US011471368B2

(12) United States Patent
Doraiswamy et al.

(10) Patent No.: US 11,471,368 B2
(45) Date of Patent: Oct. 18, 2022

(54) ELECTRO-ACTUATABLE COMPRESSION GARMENTS WITH SHAPE MEMORY ELEMENTS

(71) Applicant: Koya Medical, Inc., Oakland, CA (US)

(72) Inventors: Anand Doraiswamy, Oakland, CA (US); Connor Meehan, Pleasant Hill, CA (US); Jay Zuerndorfer, Oakland, CA (US); Ian Kovacevich, Carlsbad, CA (US); John Pamplin, Charlotte, NC (US); Jarren Baldwin, Oakland, CA (US)

(73) Assignee: Koya Medical, Inc., Oakland, CA (US)

( * ) Notice: Subject to any disclaimer, the term of this patent is extended or adjusted under 35 U.S.C. 154(b) by 0 days.

(21) Appl. No.: 17/303,951

(22) Filed: Jun. 10, 2021

(65) Prior Publication Data

US 2021/0386614 A1 Dec. 16, 2021

Related U.S. Application Data

(60) Provisional application No. 63/037,462, filed on Jun. 10, 2020.

(51) Int. Cl.
*A61H 9/00* (2006.01)

(52) U.S. Cl.
CPC ....... *A61H 9/0092* (2013.01); *A61H 2201/50* (2013.01); *A61H 2205/06* (2013.01);
(Continued)

(58) Field of Classification Search
CPC .............. A61H 9/0092; A61H 2205/06; A61H 2205/10; A61H 2201/50; A61H 2207/00;
(Continued)

(56) References Cited

U.S. PATENT DOCUMENTS 4,018,064 A 4/1977 Doslik
4,527,402 A 7/1985 Swallow et al.
(Continued)

FOREIGN PATENT DOCUMENTS

CN 101098670 B 7/2011
CN 105082129 A 11/2015
(Continued)

OTHER PUBLICATIONS

International Search Report and Written Opinion in Application No. PCT/US2021/036822, dated Sep. 28, 2021, in 16 pages.

*Primary Examiner* — Quang D Thanh

(74) *Attorney, Agent, or Firm* — Knobbe Martens Olson & Bear, LLP

(57) ABSTRACT

A compression garment having one or more flex frames that can be shortened or lengthened to apply or release a compressive force to the limb or other anatomical feature of a user. The compression garment can have a wire made of shape memory material (shape memory alloy). A controller of the compression garment can supply an electrical input to the wire, generating heat that can cause the wire to contract such that the flex frame deflects to a shorter length to apply a compressive force to the limb or other anatomical feature of the user. The one or more flex frames can be contracted in unison or in sequence to direct the flow of bodily fluids in the limb or other anatomical feature of the user.

25 Claims, 93 Drawing Sheets

(52) U.S. Cl.
CPC ...... *A61H 2205/10* (2013.01); *A61H 2207/00* (2013.01); *A61H 2209/00* (2013.01)

(58) Field of Classification Search
CPC ........ A61H 2209/00; A61H 2201/0157; A61H 2201/102; A61H 2201/0207; A61H 2201/0221; A61H 2201/1635; A61H 2201/1638; A61H 2201/164; A61H 2201/1642; A61H 2201/5007; A61H 11/00
See application file for complete search history.

(56) References Cited

U.S. PATENT DOCUMENTS

| | | | | |
|---|---|---|---|---|
| 5,787,732 | A | 8/1998 | Perron et al. | |
| 5,996,205 | A | 12/1999 | Mashiko et al. | |
| 5,997,465 | A | 12/1999 | Savage et al. | |
| 6,123,681 | A | 9/2000 | Brown, III | |
| 6,509,094 | B1 | 1/2003 | Shah et al. | |
| 7,857,777 | B2 | 12/2010 | Larson et al. | |
| 7,868,221 | B2 | 1/2011 | Munch-Fals et al. | |
| 7,896,825 | B2 | 3/2011 | Atkinson et al. | |
| 8,517,963 | B2 | 8/2013 | Larson et al. | |
| 8,523,794 | B2 | 9/2013 | Iker et al. | |
| 8,764,689 | B2 | 7/2014 | Toth | |
| 9,027,408 | B2 | 5/2015 | Toth | |
| 9,161,878 | B1 | 10/2015 | Pamplin et al. | |
| 9,248,074 | B2 | 2/2016 | Toth | |
| 9,271,890 | B1 | 3/2016 | Pamplin et al. | |
| 9,326,911 | B2 | 5/2016 | Wyatt et al. | |
| 9,463,821 | B1 | 10/2016 | Critchley et al. | |
| 10,071,012 | B2 | 9/2018 | Larson et al. | |
| 10,188,152 | B2 | 1/2019 | Stasey et al. | |
| 10,285,902 | B2 | 5/2019 | Pamplin et al. | |
| 10,426,202 | B2 | 10/2019 | Wyatt et al. | |
| 10,441,491 | B2 | 10/2019 | Wyatt et al. | |
| 10,617,593 | B2 | 4/2020 | Wyatt et al. | |
| 10,668,305 | B2 | 6/2020 | Cheatham, III et al. | |
| 10,688,007 | B2 | 6/2020 | Wyatt et al. | |
| 10,743,621 | B2 | 9/2020 | Wyatt et al. | |
| 2002/0156401 | A1 | 10/2002 | Sherman et al. | |
| 2003/0005558 | A1 | 1/2003 | Wong | |
| 2005/0043657 | A1 | 2/2005 | Couvillon, Jr. | |
| 2010/0234779 | A1 | 9/2010 | Asvadi et al. | |
| 2011/0139835 | A1 | 6/2011 | Fikes | |
| 2011/0189444 | A1 | 8/2011 | Beers | |
| 2012/0065561 | A1 | 3/2012 | Ballas et al. | |
| 2012/0101417 | A1 | 4/2012 | Joseph | |
| 2012/0232447 | A1 | 9/2012 | Gordon et al. | |
| 2013/0030335 | A1 | 1/2013 | Norton | |
| 2013/0267995 | A1 | 10/2013 | Voss et al. | |
| 2013/0303957 | A1 | 11/2013 | Bauerfeind | |
| 2014/0081187 | A1 | 3/2014 | Wyatt et al. | |
| 2015/0025426 | A1 | 1/2015 | Larson et al. | |
| 2015/0065930 | A1 | 3/2015 | Wyatt et al. | |
| 2015/0073318 | A1 | 3/2015 | Holschuh et al. | |
| 2015/0073319 | A1 | 3/2015 | Holschuh et al. | |
| 2016/0022528 | A1* | 1/2016 | Wyatt | A61H 1/008 601/152 |
| 2016/0074234 | A1 | 3/2016 | Abichandani et al. | |
| 2016/0120733 | A1 | 5/2016 | Ishikawa et al. | |
| 2016/0175179 | A1* | 6/2016 | Pamplin | A61H 7/001 601/84 |
| 2016/0193100 | A1 | 7/2016 | Toth | |
| 2016/0220808 | A1* | 8/2016 | Hyde | A61B 5/6895 |
| 2016/0331620 | A1 | 11/2016 | Kazanchyan et al. | |
| 2016/0374886 | A1 | 12/2016 | Wyatt et al. | |
| 2017/0196347 | A1* | 7/2017 | Sawhney | A63B 55/408 |
| 2017/0246073 | A1 | 8/2017 | Van-De-Velde | |
| 2017/0252252 | A1* | 9/2017 | Wyatt | A61H 11/00 |
| 2017/0304136 | A1 | 10/2017 | Holschuh et al. | |
| 2017/0304139 | A1* | 10/2017 | Ross | A61H 11/00 |
| 2017/0312161 | A1 | 11/2017 | Johnson et al. | |
| 2018/0055009 | A1 | 3/2018 | Wyatt et al. | |
| 2018/0125173 | A1 | 5/2018 | Lambert | |
| 2018/0177677 | A1 | 6/2018 | Pamplin et al. | |
| 2018/0214616 | A1 | 8/2018 | Muschalek et al. | |
| 2018/0242655 | A1 | 8/2018 | Holschuh et al. | |
| 2019/0274372 | A1 | 9/2019 | Rizzo et al. | |
| 2020/0000676 | A1 | 1/2020 | Pamplin et al. | |
| 2020/0000677 | A1 | 1/2020 | Pamplin et al. | |
| 2020/0154804 | A1 | 5/2020 | Huang | |

FOREIGN PATENT DOCUMENTS

| | | |
|---|---|---|
| CN | 105804960 | 7/2016 |
| KR | 10-1569850 | 11/2015 |
| WO | WO 2013/025481 | 2/2013 |
| WO | WO 2013/149985 | 10/2013 |
| WO | WO 2014/172248 | 10/2014 |
| WO | WO 2016/048827 | 3/2016 |
| WO | WO 2016/077150 | 5/2016 |
| WO | WO 2017/027145 | 2/2017 |
| WO | WO 2018/013188 | 1/2018 |
| WO | WO 2018/150372 | 8/2018 |
| WO | WO 2020/144437 | 7/2020 |
| WO | WO 2021/252770 | 12/2021 |

* cited by examiner

| Arm Model (Circumference cm) | | Tech Panel Dimensions (length in cm) | Total Strap Length Needed (cm) |
|---|---|---|---|
| G | 23 | 14.5 | 22 |
| F | 25.5 | 18 | 20 |
| E | 27 | 19 | 21 |
| D | 29.5 | 20 | 24 |
| C | 32 | 21 | 27 |
| B | 35.5 | 25 | 26 |
| A | 37.5 | 28 | 24 |

FIG. 14B

ELECTRO-ACTUATABLE COMPRESSION GARMENTS WITH SHAPE MEMORY ELEMENTS

CROSS REFERENCE TO RELATED APPLICATIONS

This application claims priority to U.S. Provisional Patent Application No. 63/037,462, filed Jun. 10, 2020, which is incorporated herein by reference in its entirety. Any and all applications, if any, for which a foreign or domestic priority claim is identified in the Application Data Sheet of the present application are hereby incorporated by reference under 37 CFR 1.57.

BACKGROUND

Field of the Invention

This invention relates in some aspects to compression garments, and more particularly, compression garments with flex frames that can apply pressure to a limb.

SUMMARY

A compression garment having one or more flex frames that can be shortened or lengthened to apply or release a compressive force to the limb or other anatomical feature of a user. The compression garment can have a wire made of shape memory material (shape memory alloy). A controller of the compression garment can supply an electrical input to the wire, generating heat that can cause the wire to contract such that the flex frame deflects to a shorter length to apply a compressive force to the limb or other anatomical feature (e.g., trunk, shoulder, neck, torso, waist, head, etc.) of the user. The one or more flex frames can be contracted in unison or in sequence to direct the flow of bodily fluids in the limb or other anatomical feature of the user. In some variants, the wire, which may not be made of a shape memory material, can be reeled in via a motor to shorten the flex frame to apply a compressive force to the limb or other anatomical features of the patient.

In some variants, a method for applying pressure in a controlled manner to an anatomical part of the body of an animal using electromechanical force(s) to stimulate bodily fluids in a desired fashion is described herein.

In some variants, the method can include applying force or pressure using wires made of metals, alloys or polymers with force provided by electrical power.

In some variants, the method can include applying force using wires made of metals, alloys or polymers or a combination of these materials with force provided by a mechanical motor that winds the wire in both directions to tighten or loosen the compression force.

In some variants, the method can include applying force using wires made of metals, alloys or polymers with force provided by transitional properties of shape memory polymers or shape memory alloys that can apply the set pressure based on calibrated electrical input of current, time, and frequency.

In some variants, the method can include applying force using a flexible frame that provide even transition of forces across the intended surface of application.

In some variants, the method can include applying a force using a flexible frame that is controlled using wires or cables that are powered through mechanical or electromechanical motors.

In some variants, the method can include applying force through a sensor-based closed-loop architecture where in the sensor may capture and calibrate pressure, size of limb or anatomical feature, temperature, impedance of the wire and/or tissue, pulse-rate, and other bodily metrics.

In some variants, the method can include applying force through one or more flexible frames in unison or sequential succession, all controlled by an independent microelectronic controller system, that can be further controlled using a mobile app.

In some variants, each flex-frame may have a sensor or microcontroller within its setup to individualize or personalize the level of control for each section.

In some variants, the garment may be designed from the aforementioned flex-frame into a group of panels that comprise the garment structure to encompass and surround the required anatomy to be compressed or stimulated for flow of bodily fluids.

In some variants, the aforementioned garment may have the controller unit embedded or available as a separate detachable unit with various controlling buttons, wherein the controller may hold a rechargeable battery, a blue-tooth module, or other feature.

In some variants, data may be captured to remotely monitor patient activity and patient adherence to engineer a software that may automatically remind patients to use the device or change therapy, compression, stimulation depending on progression of the disease or recovery.

In some variants, the garment holding the frame assembly or tech panel can be configured for the desired anatomy to be compressed or stimulated.

In some variants, the garment may be held in place by lace straps, hook-loop straps, belt straps and other similar mechanisms.

In some variants, the garment may be held in place by alternating straps for ease of application and providing anchor or leverage.

In some variants, cuttable straps to accommodate various sizing of desired anatomy and shape/size of subjects treated are used.

In some variants, a flexible frame for a compression garment is described herein. The flexible frame can include a first support that can have a first groove and a second groove. The flexible frame can include a second support that can have a first groove and a second groove. The flexible frame can include a first spring arm that can have first and second spaced-apart ends extending distally from interior portions of the first support, and a looped segment that extends laterally from the first and second ends. The flexible frame can include a second spring arm that can have first and second spaced-apart ends extending distally from interior portions of the second support, and a looped segment that extends laterally from the first and second ends. The flexible frame can include a bridge that can have a plurality of spaced-apart guide structures connecting the looped segments of the first spring arm and the second spring arm. The flexible frame can include a shape memory material associated with the flexible frame. The first spring arm and the second spring arm can expand or contract in response to a transformation of the shape memory material.

In some variants, the flex frame can include shape memory material that has nitinol.

In some variants, the flexible frame can include a microcontroller operably connected to the flexible frame.

In some variants, the flexible frame can include guide structures that can include a generally cylindrical shape.

In some variants, the shape memory material comprises a wire.

In some variants, the flexible frame includes no more than a single wire.

In some variants, the flexible frame can include at least one sensor that can provide feedback information to the microcontroller.

In some variants, the feedback information can include current or voltage delivered along the shape memory material.

In some variants, the first groove of the first support and the second groove of the first support can be on opposite ends of the first support.

In some variants, the second groove of the first support can include two discrete sections separated by a gap.

In some variants, the first support includes a retention feature.

In some variants, a compression garment including any number of features described herein is disclosed.

In some variants, a flexible frame including any number of features described herein is disclosed.

In some variants, a method of compressing a limb using any number of features described herein is disclosed.

In some variants, a compression garment that can be worn on an anatomical feature of a user is disclosed herein. The compression garment can include a flex frame that can have a plurality of guide structures. Each of the plurality of guide structures can have an upper channel and lower channel separated by a partition. The compression garment can include a wire or similar feature that can include shape memory material. The wire can be routed around features of the flex frame and through the upper and lower channels of the guide structures to cross over itself. The partition can separate portions of the wire disposed through the upper and lower channels. The compression garment can include a controller that can apply an electrical current to the wire to generate heat, causing the wire to contract such that the flex frame deflects to a shorter length to apply a compressive force to the anatomical feature of the user to urge a flow of fluids therein when the compression garment is worn by the user.

In some variants, the compression garment can have a plurality of primary straps that can secure the compression garment around the anatomical feature of the user.

In some variants, the primary straps can include protrusions that can break up fibrotic tissue of the user.

In some variants, the compression garment can have a plurality of secondary straps that can secure the compression garment around the anatomical feature of the user.

In some variants, the compression garment can include a liner that can be disposed between the flex frame and the anatomical feature of the user.

In some variants, the compression garment can have protrusions configured to face inward toward the anatomical feature of the user. The protrusions can break up fibrotic tissue of the user.

In some variants, the flex frame can include protrusions that can break up fibrotic tissue of the user.

In some variants, the compression garment can have a plurality of flex frames and a plurality of wires.

In some variants, the controller is configured to control the contraction of the wires such that an electrical current can be applied to select wires of the plurality of wires to facilitate localized compression to the anatomical feature of the user.

In some variants, the flex frame can include a first support that can have a first groove and a second groove. The flex frame can include a second support that can have a first groove and a second groove. The flex frame can include a first spring arm that can have first and second spaced-apart ends extending distally from interior portions of the first support, and a looped segment that extends laterally from the first and second ends. The flex frame can include a second spring arm that can include first and second spaced-apart ends extending distally from interior portions of the second support, and a looped segment that extends laterally from the first and second ends. The flex frame can include a bridge that can include the guide structure. The bridge can connect the looped segments of the first spring arm and the second spring arm. The first spring arm and second spring arm can expand or contract in response to the contraction of the wire.

In some variants, the first and second grooves can be on opposing ends of the first support and second support.

In some variants, the wire can be routed through the first and second grooves of the first and second supports.

In some variants, the compression garment can include backing disposed on an outer surface of the compression garment. The backing can vent heat.

In some variants, a flex frame for a compression garment that can be worn by a user to apply a compressive force to an anatomical feature is described herein. The flex frame can include a first support that can have a first groove and a second groove disposed on opposing sides of the first support. The flex frame can include a second support that can include a first groove and a second groove disposed on opposing sides of the second support. The flex frame can include a first spring arm that can have first and second spaced-apart ends extending distally from interior portions of the first support, and a looped segment that extends laterally from the first and second ends. The flex frame can include a second spring arm that can have first and second spaced-apart ends extending distally from interior portions of the second support, and a looped segment that extends laterally from the first and second ends. The flex frame can include a bridge having a guide structure that can have an upper and lower channel separated by a partition. The flex frame can include a wire routed through various features of the flex frame away from a controller and back to the controller. The wire can be routed away from the controller through the first groove of first support, upper channel of the guide structure, and the second groove of a second support. The wire can be routed toward the controller through the first groove of the second support, lower channel of the guide structure, and the second groove of the first support. The partition can separate an intersection of the wire at the guide structure. The controller can apply an electrical current to the wire to generate heat, causing the wire to contract such that the flex frame deflects to a short length to apply a compressive force to the anatomical feature when incorporated into the compression garment worn by the user.

In some variants, the flex frame can include protrusions that can break up fibrotic tissue of the user.

In some variants, the protrusions can be disposed on the first and second supports.

In some variants, the first and second supports can include tabs that can help to retain the wire in the first and second grooves.

In some variants, the wire is made of nitinol.

In some variants, the bridge can include a ramp configured to retain the wire in the lower channel.

In some variants, the bridge and/or guide structure can be made of a nonconductive material (e.g., a polymer) to electrically insulate the portions of the wire routed through the upper and lower channels from each other.

In some variants, a compression garment that can be worn on an anatomical feature of the user is described herein. The compression garment can include a plurality of flex frames that can include a plurality of guide structures. Each of the plurality of guide structures can have a partition separating an upper portion and a lower portion. The compression garment can include a plurality of wires. Each of the plurality of wires can include shape memory material. Each wire can be wrapped around features of one flex frame of the plurality of flex frames and cross over itself at one or more intersections. The partition of the guide structures can electrically isolate the wire from itself in the upper and lower portions at the intersections. The compression garment can include a plurality of microcontrollers. Each of the plurality of microcontrollers can apply an electrical current to one wire of the plurality of wires to generate heat, causing the one wire to contract such that the one flex frame deflects to a shorter length to apply a compressive force to the anatomical feature of the user to urge a flow of fluids therein when the compression garment is worn by the user.

In some variants, the compression garment can include a plurality of primary straps that can secure the compression garment around the anatomical feature of the user.

In some variants, the primary straps can include protrusions that can break up fibrotic tissue of the user.

In some variants, the compression garment can include a plurality of secondary straps that can secure the compression garment around the anatomical feature of the user.

In some variants, the compression garment can include a liner that can be disposed between the plurality of flex frames and the anatomical feature of the user.

In some variants, the compression garment can include protrusions that can face inward toward the anatomical feature of the user. The protrusions can break up fibrotic tissue of the user.

In some variants, the plurality of flex frames can include protrusions configured to break up fibrotic tissue of the user.

In some variants, the plurality of microcontrollers can apply electrical current to the plurality of wires in a sequence in a longitudinal direction of the compression garment to direct a flow of fluid in the anatomical feature.

In some variants, each of the plurality of flex frames can include a first support having a first groove and a second groove. Each of the plurality of flex frames can include a second support that can have a first groove and a second groove. Each of the plurality of flex frames can include a first spring arm that can have first and second spaced-apart ends extending distally from interior portions of the first support, and a looped segment that extends laterally from the first and second ends. Each of the plurality of flex frames can include a second spring arm comprising first and second spaced-apart ends extending distally from interior portions of the second support, and a looped segment that extends laterally from the first and second ends. Each of the plurality of flex frames can include a bridge that can have the guide structure. The bridge can connect the looped segments of the first spring arm and the second spring arm. The first spring arm and second spring arm can expand or contract in response to the contraction of the wire.

In some variants, the compression garment can include backing that can be disposed on an outer surface of the compression garment. The backing can vent heat.

In some variants, the compression garment can include one or more sensors to measure one or more parameters of the user.

BRIEF DESCRIPTION OF THE DRAWINGS

Various embodiments are depicted in the accompanying drawings for illustrative purposes and may not be drawn to scale, and should in no way be interpreted as limiting the scope of the embodiments. In addition, various features of different disclosed embodiments can be combined to form additional embodiments, which are part of this disclosure.

FIGS. 3A-1, 3A-2 and 3A-3 illustrate various flex frames.

FIGS. 3B-1, 3B-2 and 3B-3 illustrate various flex frames.

FIG. 14B provides a table of example strap sizes.

DETAILED DESCRIPTION

Although certain embodiments and examples are described below, this disclosure extends beyond the specifically disclosed embodiments and/or uses and modifications and equivalents thereof. Thus, it is intended that the scope of this disclosure should not be limited by any particular embodiments described below.

The compression garments systems, apparatuses, and methods disclosed herein can be used and/or modified for use with systems and methods described in U.S. Pub. No. 2020/0000677 to Pamplin et al., filed Aug. 15, 2019, which is hereby incorporated by reference in its entirety. Compression garment systems can include flex frames, which can be made of polymers such as plastics, thermoplastics, etc., that are configured to deflect or flex to shorten under compression. Compression can be applied via providing a thermal or electrical input to a wire made of a shape memory material that is wrapped around features of the flex frame. For example, the wire can be made of shape memory materials such alloys, nickel-titanium (Nitinol) alloy (preferred), and/or copper-aluminum-nickel alloy or any other alloy (e.g., Fe—Mn—Si, Cu—Zn—Al, Cu—Al—Ni, etc.) or shape memory polymers and composites, configured to morphologically change in response to a stimulus (e.g., temperature change). The electrical input from a controller of the compression garment can heat the wire, causing it to contract, which can shorten the flex frame and apply compression to a limb or other anatomical feature of a user (e.g., trunk, shoulder, neck, torso, waist, head, etc.). Alternatively and/or in combination, the flex frames can include shape memory material that can contract as explained above. Alternatively and/or in combination, compression can be applied via reeling in a wire that is wrapped around the features of the flex frame with a motor, which can shorten the flex frame and apply compression to a limb of other anatomical feature of the user. In some embodiments, the shape memory material can include one or more shape memory polymers, including but not limited to shape memory polymer foams and polyurethanes.

Figure 1:
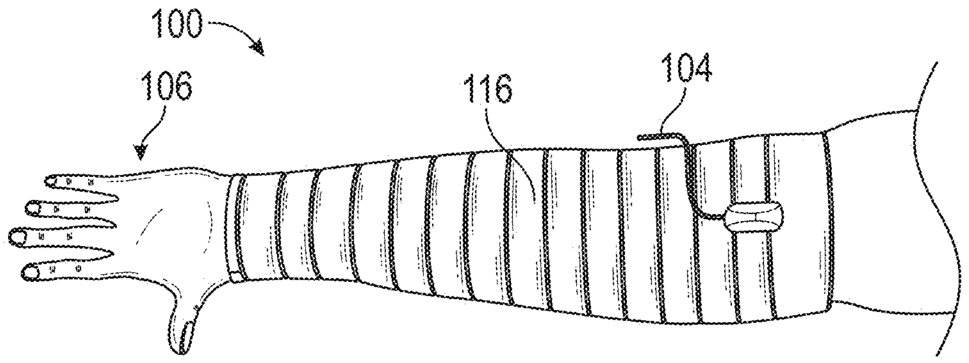
FIG. 1 illustrates a compression garment on the limb of a user.

FIG. 1 illustrates a compression garment 100. The compression garment 100 can be disposed on a limb 106, such as an upper or lower extremity, or other anatomical feature such as a shoulder, trunk, torso, neck, etc. As illustrated, the limb 106 is the arm, but in some variants, the limb 106 can be another limb or other anatomical features of a human, such as a leg, arm, trunk, shoulder, neck, torso, waist, head, eyes, ears, etc. or the limb or other anatomical feature (e.g., trunk, shoulder, neck, torso, waist, head, etc.) of an animal, such as the leg of a dog, cat, etc. The compression garment 100 can include a backing 116. The backing 116 can enclose or cover internal components of the compression garment 100, which can help prevent internal components of the compression garment 100 from snagging on objects and/or protect the internal components of the compression garment 100 from damage. The backing 116 can vent heat to the ambient environment as a wire made of shape memory material is heated to contract. The compression garment 100 can include a wired connection 104 to a controller and/or power supply described in more detail elsewhere herein.

The compression garment 100 can be used to selectively apply pressure (e.g., compressive forces) to the limb 106 of a user or other anatomical feature (e.g., trunk, shoulder, neck, torso, waist, head, etc.) of the user. In some variants, the compression garment 100 can apply pulses of pressure to the limb 106 or other anatomical feature. In some variants, the compression garment 100 can apply compressive forces along the length of the limb 106 or other anatomical feature covered by the compression garment 100. In some variants, the compression garment 100 can sequentially provide pressure along the length of the limb 106 or other anatomical feature to direct the flow of fluid within the limb 106 or other anatomical feature. In some variants, the compression garment 100 can apply preprogrammed treatment plans. In some variants, the compression garment 100 can include one or more sensors to capture and calibrate an applied pressure based on the size of the limb 106 or anatomical feature, temperature, impedance of the tissue of the limb 106/anatomical feature and/or wire facilitating compression, pulse rate, and/or other bodily metrics. The sensors can include bioimpedance sensors to measure the tissue for edema, temperature sensor to measure the tissue for inflammation, and other metrics such as SPO2 and PPG of bodily fluids.

The compression garment 100 can be used to improve circulation, enhance muscle recovery, and/or assist in recovery from injuries, such as sports injuries. In some variants, the compression garment 100 can be used to assist in treating primary and secondary lymphedema and/or edema. In some variants, the compression garment 100 can be used to help prevent deep vein thrombosis (DVT), cellulitis, and/or ulceration. In some variants, the compression garment 100 can be used to prevent and/or treat restless leg syndrome (RLS) using application on lower extremity, thigh area, knee, ankle, and/or feet. In some variants, the compression garment 100 can be used to treat and/or provide relief for rheumatoid arthritis (RA), which can include RA of at least the hand, knuckle, wrist, knee, hip, shoulder, elbow, or other joints. In some variants, the compression garment 100 can be a treatment to provide an arterial flow increase using enhanced external counter pulsation procedure. In some variants, the compression garment 100 can be used to treat ghost pain in amputees. In some variants, the compression garment 100 can be used to treat plantar fasciitis.

Figure 2:
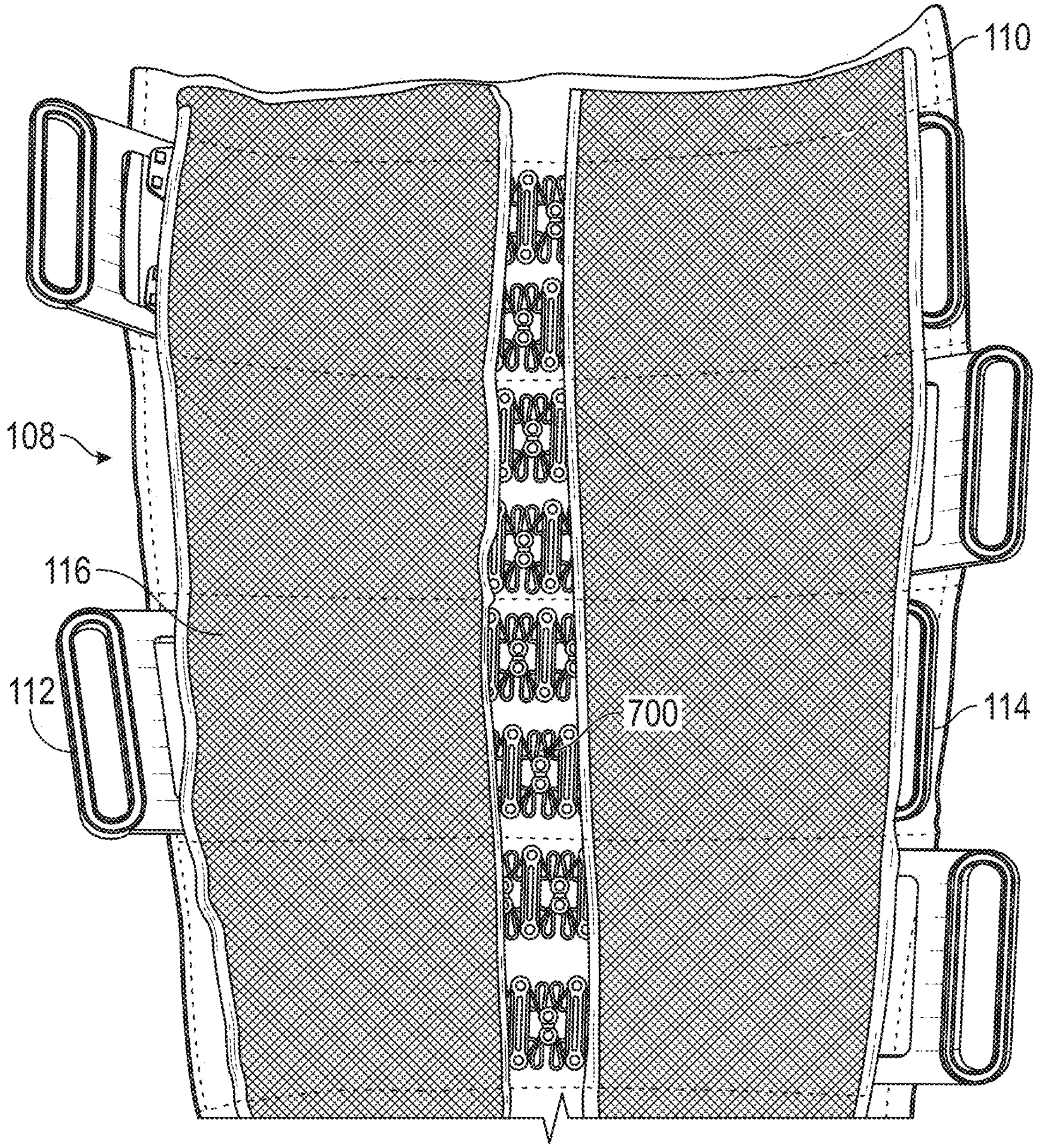
FIG. 2 illustrates a panel that is incorporated into the compression garment. Samuel

FIG. 2 illustrates a panel 108 that can be incorporated in the compression garment 100. In some variants, one or more panels 108 can be incorporated into the compression garment 100 to apply compressive forces to the limb 106 of the user. In some variants, one or more panels 108 can be incorporated into the compression garment 100 to encompass and/or surround a limb 106 and/or portion of a limb 106 to apply compressive forces and/or stimulate the flow of bodily fluids of the user.

The panel 108 can include one or more of the flex frame(s) 700 which can be one or more of the flex frame(s) 200, flex frame(s) 300, flex frame(s) 400, flex frame(s) 500, and/or flex frame(s) 600, described in more detail herein. The flex frame(s) 700 can facilitate providing compressive forces to the limb 106 of the user upon contraction of the wire described herein. The flex frame(s) 700 can shorten or length via an electromechanical mechanism acting on the wire and/or flex frame(s) 700 to selectively apply more or less compressive forces, as detailed elsewhere herein.

The number of flex frames 700 can depend on the size of the limb 106 to be treated. In some variants, each of the flex frames 700 included in the panel 108 can be independently controlled to provide targeted compression and/or compression patterns or sequences. The flex frame 700 can include a first strap interface 112 and/or a second strap interface 114, which can be disposed on opposing ends of the flex frame 700. The first strap interface 112 and second strap interface 114 can interface with straps, belts, ties, and/or other similar devices to secure the panel 108 to the limb 106 of the user. In some variants, the first strap interface 112 and/or second strap interface 114 are loops, openings, hooks, rings, hoops, D rings, and/or other similar features that can engage with the straps (e.g, Velcro straps, lace straps, hook-loop straps, belt straps, and/or other varieties).

The panel 108 can include a liner 110. The liner 110 can be disposed between the flex frame 700 and the limb 106 of the user. The liner 110 can thermally insulate the limb 106 of the user from heat generated from electronic components and/or heating of the wire to control the flex frame 700. The liner 110 can be flexible to facilitate movement of the user. The liner 110 can help to protect the limb 106 of the user from the flex frame 700. In some variants, the user may have another material (e.g., sleeve, wrap, etc.) disposed between the liner 110 and the limb 106 for protection.

The panel 108 can include backing 116. The backing 116 can be disposed on the outer side of the flex frame 700 that is opposite the limb 106 of the user. The backing 116 can be disposed between the flex frame 700 and a sleeve of the compression garment 100. In some variants, the compression garment 100 does not include a sleeve and the backing 116 alone can protect the flex frame 700. The backing 116 can include a breathable material, such as mesh, to ventilate the heat generated in contracting and/or releasing the flex frame(s) 700 via the wire(s). In some variants, the liner 110 and/or backing 116 can be divided into multiple pieces having gaps therebetween, which can facilitate movement of the user. In some variants, the liner 110 and/or backing 116 can be monolithic.

FIGS. 3A-1, 3A-2 and 3A-3 illustrate the flex frame 200, flex frame 300, and flex frame 400, each having different geometries, according to some embodiments. One or more of the flex frame 200, flex frame 300, and/or flex frame 400 can be incorporated into the panel 108. The flex frame 200, flex frame 300, and/or flex frame 400 can shorten or length to apply compressive forces to the limb 106 of the user via the wire contraction or withdraw. The flex frame 200, flex frame 300, and/or flex frame 400 can provide pressure to the limb 106 of the user via the wire contraction or withdrawal. The flex frame 200, flex frame 300, and/or flex frame 400 can be wrapped circumferentially around the limb 106 of the user to apply a compressive force. The flex frame 200, flex frame 300, and/or flex frame 400 can provide an even transition of forces across the intended surface of application, e.g., across the surface of the limb 106 of the user.

Figures 1, 2, 3, 3A:
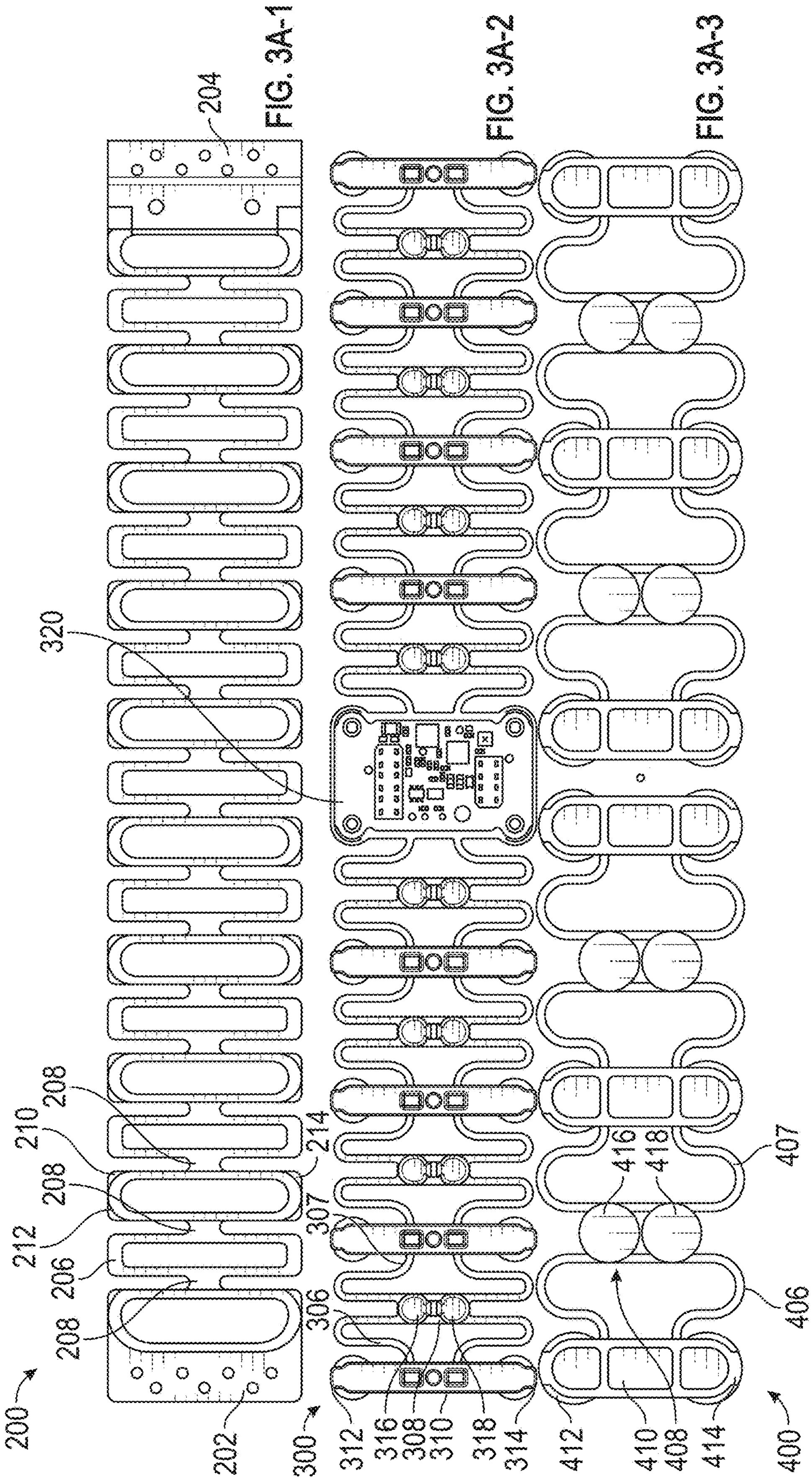

As illustrated in FIG. 3A-1, the flex frame 200 can include a first end 202 and a second end 204. The first end 202 and/or second end 204 can be configured to couple with one or more of the first strap interface 112, second strap interface 114, and/or liner 110 to enable the flex frame 200 to be secured into position around the limb 106 of the user.

The flex frame 200 can include a plurality of protruding support regions 210 that are deposed between enclosed openings 206. The flex frame 200 can include bridges 208 disposed between the protruding support regions 210 and the enclosed openings 206. The enclosed opening 206 can be configured to flex, deflect, and/or otherwise change to allow the longitudinal length of the flex frame 200 to shorten or lengthen to apply compressive forces to the limb 106 of the user. The protruding support regions 210 can include first grooves 212 and second grooves 214 to guide a wire. In some variants, the protruding support region 210 can include a first groove 212 disposed on a first edge and a second groove 214 disposed on a second edge which can be opposite the first edge. In some variants, the first groove 212 and/or second groove 214 can be curved to facilitate movement of a wire that extends or retracts to shorten or lengthen the flex frame 200.

Figures 1, 2, 3, 3B:
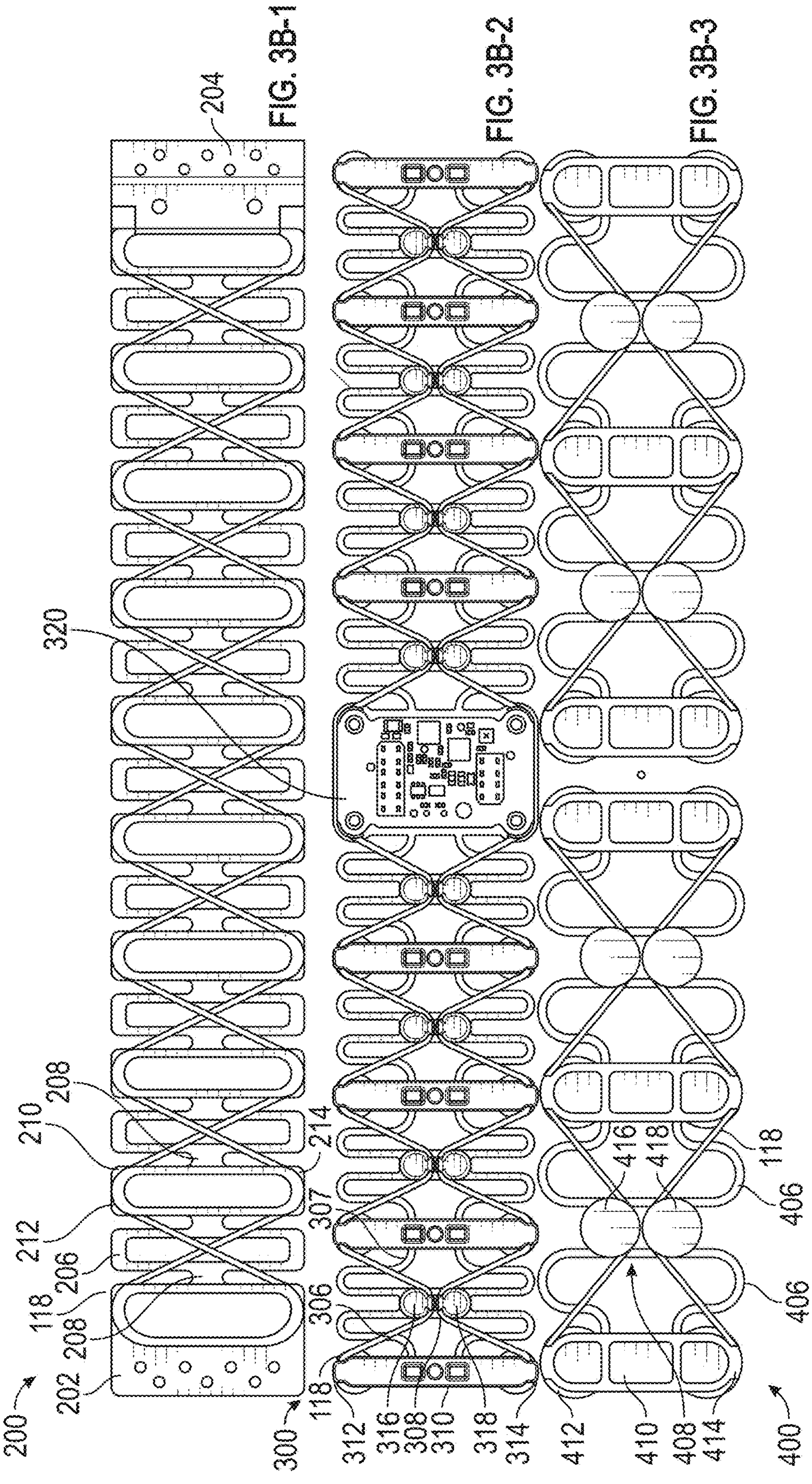

As schematically illustrated in FIG. 3B-1, a wire 118, also referred to as a cable or band, can be threaded, routed, and/or otherwise incorporated with the flex frame 200. The wire 118 can impart a force on the flex frame 200 to apply a compressive force to the limb 106 of the user. The wire 118 can wrap around various features of the flex frame 200. The wire 118 can extend from the first end 202 to the second end 204. In some variants, the wire 118 can extend from the first end 202 to the second end 204 and back to the first end 202. The wire 118 can curve around the first groove 212 and second groove 214 of the protruding support regions 210. The wire 118 can be routed around a first groove 212 of one protruding support region 210 to around a second groove 214 of another protruding support region 210 to around another first groove 212 of another protruding support region 210 as the wire 118 extends between the first end 202 and second end 204. At the second end 204, the wire 118 can wrap around the first groove 212 and second groove 214 of a last protruding support region 210 before being routed back to the first end 202. In some variants, the wire 118 can cross itself as the wire 118 is routed from the first end 202 to the second end 204 and back to the first end 202. In some variants, the wire 118 can cross over itself over the enclosed opening 206.

The wire 118 can be used to apply a force to the flex frame 200 to apply or release compressive forces to the limb 106 of the user. In some variants, electromechanical forces can be applied using the wire 118 to apply or release compressive forces. In some variants, electrical power can be used to apply a force to the flex frame 200 via the wire 118 resulting in the application or release of compressive forces to the limb 106 of the user. In some variants, a motor (e.g., electromechanical, mechanical motor, electrical motor, etc.) can wind (e.g., reel) or unwind (e.g., unreel) the wire 118 to apply, apply more, release, or apply less compressive force to the limb 106 of the user. For example, the wire 118 may be unwound length the flex frame 200 to release compressive forces and wound to shorten the length of the flex frame 200 to apply compressive forces.

In some variants, the wire 118 is made of a shape memory material (e.g., shape memory metal(s), metal alloy(s), and/or polymer(s)) having transitional properties that can transition between phases or structures to apply a set pressure to the limb 106 of the user based on an electrical input of current, time, and/or frequency. For example, the wire 118 may lengthen to a set length causing the flex frame 200 to lengthen, releasing compressive forces, upon the application of an electrical input of a given current, time, and/or frequency. The wire 118 may shorten to a set length causing the flex frame 200 to shorten, applying compressive forces, upon the application of an electrical input of a given current, time, and/or frequency. In some variants, the flex frame 200 and/or portions of the flex frame 200 (e.g., enclosed opening 206) can be made of a shape memory material (e.g., shape memory metal(s), metal alloy(s), and/or polymer(s)) having transitional properties that can transition between phases or structures to apply a set pressure to the limb 106 of the user based on an electrical input of current, time, and/or frequency, which can work in conjunction with the wire 118 and/or without the wire 118. The wire 118 used with flex frame 200 can have a radius of about 3.3 millimeters but, in some variants, other sizes are possible such as 1, 1-2, 2-3, 3-4, 4-5, or greater than 5 millimeters.

Returning to FIG. 3A-2, the flex frame 300 is illustrated. The flex frame 300 can include a first spring arm 306 and second spring arm 307 connected by a bridge 308 disposed between protruding support regions 210. The first spring arm 306 and second spring arm 307 can flex, deflect, move, undergo a phase change, and/or otherwise change to reduce and/or increase the length of the flex frame 300. The first spring arm 306 can extend from a central portion of a first support 310, curve outward towards opposing longitudinal edges of the flex frame 300, and curve inward towards the bridge 308. The first spring arm 306 can include an opening therethrough to facilitate flexion, deflection, and/or movement of the first spring arm 306. The bridge 308 can be disposed along a longitudinal axis of the flex frame 300. The second spring arm 307 can mirror the first spring arm 306 relative to the bridge 308. The second spring arm 307 can curve outward from the bridge 308 towards opposing longitudinal edges of the flex frame 300 and then curve inward to a central portion of a second support 310. The second spring arm 307 can include an opening therethrough to facilitate flexion, deflection, and/or movement of the first spring arm 306.

The bridge 308 can include a first guide structure 316 and/or second guide structure 318. The first guide structure 316 and/or second guide structure 318 can be a protuberance, rounded protrusions, grooved cylindrical structures, and/or other structures that can guide a wire. The support 310 can include a first groove 312 and/or second groove 314 disposed on opposing sides to guide a wire. The first groove 312 and/or second groove 314 can be curved to facilitate the extension and/or retraction of the wire 118 to shorten or lengthen the length of the flex frame 300.

The flex frame 300 can include a micro-electronic controller 320, which can be used with any of the flex frames disclosed herein. In some variants, the micro-electronic controller 320 can include one, two, or more sensors configured to receive feedback regarding the current and/or voltage signal passing through the wire 118, performance of the flex frame 300, and/or detect biometric information which can be used to make changes to applied compressive forces. The micro-electronic controller 320 can be disposed at various locations on flex frame 300. For example, the micro-electronic controller 320 can be disposed at the end, middle, and/or other portion of the flex frame 300 or other flex frame described herein. As illustrated, the micro-electronic controller 320 is disposed between two segments of the flex frame 300 and can control the segments individually to apply or release compressive forces.

In some variants, the flex frame 200, flex frame 300, flex frame 400, flex frame 500, flex frame 600, and/or flex frame 700 can include a micro-electronic controller 320. In some variants, each of the flex frame 200, flex frame 300, flex frame 400, flex frame 500, flex frame 600, and/or flex frame 700 can include a micro-electronic controller 320 that can control the compressive force applied to the limb 106 of the user. For example, the micro-electronic controller 320 can control whether the wire contracts to shorten or lengthen the flex frame 200, flex frame 300, flex frame 400, flex frame 500, flex frame 600, and/or flex frame 700 to apply more or less compressive forces. In some variants, the micro-electronic controller 320 can control a motor to unwind or wind the wire 118 to apply compression or release. In some variants, the micro-electronic controller 320 can control an electrical input applied to a shape memory material in the wire 118 and/or the flex frame 200, flex frame 300, flex frame 400, flex frame 500, flex frame 600, and/or flex frame 700 to lengthen or shorten the flex frame 200, flex frame 300, flex frame 400, flex frame 500, flex frame 600, and/or flex frame 700 to apply or release compressive forces to the limb 106. In some variants, the flex frame 200, flex frame 300, flex frame 400, flex frame 500, flex frame 600, and/or flex frame 700 does not have a micro-electronic controller and the flex frames are directly controlled by a main controller. In other variants, the micro-electronic controller controls multiple flex frames.

FIG. 3B-2 illustrates the flex frame 300 with the wire 118. The wire 118 can extend from the micro-electronic controller 320 to a end support 310 and back to the micro-electronic controller 320. In some variants, the wire 118 can extend from the micro-electronic controller 320 to around the first guide structure 316 up to the first groove 312 of a first support 310 around a second first guide structure 316 up to the second first groove 312 of a second support 310 and continue in a similar manner until reaching a last support 310. At the last support 310, the wire 118 can loop around the first groove 312 and second groove 314 before being routed back to the micro-electronic controller 320 via looping around the second guide structures 318 and second grooves 314 of the supports 310.

In some variants, the wire 118 can cross itself. For example, the wire 118 can extend from the micro-electronic controller 320 between the first guide structure 316 and second guide structure 318 to around the second groove 314 of a support 310 to between another first guide structure 316 and second guide structure 318 to around first groove 312 of another support 310 and continue in a similar manner until reaching the support 310. At the end support 310, the wire 118 can loop around the first groove 312 and second groove 314 before being routed back to the micro-electronic controller 320 via extending between the first guide structure 316 and second guide structure 318 to cross itself and extend around first grooves 312 and second grooves 314 of the supports 310. The wire 118 and/or flex frame 300 can be extended or lengthened via the methods described elsewhere herein to apply or release compressive forces. The wire 118 used with flex frame 300 can have a radius of about 2 millimeters but, in some variants, other sizes are possible such as 1, 1-2, 2-3, 3-4, 4-5, or greater than 5 millimeters, or ranges including any two of the foregoing values.

Returning to FIG. 3A-3, the flex frame 400 is illustrated. The flex frame 400 can include a first spring arm 406 and second spring arm 407 connected by a bridge 408 disposed between supports 410. The first spring arm 406 and second spring arm 407 can flex, deflect, move, undergo a phase change, and/or otherwise change to reduce and/or increase the length of the flex frame 400. The first spring arm 406 can extend from a central portion of a first support 410, curve outward towards opposing longitudinal edges of the flex frame 400, and curve inwards toward the bridge 408. The first spring arm 406 can include an opening therethrough to facilitate flexion, deflection, and/or movement of the first spring arm 406. The bridge 408 can be disposed along a longitudinal axis of the flex frame 400. The second spring arm 407 can mirror the first spring arm 406 relative to the bridge 408. The second spring arm 407 can curve outward from the bridge 408 towards opposing longitudinal edges of the flex frame 400 and then curve inward to a central portion of a second support 410. The second spring arm 407 can include an opening therethrough to facilitate flexion, deflection, and/or movement of the first spring arm 406.

The bridge 408 can include a first guide structure 416 and/or second guide structure 418. The first guide structure 416 and/or second guide structure 418 can be protuberances, rounded protrusions, grooved cylindrical structures, and/or other similar structures that can guide a wire. The support 410 can include a first groove 412 and/or second groove 314 disposed on opposing sides to guide a wire. The first groove 412 and/or second groove 314 can be curved to facilitate the extension and/or contraction of the wire 118 to shorten or lengthen the flex frame 400.

The micro-electronic controller 320 can be disposed between segments of the flex frame 400 to control lengthening and/or shortening of the flex frame 400 via the wire to apply or release compressive forces to the limb 106 of the user. In some variants, the micro-electronic controller 320 can be disposed at the end of the flex frame 400.

FIG. 3B-3 illustrates the flex frame 400 with the wire 118. The wire 118 can extend from a micro-electronic controller 320 disposed between the segments of the flex frame 400 to an end support 410 and back to the micro-electronic controller 320. In some variants, the wire 118 can extend from the micro-electronic controller 320 to around the first guide structure 416 up to the first groove 412 of a first support 410 around a second guide structure 416 up to the first groove 412 of a second support 410 and continue in a similar manner until reaching an end support 410. At the end support 410, the wire 118 can loop around the first groove 412 and second groove 414 before being routed back to the micro-electronic controller 320 via looping around the second guide structures 418 and second grooves 414 of the supports 410.

In some variants, the wire 118 can cross itself. For example, the wire 118 can extend from the micro-electronic controller 320 between the first guide structure 416 and second guide structure 418 to around the second groove 414 of a support 410 to between another first guide structure 416 and second guide structure 418 to around the first groove 412 of another support 410 and continue in a similar manner until reaching a end support 410. At the end support 410, the wire 118 can loop around the first groove 412 and second groove 414 before being routed back to the micro-electronic controller 320 via extending between the first guide structure 416 and second guide structure 418 to cross itself and extend around first grooves 412 and second grooves 414 of the supports 410. The wire 118 and/or flex frame 400 can be extended or contracted via the methods described elsewhere herein to apply or release compressive forces. The wire 118 used with flex frame 400 can have a radius of about 4 millimeters but, in some variants, other sizes are possible such as 1, 1-2, 2-3, 3-4, 4-5, 5-6, 6-7, 7-8, or greater than 8 millimeters, or ranges including any two of the foregoing values.

Figure 3C:
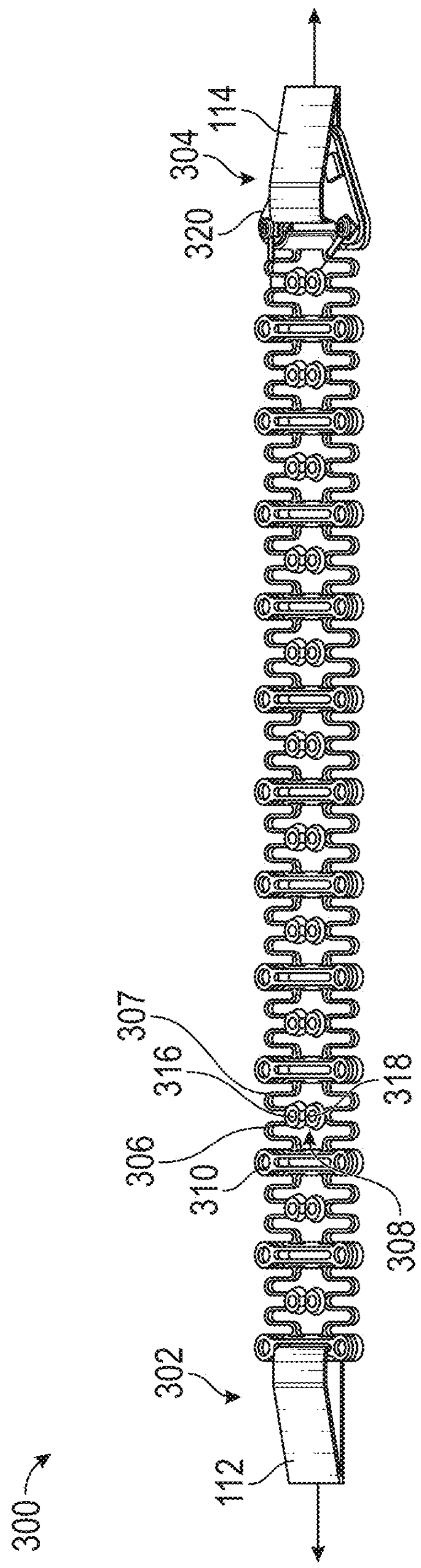
FIG. 3C illustrates a flex frame experiencing a tensile force.

FIG. 3C illustrates the flex frame 300. The flex frame 300 can have a first end 302 and a second end 304. The first end 302 can include a first strap interface 112. The second end 304 can include a second strap interface 114. The first strap interface 112 and second strap interface 114 can couple to a strap to facilitate wrapping the flex frame 300 around the limb 106 of the user. As described elsewhere herein, the flex frame 300 can include a micro-electronic controller 320 that is configured to apply an electrical input to the wire 118 to shorten or lengthen the wire 118 to apply compressive forces or release compressive forces to the limb 106 of the user. As the wire 118 shortens, the flex frame 300 can shorten which can result in the flex frame 300 experiencing tensile forces as the flex frame 300 pulls on the straps secured around the limb 106 of the user. As illustrated, the micro-electronic controller 320 can be disposed on an end of the flex frame 300, which can at least include the second end 304.

Figure 3D:
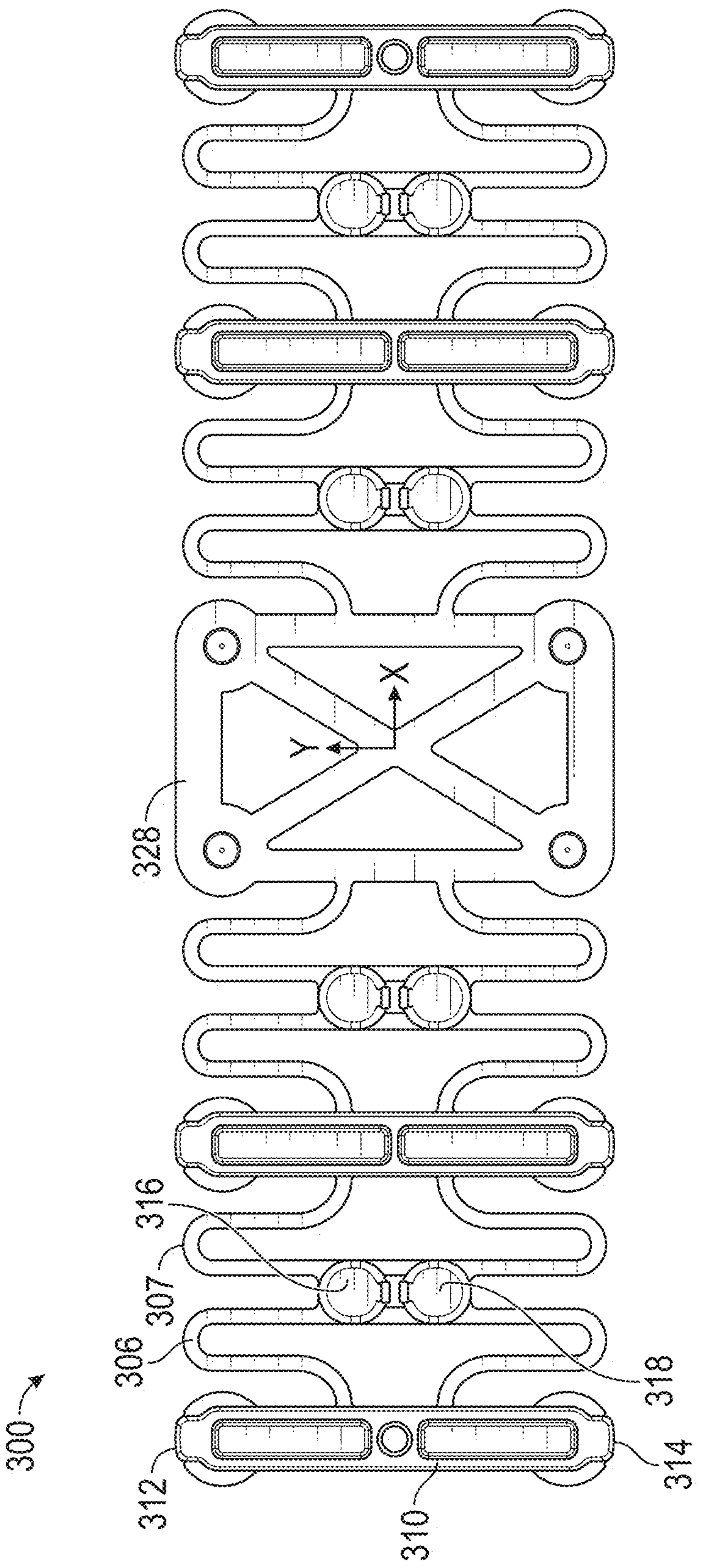
FIG. 3D illustrates a flex frame.
Figure 3E:
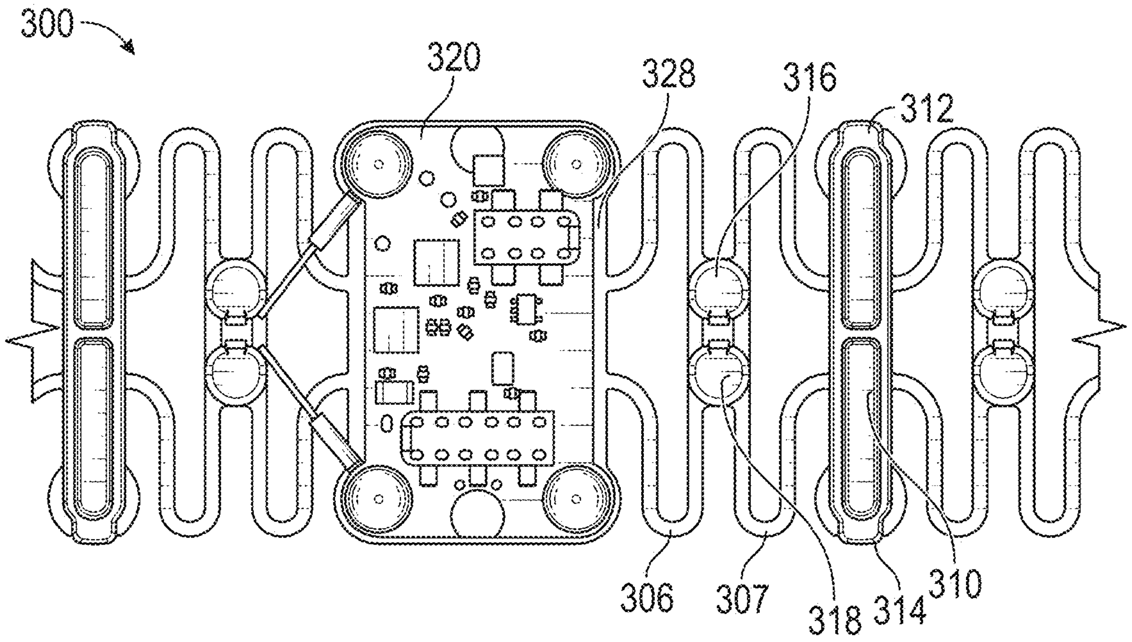
FIGS. 3E-3H illustrate various views of a flex frame.

FIG. 3D illustrates the flex frame 300. The flex frame 300 can have a mounting frame 328. The micro-electronic controller 320 can be mounted onto the mounting frame 328, which can be via screws (e.g., four screws), bolts, rivets, and/or other mechanisms such as adhesives, ultrasonic welding, heat staking, snap-fitting, as is illustrated in FIGS. 3E-3H. In some variants, the mounting frame 328 does not flex or deflect to lengthen or shorten the flex frame 300, but instead, the first spring arm 306 and/or second spring arm 307 deflect or flex.

Figure 3F:
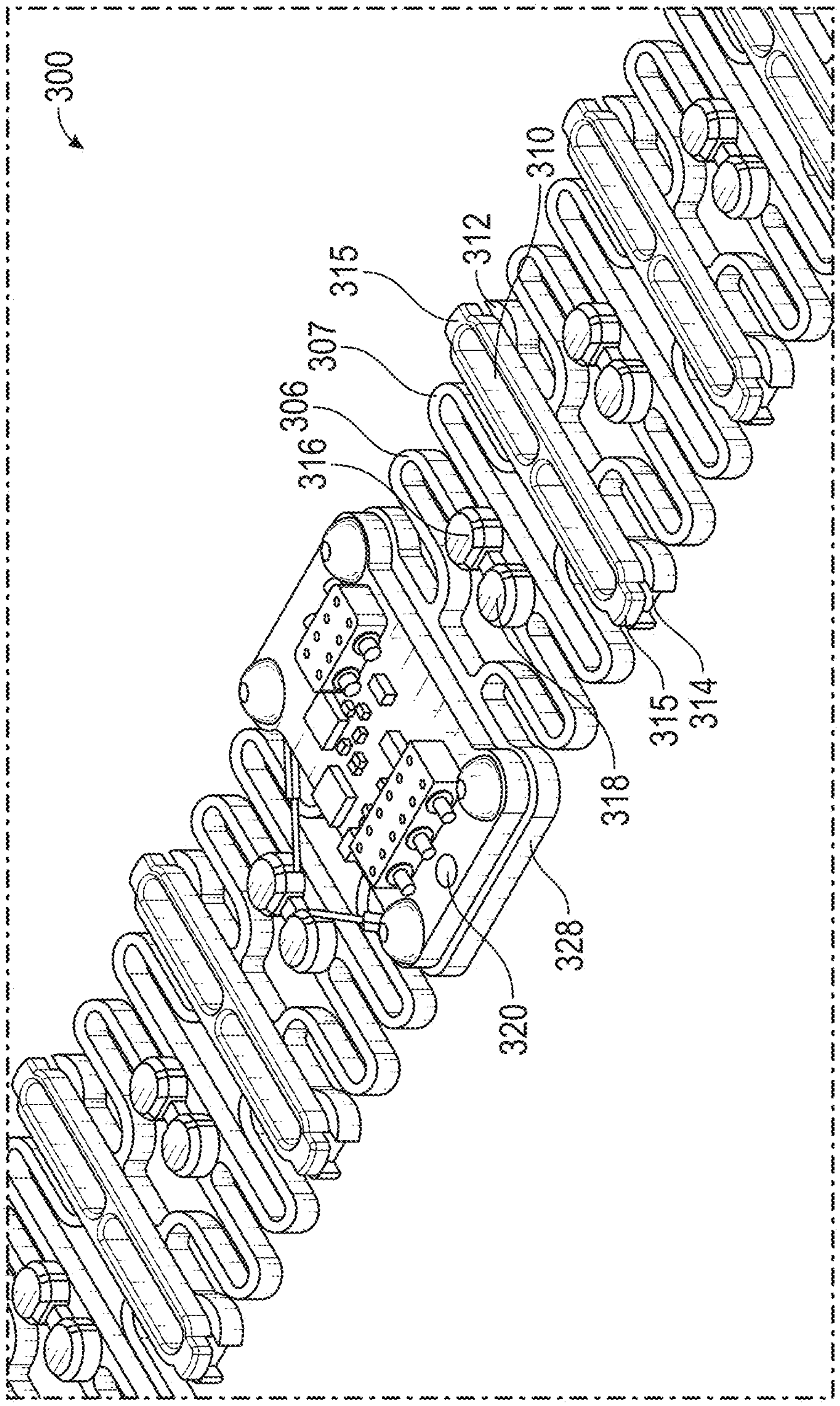
Figure 3G:
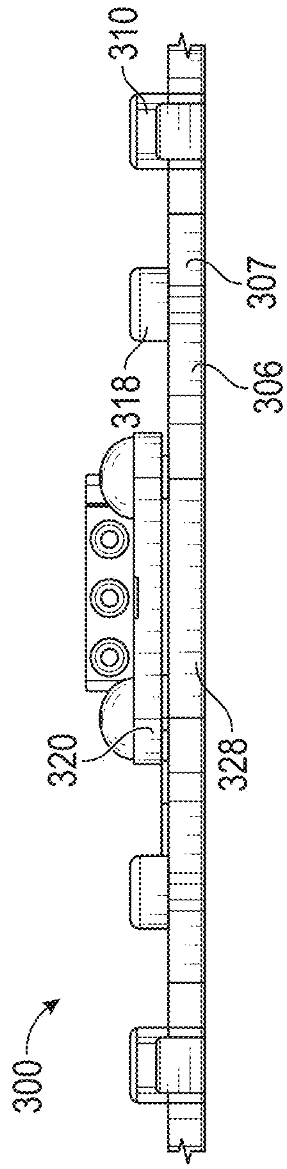
Figure 3H:
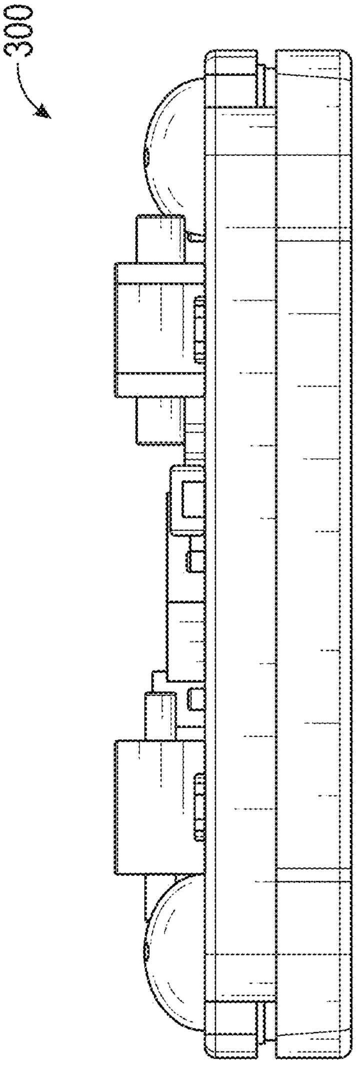

As illustrated in FIGS. 3F and 3G, the support 310, first guide structure 316, and/or second guide structure 318 can extend away from the plane of the first spring arm 306, second spring arm 307, and/or mounting frame 328. In some variants, the support 310, first guide structure 316, and/or second guide structure 318 equidistantly extend away from the plane of the first spring arm 306, second spring arm 307, and/or mounting frame 328 which can allow for a more direct path of the wire 118 along the flex frame 300. In some variants, the extension of the support 310, first guide structure 316, and/or second guide structure 318 can protect the wire 118 from engagement with the flexing features of the flex frame 300 (e.g., the first spring arm 306 and/or second spring arm 307).

Figure 3I:
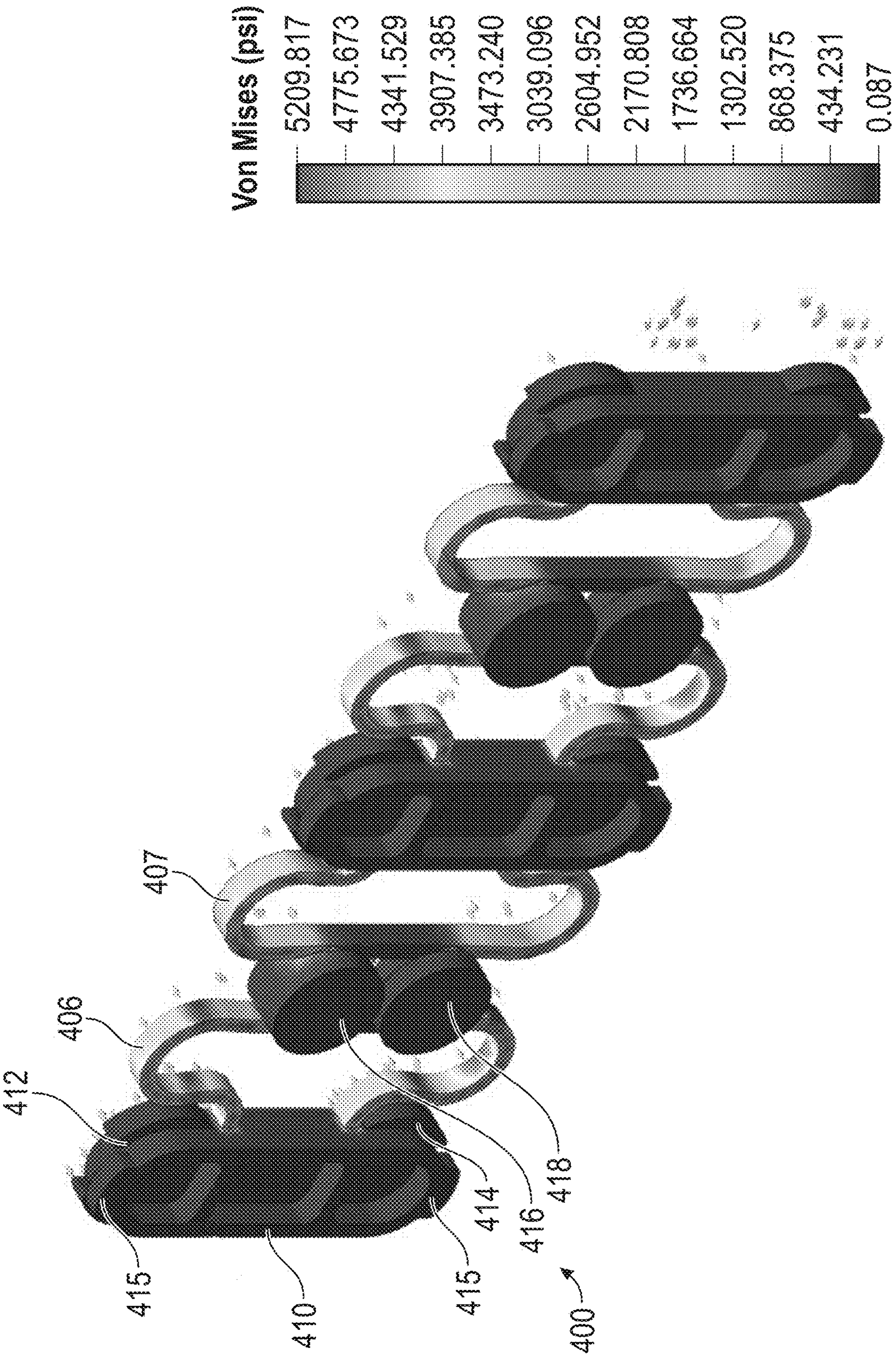
FIG. 3I illustrates the stresses experienced by a flex frame.

FIG. 3I illustrates the flex frame 400. As illustrated, the support 410 can have a first groove 412 (channel) on a first end and a second groove 414 on a second end. The first groove 412 and second groove 414 can receive and/or direct the wire 118 around the ends of the support 410. Each of the first groove 412 and second groove 414 can be distributed into multiple portions which can be separated by one or more gaps. For example, as illustrated, the first groove 412 is distributed in two parts that are separated by a gap. A tab 415, also known as a retention feature, can be disposed on one or more ends of the support 410, which can include proximate the first groove 412 and second groove 414. The tabs 415 can contain and/or electrically isolate the wire 118 in the first groove 512 and/or second groove 514. For example, the tabs 415 and first groove 412 and/or second groove 414 can retain the wire 118 in the event that the flex frame 400 is subject to an external compression causing slack in the wire 118 or in the event of the wire 118 breaking.

FIG. 3I illustrates the results of a Finite Element Analysis (FEA) for the flex frame 400. As shown, the portions of the flex frame 400 that flex or deflect to enable the flex frame 400 to shorten or lengthen can experience the most stress. For example, the first spring arm 406 and second spring arm 407 can flex or deflect such that the first spring arm 406 and second spring arm 407 experience the highest stress as the flex frame 400 is compressed. The support 410, first guide structure 416, and/or second guide structure 418 can experience no or insubstantial stress. In some variants, this can be due to the support 410, first guide structure 416, and/or second guide structure 418 not flexing or deflecting as the flex frame 400 is shortened or lengthened to apply compression to the user.

Figure 4A:
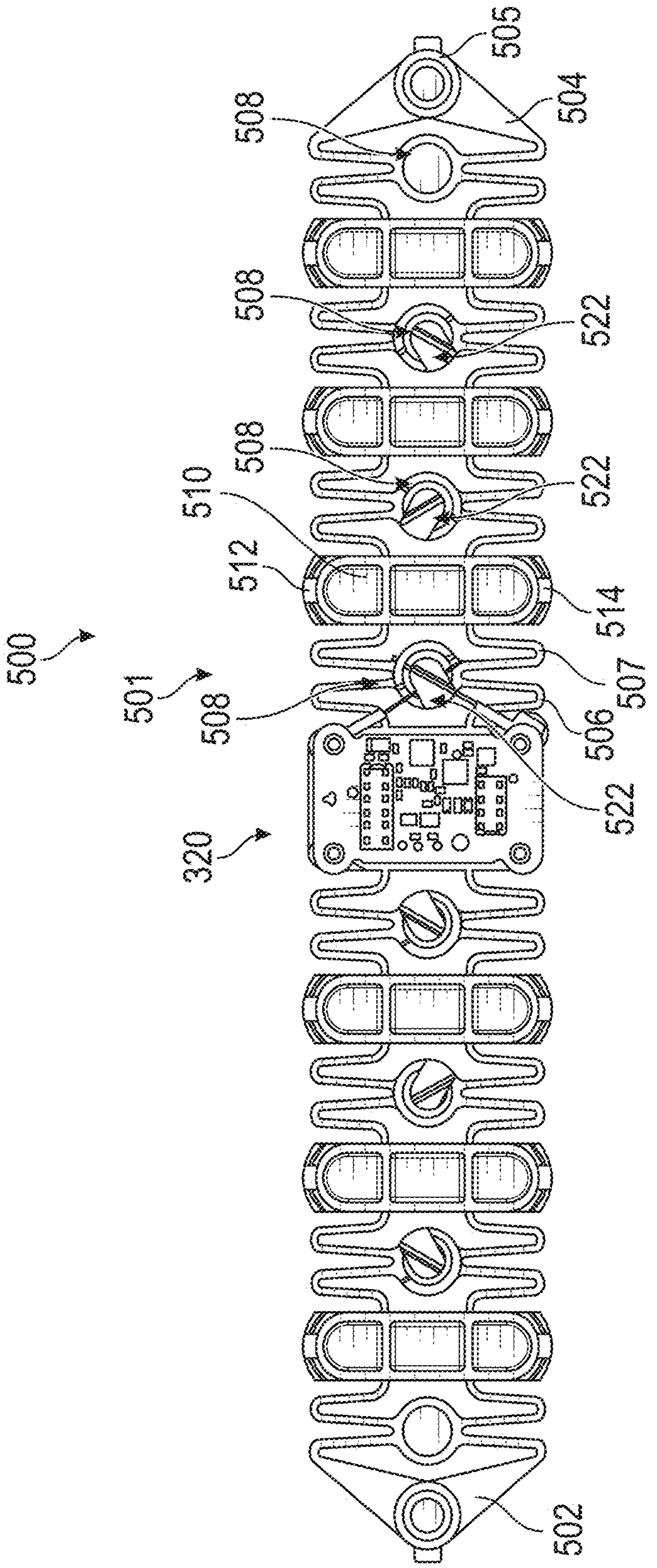
FIG. 4A illustrates a flex frame with a micro-electronic controller.

FIG. 4A illustrates a flex frame 500. The flex frame 500 can include a micro-electronic controller 320 disposed between segments of the flex frame 500. The flex frame 500 can convert electrical energy provided via the micro-electronic controller 320 to mechanical work via a reversible phase change of the wire 118, which can include a shape memory material, Nitinol, nickel titanium alloy, and/or other materials. The flex frame 500 can provide mounting and constraint of the wire 118 and provide rotational and lateral stability of the wire 118 and greater structure while allowing for longitudinal compression via a longitudinal bias force.

The flex frame 500 can include units 501 which can have a first spring arm 506, second spring arm 507, bridge 508, guide structure 522, and/or support 510. The first spring arm 506 and/or second spring arm 507 can flex, deflect, deform, bend, and/or otherwise move to allow the flex frame 500 to lengthen or shorten to apply or release compressive forces to the limb 106 of the user.

The first spring arm 506 can extend from a central portion of a side of the micro-electronic controller 320 or a first support 510, curve outward toward the outer longitudinal edges of the flex frame 500, and curve inward toward a bridge 508. The first spring arm 506 can have an opening extending therethrough to facilitate flexion, deflection, and/or other movement. The bridge 508 can be disposed between the first spring arm 506 and the second spring arm 507. The bridge 508 can include a guide structure 522 that is described herein. The second spring arm 507 can be in a mirrored arrangement as the first spring arm 506 relative to the bridge 508. The second spring arm 507 can extend from a central portion of a second support 510, curve outward toward the outer longitudinal edges of the flex frame 500, and curve inward toward the bridge 508. The second spring arm 507 can have an opening extending therethrough to facilitate flexion, deflection, and/or other movement.

The support 510 can include a first groove 512 and/or a second groove 514. The first groove 512 and second groove 514 can be disposed on opposing sides of the support 510. The first groove 512 and second groove 514 can receive the wire. The first groove 512 and second groove 514 can be curved.

Figure 4B:
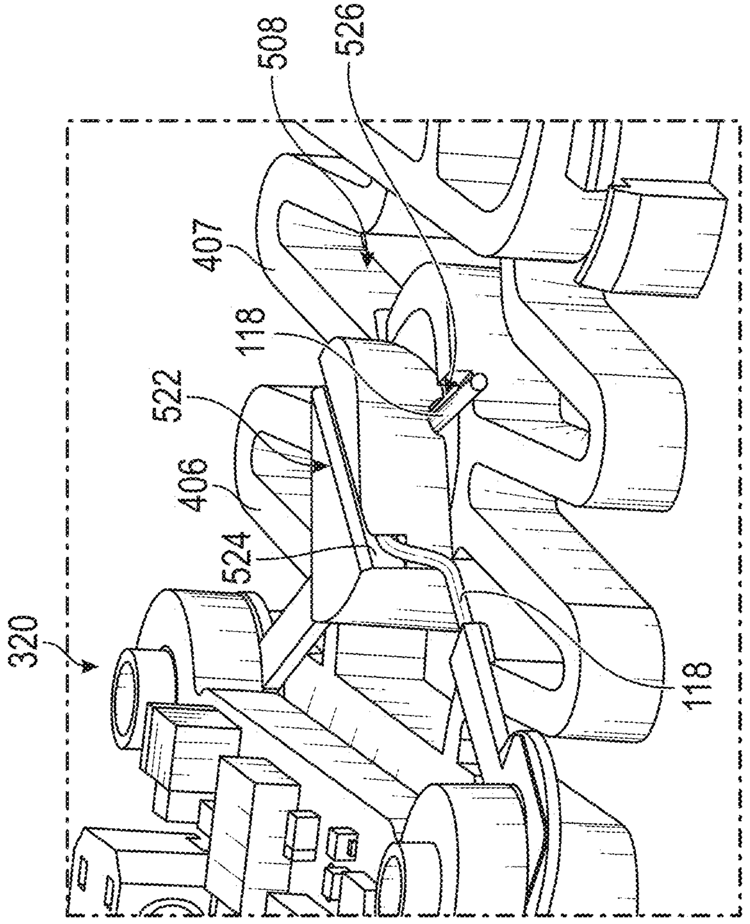
FIG. 4B illustrates an enlarged partial view of the flex frame of FIG. 4A.

FIG. 4B illustrates an enlarged view of the guide structure 522. The wire 118 can be laced within and/or through the guide structure 522. The guide structure 522 can include a top channel 524 and bottom channel 526. The top channel 524 and bottom channel 526 can guide the wire 118 as it is routed from the micro-electronic controller 320 to a second end 504 and/or first end 502 of the flex frame 500. The top channel 524 and bottom channel 526 can separate the wire 118 at an intersection of the wire 118 using an under-over-pattern. The guide structure 522 can electrically isolate, which can include complete electrical isolation, the wire 118 from itself at intersections. The guide structure 522 can be made of a polymer (e.g., creating a polymer barrier), which can facilitate electrical isolation. In some variants, the wire 118 can be guided through the top channels 524 of the guide structures 522 as the wire 118 is routed from the micro-electronic controller 320 to the second end 504 and guided through the bottom channel 526 of the guide structure 522 as the wire 118 is routed from the second end 504 back to the micro-electronic controller 320 or in a flipped configuration.

Figure 4C:
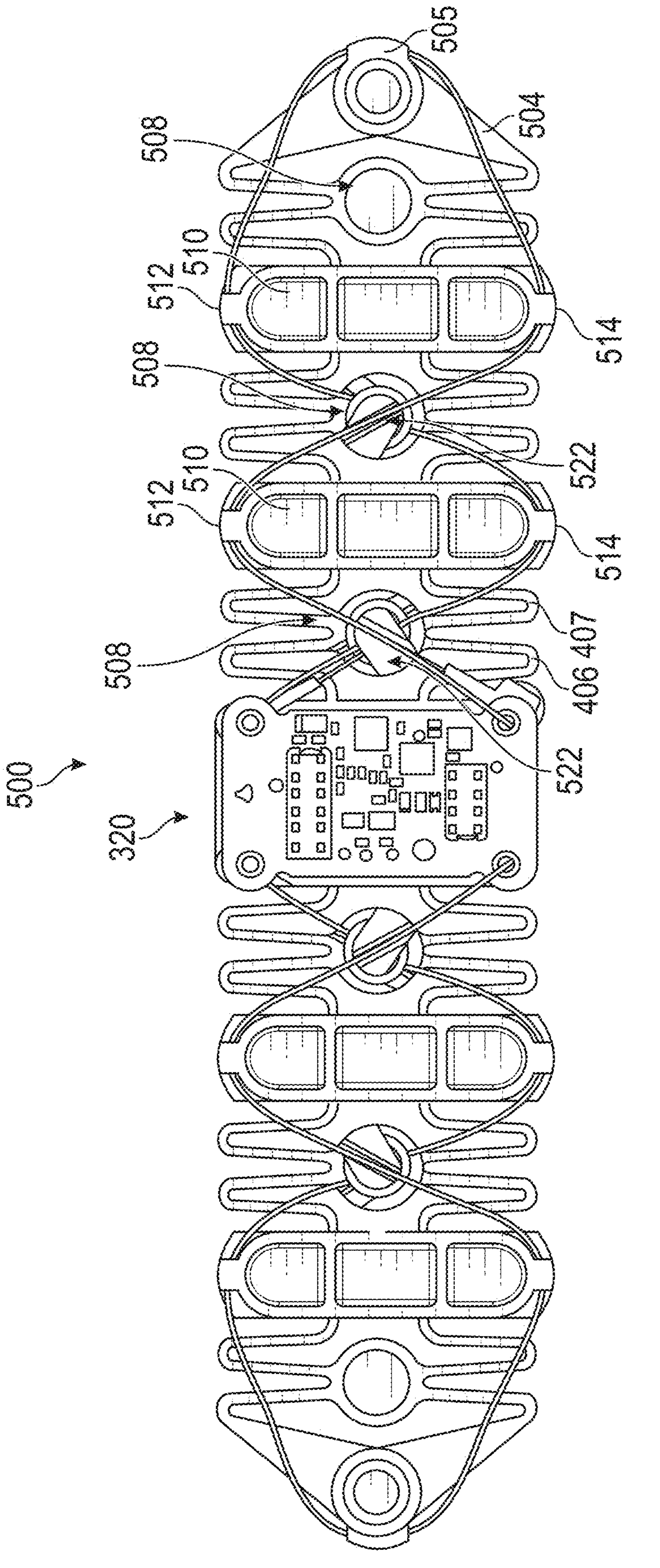
FIG. 4C illustrates the flex frame of FIG. 4A with a wire.

FIG. 4C shows the wire 118 incorporated into the flex frame 500. The wire 118 extends from the micro-electronic controller 320 to the second end 504 via extending through the top channel 524 of the first guide structure 522, wrapping around the first groove 512 of the first support 510, extending through the top channel 524 of the second guide structure 522, and wrapping around the second groove 514 of the second support 510. At the second end 504, the wire 118 can wrap around the second end groove 505 to be directed back toward the micro-electronic controller 320. The wire 118 can extend from the second end groove 505 to the micro-electronic controller 320 via extending through the bottom channel 526 of the second guide structure 522, wrapping around the first groove 512 of the second support 510, and extending through the bottom channel 526 of the first guide structure 522. As illustrated, the top channel 524 and bottom channel 526 can be oriented to direct the wire 118 as described above.

Figure 4D:
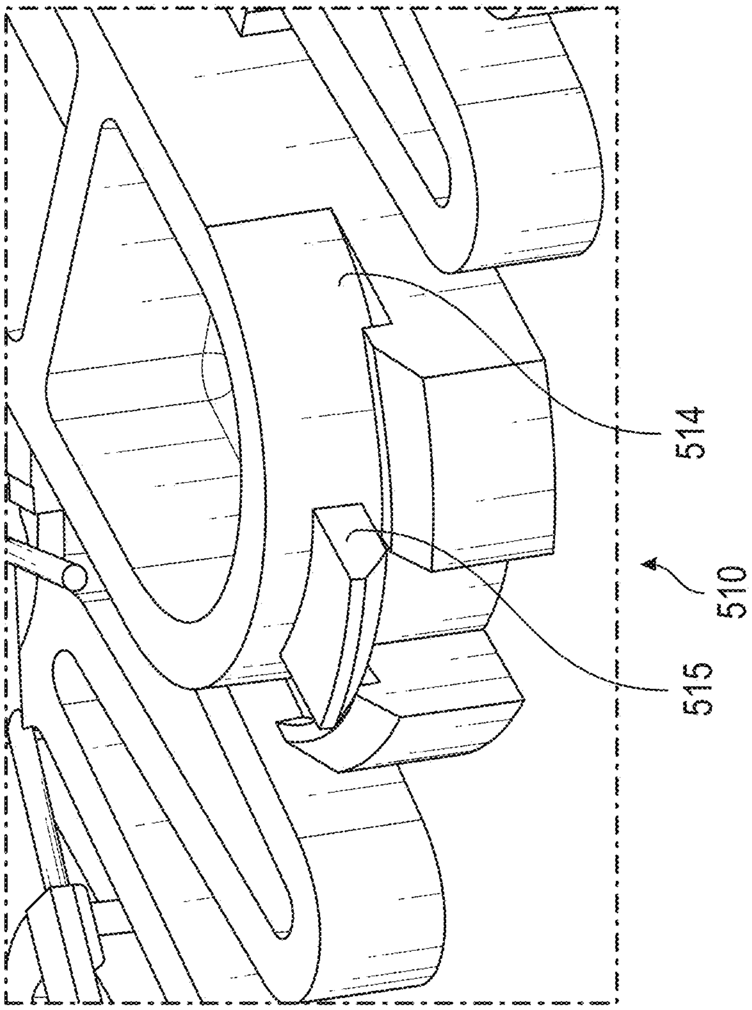
FIG. 4D illustrates an enlarged partial view of the flex frame of FIG. 4A.

FIG. 4D illustrates an enlarged view of an end of the support 510. As detailed above, the support 510 can have a first groove 512 and/or second groove 514 that can receive and/or direct the wire 118 around an end of the support 510. The second groove 514 can be distributed into multiple portions which can be separated by one or more gaps. For example, as illustrated, the second groove 514 is distributed in two parts that are separated by a gap. A tab 515, also known as a retention feature, can be disposed on one or more of the ends of the support 510. The tab 515 can contain and/or electrically isolate the wire 118 in the second groove 514. For example, tab 515 and second groove 514 can retain the wire 118 in the event that the flex frame 500 is subject to an external compression causing slack in the wire 118 or in the event of the wire 118 breaking.

Figure 4E:
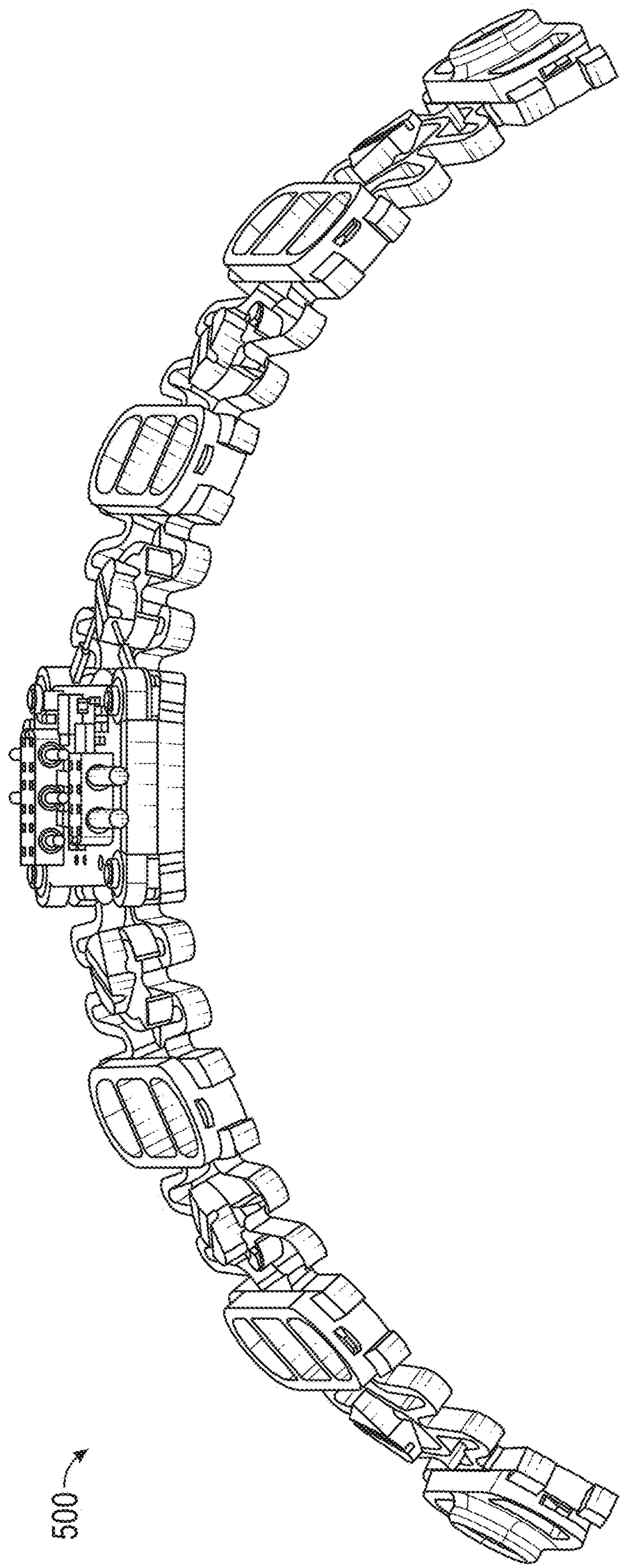
FIG. 4E illustrates the flex frame of FIG. 4A bending thru-plane.
Figure 4F:
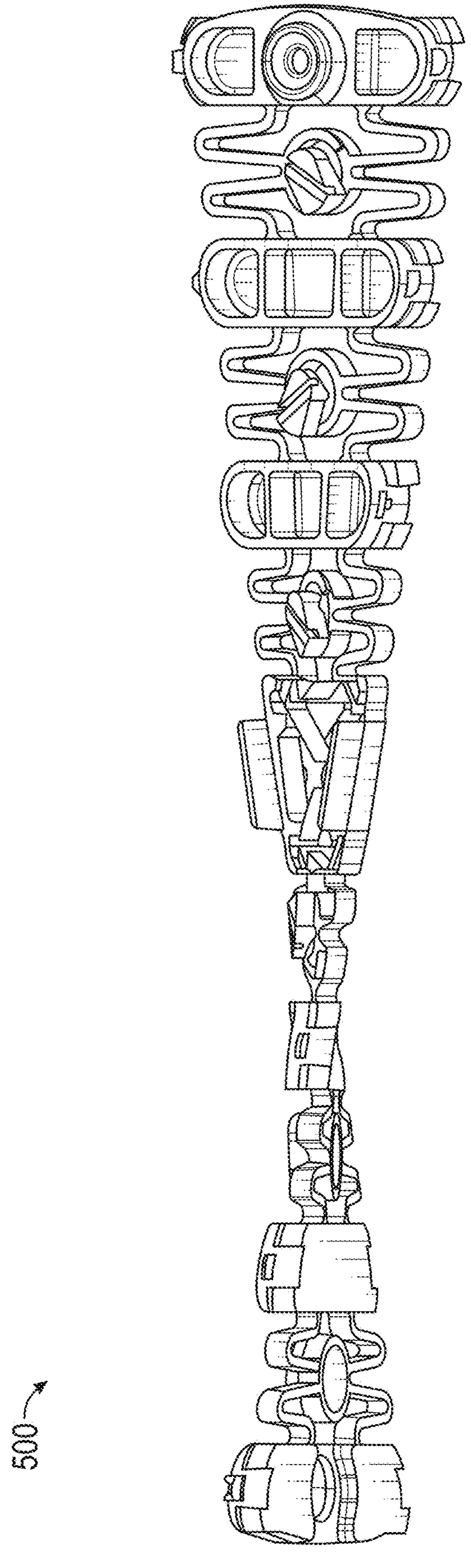
FIG. 4F illustrates the flex frame of FIG. 4A twisting in-plane.

The flex frame 500 can be made of, which can include partially made of, a thermoplastic polymer with a moderate yield strength and/or low flexural modulus (e.g., polyamide 12). The flex frame 500 can, as illustrated in FIG. 4E, facilitate thru plane bending, which can help enable the user to move with the compression garment 100 worn on the limb 106 of the user. The flex frame 500, however, can be structured, as described above, to reduce allowable in-plane bending (e.g., bending about a longitudinal axis of the flex frame 500), as illustrated in FIG. 4F.

Figure 5A:
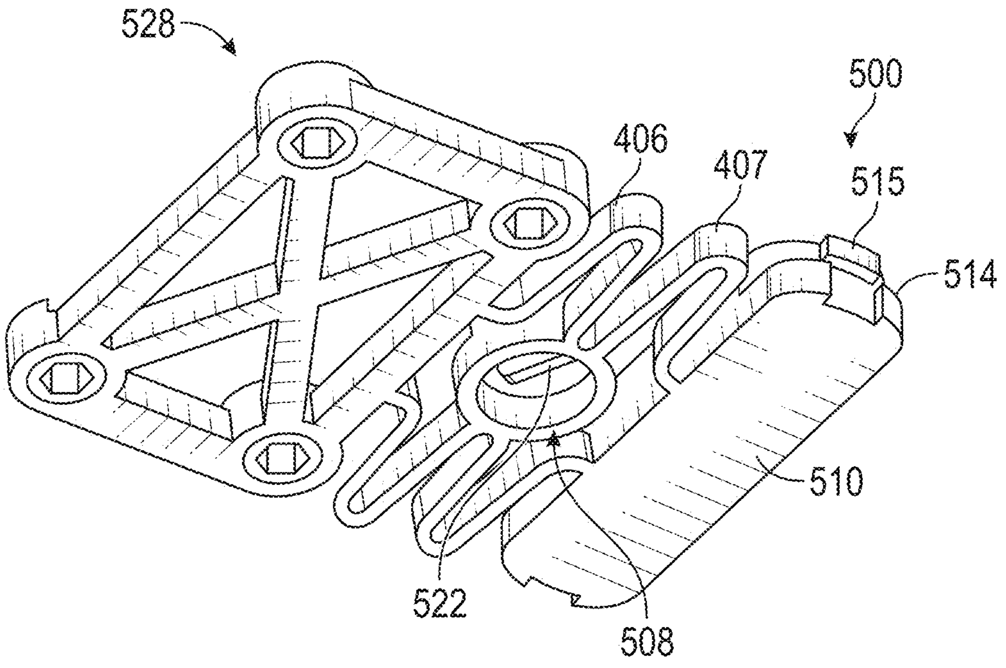
FIG. 5A illustrates a unit of the flex frame of FIG. 4A.
Figure 5B:
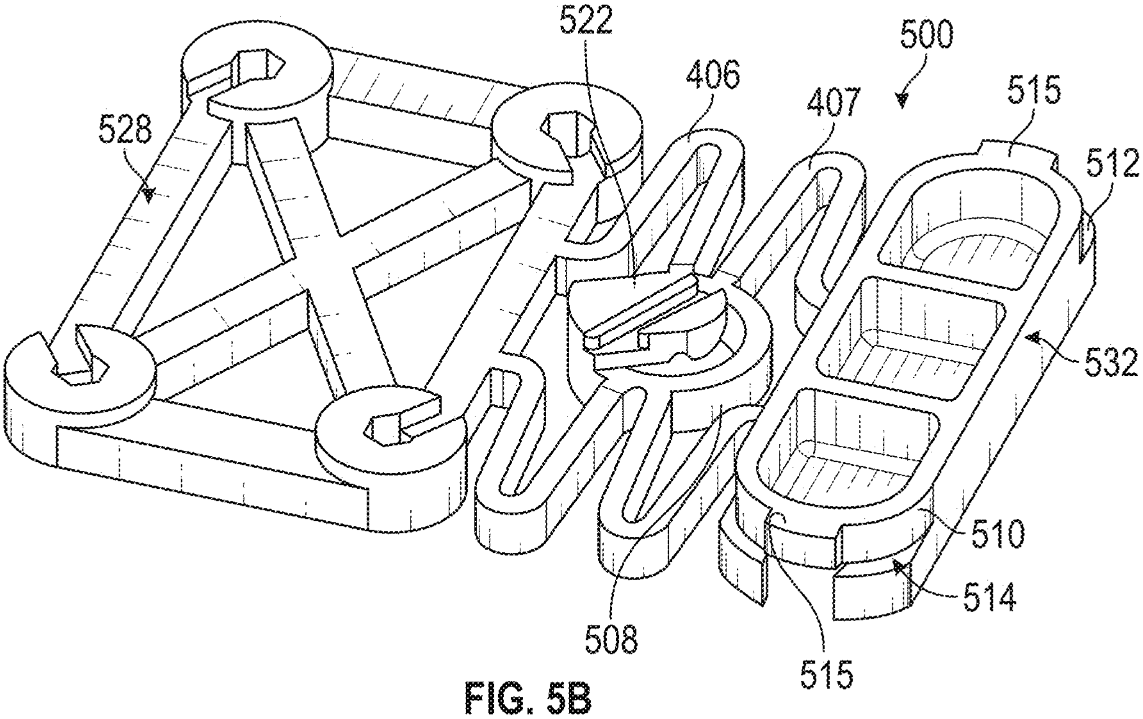
FIG. 5B illustrates the unit of FIG. 5A.

As described above, the flex frame 500 can include one or more units 501 (e.g., nodes). Each unit 501 can include the first spring arm 406, second spring arm 407, bridge 508, guide structure 522, and/or support 510. As described in more detail below, the first spring arm 406 and second spring arm 407 can facilitate the lengthening and/or shortening of the flex frame 500. Each unit 501 can be configured to deflect, flex in the longitudinal direction by approximately 3 millimeters, but in some variants, each unit 501 can deflect less than 1, 1-2, 2-3, 3-4, 4-5, 5-6, or more than 6 millimeters. A first unit 501 can be coupled to a mounting frame 528, as shown in FIG. 5A, that can support the micro-electronic controller 320. The mounting frame 528 can remain in a fixed position, not deflecting or substantially deflecting when the flex frame 500 lengthens or shortens. As illustrated in FIG. 5B, the unit 501 can compress or shorten in the direction of arrow 532 when the wire 118 is shortened via a phase change as an electrical input is applied to the shape memory material of the wire 118 and/or as the motor winds in the wire 118.

Figure 5C:
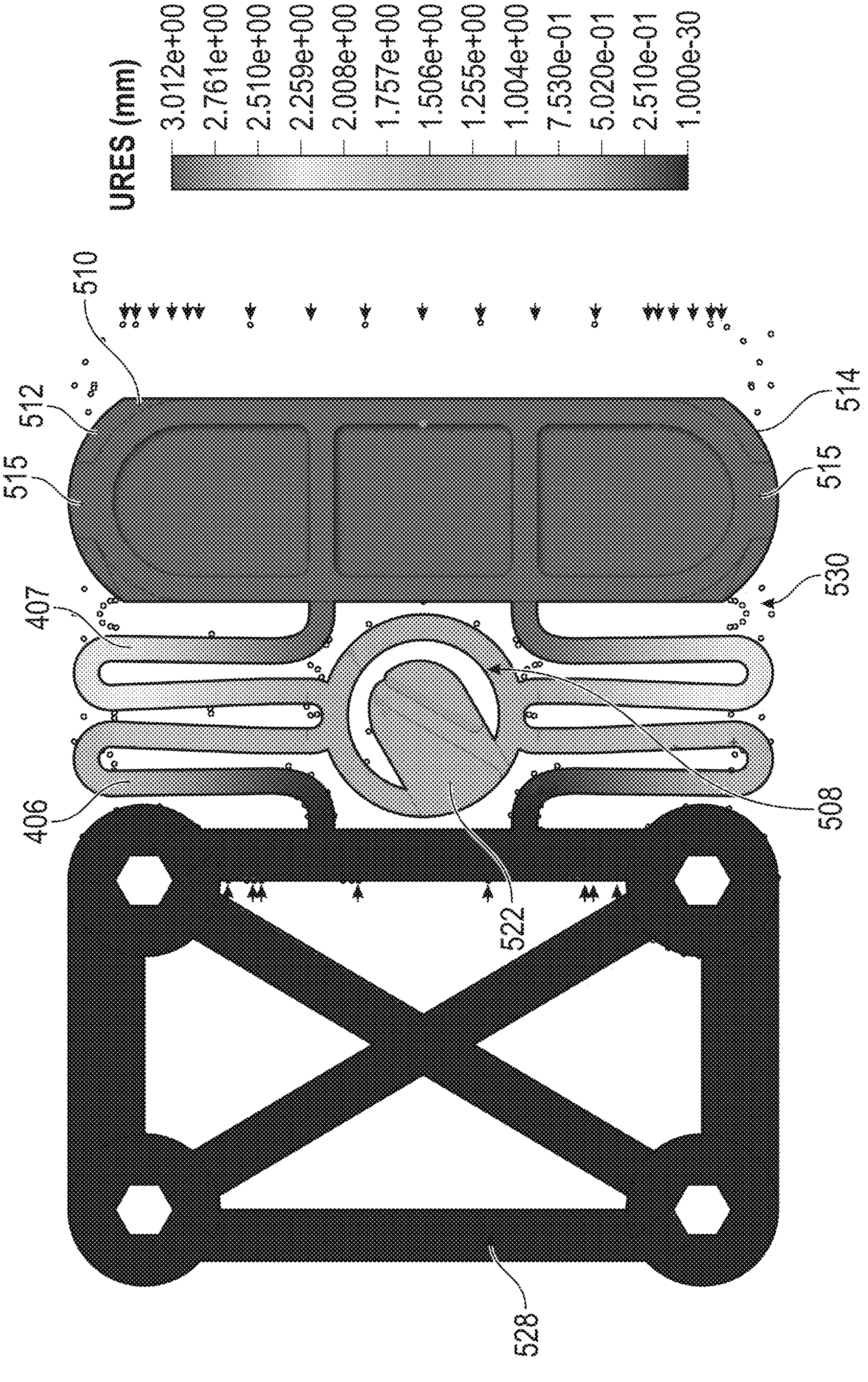
FIG. 5C illustrates the unit of FIG. 5A deflected.

FIG. 5C shows the deflection of the unit 501 by 3 millimeters toward the mounting frame 528. As illustrated, the support 510 undergoes the full displacement of 3 millimeters, while the portions of the first spring arm 406 and second spring arm 407 closer to the mounting frame 528 displace progressively less the closer to the mounting frame 528. For example, the first spring arm 406 is displaced less than the second spring arm 407. More specifically, the portions of the first spring arm 406 closer to the mounting frame 528 displace less than the portions of the first spring arm 406 farther away from the mounting frame 528 and the portions of the second spring arm 407 closer to the mounting frame 528 displace less than the portions of the second spring arm 407 that are father away from the mounting frame 528. As illustrated, the entirety of the support 510 displaces uniformly which can, in some variants, be because the support 510 does not itself deflect when the unit 501 deflects. The bridge 508 and guide structure 522, similarly to the support 510 displace uniformly, which can, in some variants, be because the bridge 508 and guide structure 522 do not themselves deflect when the unit 501 deflects. In some variants, the mounting frame 528 does not displace but, instead, is fixed in position.

Figure 5D:
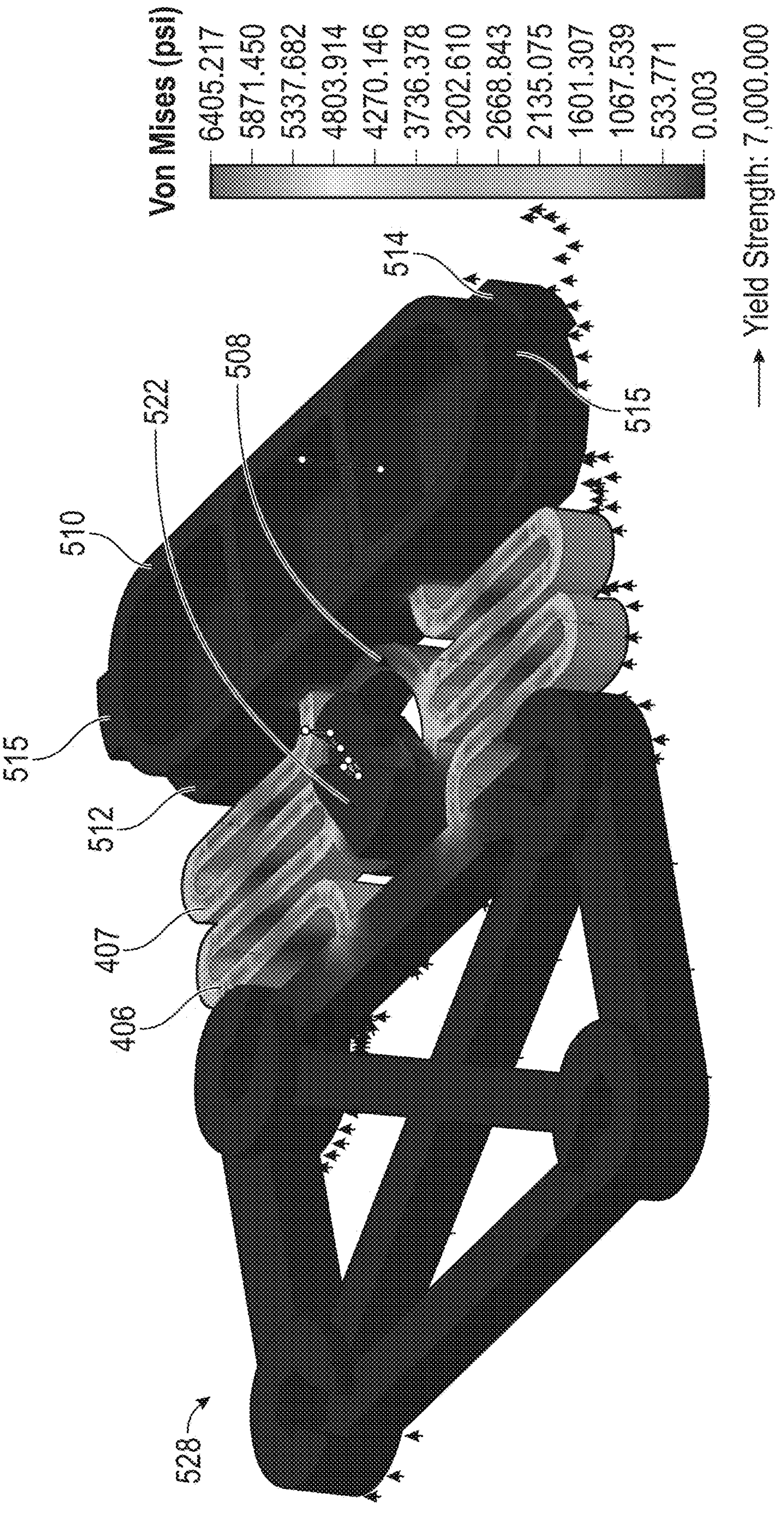
FIG. 5D illustrates the stresses experienced by the unit deflected as shown in FIG. 5C.
Figure 5E:
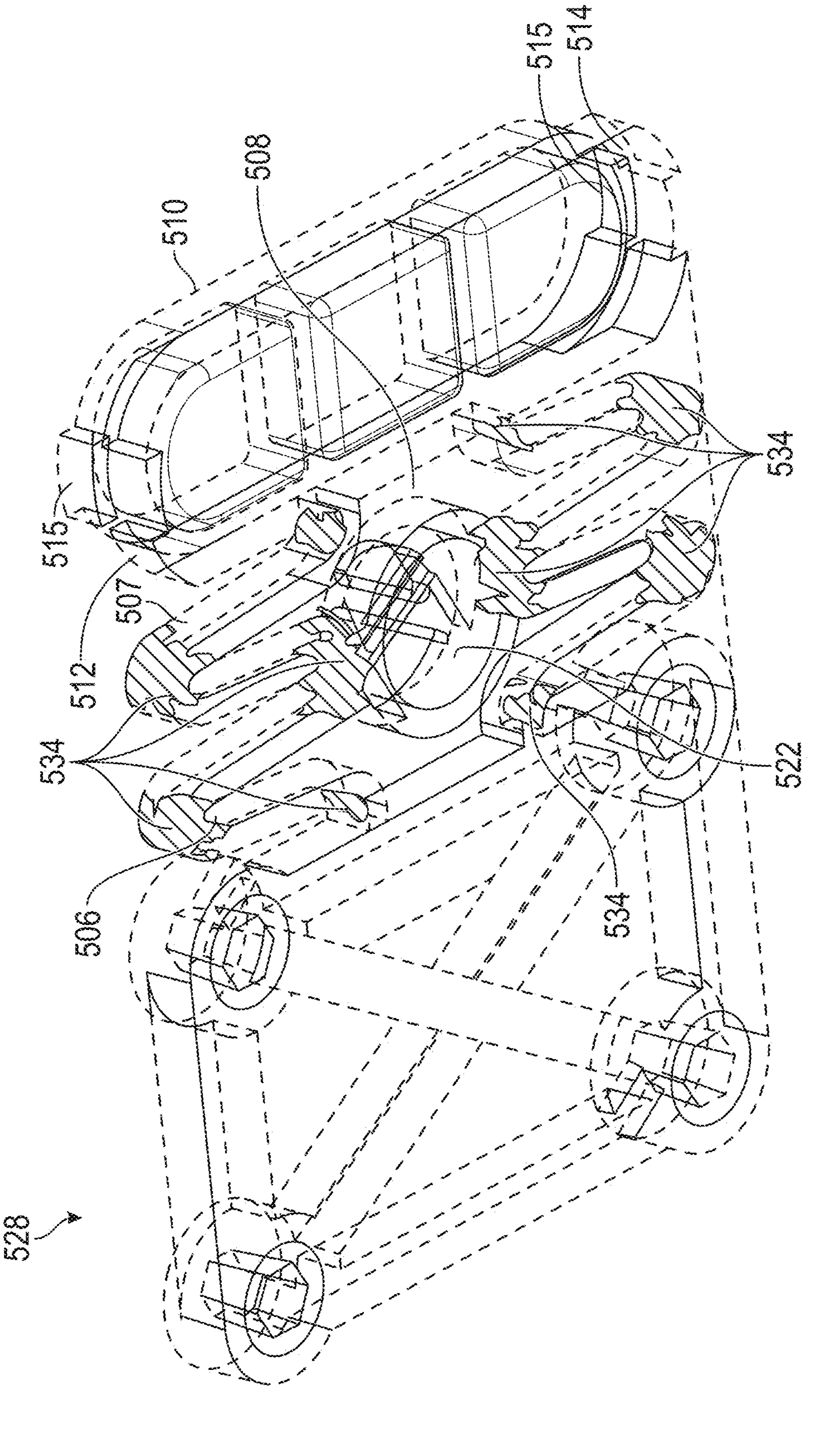
FIG. 5E illustrates the areas of highest stress on the unit deflected as shown in FIG. 5C.

FIG. 5D illustrates the stresses that are experienced by the mounting frame 528 and unit 501 when the unit 501 is shortened by 3 millimeters via the results of a Finite Element Analysis (FEA) model. As indicated, portions of the unit can experience a stress of 6,405 PSI when the unit 501 is shortened by 3 millimeters. As described elsewhere herein, in some variants, the flex frame 500, which can include the mounting frame 528 and/or unit 501, can be made of polyamide 12 (Nylon 12) which can have a yield strength of approximately 7000 PSI. In some variants, the support 510, mounting frame 528, bridge 508, and/or guide structure 522 can experience no or insubstantial stress. In some variants, the first spring arm 406 and/or second spring arm 407 can experience the most stress of the unit 501, which can be due to the first spring arm 406 and second spring arm 407 facilitating the deflection of the unit 501. In some variants, the highest stress experienced by the unit 501 can be at the inflection points 534 of the first spring arm 406 and second spring arm 407, as illustrated in FIG. 5E. The curvature of the inflection points 534 can facilitate avoiding stress concentrators such as corners.

Figure 6A:
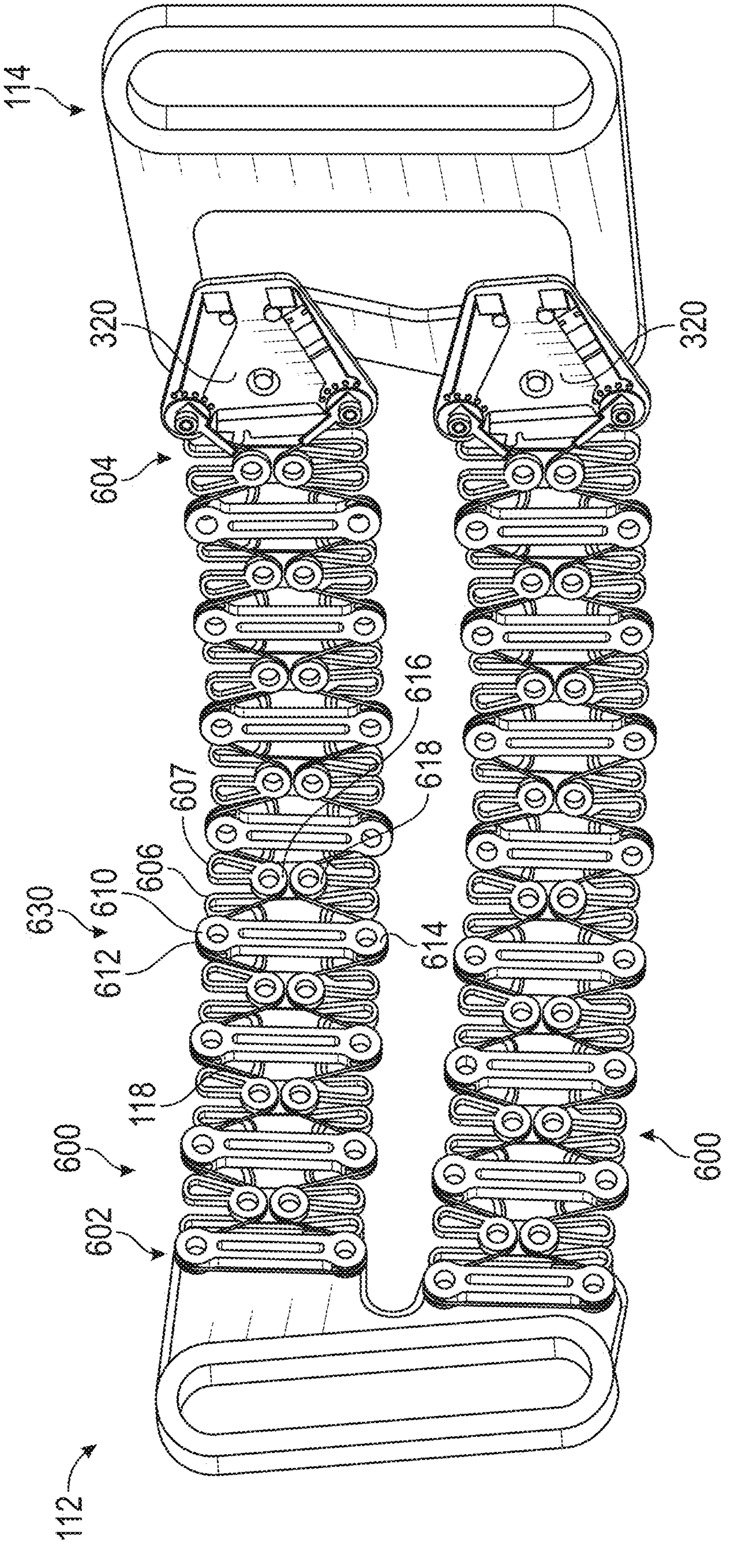
FIG. 6A illustrates two flex frames coupled to strap interfaces.

FIG. 6A illustrates first and second flex frames 600 coupled to a first strap interface 112 and second strap interface 114. The flex frame 600 can be similar to the flex frame 300. The flex frame 600 can be an elongate structure that is configured to wrap around at least a portion of the limb 106 or other portion of the user. The flex frame 600 can include a first end 602 and second end 604. The first end 602 can be coupled to the first strap interface 112. The second end 604 can be coupled to the second strap interface 114 and/or the micro-electronic controller 320 or mounting frame upon which the micro-electronic controller 320 is mounted. As explained elsewhere herein, the first strap interface 112 and the second strap interface 114 can be coupled to straps that wrap around the limb 106 or other portion of the user.

The flex frame 600 can include one or more units 630. The one or more units 630 can enable the flex frame 600 to flex to shorten or lengthen. The one or more units 630 can each include a support 610, first spring arm 606, second spring arm 607, first guide structure 616, and/or second guide structure 618. The support 610 can be an elongate structure with an elongate opening disposed between two circular openings positioned proximate ends of the support 610. The ends of the support 610 can be curved. One end of the support 610 can include a first groove 612. Another end of the support 610, opposite the first groove 612, can include a second groove 614. The first groove 612 and/or second groove 614 can receive and/or guide the wire 118 around the ends of the support 610.

The first spring arm 606 and/or second spring arm 607 can facilitate the flexion and/or deflection of the unit 630. The first spring arm 606 can extend away from a side of a support 610, curve towards the opposing longitudinal edges of the 600, and curve back to the first guide structure 616 and second guide structure 618. The second spring arm 607 can extend away from a second support 610, curve towards the opposing longitudinal edges of the 600, and curve back to the first guide structure 616 and second guide structure 618. The first spring arm 606 and/or second spring arm 607 can each include an opening therethrough to facilitate deflection.

The first guide structure 616 and second guide structure 618 can be rounded protuberances, projections, etc. The first spring arm 606 and/or second guide structure 618 can include an opening extending therethrough. The first guide structure 616 and second guide structure 618 can be in a mirrored configuration relative to the longitudinal axis of the flex frame 600. The first guide structure 616 and/or second guide structure 618 can include grooves to receive and/or guide the wire 118. The wire 118 can wrap around and/or between the first guide structure 616 and/or second guide structure 618 in route to the first groove 612 or second groove 614 of the support 610.

The wire 118 can extend from the micro-electronic controller 320 to the first end 602 and back to the micro-electronic controller 320. In some variants, the first end 602 includes a support 610 and the wire 118 wraps around the first groove 612 and second groove 614 before being routed back to the micro-electronic controller 320. In some variants, the wire 118 can extend from the micro-electronic controller 320 to around the first guide structure 616 up to the first groove 612 of a first support 610 around a second first guide structure 616 up to the second first groove 612 of a second support 610 and continue in a similar manner until reaching an end support 610 at the first end 602. At the end support 610, the wire 118 can loop around the first groove 612 and second groove 614 before being routed back to the micro-electronic controller 320 via looping around the second guide structures 618 and second grooves 614 of the supports 610.

In some variants, the wire 118 can cross itself. For example, the wire 118 can extend from the micro-electronic controller 320 between the first guide structure 616 and second guide structure 618 to around the second groove 614 of a support 610 to between another first guide structure 616 and second guide structure 618 to around first groove 612 of another support 610 and continue in a similar manner until reaching the end support 610 (e.g., first end 602). At the end support 610 (e.g., first end 602), the wire 118 can loop around the first groove 612 and second groove 614 before being routed back to the micro-electronic controller 320 via extending between the first guide structure 616 and second guide structure 618 to cross itself and extend around first grooves 612 and second grooves 614 of the supports 610. The wire 118 and/or flex frame 600 can be extended or lengthened via the methods described elsewhere herein to apply or release compressive forces.

The two flex frames 600 illustrated in FIG. 6A can each be independently controlled by separate micro-electronic controllers 320. For example, one of the micro-electronic controller 320 can cause the flex frame 600 to compress while the other micro-electronic controller 320 can cause the other flex frame 600 to loosen, compress to a different degree, perform no action, etc. In some variants, the two flex frames 600 can sequentially apply compressive forces to the limb 106 of the user to move bodily fluids therein in a direction. In some variants, the same micro-electronic controller 320 can control the two flex frames 600.

Figure 6B:
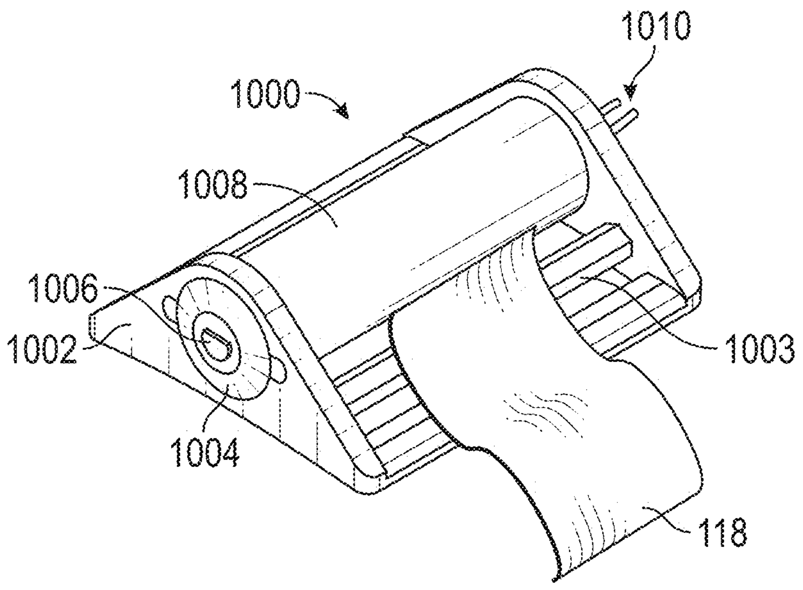
FIG. 6B illustrates an example reel mechanism that can be used to reel in or out wire(s) (e.g., cable(s)) to apply or release a compressive force to an anatomical feature of a user via the compression garment.

FIG. 6B illustrates a reel mechanism (reel tension mechanism, winder mechanism, spool mechanism) 1000. The reel mechanism 1000 can be used in conjunction with any of the flex frames described herein. The reel mechanism 1000 can be used to reel in or out the wire (cable, band, shape memory alloy feature, etc.) 118. The reel mechanism 1000 can reel in the wire 118 (applying tension to the flex frame) to shorten the flex frame, causing the flex frame to apply compressive forces to the limb or other anatomical feature of the user. The reel mechanism 1000 can reel out the wire 118 to lengthen the flex frame, causing the flex frame to lengthen such that less or no compressive forces are applied to the limb or other anatomical feature of the user. The reel mechanism can be used with any of the flex frames described herein.

Figure 6C:
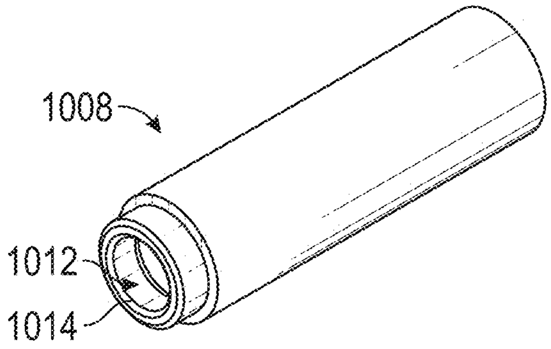
FIG. 6C illustrates an example bobbin from the reel mechanism illustrated in FIG. 6B.
Figure 6D:
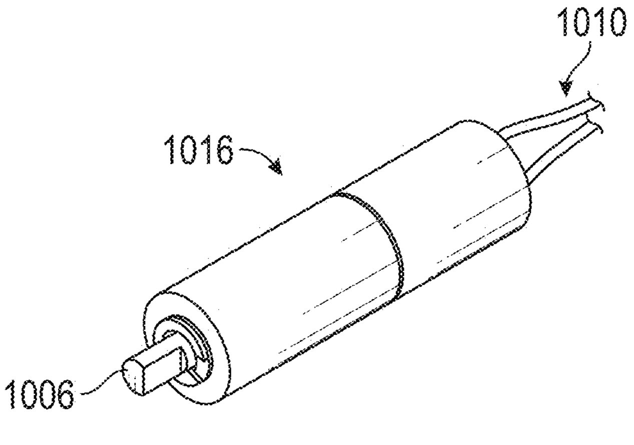
FIG. 6D illustrates an example motor from the reel mechanism illustrated in FIG. 6B.

The reel mechanism 1000 can have a frame 1002. The frame 1002 can support a bobbin (reel, spool, cylinder, winder) 1008. The bobbin 1008 can rotate to reel in or out the wire 118. As the bobbin 1008 rotates in a first direction, the wire 1008 can be wrapped around the bobbin 1008. As the bobbin 1008 rotates in a second direction opposite the first direction, the wire 1008 can be unwrapped from around the bobbin 1008. The bobbin 1008 can be rotated by the motor 1016. As illustrated in FIG. 6C, the bobbin 1008 can have a cavity 1012 to house a motor 1016 therein that can drive rotation of the bobbin 1008 as discussed herein. The bobbin 1008 can have an opening 1014 through which the shaft 1006, illustrated in FIG. 6D, of the motor 1008 can extend. The shaft 1006 can engage with a locking collar 1004 that is disposed in the frame 1002, as illustrated in FIG. 6B. The motor 1016 can be powered via wires 1010 to drive the bobbin 1008 to wind or unwind the wire 1008 to apply or reduce compressive forces on the limb or other anatomical feature of the user. The frame 1002 can include a guide bar or rod 1003 to guide the wire 118 during winding or unwinding. As discussed elsewhere herein, the reel mechanism 1000 can be used in place of or in combination with using shape memory alloys to apply or release compressive forces.

Figure 7A:
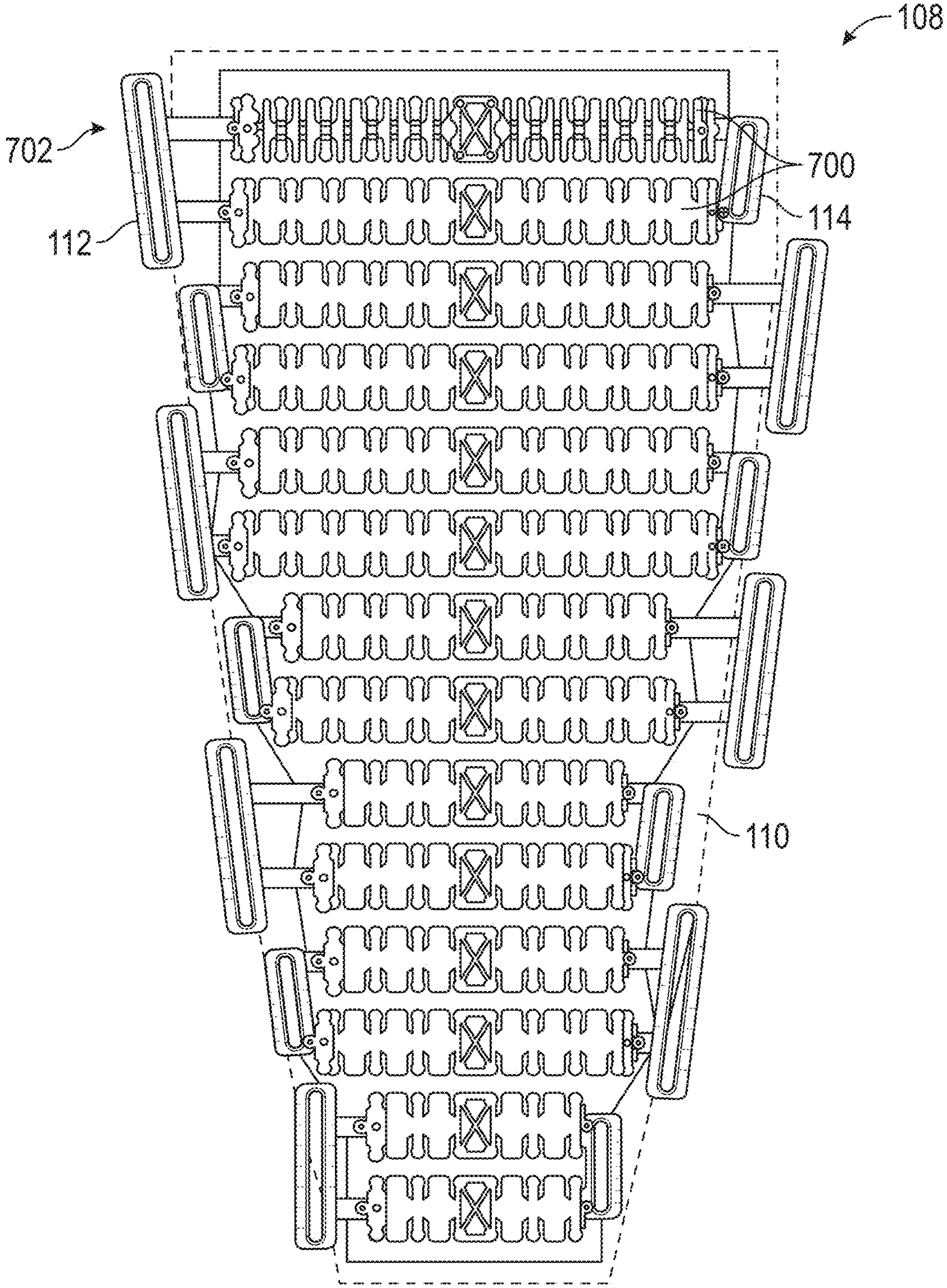
FIGS. 7A, 7B, and 7C illustrate a panel.
Figure 7B:
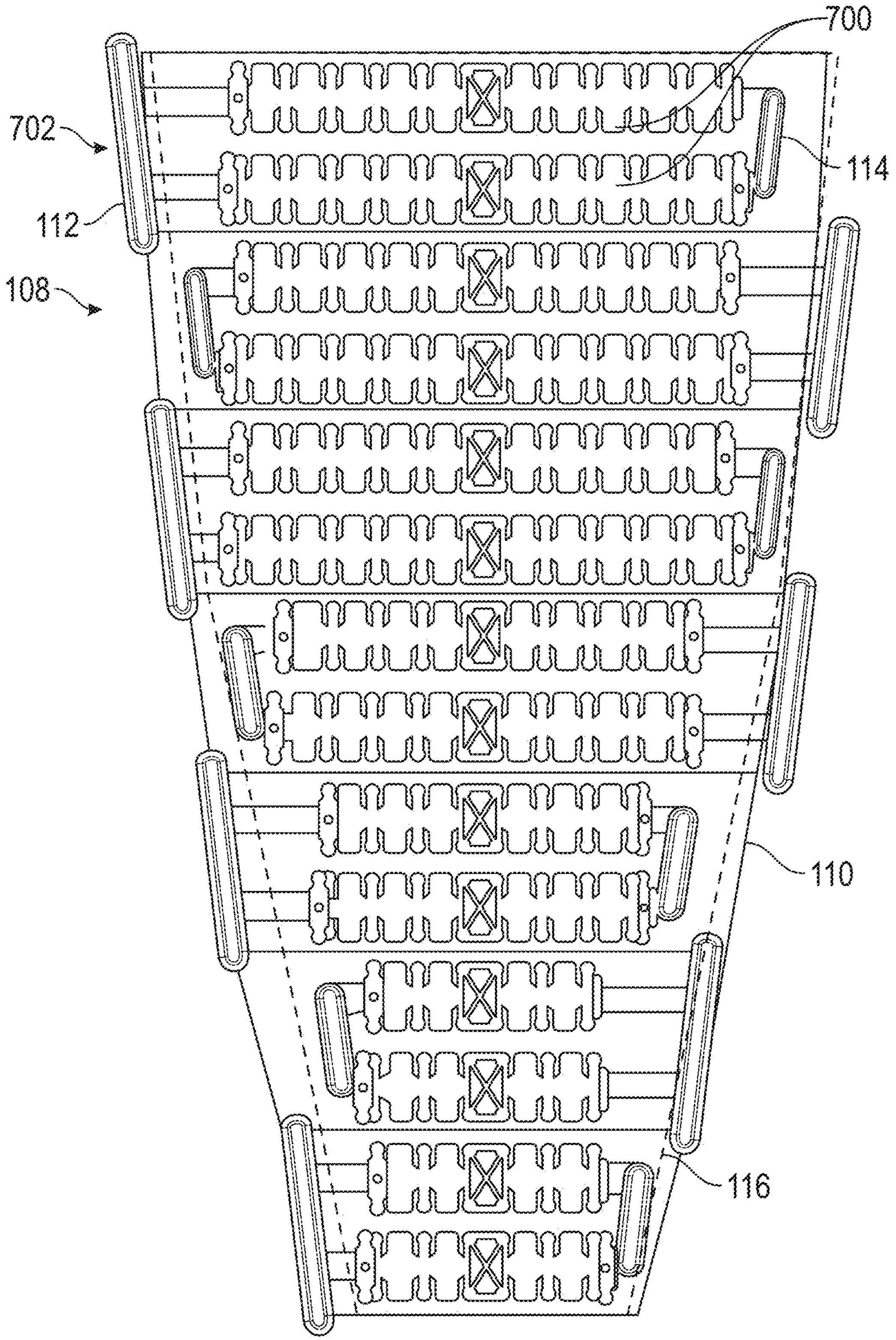
Figure 7C:
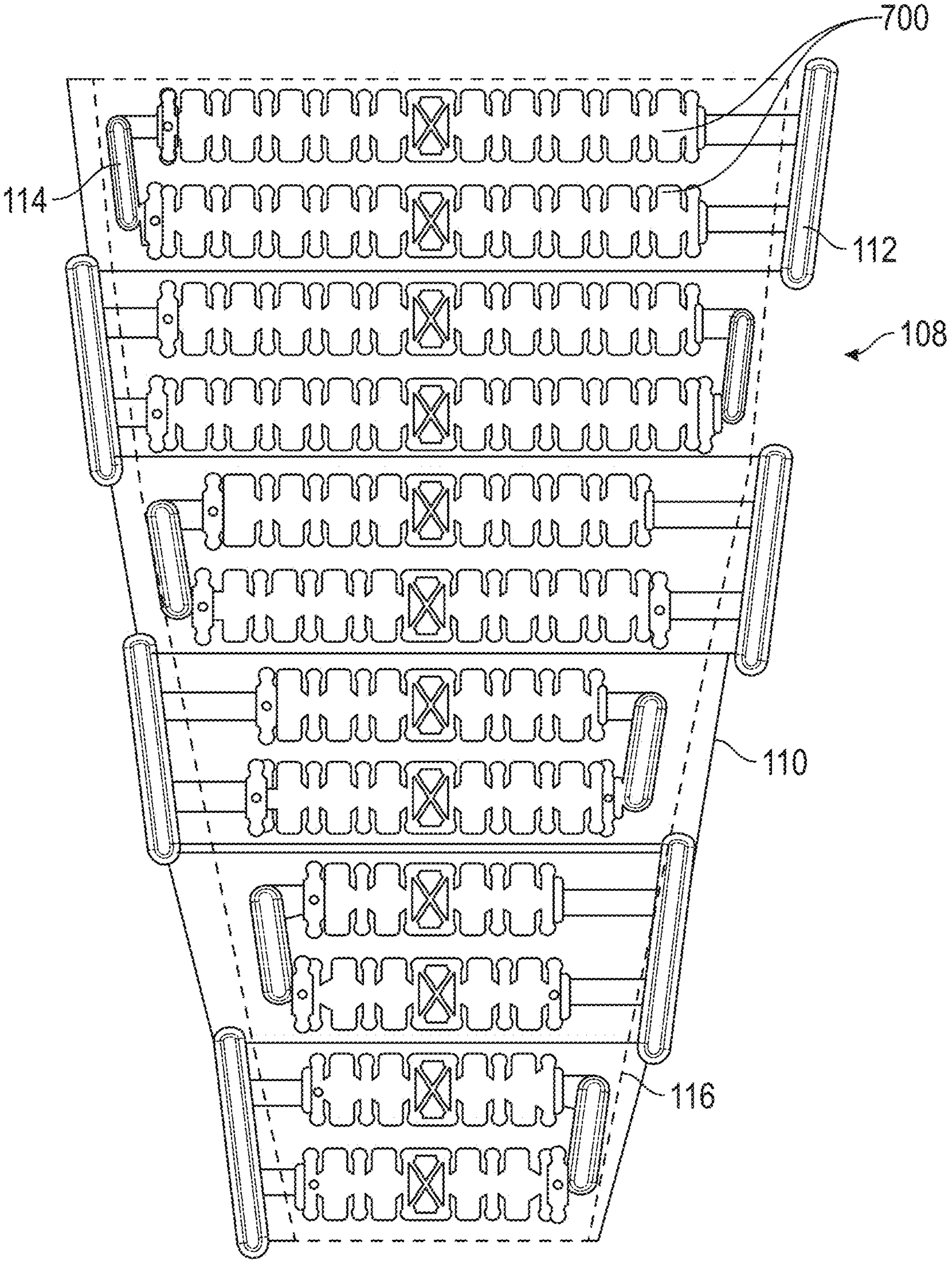

FIG. 7A-7C illustrates a panel 108. The panel 108 can include a plurality of flex frame assemblies 702. The flex frame assemblies 702 can each include one or more flex frames 700 (e.g., two) that are coupled to a first strap interface 112 and second strap interface 114. The flex frame assemblies 702 can decrease in length from one end of the panel 108 to the other, which can be based on the structure of the anatomical structure of the user. For example, limbs typically become progressively smaller in circumference moving away from the trunk of the user. Accordingly, the circumferential length to be surrounded by the panel 108 can become progressively smaller such that the lengths of the flex frame assemblies 702 can be smaller. The positioning of the first strap interface 112 and second strap interface 114 can be alternated for each flex frame assemblies 702 moving from one end of the panel 108 to the other. This can help securely strap the panel 108 to the user. For example, in some variants, the second strap interface 114 can fixedly couple to a strap. The user can extend the end of the strap through the first strap interface 112 and fold the first strap interface 112 back on itself to Velcro or otherwise fix the strap in position. Alternating which direction the user pulls the strap via alternating the side of the panel 108 having the first strap interface 112 can require the user to pull the strap in alternating directions to avoid shifting the positioning of the panel 108 as the panel 108 is secure in place. This can also ease application and/or provide bettering leverage or anchoring when securing the straps. As explained elsewhere herein, each of the flex frame assemblies 702 can include a micro-electronic controller 320 to individually control the flex frame assemblies 702, which can allow targeted compression and/or the directed movement of bodily fluids. The panel 108 as explained elsewhere herein can include a liner 110 that can be disposed between the flex frame assemblies 702 and the user, which can protect the user from the flex frames 700 and/or generated heat. The panel 108 can include backing 116 which can be disposed on the opposite side of the flex frame assemblies 702, which can be an outside of panel 108. The backing 116 can protect the flex frame assemblies 702 and/or help release heat generated by the flex frame assemblies 702.

Figure 8A:
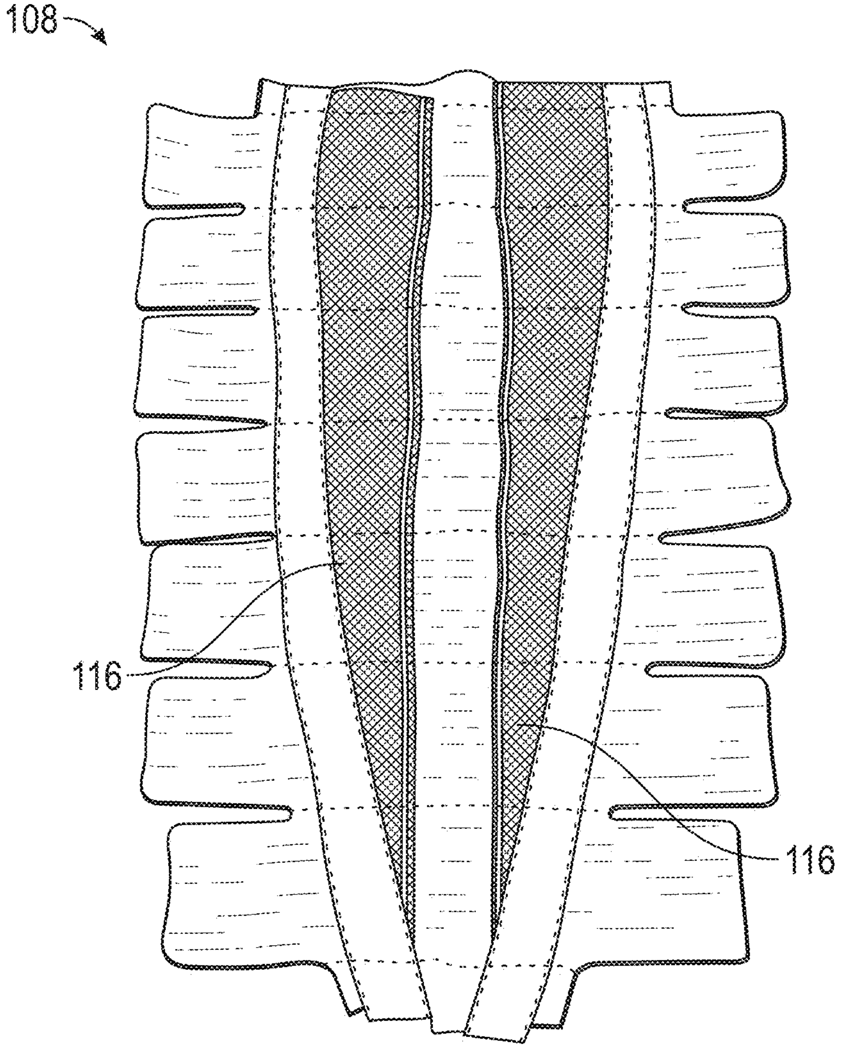
FIGS. 8A and 8B illustrate a panel.
Figure 8B:
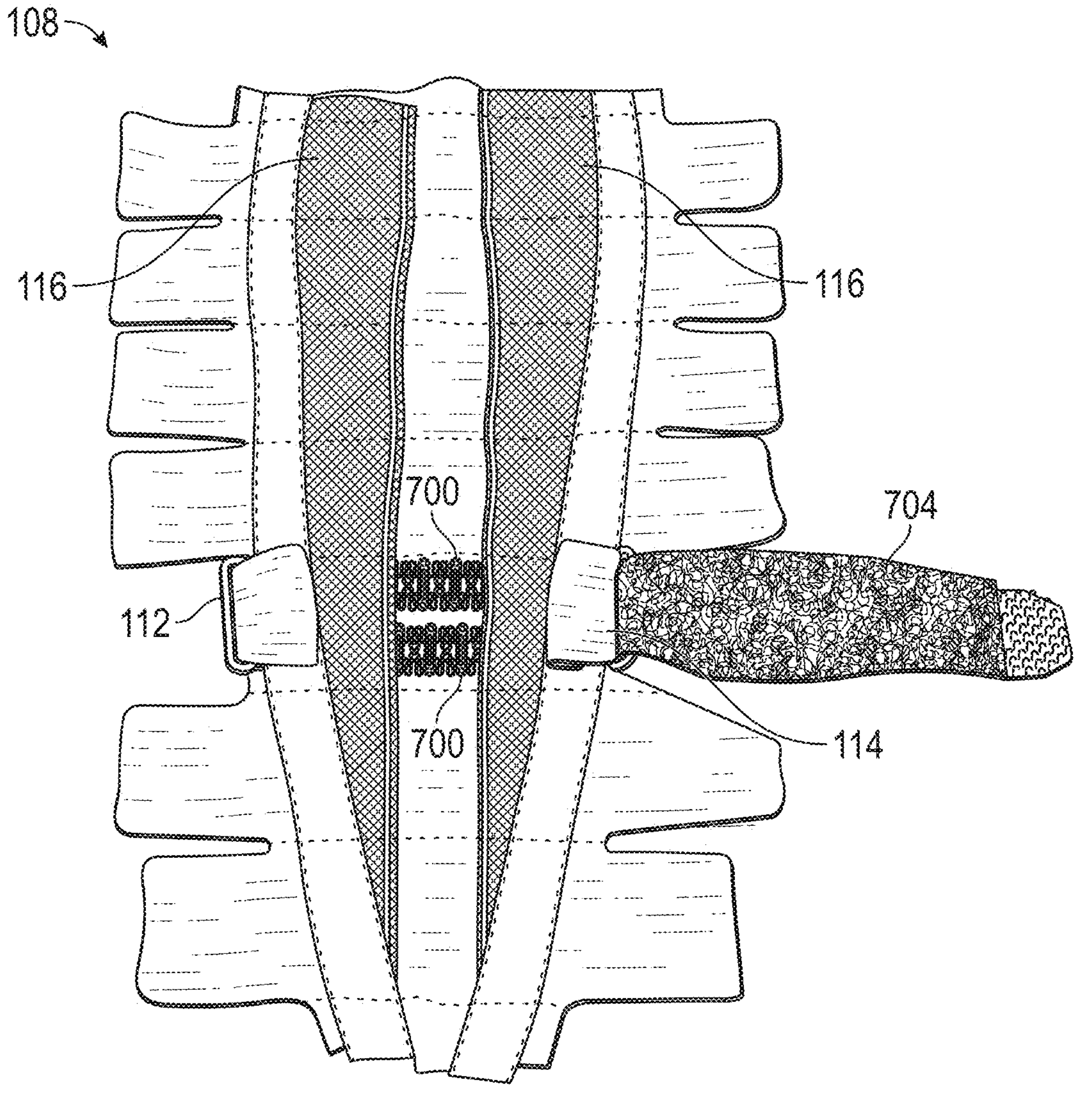

FIGS. 8A and 8B illustrate a panel 108. The panel 108 includes backing 116 that can be disposed on the outside of the panel 108 when secured to the user. The panel 108 includes a strap 704. As explained elsewhere herein, the strap 704 can be fixedly coupled to the second strap interface 114. The user can position the panel 108 on a limb 106 and wrap the strap 704 around the limb 106, through the first strap interface 112, and back on the strap 704 to fix the strap 704 to itself, which can be via Velcro. The panel 108 can be tapered from one end to the other.

Figure 9B:
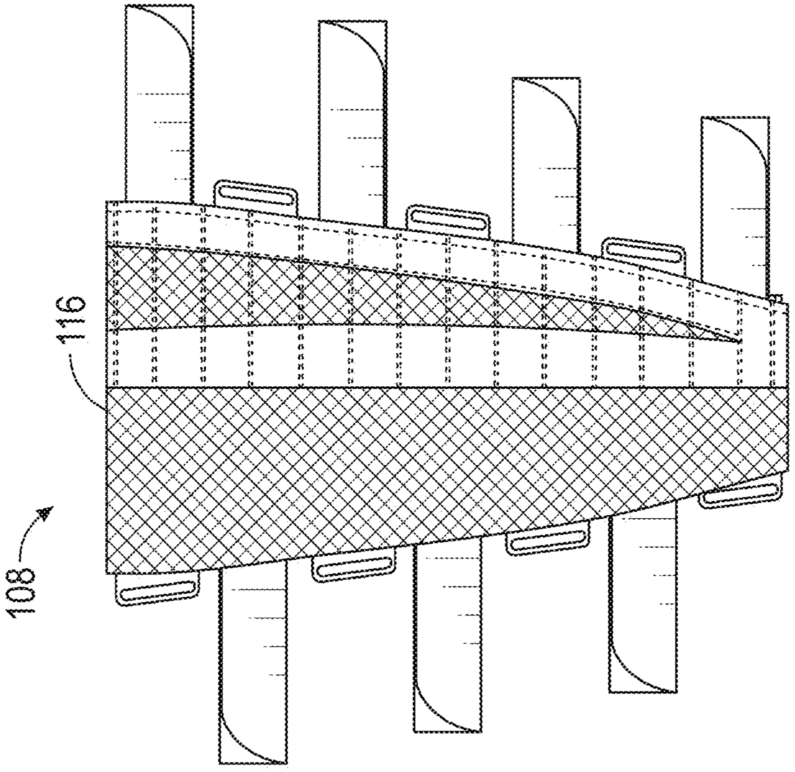
FIGS. 9A and 9B illustrate a panel with straps.
Figure 9A:
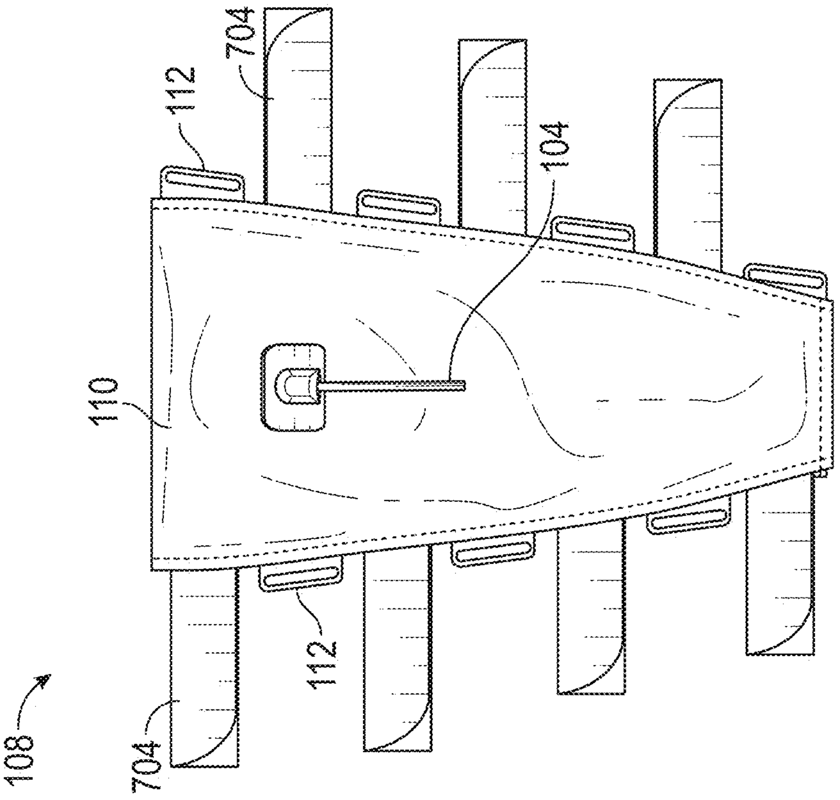

FIGS. 9A and 9B illustrates a panel 108. FIG. 9A illustrates an external side of the panel 108. The panel 108 can be tapered from one end to the other. The panel 108 can have a wired connection 104 which can connect to a controller and/or power supply that can power the micro-electronic controller(s) 320 to control the flex frame assemblies 702. The panel 108 can include straps 704 positioned on alternating sides of the panel 108 moving from one end to the other, which as explained elsewhere herein can help the user securely position the panel 108 on a limb 106 without excessive shifting of the panel 108. The straps 704 can be fixedly coupled to second strap interfaces 114. The user can secure the panel 108 to a limb 106 by placing the panel 108 on the limb 106 and wrapping the strap 704 around the limb 106, through the first strap interface 112, and back onto itself, which can be fixed in place via a hook and loop fastening system or another mechanism such as Velcro. The panel 108 can include the backing 116 on an external surface thereof which can help vent heat and/or protect the flex frame assemblies 702. FIG. 9B illustrates an internal side of the panel 108. The internal side of the panel 108 can include liner 110 which can protect the limb 106 of the user from the flex frame assemblies 702 and/or heat (e.g., thermally insulate the limb 106 of the user).

Figure 10B:
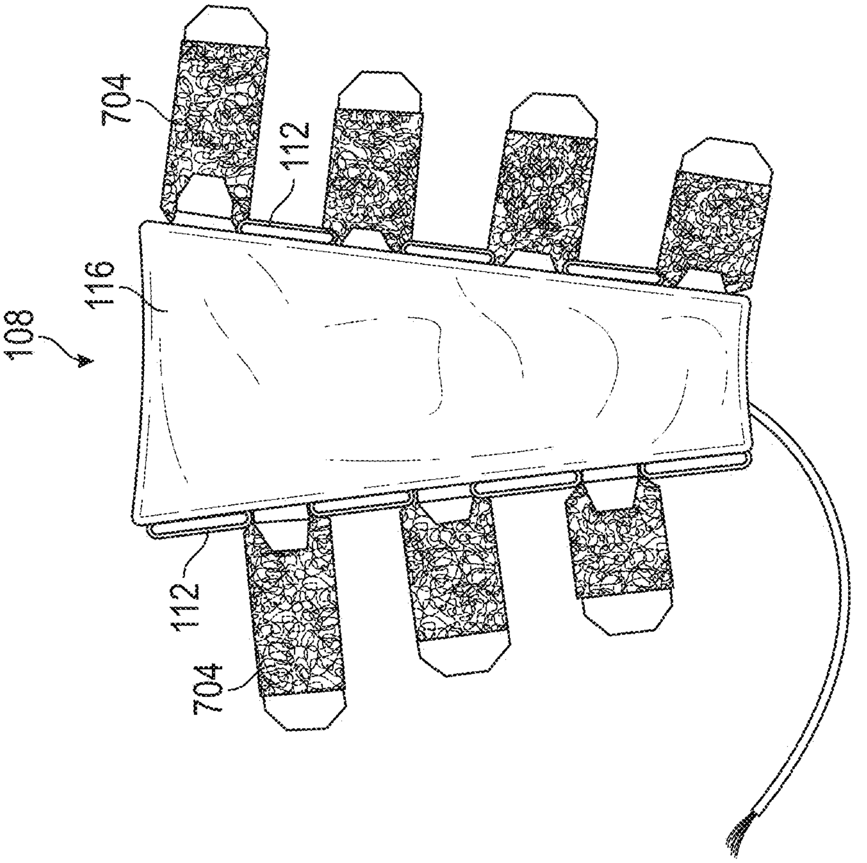
FIGS. 10A and 10B illustrate a panel with straps.
Figure 10A:
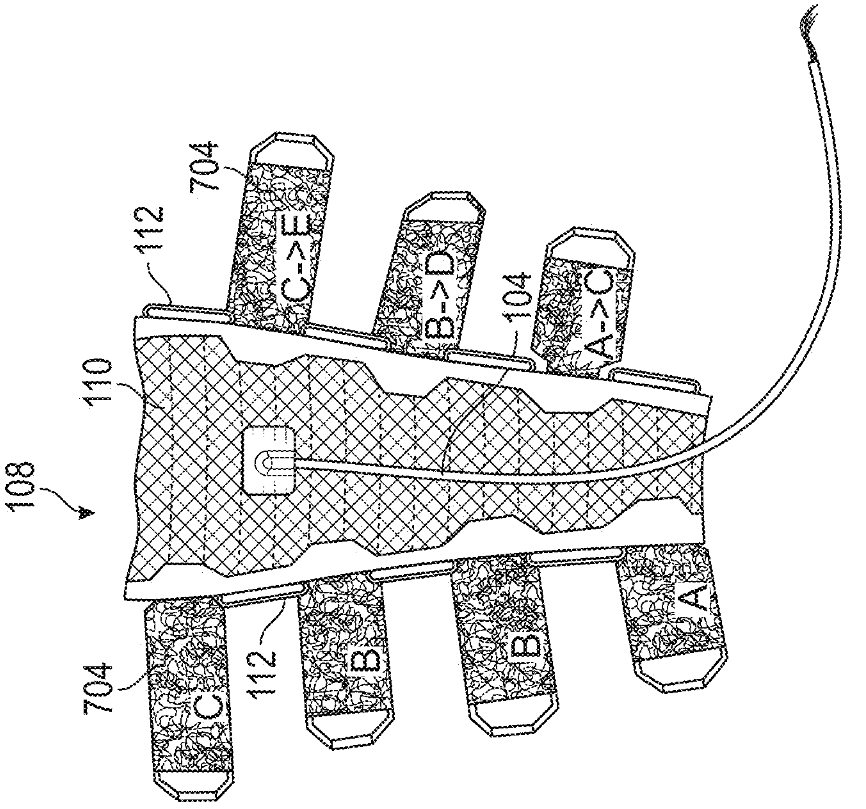
Figure 11:
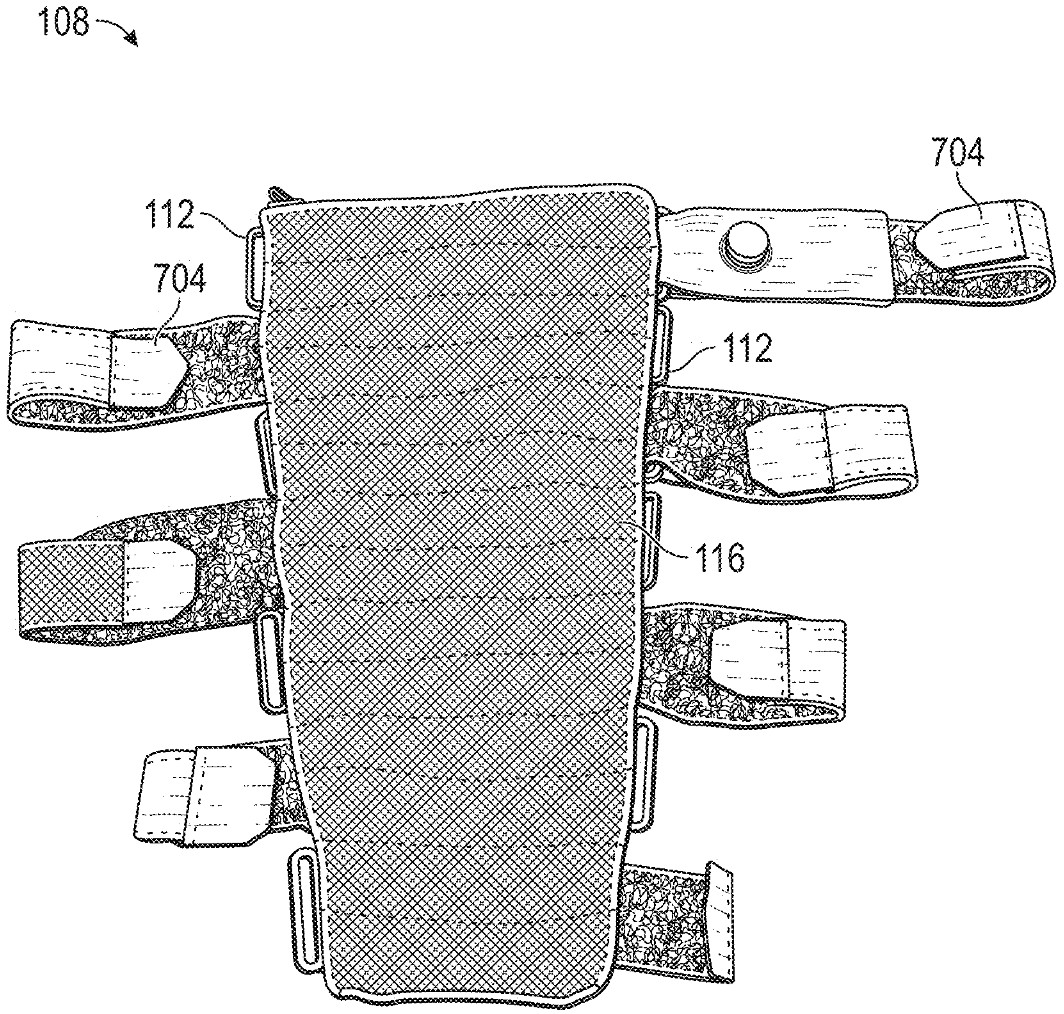
FIG. 11 illustrates a panel with straps.

FIGS. 10A and 10B illustrate a similar panel 108 to that shown in FIGS. 9A and 9B with 10A showing an external side and 10B showing an internal side. FIG. 11 illustrates the internal side of another similar panel 108.

FIGS. 12A-12D illustrates the panel 108 and components of an envelope to receive the panel 108. As described elsewhere herein, the compression garment 100 can include electronics, shape memory material (shape memory alloy), etc. that an increase the heat emitted by the compression garment 100. Accordingly, it can be beneficial to provide improved thermal management to ensure that surface temperatures in contact with the user is save, the compression garment 100 is comfortable to use, and the components and/or electronics of the compression garment 100 are protected. Accordingly, the compression garment 100 can include multiple layers that can impede heat transfer toward the user and encourage heat dissipation to the ambient environment. Thermal release into the ambient environment can be achieved through one or more methods. Thermal release can also be used to drive a thermoelectric generator to restore some or most of the energy back into the battery or power system of the electronic controller. Convection heat transfer can be created by designing the external material (e.g., fabric) with a mesh pattern to allow heat to be moved and diffused through air flow, which can also prevent the user from accessing a shape memory alloy wire 118. A thermally conductive heat exchanger can allow heat to easily and/or readily transfer from the electrical components and/or shape memory alloy to the exterior of the compression garment 100. Incorporating phase changing materials (PCMs) into the garment to store thermal energy when in use and release the thermal energy after use. FIGS. 12A-12D illustrate an example of implementing convection as the thermal management method. In some variants, heat and thermal release can be used to drive or channel to a specific part or anatomical feature of the body for a desired relief or dilation or fluid transfer.

Figure 12A:
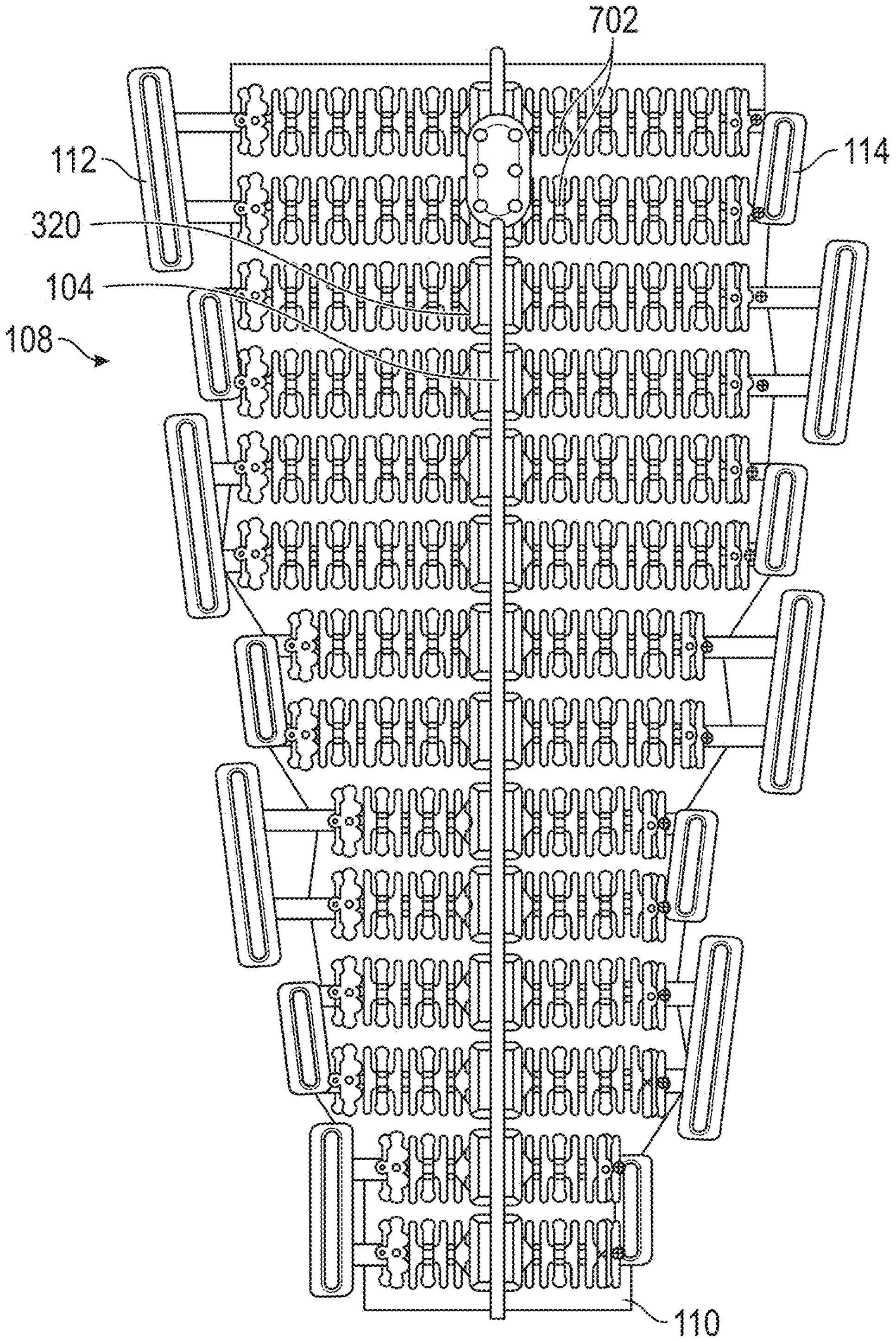
FIG. 12A illustrates a panel.
Figure 12C:
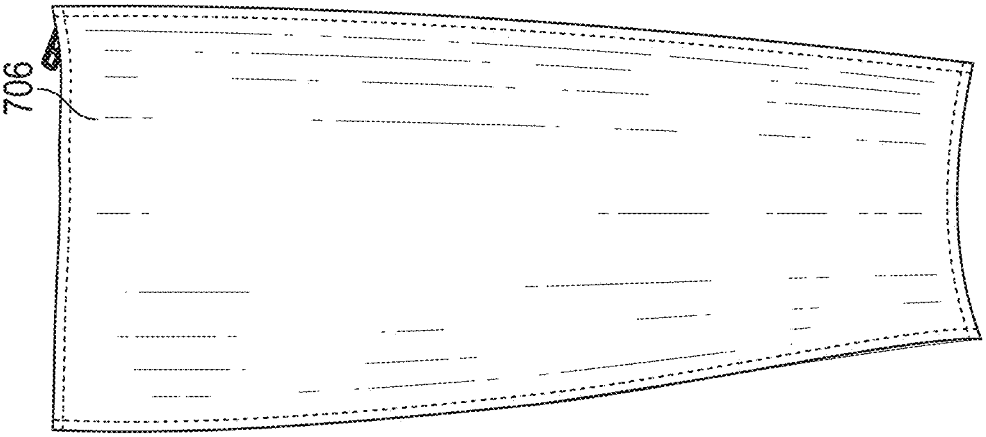
FIG. 12C illustrates an internal lining.

FIG. 12A illustrates a panel 108 having plurality of flex frame assemblies 702 coupled to first strap interfaces 112 and second strap interfaces 114. The first strap interface 112 and second strap interface 114 are disposed on alternating sides of the panel 108 from one side of the panel 108 to the other. The panel 108 is tapered from one side to the other. Each of the flex frame assemblies 702 can include a micro-electronic controller 320 which are connected to a wired connection 104 which can connect to a controller and/or power supply. The flex frame assemblies 702 and/or first strap interface 112 and second strap interface 114 are coupled to the liner 110. The liner 110 can be thermally insulating to protect the user from heat and/or the flex frame assemblies 702 during shortening and/or lengthening.

Figure 12B:
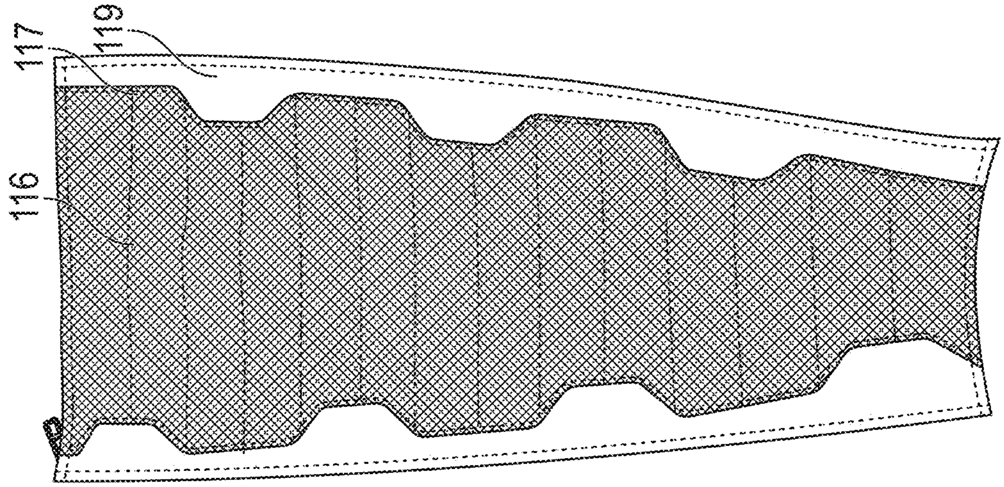
FIG. 12B illustrates an external backing.
Figure 12D:
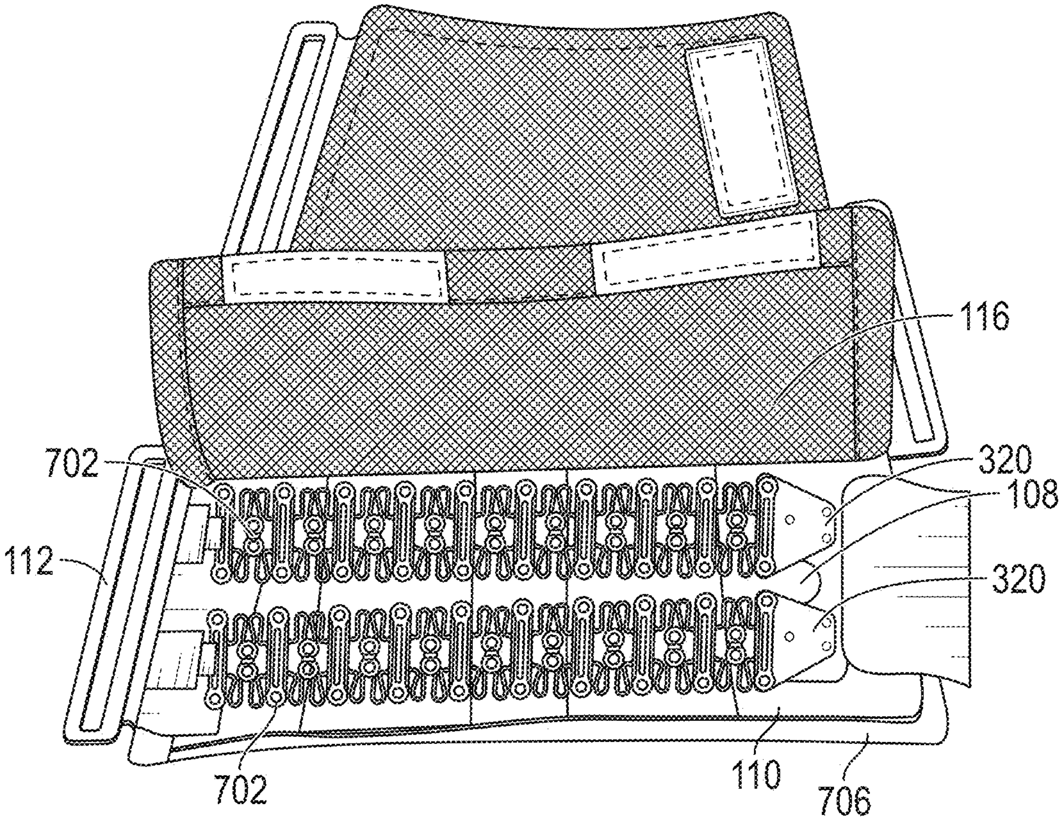
FIG. 12D shows the features of FIGS. 12A-12C assembled together.

FIG. 12B illustrates the backing 116 which can be disposed on the external side of the panel 108. The backing 116 can include a mesh pattern to help ventilate heat to the ambient environment. In some variants, the backing 116 can be made of a mesh garment material. The backing 116 can include tabs 119 with gaps 117 disposed therebetween. The gaps 117 can enable the first strap interfaces 112 to extend outside an envelope formed with the backing 116 and internal lining 706, illustrated in FIG. 12C. The internal lining 706 can be disposed between the panel 108 and the user. In some variants, the internal lining 706 is made of a garment fabric that is comfortable on the skin of the user. FIG. 12D illustrates the panel 108 positioned between the backing 116 and the internal lining 706, which can also be referred to as a liner 110. As illustrated, the flex frame assemblies 702 are positioned between the internal lining 706, e.g., liner 110, and the backing 116 such that heat can be emitted through the backing 116 to the ambient environment. In use, straps can be secured to the first strap interfaces 112 and the panel 108 disposed between the backing 116 and internal lining 706 (e.g., positioned in the envelope) can be secured to the limb 106 of the user.

Figure 13A:
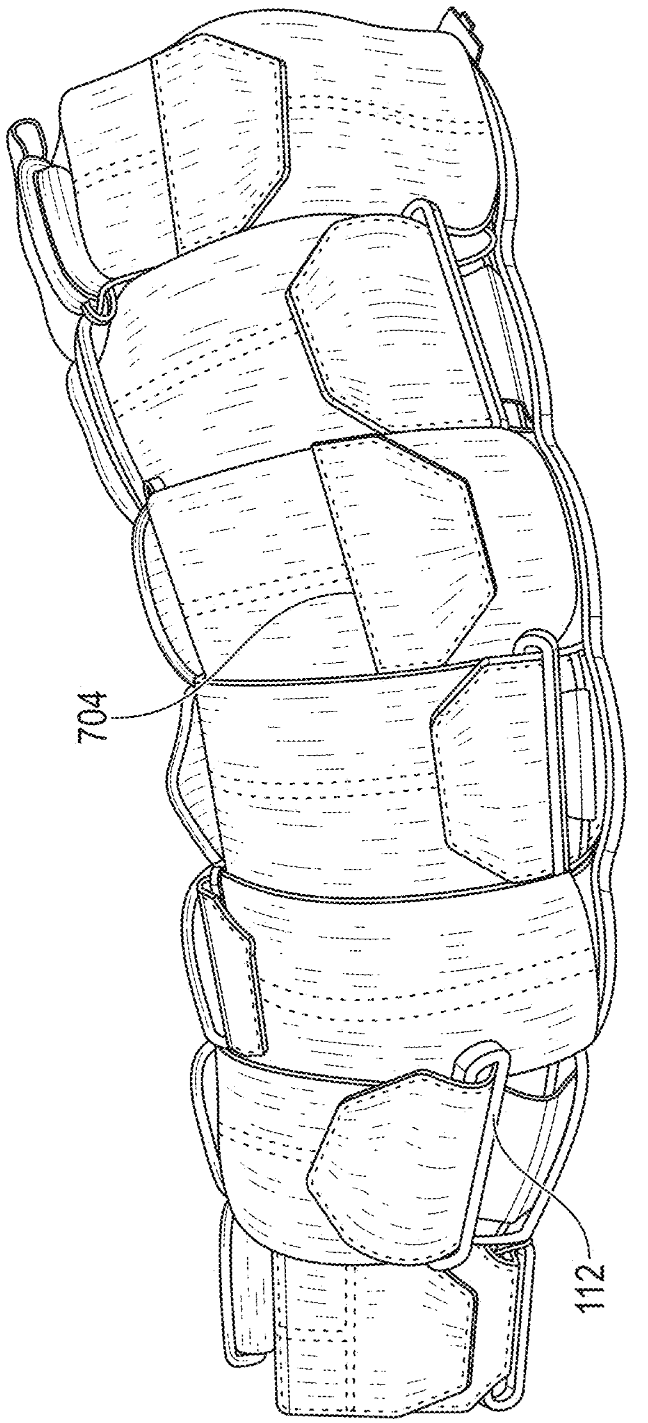
FIGS. 13A, 13B, and 13C illustrate the compression garment on the limb of the user.
Figure 13B:
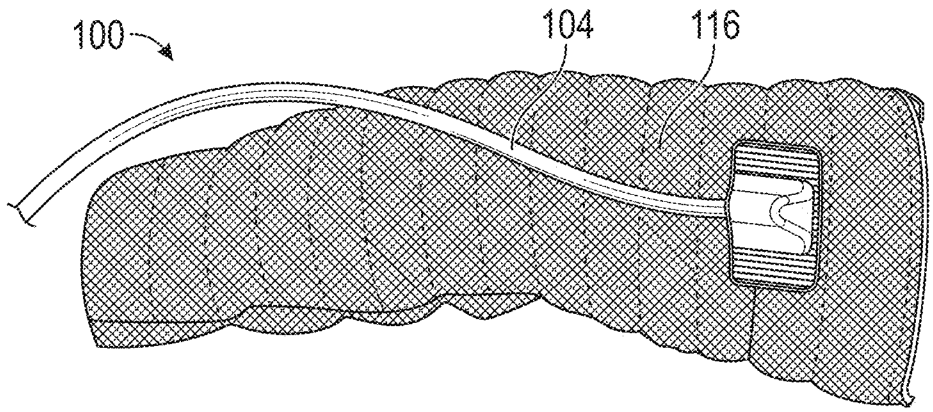
Figure 13C:
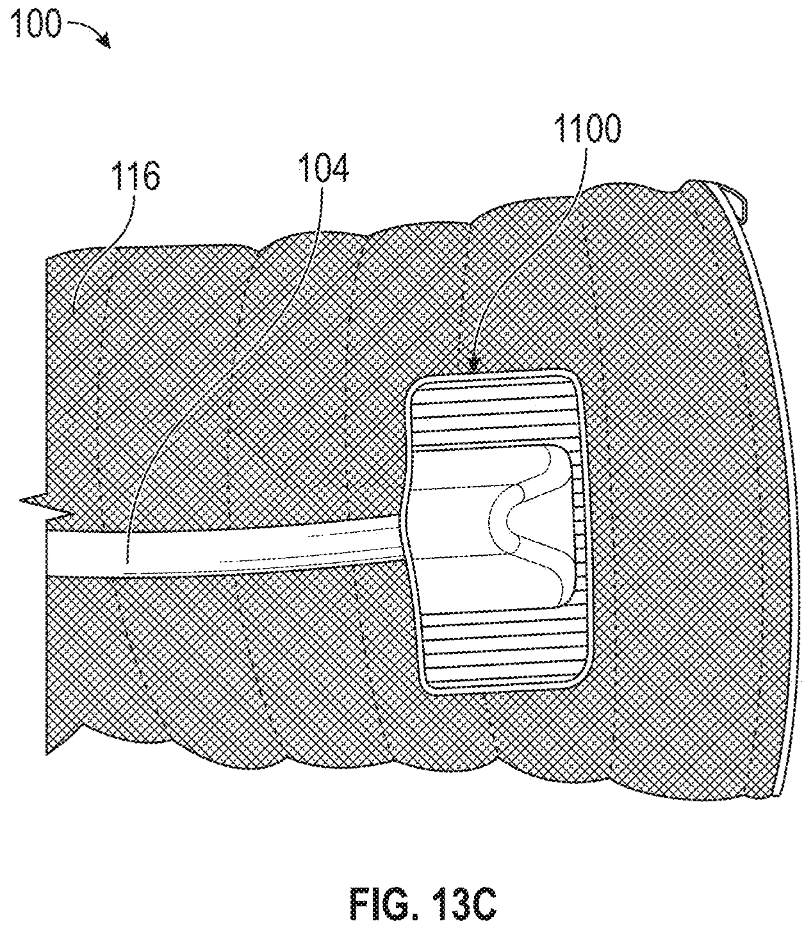

FIG. 13A-13C illustrates the compression garment 100 strapped to the limb 106 of the user. As illustrated, the straps 704 are wrapped around the limb 106, threaded through the first strap interface 112, and folded back onto itself for securing via Velcro. As illustrated in FIGS. 13B and 13C, the backing 116 can include a mesh pattern to vent heat to the ambient environment. A wired connection (cable) 104 can connect to a controller and/or power supply which can control and/or power the compression garment 100. FIG. 13C also illustrates an anchoring mechanism or system 1100. The anchoring system 1100 can include interior and exterior anchor components, which can be made of a rigid polymer. The anchor components can simultaneously apply compressive forces on the cable jacket and exterior backing 116 to fixate the cable 104 with respect to the backing 116. Interior and exterior parts can be connected via screws, rivets, snap-fit, etc.

Figure 13D:
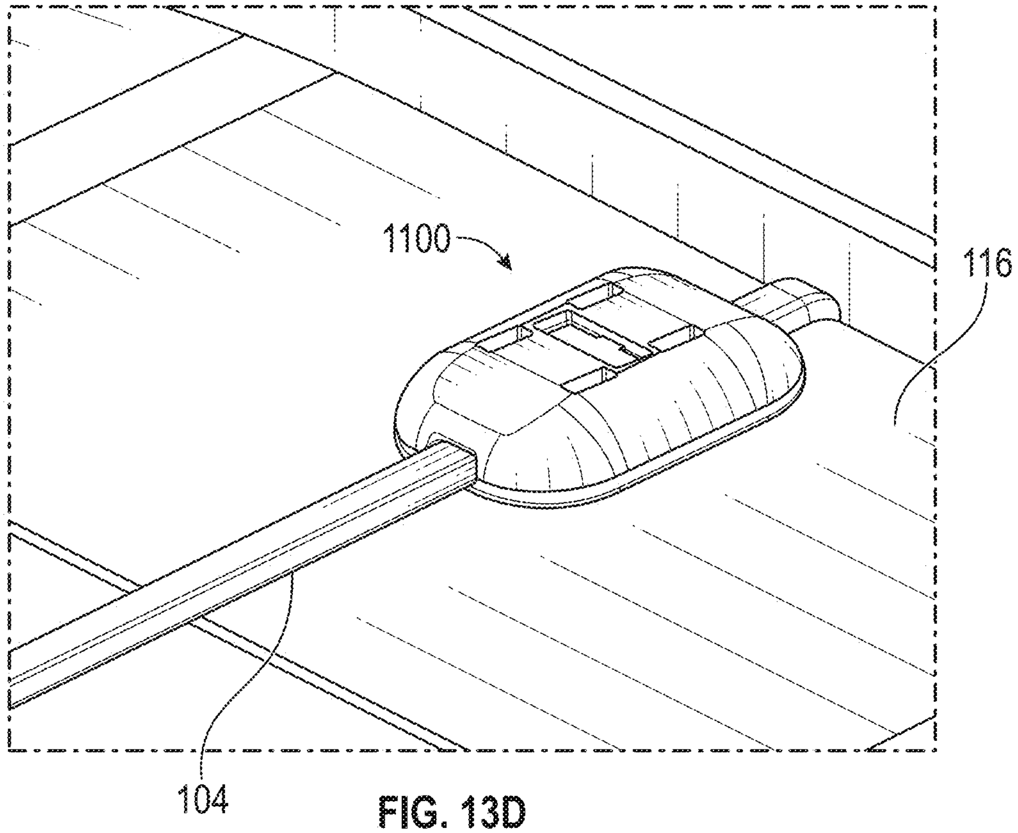
FIGS. 13D and 13E illustrate an anchor mechanism.
Figure 13E:
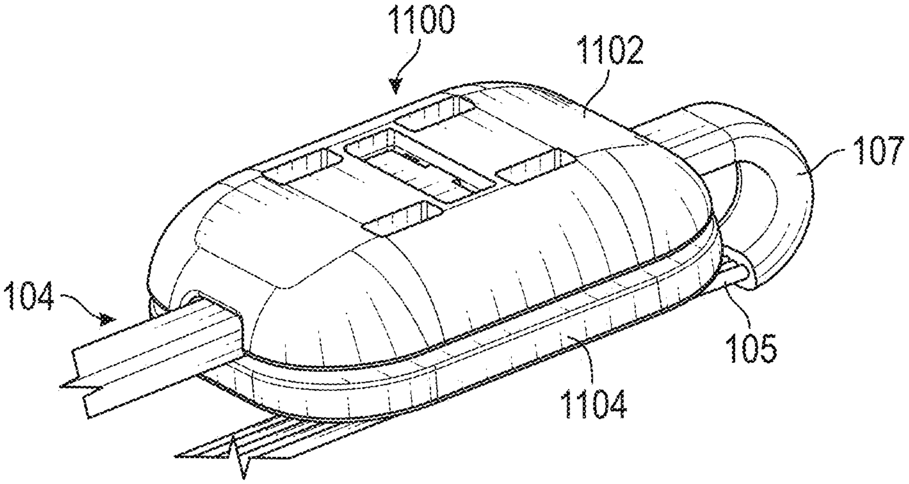
Figure 13F:
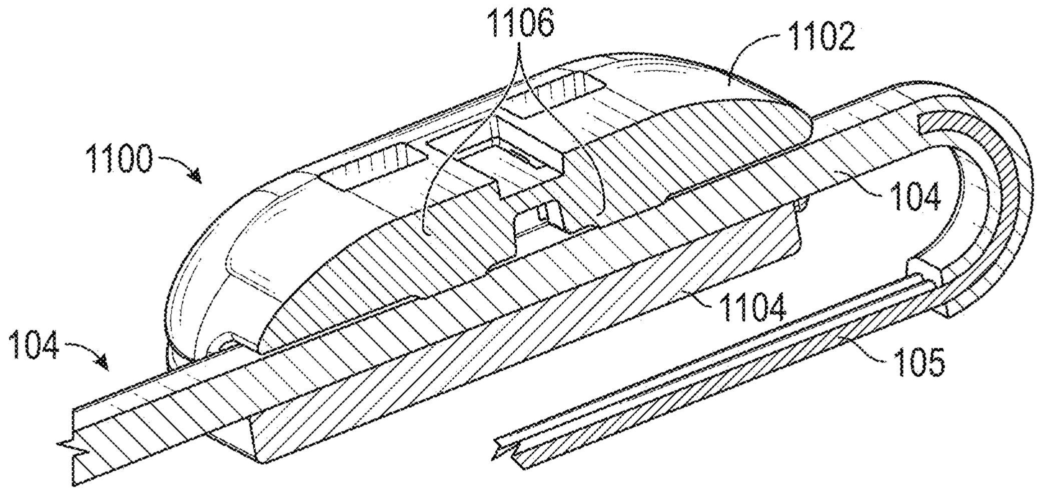
FIG. 13F illustrates a section view of the anchor mechanism of FIGS. 13D and 13F.

FIGS. 13D-13F illustrate an example anchoring mechanism (cable anchor) 1100. The anchoring mechanism 1100 can fix the cable 104 to the backing 116, as shown in FIG. 13D. The cable 104 can connect to a controller, power supply, and/or motor which can control and/or power the compression garment 100. The cable 104 can include one or more wires 105 that are covered by a coating 107, which can be an insulated coating.

The anchoring mechanism 1100 can include an external component 1102 and an internal component 1104, as shown in FIGS. 13E and 13F. In some variants, the external component 1102 can be disposed outside the backing 116, as shown in FIG. 13D, while the internal component 1104 can be disposed inside the backing 117 (e.g., closer to the user), which can secure the external component 1102 and internal component 1104 to the backing 116. The external component 1102 and internal component 1104 can be coupled together via a snap-fit connection, screws, rivets, bolts, interference fit, etc. As shown in FIG. 13F, the cable 104 can be disposed between the external component 1102 and internal component 1104, which can secure the cable 104 to the backing 116 and/or external component 1102 and internal component 1104. The external component 1102 can include protrusion(s) (bump(s)) 1106 that can push against the cable 1104 to secure the cable 104 in place.

Figure 13G:
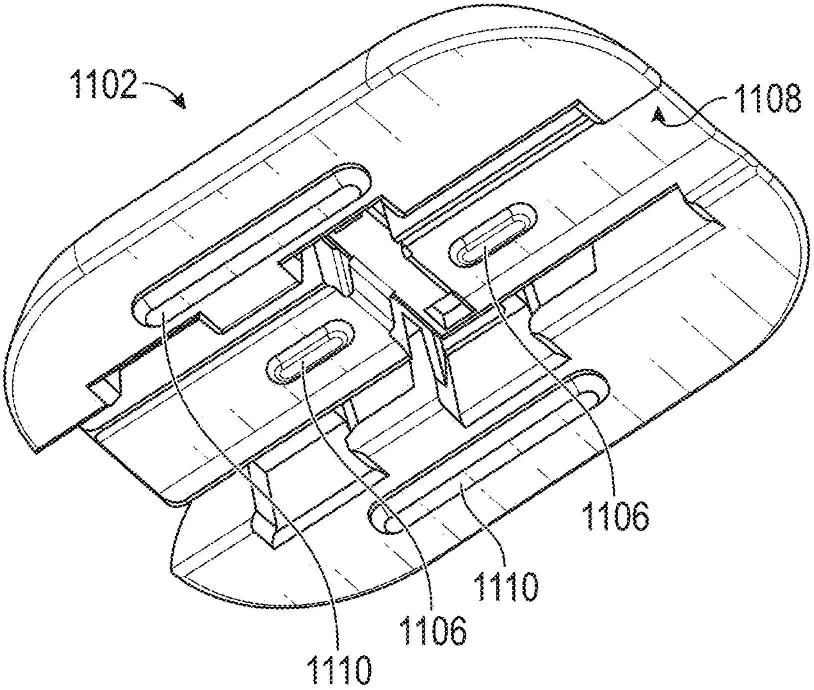
FIGS. 13G and 13H illustrate views of an exterior component of the anchor mechanism shown in FIGS. 13D and 13F.
Figure 13H:
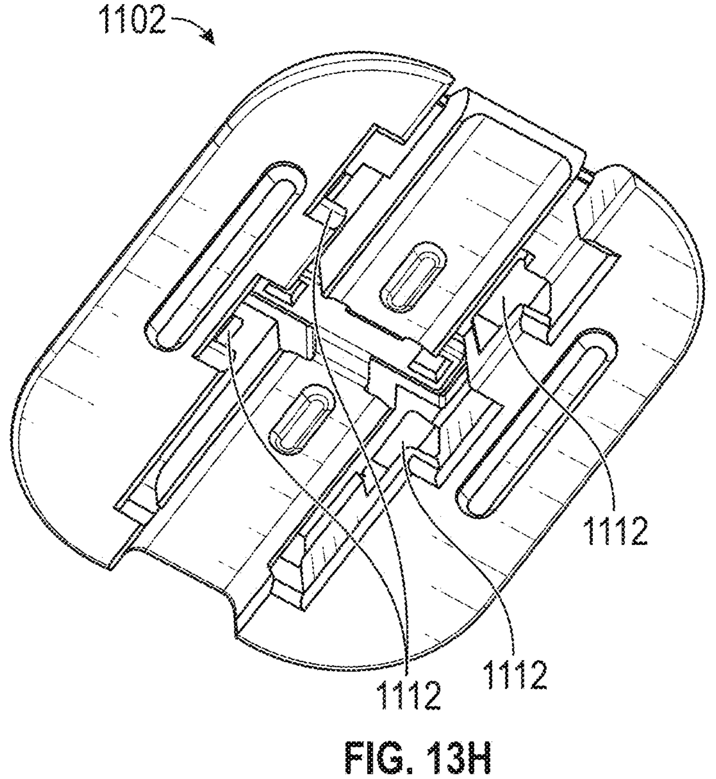

FIGS. 13G and 13H illustrate views of the external component 1102. The external component 1102 can have a channel 1108 that can receive the cable 104. The external component 1102, as described above, can have protrusion(s) 1106. The external component 1102 can have elongate protrusion(s) 1106 that can interface with elongate recess(es) (groove(s), channel(s)) 110 of the internal component 1104 to help facilitate a secure connection between the external component 1102 and the internal component 1104. The external component 1102 can include one or more ledges (surface(s), edge(s)) 1112 that can engage with hook(s) (tab(s), flange(s)) 1116 of the internal component 1104, illustrated in FIGS. 13I and 13J, to facilitate a snap-fit connection. The hook(s) 1116 can deflect as the external component 1102 and internal component 1104 are pushed together and snap into place around the ledge(s) 1112 to facilitate a snap-fit connection between the external component 1102 and internal component 1104.

Figure 13I:
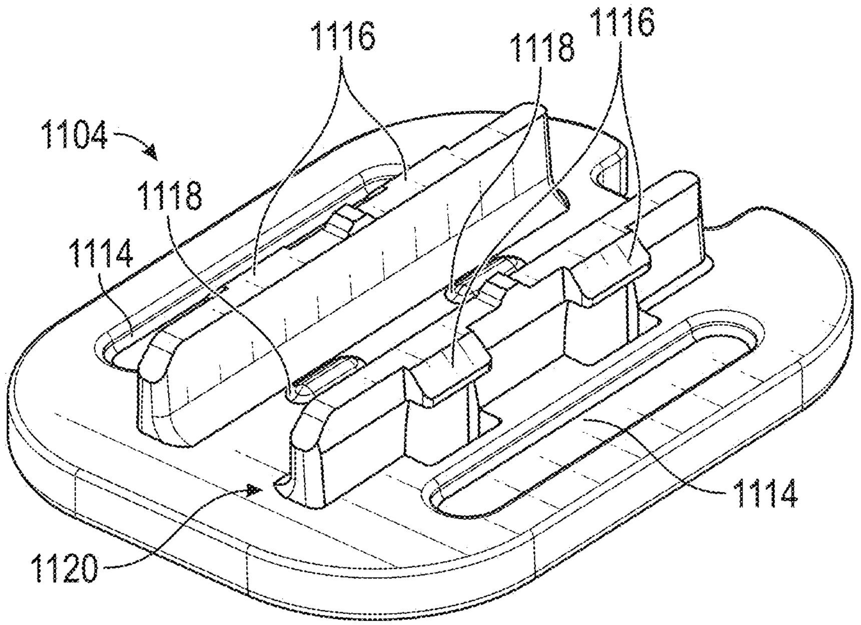
FIGS. 13I and 13J illustrate views of an interior component of the anchor mechanism shown in FIGS. 13D and 13F.
Figure 13J:
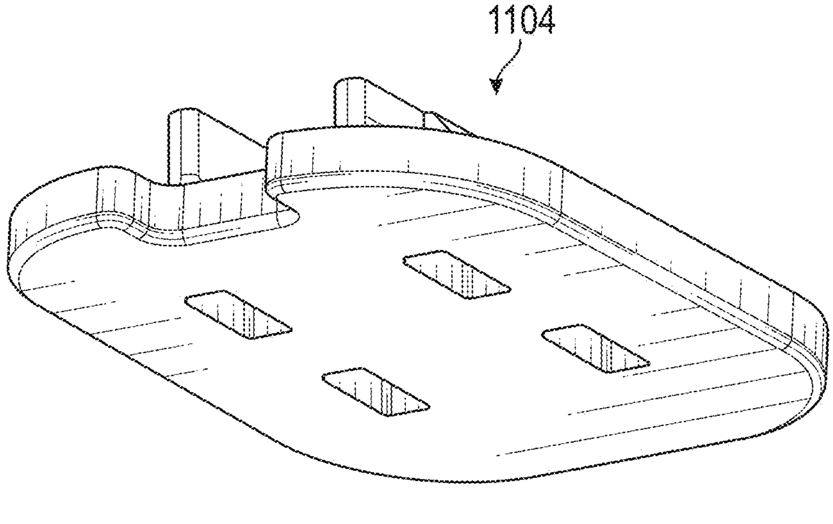

FIGS. 13I and 13J illustrate views of the internal component 1104. The internal component 1104 can include a channel 1120 that can receive the cable 104. The internal component 1104 can include one or more protrusions 1118 disposed in the channel 1120 that can push the cable 104 against the external component 1102 to secure the cable 104 in place. The channel 1120 of the internal component 1104 can be at least partially disposed in the channel 1108 of the external component 1102 when the internal component 1104 and external component 1102 are coupled together. The external component 1102 and/or internal component 1104 can be made of a polymer (i.e., rigid polymer). In some variants, the external component 1102 and/or internal component 1104 can be made of a metal or metal alloy.

Figure 14A:
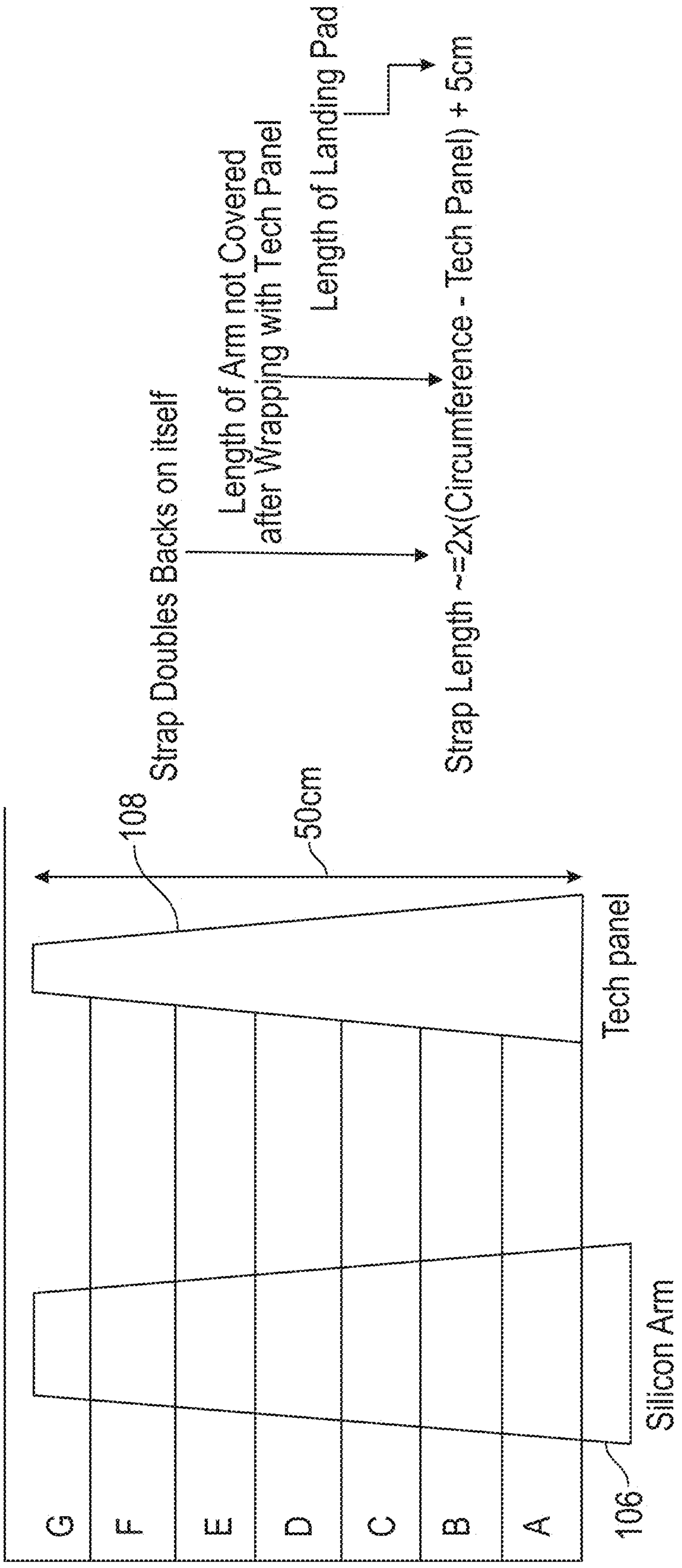
FIG. 14A schematically illustrates the panel and limb of the user segmented into portions.

FIG. 14A schematically illustrates a panel 108 and limb 106 segmented into portions A, B, C, D, E, F, and G. The panel 108 is 50 centimeters in length but other lengths can be implemented. The limb 106 and panel 108 are tapered. The panel 108 has a length that is smaller than that of the limb 106. In some variants, the panel 108 does not wrap completely around the limb 106. Accordingly, the straps 704 may connect the opposing sides of the panel 108 around the limb 106. The length of the straps 704 can be calculated using the formula:

$$\text{Strap Length} \approx 2\times(\text{Circumference of Limb} - \text{Panel Width}) + 5\ \text{centimeters}$$

The circumference of the limb minus the width of the panel 108 can determine the portion of the circumference not covered by the panel 108 after wrapping the panel 108 around the limb 106 of the user. That uncovered portion can be doubled to account for the straps 704 doubling back on themselves to be secured via Velcro. The 5 centimeters can be the length of the landing pad. FIG. 14B includes a table with the circumference of segmented portions of the limb 106, the width of the panel 108 in centimeters, and the total length of the strap 704 that is determined based on the above formula.

Figure 15A:
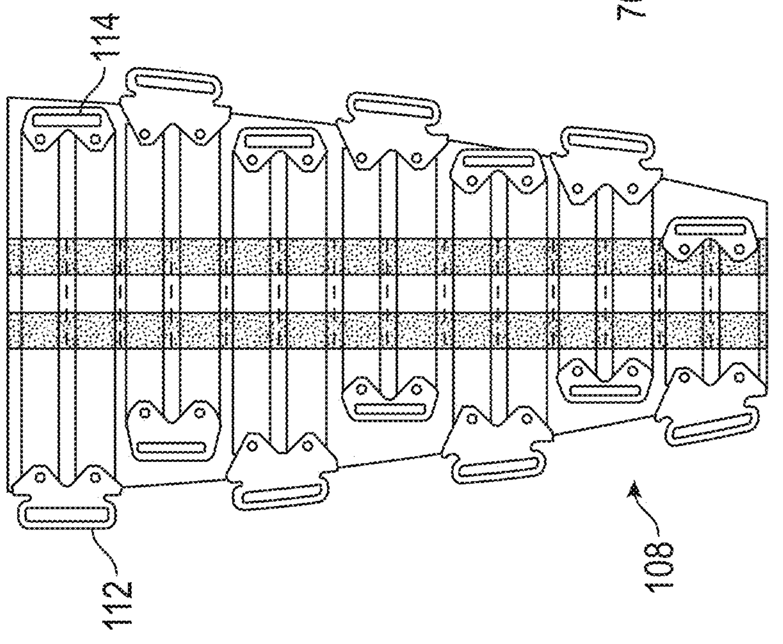
FIG. 15A illustrates a panel.
Figure 15B:
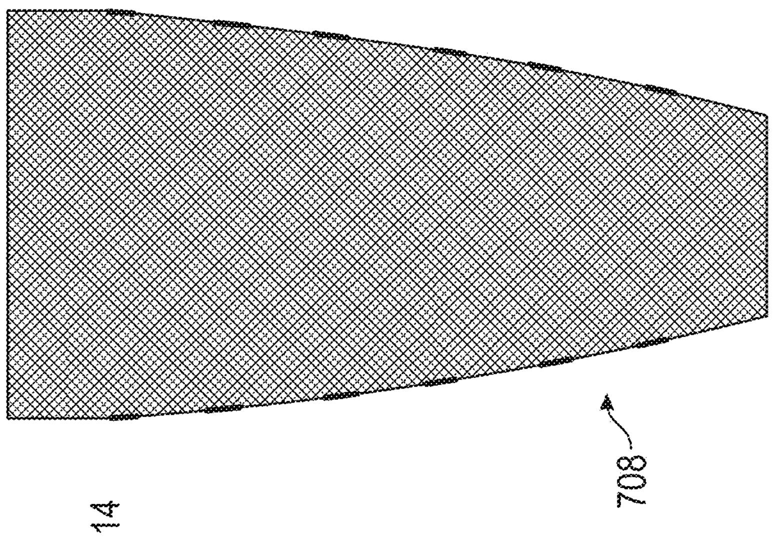
FIG. 15B illustrates a sleeve that can receive the panel.
Figure 15C:
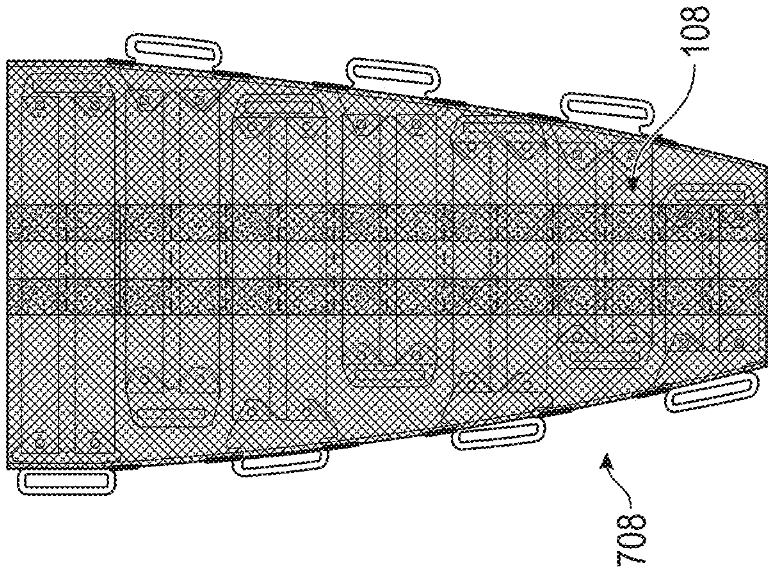
FIG. 15C illustrates the panel of FIG. 15A in the sleeve of FIG. 15B.
Figures 16A, 16B, 16C, 16D:
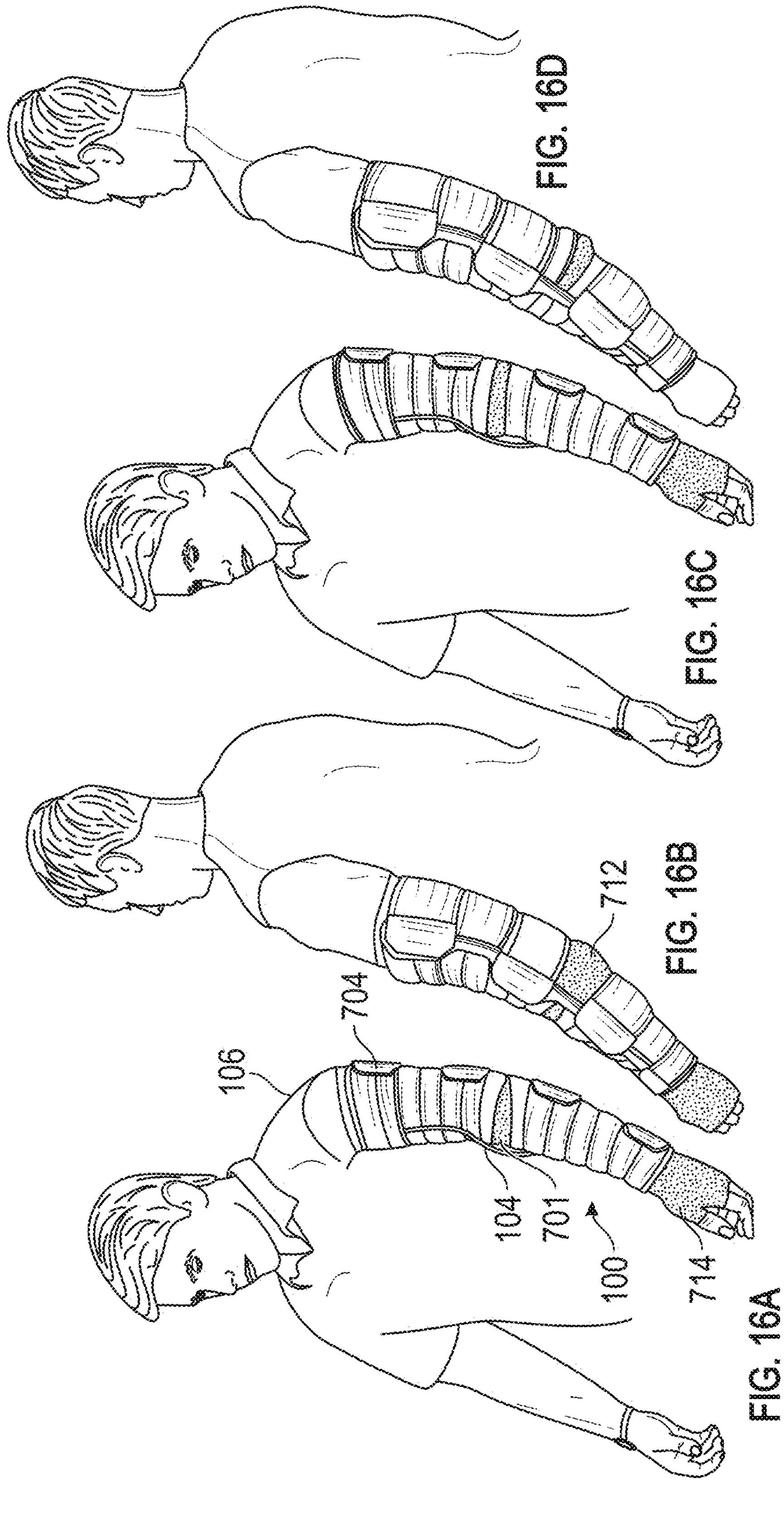
FIGS. 16A-D illustrate various views of the compression garment on the arm of the user.

FIGS. 15A-15C illustrate the panel 108 and sleeve 708. The sleeve 708 can include the backing 116 and internal lining 706. The sleeve 708 can receive the panel 108. The sleeve 708 can have gaps to enable the first strap interfaces 112 to extend outside the sleeve 708 to engage with straps 704. In such variants, the interfaces 112 lock the straps 704 at the tech panel 108. For these variants, the length of the straps 704 can be calculated using the formula:

$$\text{Strap Length} \approx (\text{Circumference of Limb} - \text{Panel Width}) + \tfrac{1}{2}(\text{Circumference of Limb} - \text{Panel Width})$$

FIGS. 16A-D illustrate various views of the compression garment 100 on the limb 106 of the user—specifically the arm of the user. The compression garment 100 includes a front flex region 710, also referred to as a stretch panel and/or joint panel, positioned over the front of the elbow of the user. The compression garment 100 includes a back flex region 712, as referred to as a stretch panel and/or joint panel, positioned over the back of the elbow of the user. The front flex region 710 and/or back flex region 712 can facilitate bending of the elbow of the user, which can improve the mobility and comfort of the user.

Figure 17A:
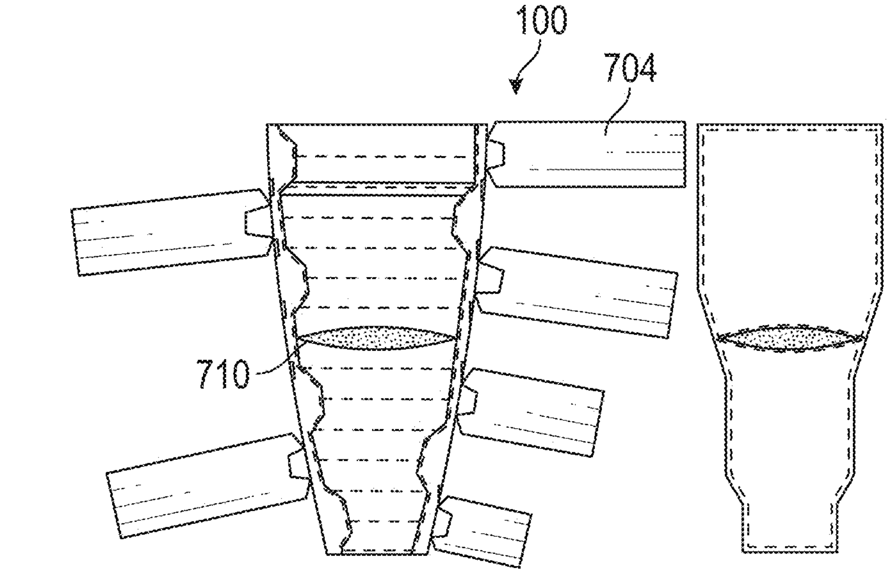
FIGS. 17A and 17B illustrate the compression garment with flex regions at the elbow.
Figure 17B:
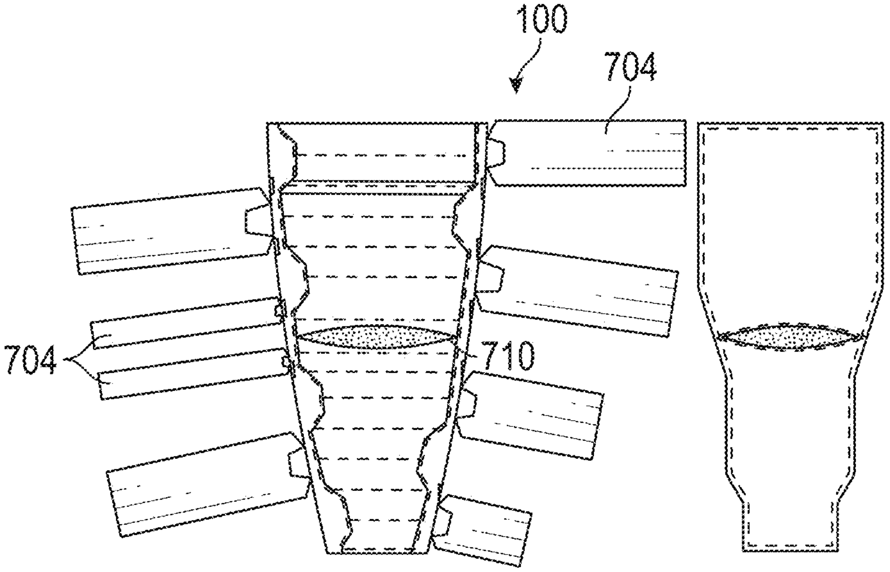

FIGS. 17A and 17B illustrate the compression garment 100 with the front flex region 710. As illustrated in 17A, the compression garment 100 can omit a strap 704 and/or one or more flex frame assemblies 702 to provide room for the front flex region 710. As illustrated in 17B, alternatively, smaller straps 704 can be disposed on either side of the front flex region 710 and/or one or more flex frame assemblies 702 repositioned on either side of the front flex region 710. The garment holding the panel 108 and/or flex frame assemblies 702 can be configured for the desired anatomy to be compressed or stimulated.

Figure 18A:
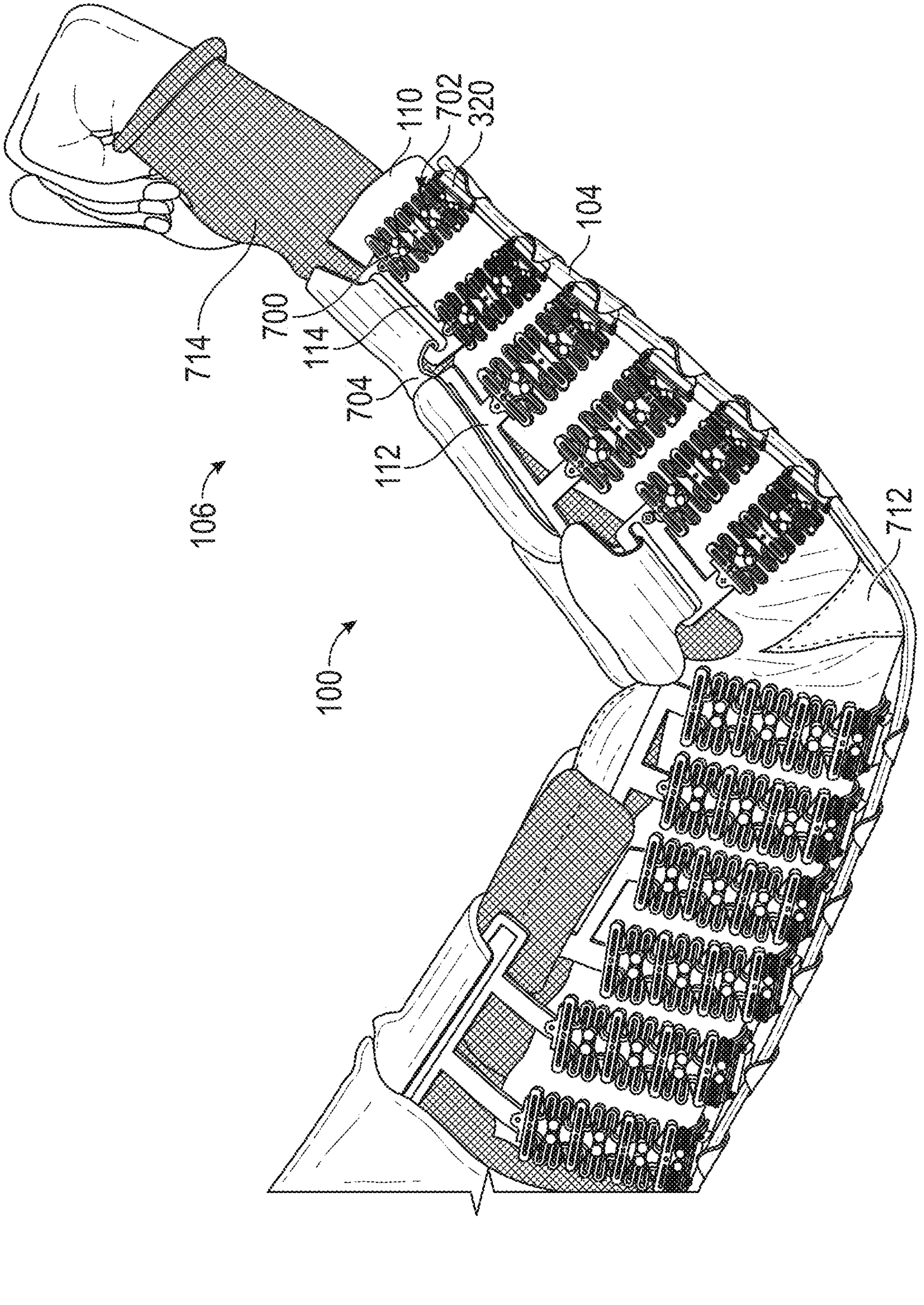
FIGS. 18A, 18B, 18C, and 18D show the compression garment on the arm of the user.
Figure 18B:
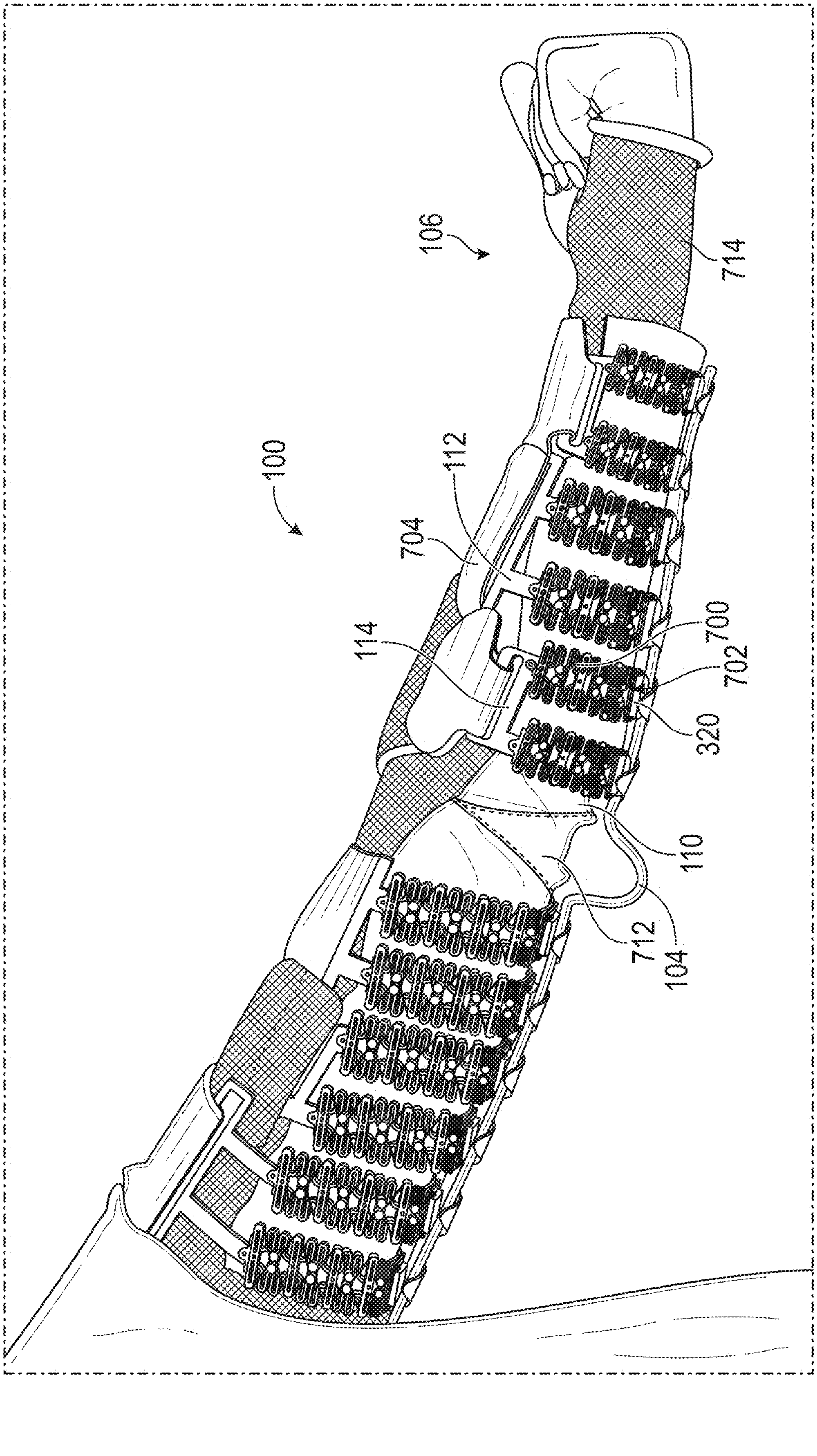
Figure 18C:
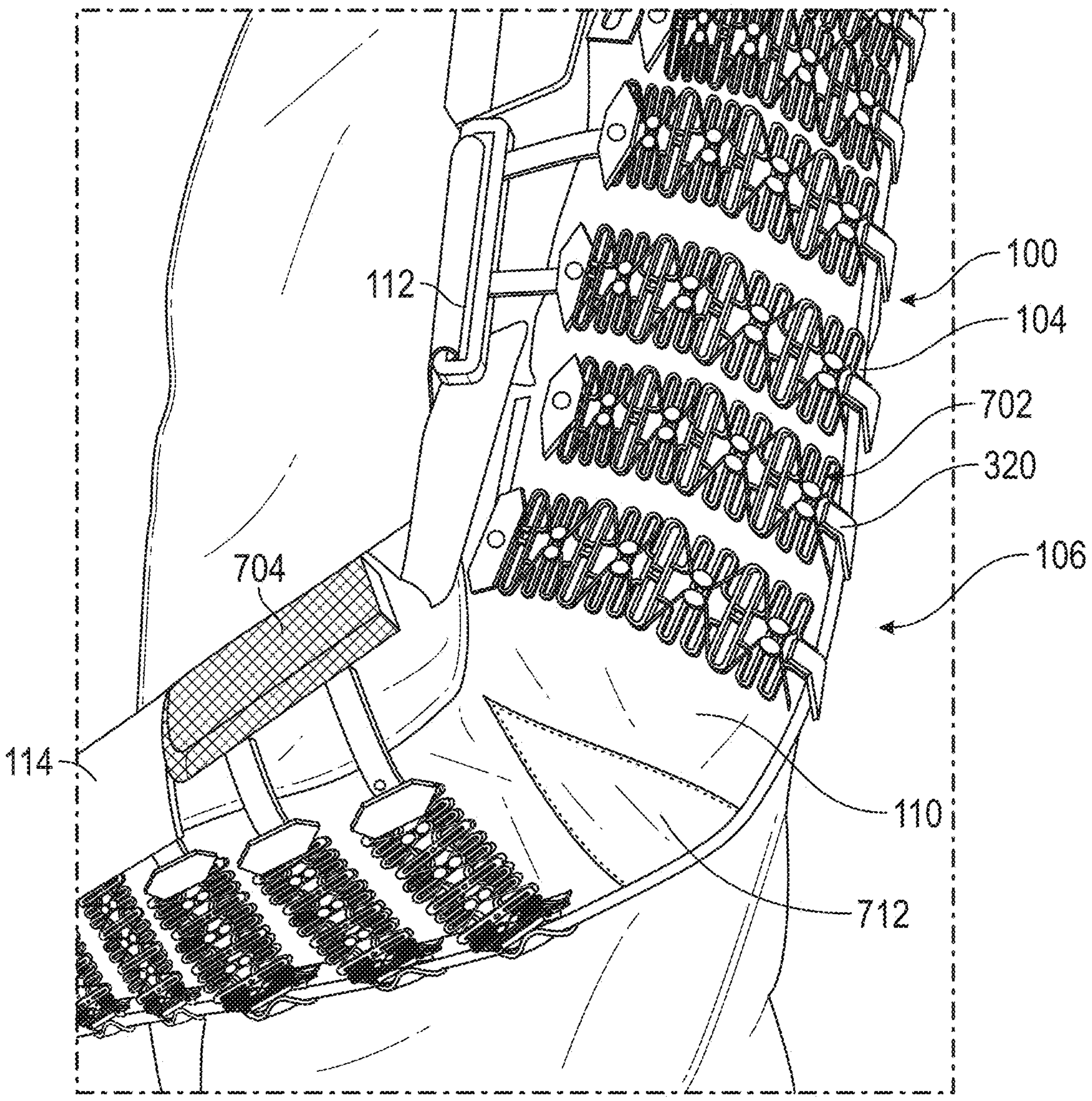
Figure 18D:
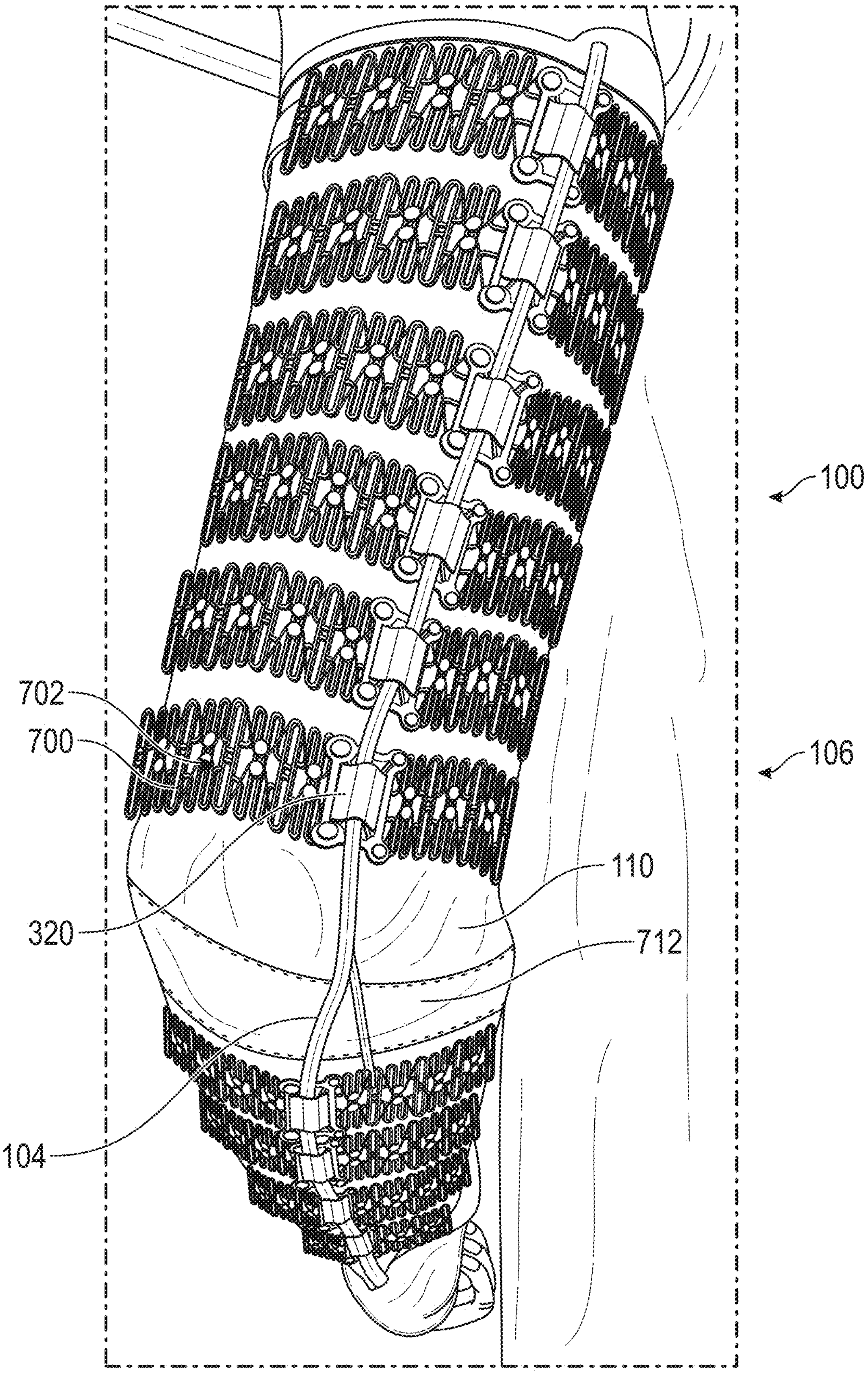

FIGS. 18A-18D illustrate the compression garment 100 disposed on the limb 106 (arm) of the user. The compression garment 100 is securely strapped to the user with the straps 704. The liner 110 is disposed between the user and the flex frame assemblies 702 to help protect the user from heat generated by the electrical components, flex frames 700, and/or shape memory materials. The user is also wearing a limb covering 714 to further protect the skin of the user. The compression garment 100 includes a back flex region 712 positioned over the elbow to improve movement such that the user can bend the elbow such as seen in FIG. 18A and/or straighten the elbow as shown in FIG. 18B. The compression garment 100 can include a plurality of flex frame assemblies 702 with individual micro-electronic controllers 320 that are operatively connected to a wired connection 104 which can be connected to a controller or power supply. The wired connection 104 can include enough slack such that the wired connection 104 bends away from the elbow upon straightening, as shown in FIG. 18B, and pulls into the elbow or proximate the elbow upon bending, as shown in FIG. 18A.

Figure 19:
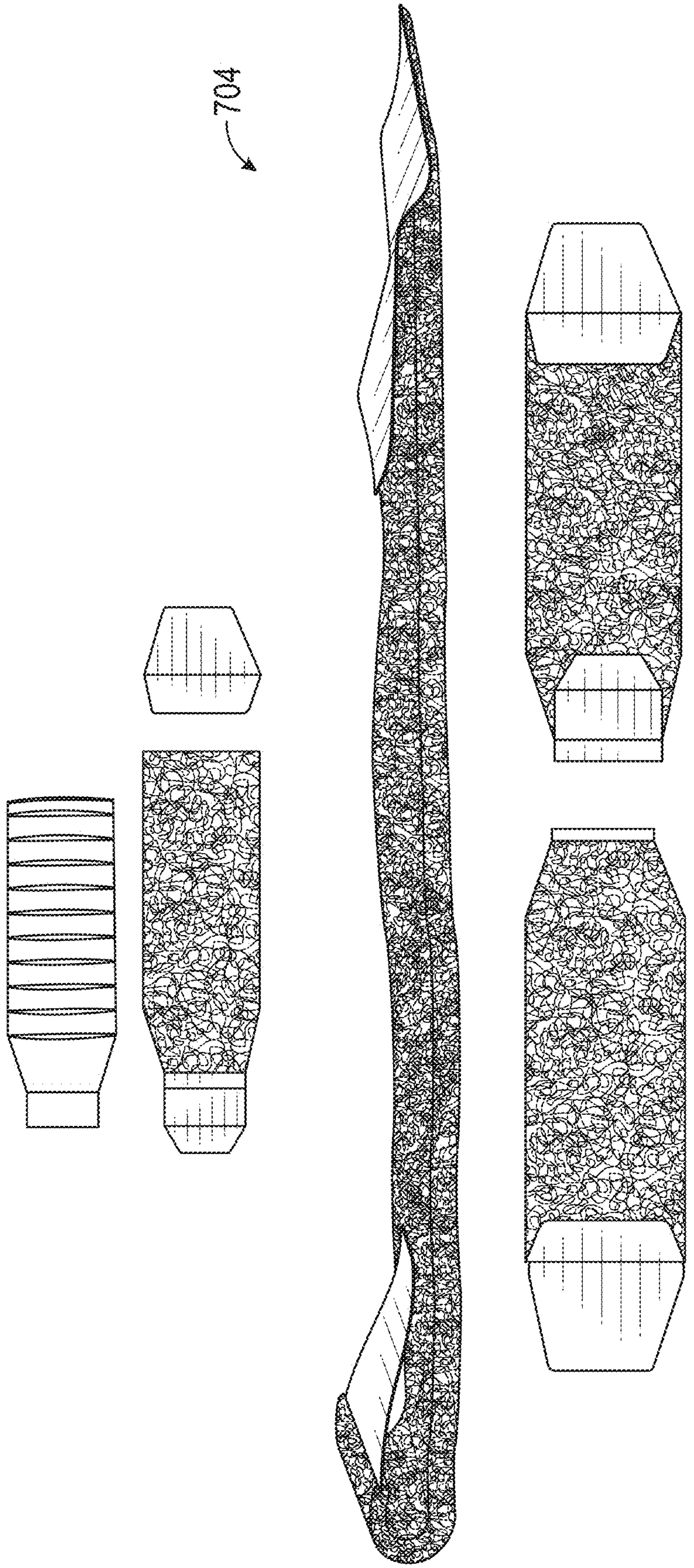
FIG. 19 shows cuttable straps.

As illustrated in FIG. 19, the straps 704 can be cut to fit various sizes/shapes. This can be beneficial in accommodating various sizing of desired anatomy of users to be treated.

Figure 20A:
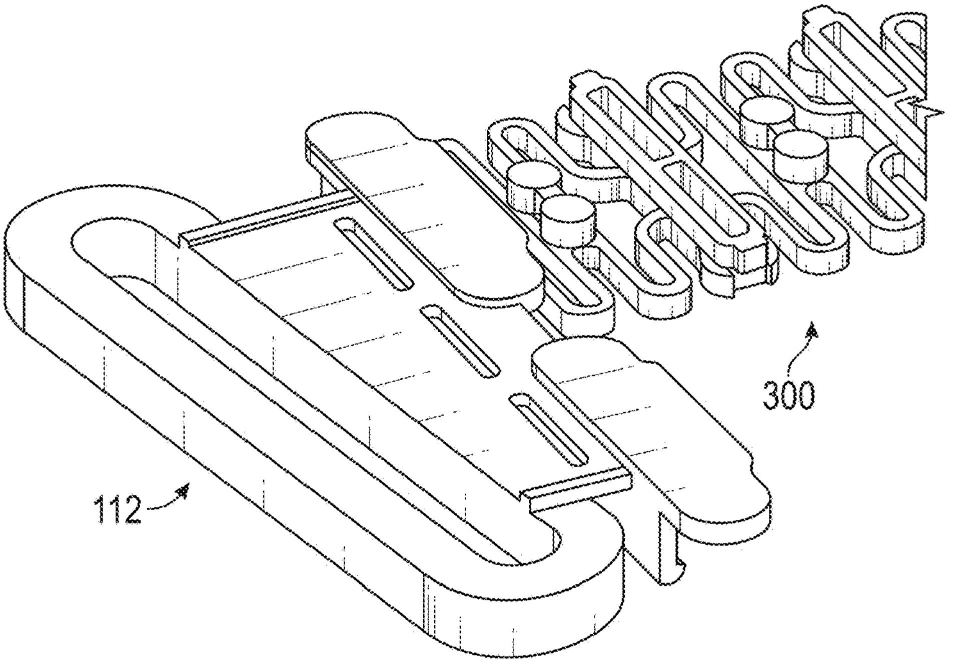
FIGS. 20A, 20B, and 20C illustrate strap interfaces.
Figure 20B:
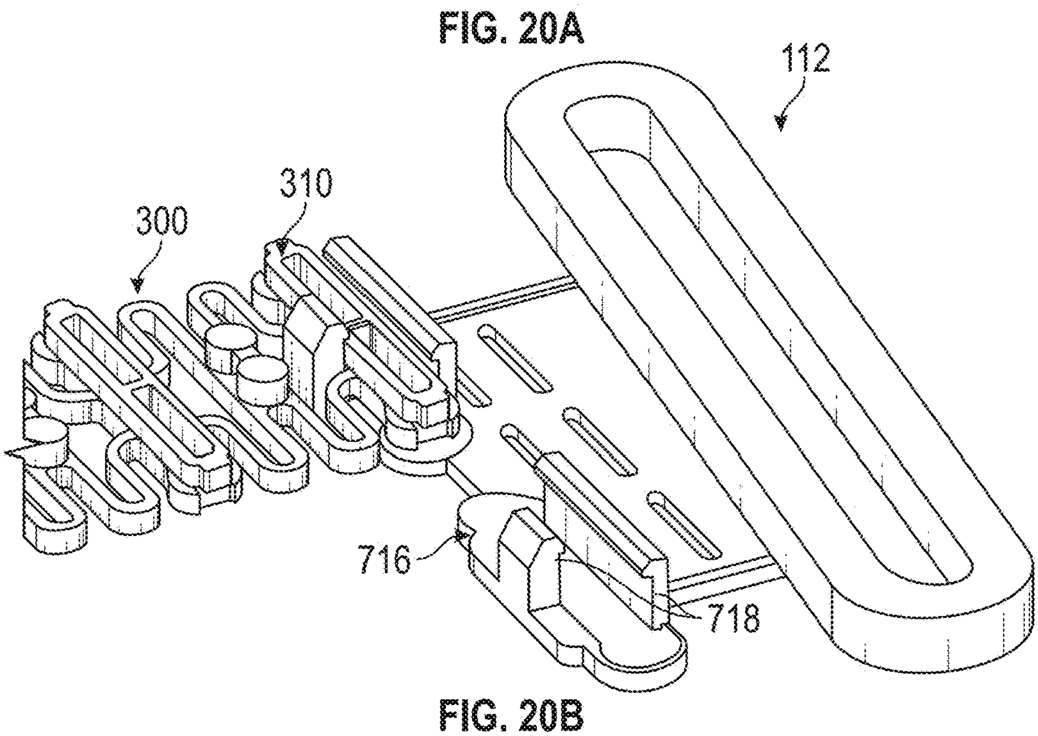
Figure 20C:
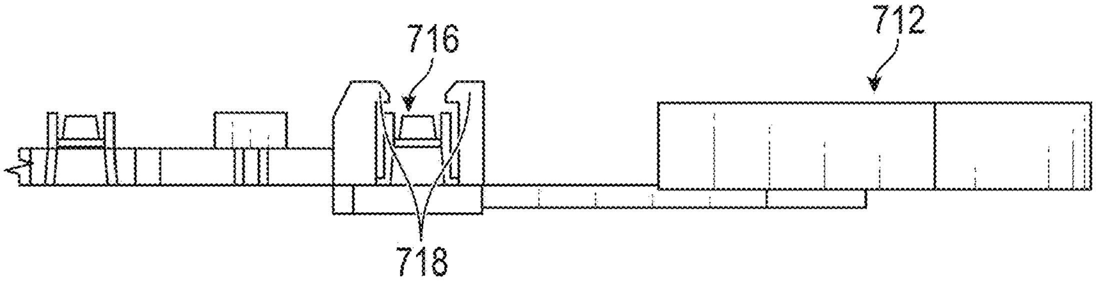

FIGS. 20A-20C illustrate the first strap interface 112 coupled to the flex frame 300 but other flex frames described herein can be coupled to the first strap interface 112 as described herein. In some variants, the first strap interface 112 can be described as a D ring. In some variants, the flex frame 300 can snap fit with the first strap interface 112 to couple thereto. Specifically, the first strap interface 112 can have a slot 716 into which a support 310 (e.g., last support 310, end support 310) of the flex frame 300 can be positioned. The first strap interface 112 can have hooks 718 disposed proximate the slot 716 that can retain a support 310 once positioned therein. In some variants, the hooks 718 can deflect to enable the support 310 to be positioned in the slot 716. As explained elsewhere herein, the first strap interface 112 can include loops, hoops, and/or rings with which straps can be coupled, threaded through, and/or otherwise interface. The centerline of the first strap interface 112 can align with the centerline of the flex frame 300.

As described elsewhere herein, the compression garment 100 can include zero, one, two, or more controllers. The controller can include microelectronics, a battery or other power source, a processor, a memory which can be read from and/or written to, instructions which can be stored on the memory, a power supply that can be charged, a communication interface (e.g., facilitate wired or wireless communication, such as via Wi-Fi, Bluetooth (Bluetooth module, etc.), RFID, cellular modem, NFC, etc.), display(s), button(s), switch(es), light(s), indicator(s), and/or other features that can help in the administration of the compression garment 100. The controller can receive user input to change pressures, sequences, and/or programmed treatments of the compression garment 100. The controller may include an accelerometer, GPS, gyroscope, and/or other sensors to aid in providing user activity-based feedback and control. The controller can include sensors to detect the state of the shape memory material when it expands and contracts to feedback real-time status and strain in compressing an anatomical feature. The controller can include sensors to track biometric information of the user, such as heart rate, blood pressure, temperature, and/or other information and adjust pressures, sequences, heat, treatments, etc. accordingly. In some variants, biometric sensors can, using pulsed oximetry and/or temperature detection, be used to evaluate potential for ulceration and cellulitis, which in turn can be fed back to the compression sequence and pressure settings to prophylactically treat and/or prevent worsening of the disease and/or other diseases.

The controller and/or micro-electronic controller can include mechanical, electrical, and/or winding motors to apply a desired force to a flex frame described herein. The controller can communicate with and/or be controlled by a portable device of the user such as the user's mobile phone, smart phone, etc. via a wired or wireless connection. The user can control the controller via an application on the user's phone. The controller can have LCD and/or LED displays to indicate the state of the controller, help guide the user through the use of the compression garment 100, and/or set desired pressures, sequences, etc. In some variants, the controller can be fit into a pocket of the user, clip onto the pant of the user, and/or be worn on a lanyard. The controller can have battery indicators and time of treatment indicators. The controller can have detachable features for a battery and/or chargers.

In some variants, the controller can capture data to monitor user activity, information, and/or adherence to a treatment program that can be relayed to a server or database accessible by a clinician. In some variants, the controller and/or application on the user's phone may automatically remind users to use the device, change therapy, compression, and/or stimulation depending on progression of a disease or recovery.

Figure 21B:
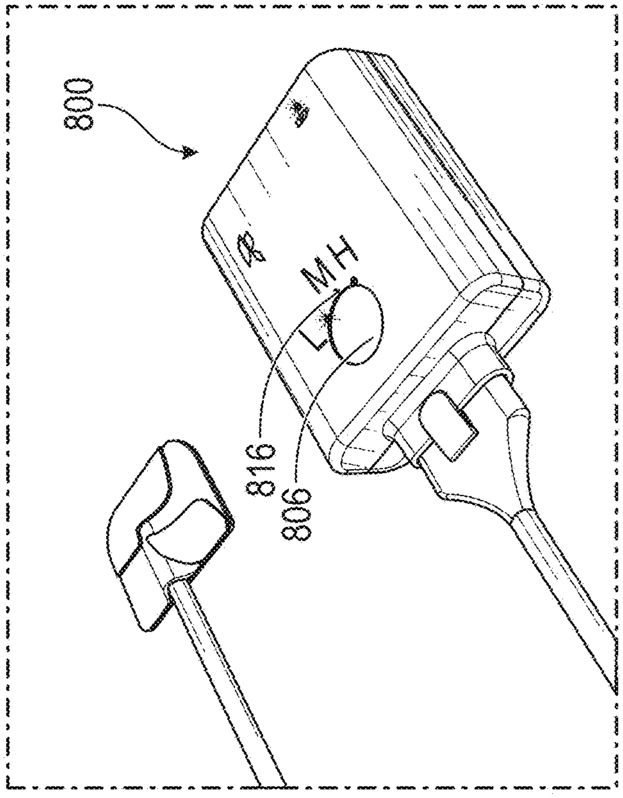
FIGS. 21A-25 illustrate a controller.
Figure 21A:
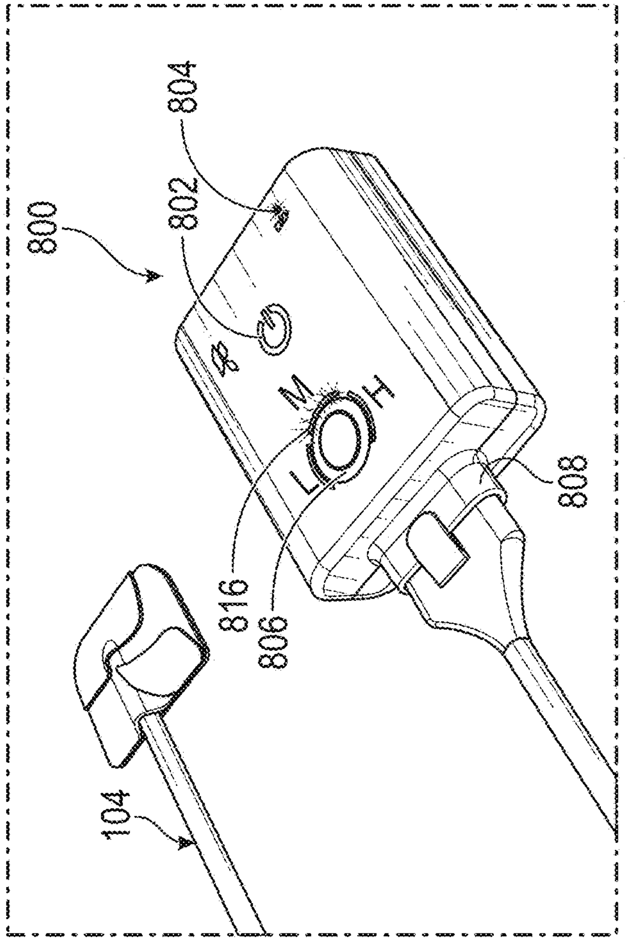
Figure 21C:
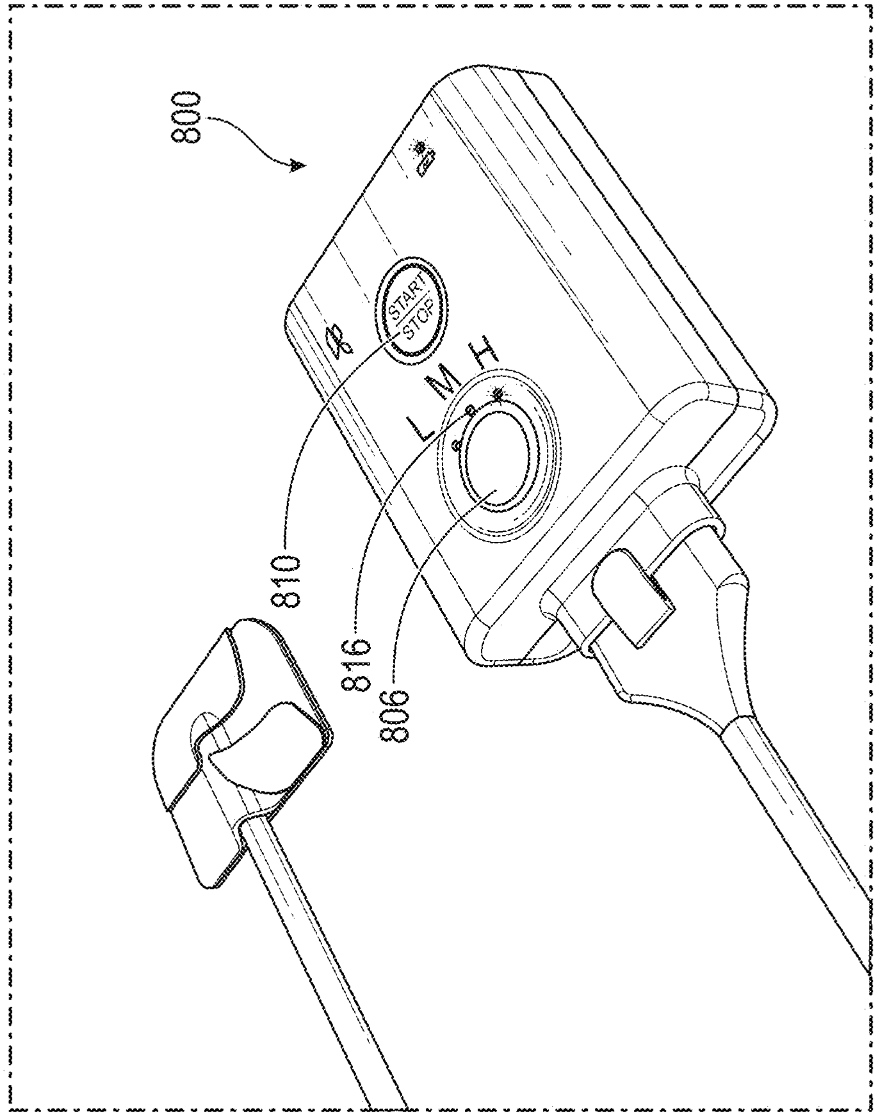

FIGS. 21A-25 illustrate a controller 800. As illustrated in FIGS. 21A and 21B, the controller 800 can have a power button 802, battery indicator 804, port 808 for connecting to the wired connection 104 which can be connected to the compression garment 100, selector 806 for selecting different pressures, sequences, and/or other features, and/or indicators 816. The indicators 816 can, in some variants, indicate whether the user has selected that the controller 800 apply a lower, medium, or high pressure to the limb 106 of the user. The indicator 816 can light up to indicate the user's selection. In some variants, the controller 800 can be charged, which can be via the port 808. As illustrated in FIG. 21C, the controller 800 can have a start/stop button 810 to start or stop applying pressure to the limb 106.

Figure 22A:
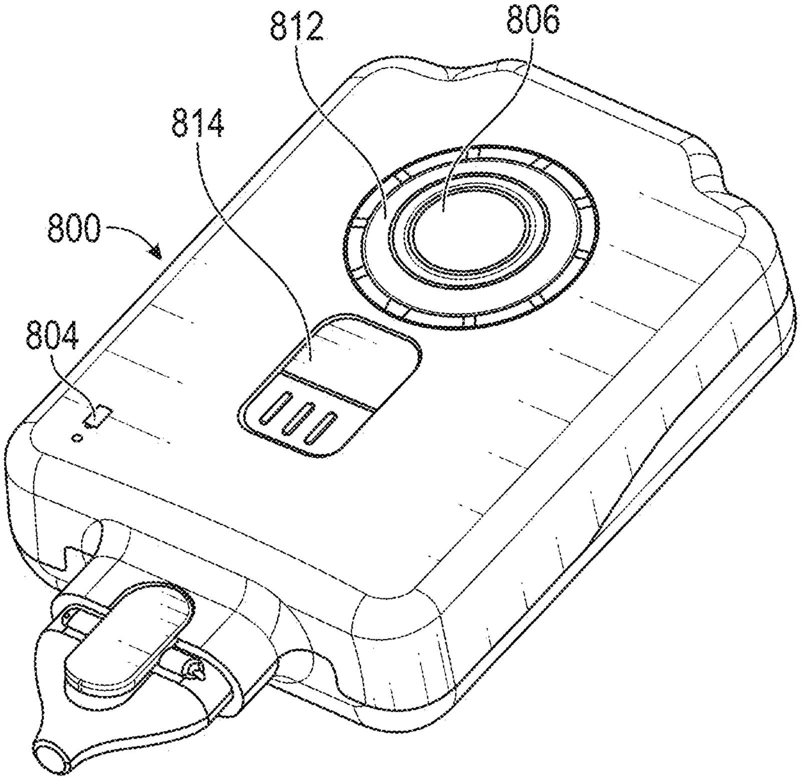
Figure 22B:
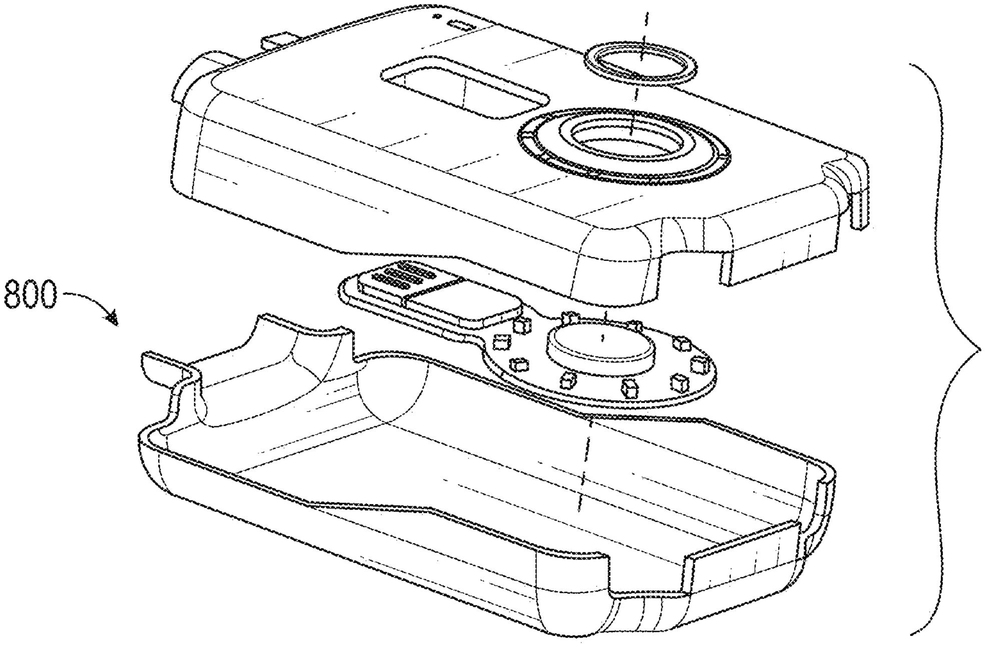
Figure 22C:
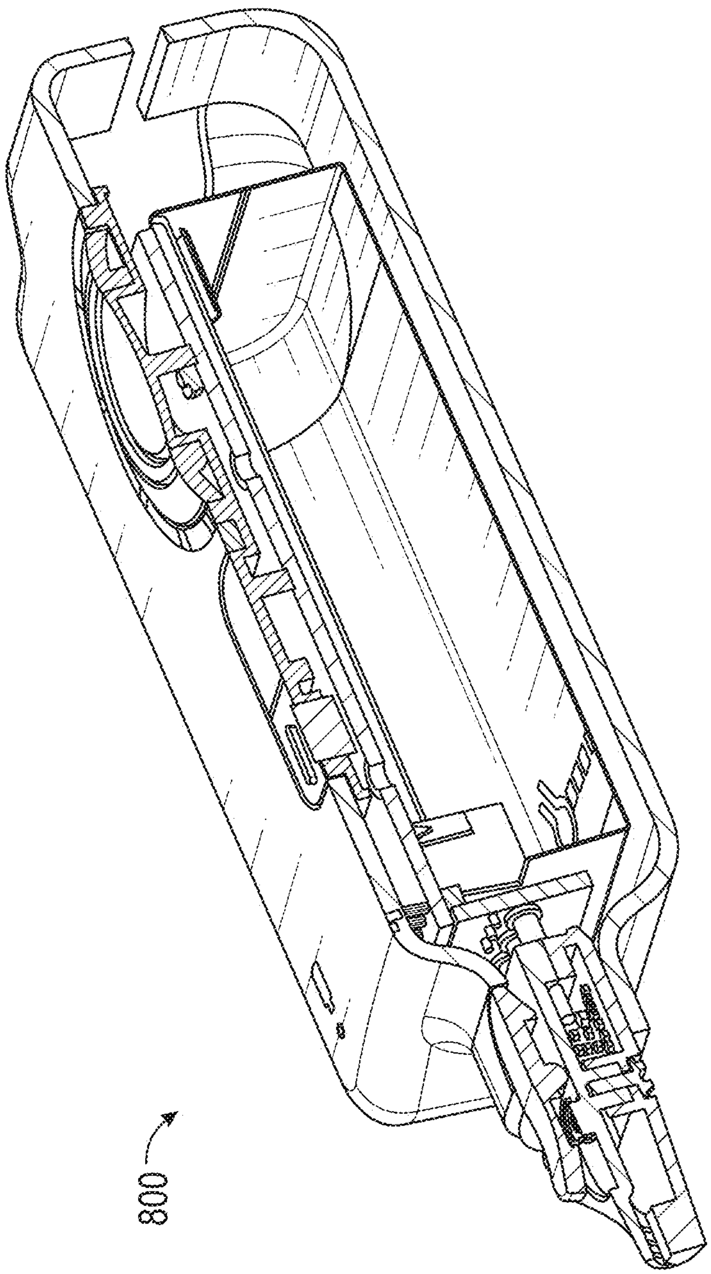

As shown in FIGS. 22A-22C, the controller 800 can include a selector 806 through which the user can indicate more or less pressure and/or make other selections. The controller 800 can include the wheeled indicator and/or selector 812. In some variants, the wheeled indicator and/or selector 812 displays to the user the user's current selection, such as intensity by lighting up more or less lights, and/or allows the user to rotate through various selections. The controller 800 can include a selector and/or indicator 814 which can be used to make and/or view selections. FIG. 22B illustrates an exploded view of the controller 800. FIG. 22C illustrates a section view of the controller 800.

Figure 23A:
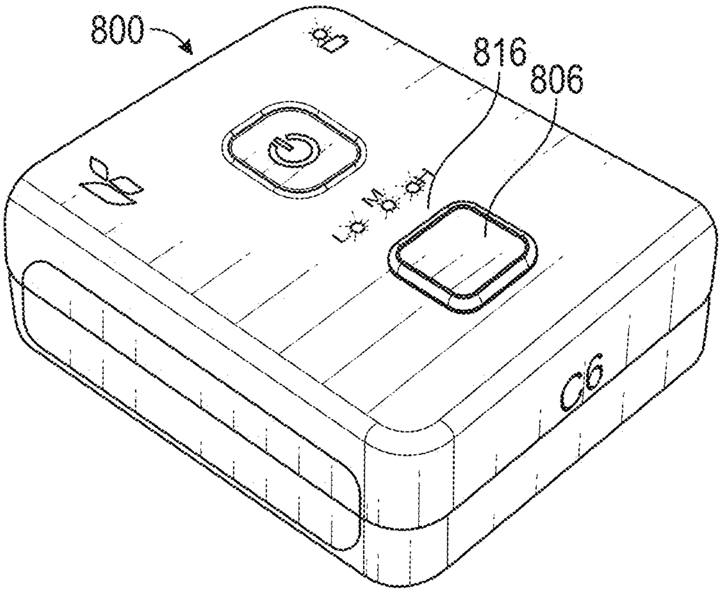
Figure 23B:
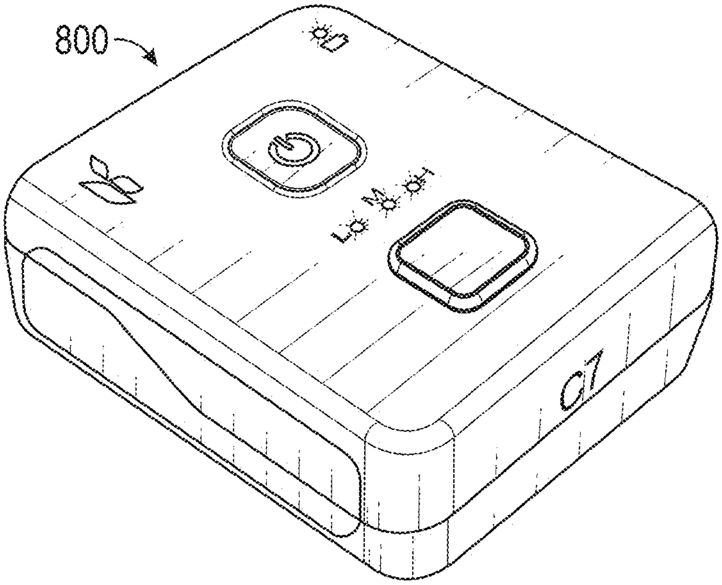
Figure 23C:
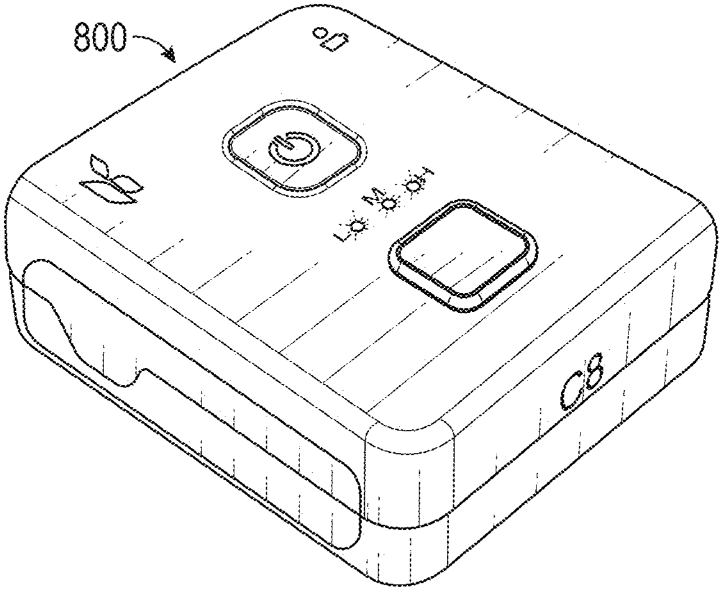
Figure 23D:
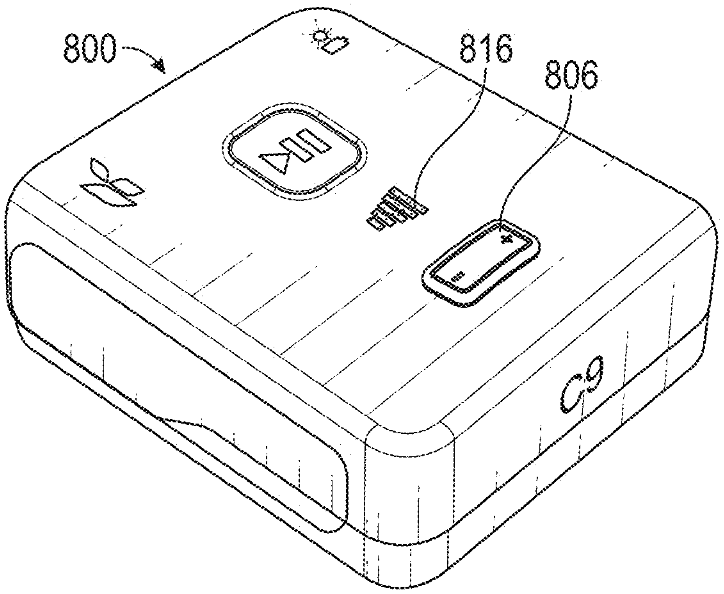
Figure 23E:
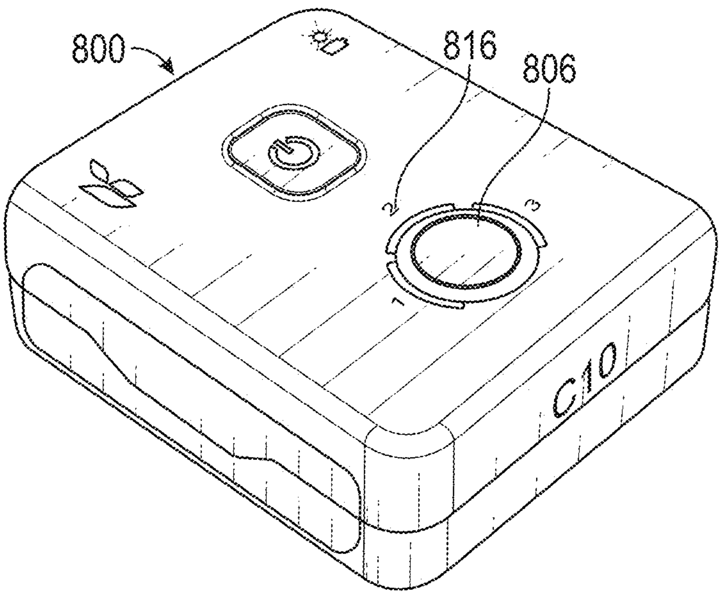
Figure 23F:
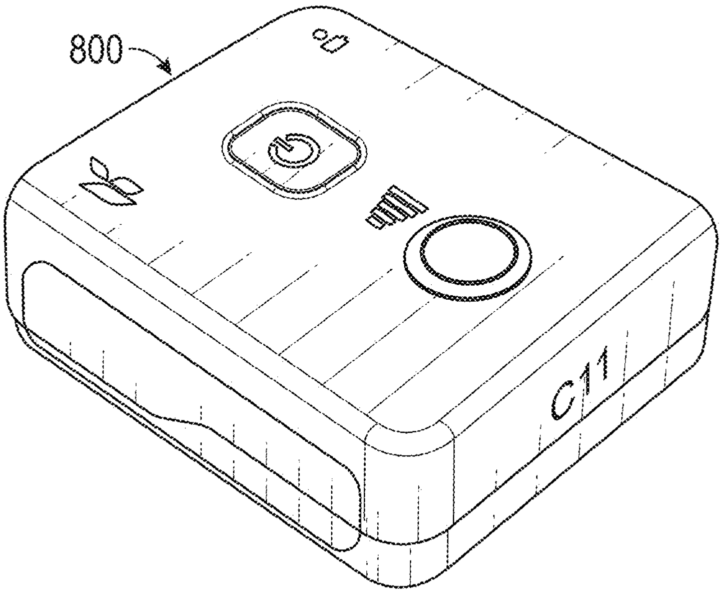

FIGS. 23A, 23B, and 23C illustrate a controller 800 with indicators 816, indicating low, medium, and high settings, and a selector 806. As shown in FIG. 23D, the controller 800 can include a selector 806 that has a plus and minus to allow the user to select more or less pressure. The controller 800 can include an indicator 816 that includes bars to show the user's selected intensity—e.g., more bars signifies more intensity. FIG. 23E illustrates that the controller 800 can include an indicator 816 with numerals to indicate the user's selection, such as 1, 2, and 3, to convey the user's selected intensity. FIG. 23F illustrates another controller similar to the controller shown in FIG. 23D.

Figure 24A:
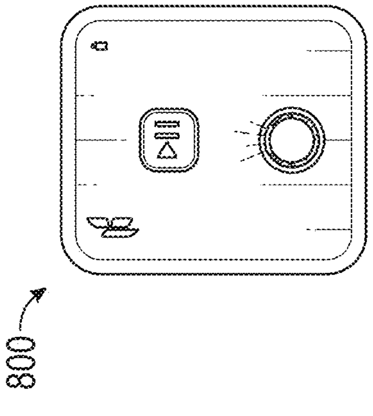
Figure 24B:
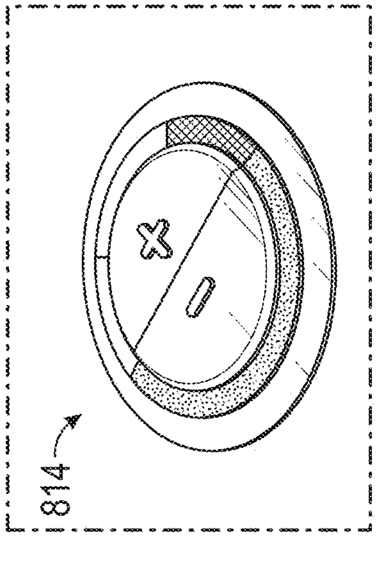
Figure 24C:
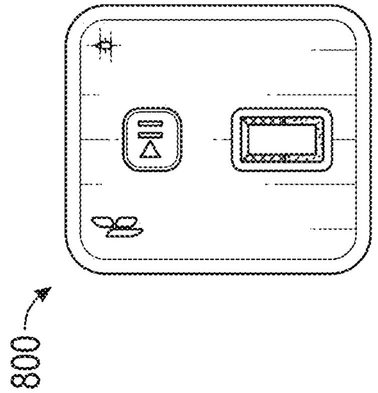
Figure 24D:
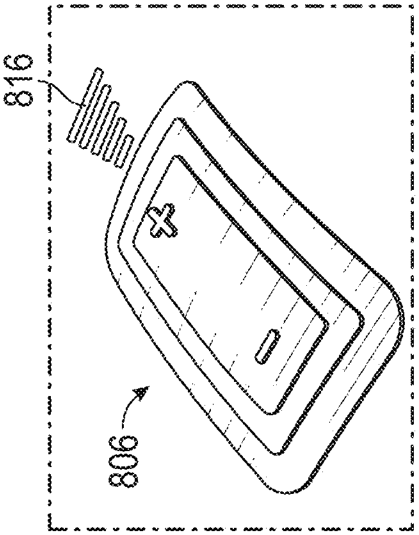
Figure 24E:
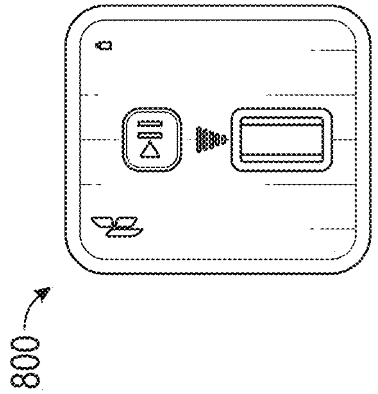
Figure 24F:
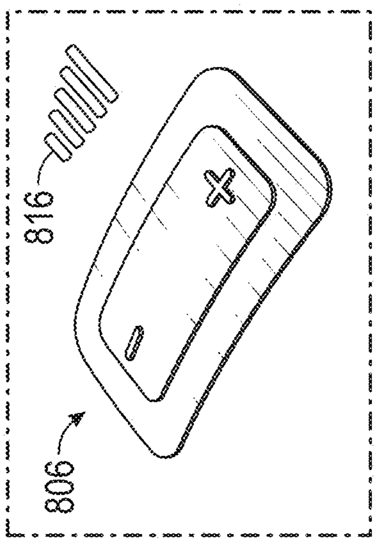
Figure 25:
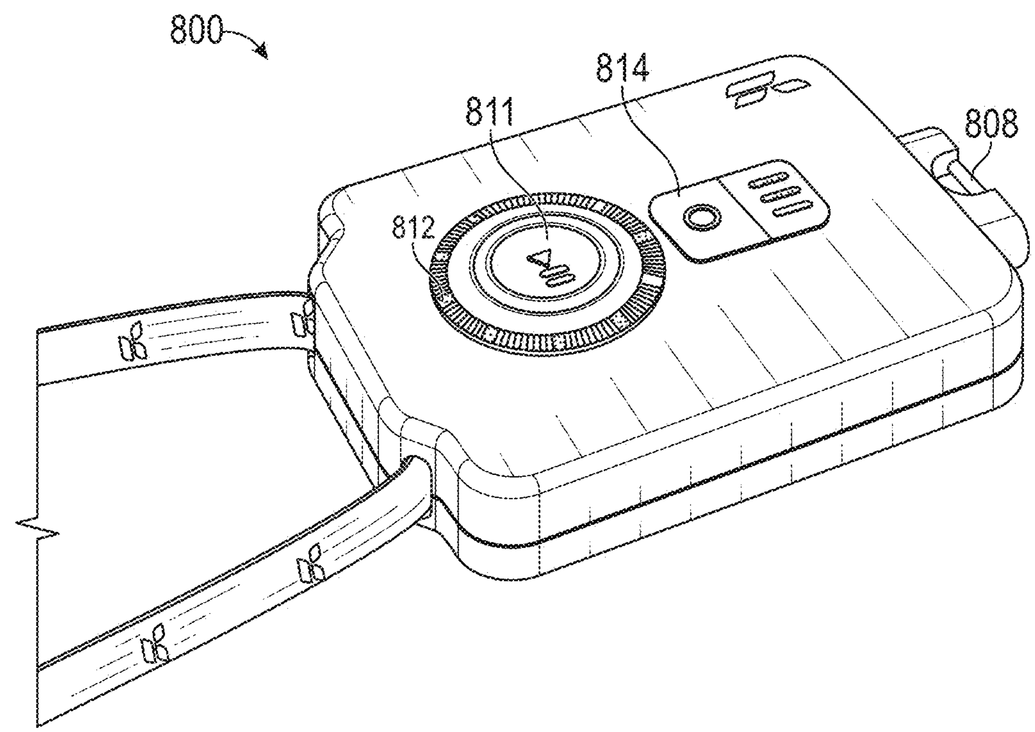

FIGS. 24A and 24B illustrate that the controller 800 can have a selector and/or indicator 814 with plus or minus buttons that can be used to make selections and that light up around the periphery to show the user's selections. FIGS. 24C, 24D, 24E, and 24F illustrate that the controller 800 can include longitudinally or transverse oriented selectors 806 with a plus or minus input capability that can be indicated via bars of the indicator 816 that light up. FIG. 25 illustrates another controller, similar to that shown in FIGS. 22A-22C, with a port 808 for connecting to the wired connection 104, selector and/or indicator 814, wheeled indicator and/or selector 812, and/or pause/run interface (e.g., button) 811. Any features of the controller 800 illustrated in FIGS. 21A-25 can be combined together as part of this disclosure.

Figure 26:
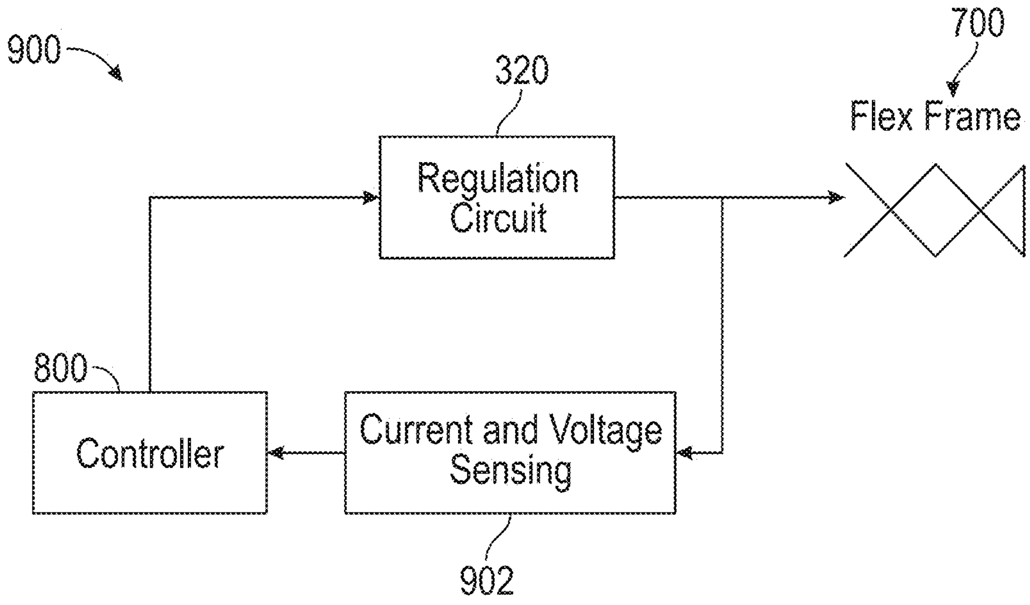
FIG. 26 illustrates a block diagram.

As described elsewhere herein, the compression garment 100 can utilize shape memory material, such as shape memory alloy (SMA) to apply compression to the limb 106 of a patient. Electricity is conveyed to the SMA wire 118 to generate heat, which causes the wire to contract to shorten the flex frame 700 and apply compressive forces. When the wire contracts, the resistance of the wire 118 decreases. Regulated current or voltage can be applied to the SMA wire 118 to produce a contract. FIG. 26 displays a block diagram 900 that can incorporate these features. The controller 800 can provide an electrical input via the micro-electronic controller 320 (regulation circuit) to the wire 118 of the flex frame 700 and current and/or voltage sensor(s) 902 can monitor the current or voltage signal across the SMA wire 118. If the voltage is regulated, a current signal through the SMA wire 118 can be monitored to determine to what degree the SMA wire 118 has contracted. For a regulated current signal, the voltage across the SMA can be monitored to determine the degree of contraction. In some variants, the current and/or voltage sensor 902 can evaluate impedance or resistance from the SMA wire 118 which can be indicative of pressure applied to the limb 106 or anatomical feature. Current feedback can be used to detect the phase change of compression of the flex frame 700 or SMA wire 118 to modulate output pressure applied. Resistance feedback can be used to detect the phase change in the flex frame 700 or SMA wire 118 to detect output pressure.

Figure 27:
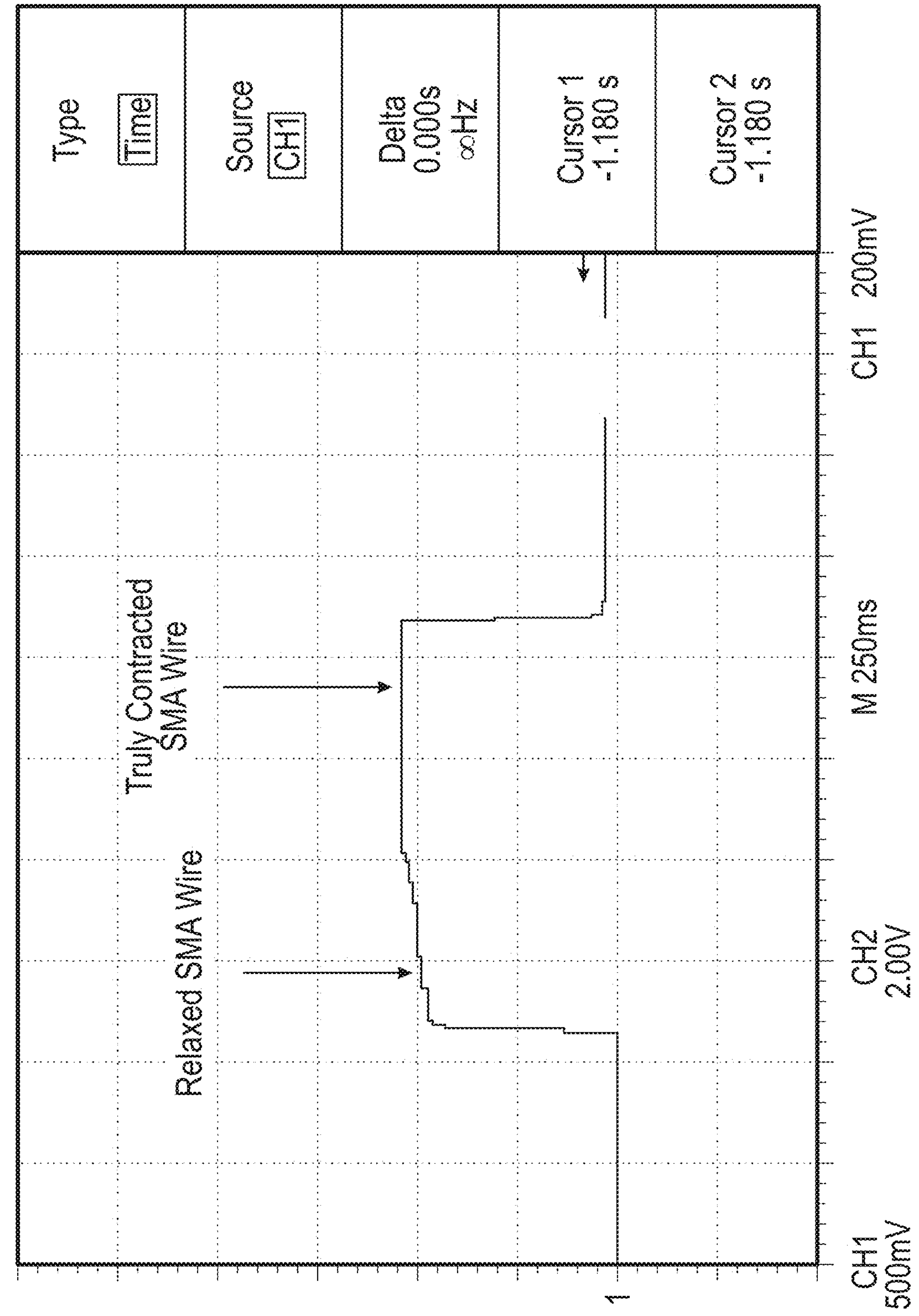
FIG. 27 illustrates a graph of current signal current signal through the wire during temperature increase and full contraction.
Figure 28:
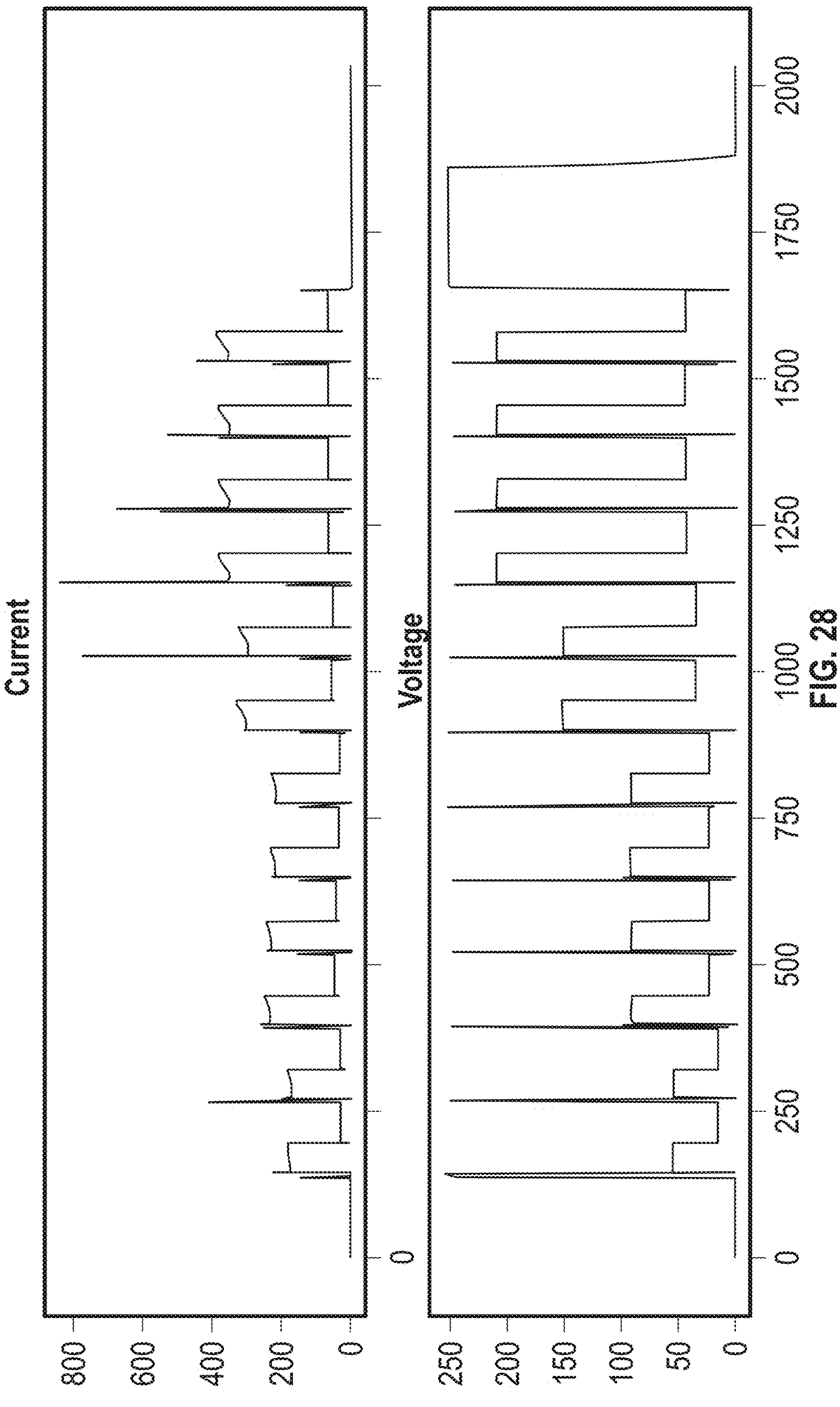
FIG. 28 illustrates a graph of current signal current signal through the wire during temperature increase and full contraction.

FIGS. 27 and 28 show examples of the current signal through the wire as the SMA's temperature increases and fully contracts. The compression force applied to the patient's arm can be proportional to the degree of SMA contraction. Actively monitoring this contraction allows this applied force to be controlled.

The voltage across or the current going through the wire can be precisely controlled to prevent overheating which can lead to underperformance of the SMA wire 118. The output circuit can include voltage regulated output with both voltage and current monitoring so that compression garment 100 can operate safely and effectively.

Figure 29A:
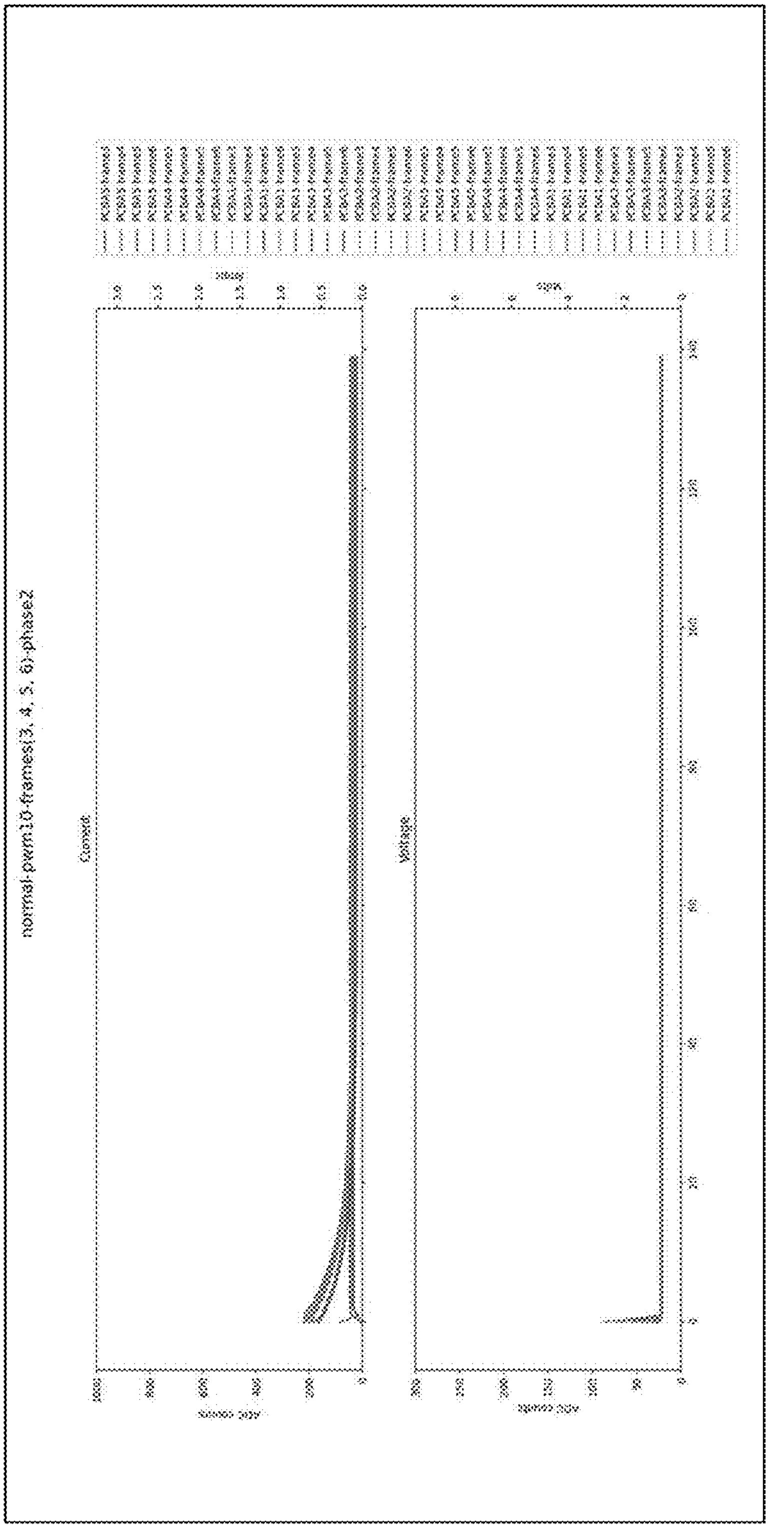
FIG. 29A illustrates detected voltage and current differences at a low power setting.
Figure 29B:
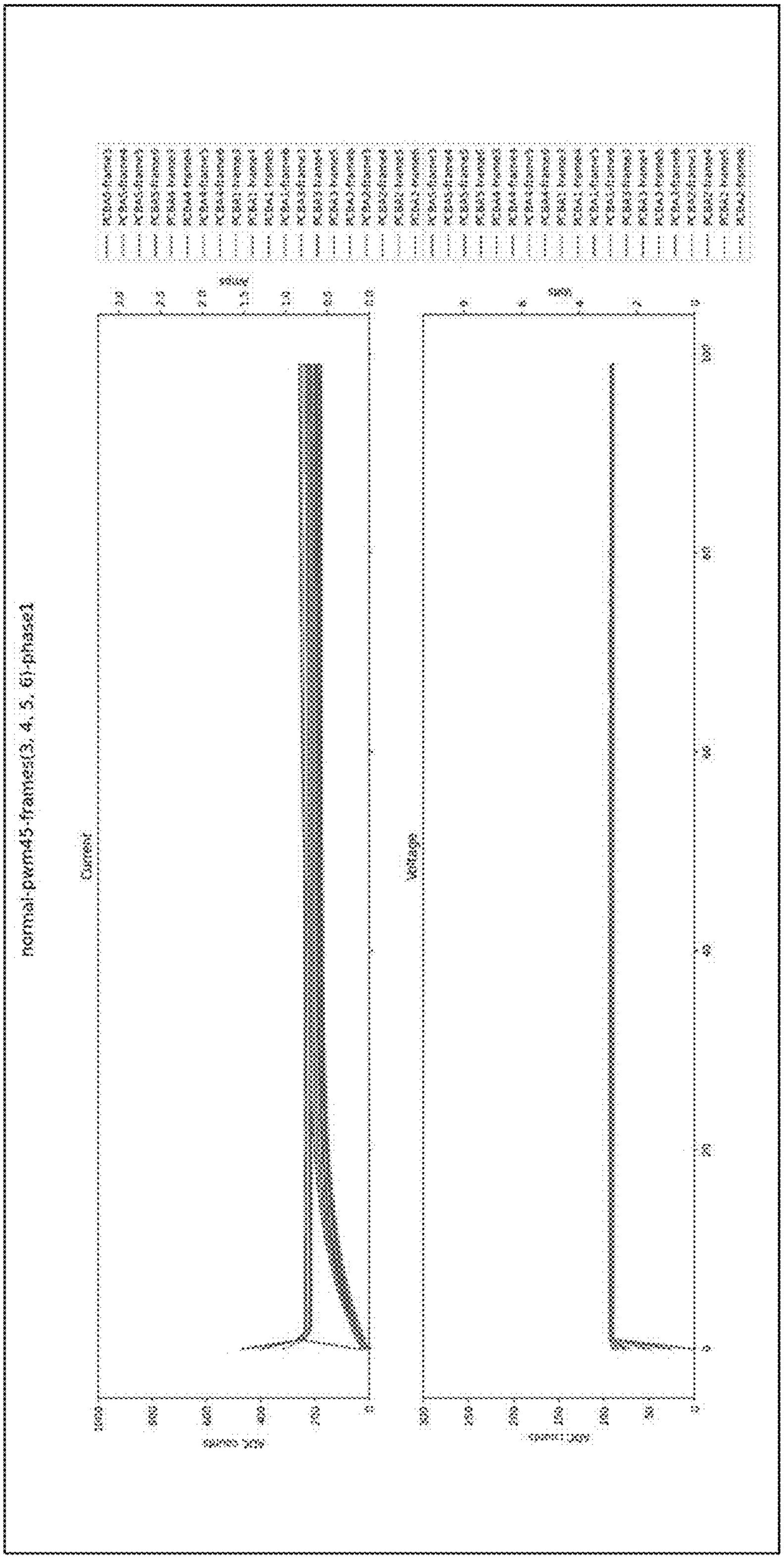
FIG. 29B illustrates detected voltage and current differences at a high power setting.
Figure 30A:
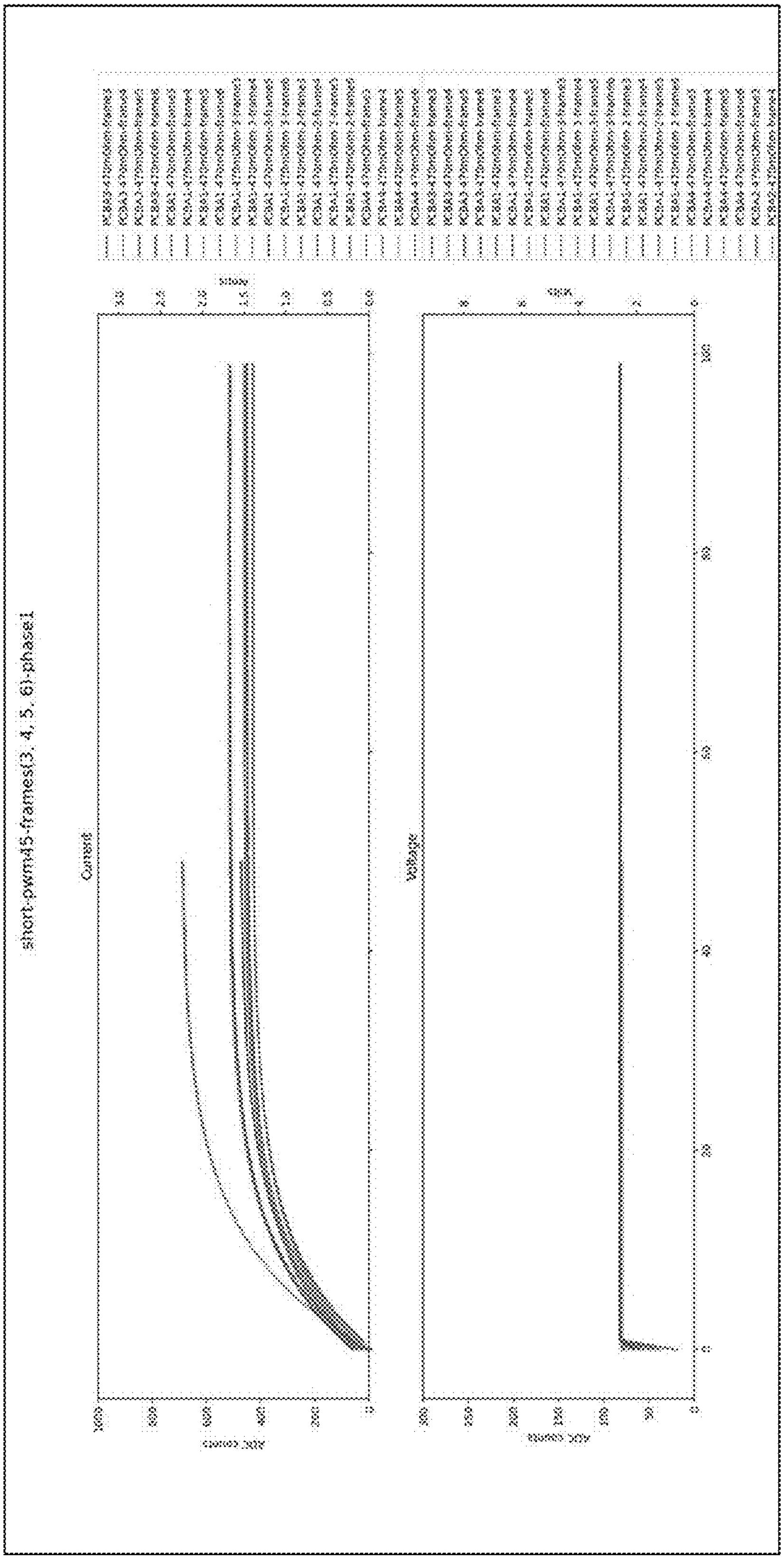
FIG. 30A illustrates a short-circuit condition.
Figure 30B:
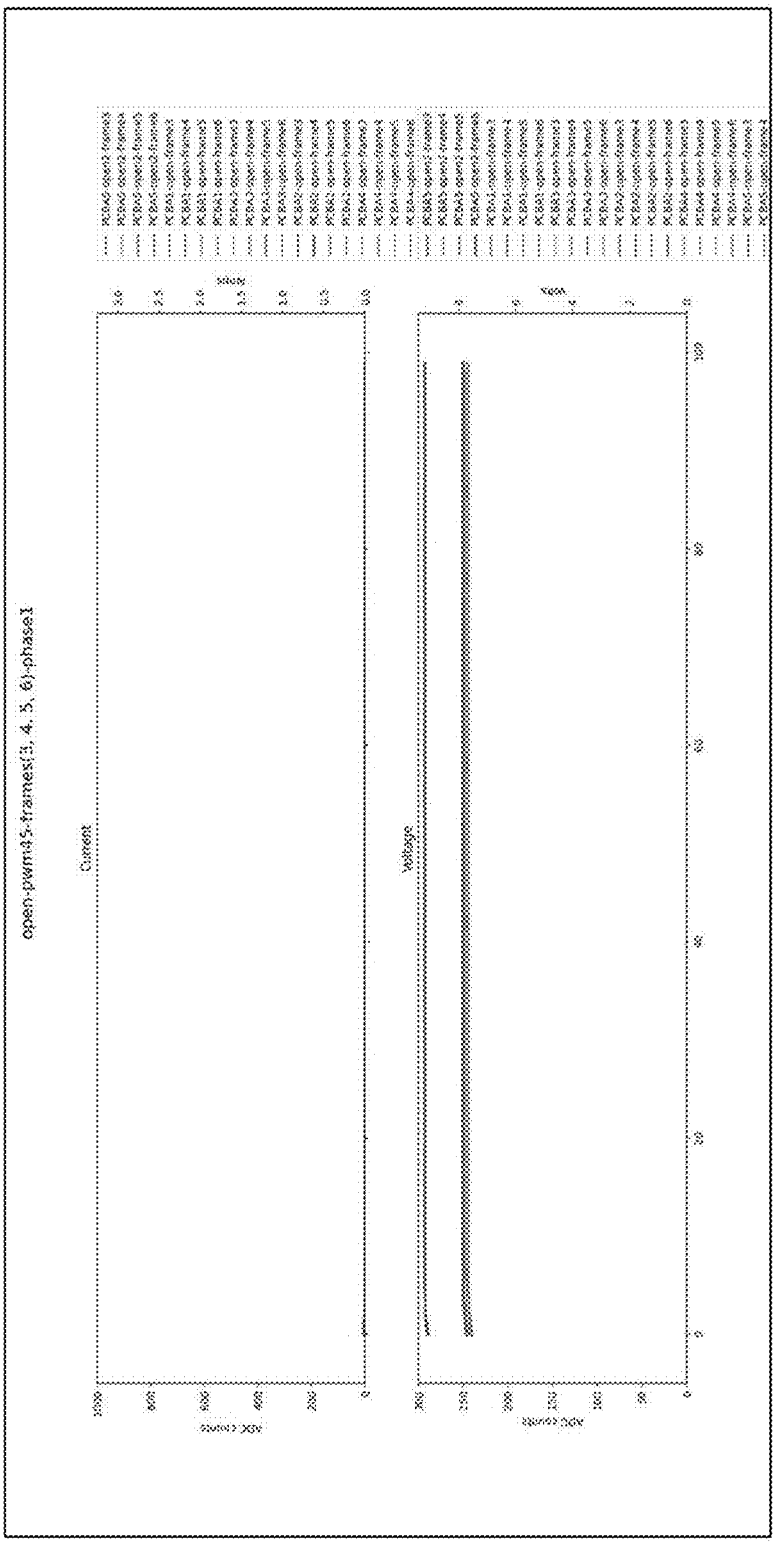
FIG. 30B illustrates an open-circuit condition.

This sensing, in practice, has shown to be a reliable indicator that the output is working properly. Checking that the voltage is within a predetermined range can ensure that the SMA wire 118 is connected correctly and that the electrical output is driving as expected. Current sensing can allow for the detection of open or short circuits, which may happen if there is physical damage to the SMA wire 118. FIGS. 29A and 29B show the detected voltage and current differences between low and high power settings, respectively. FIGS. 30A and 30B illustrate the differences during a short-circuit condition and during an open-circuit condition, respectively. In some variants, the sensing can be prior to activation or during activation or post activation of the shape memory members.

Figure 31:
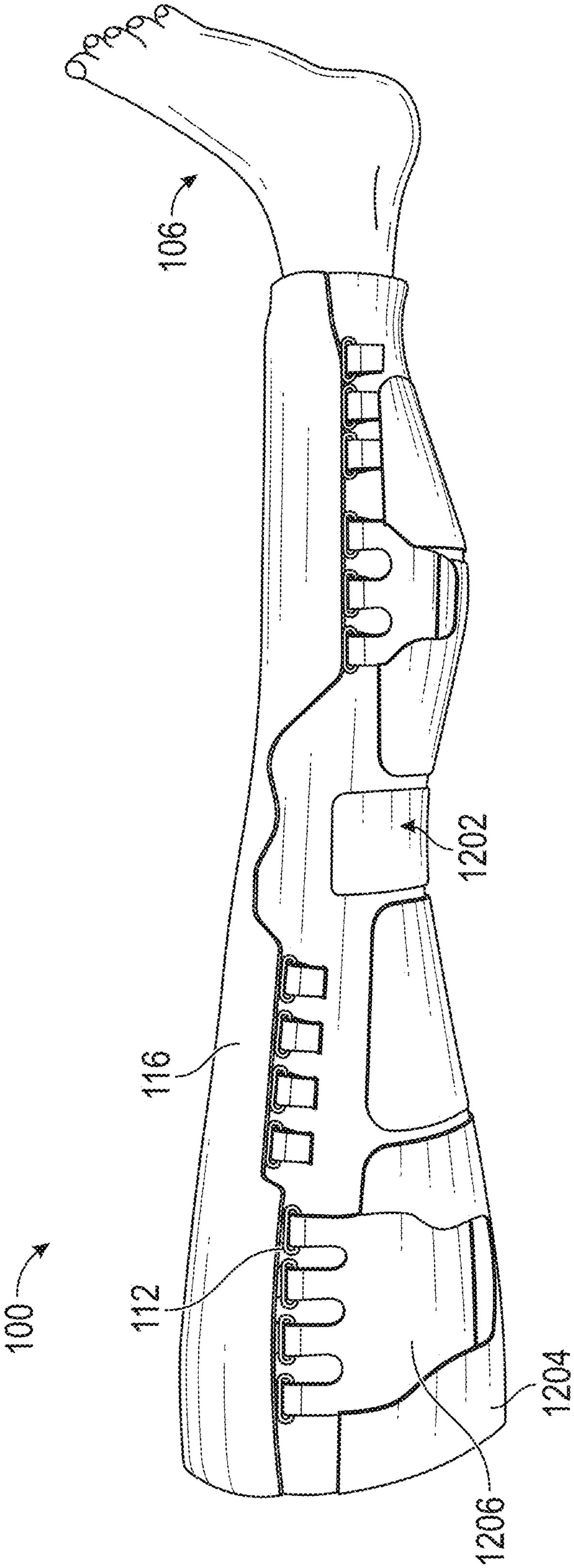
FIG. 31 illustrates a compression garment on a limb.

FIG. 31 illustrates a compression garment 100. The compression garment 100, as described herein, can be disposed on a limb 106 or other anatomical feature of a human or animal body. As illustrated, the limb 106 is a human leg. The compression garment 100 can apply compression to the limb 106, which can include applying a compressive force along the entirety of the limb 106 and/or a portion of the limb 106. The compression garment 100 can, in some variants, sequentially apply a compressive force to the limb 106 along a length thereof to urge fluid within the limb 106 to flow in a direction (e.g., toward a trunk of the user). In some variants, the compression garment 100 can apply consistent pressure. In some variants, the compression garment 100 can apply pulses of pressure. In some variants, the compression garment 100 can apply preprogrammed treatments and/or selectively apply pressures to varying degrees and at varying locations. The compression garment 100 can include one or more sensors, as described herein. As described herein, the compression garment 100 can be used to help with recovery after physical activity, enhance circulation, promote comfort, and/or treat one or more diseases.

The compression garment 100 can include backing 116. The backing 116 can enclose or cover at least a portion of the internal components of the compression garment 100. In some variants, the backing 116 can vent heat to the ambient environment as a wire made of shape memory material is heated to contract and/or electronic components of the compression garment 100 are run.

The compression garment 100 can be secured to the limb 106 and/or other anatomical feature of the user via a variety of techniques. For example, the compression garment 100 can include one or more straps to couple the compression garment 100 to the user. The compression garment 100 can include primary straps 1204 and/or secondary strap 1206. The primary strap 1204 and/or secondary strap 1206 can be coupled to the backing 116, liner, internal flex frame, and/or compression garment 100. The primary strap 1204 and/or secondary strap 1206 can extend, respectively, through a strap interface 112, which can be described as a D ring, ring, and/or similar device, and be folded back to be secured via a hook and loop mechanism (e.g., VELCRO) and/or another technique described herein to fix the primary strap 1204 and/or secondary strap 1206 in place and secure the compression garment 100 on the user. The primary strap 1204 and/or secondary strap 1206 can be oriented in different directions to help prevent shifting of the compression garment 100 on the limb 106 of the user while being strapped on and/or used.

The compression garment 100 can include a joint strap or section 1202 disposed around the joint of the user (e.g., the knee, elbow, etc.). The joint strap 1202 can have increased flexibility to allow the limb 106 to be easily moved, bent, etc. In some variants, the backing 116 can be altered or omitted at the joint to improve movement, which can include narrowing the width of the backing 116 at the joint. The compression garment 100 can at least include all the features of the other compression garments described herein.

Figure 32B:
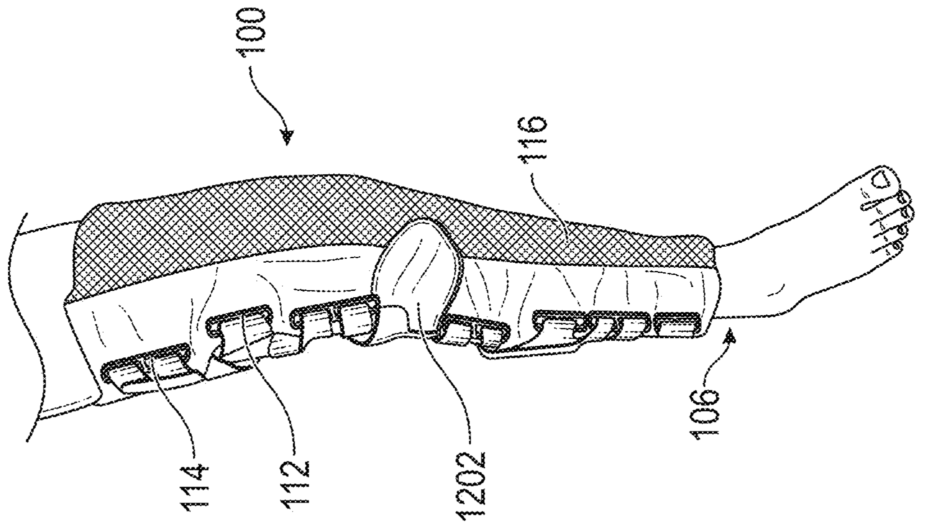
FIGS. 32A and 32B illustrate a compression garment on a limb.
Figure 32A:
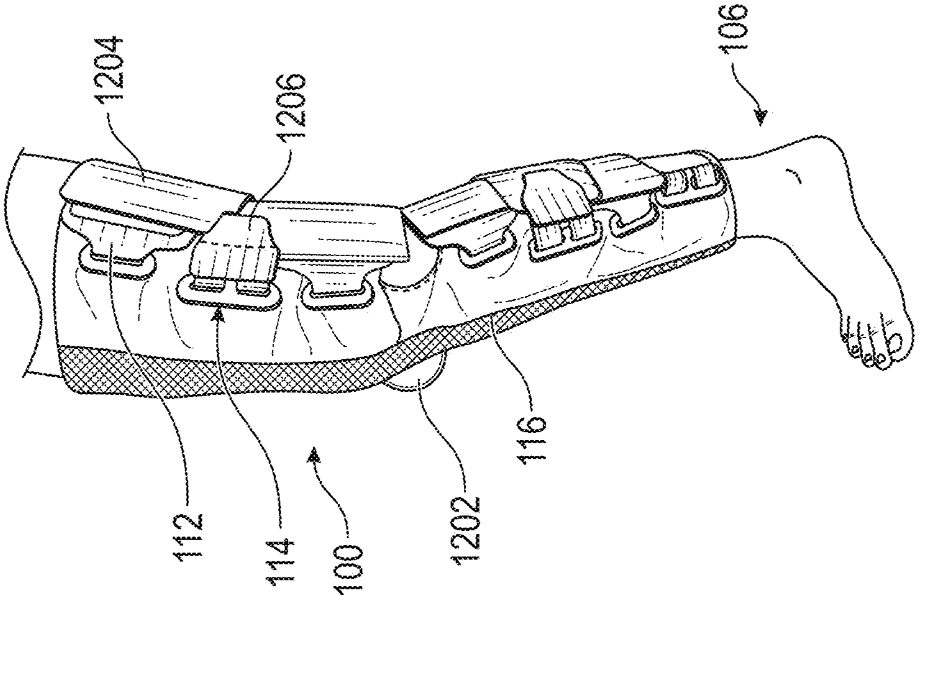

FIGS. 32A and 32B illustrate a compression garment 100 disposed on a limb 106 of the user. The compression garment 100 can include primary straps 1204 and/or secondary straps 1206 in an alternating pattern extending along the length or at least a part of the length of the limb 106. The primary straps 1204 and/or secondary strap 1206 can be coupled to the backing 116, flex frames, liner, and/or compression garment 100, as described herein. The primary strap 1204 and/or secondary strap 1206 can be oriented in alternating circumferential directions such that, as the primary strap 1204 and/or secondary strap 1206 are tightened, the compression garment 100 does not overly shift on the limb 106 of the user. The primary strap 1204 and/or secondary strap 1206 can be, respectively, threaded through the first strap interface 112 and/or second strap interface 114 and folded back on themselves to be secured via a hook and loop mechanism (e.g., VELCRO), buckle, fastener, clip, and/or other device to secure the compression garment 100 to the limb 106 of the user. As described herein, the backing 116 can include a material (e.g., mesh) that can vent heat.

Figure 33A:
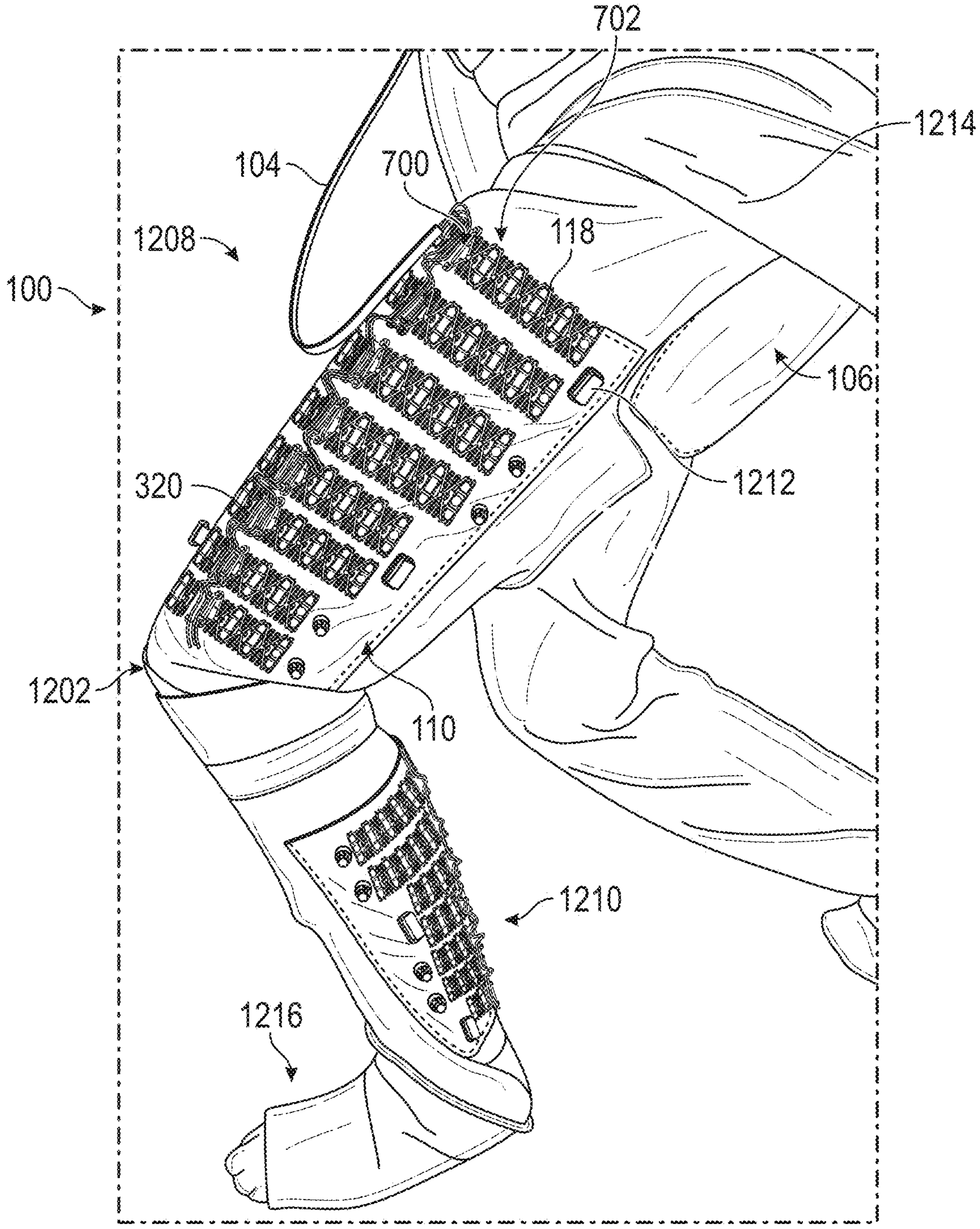
FIGS. 33A and 33B illustrate a compression garment on a limb with a backing removed to show flex frame assemblies.
Figure 33B:
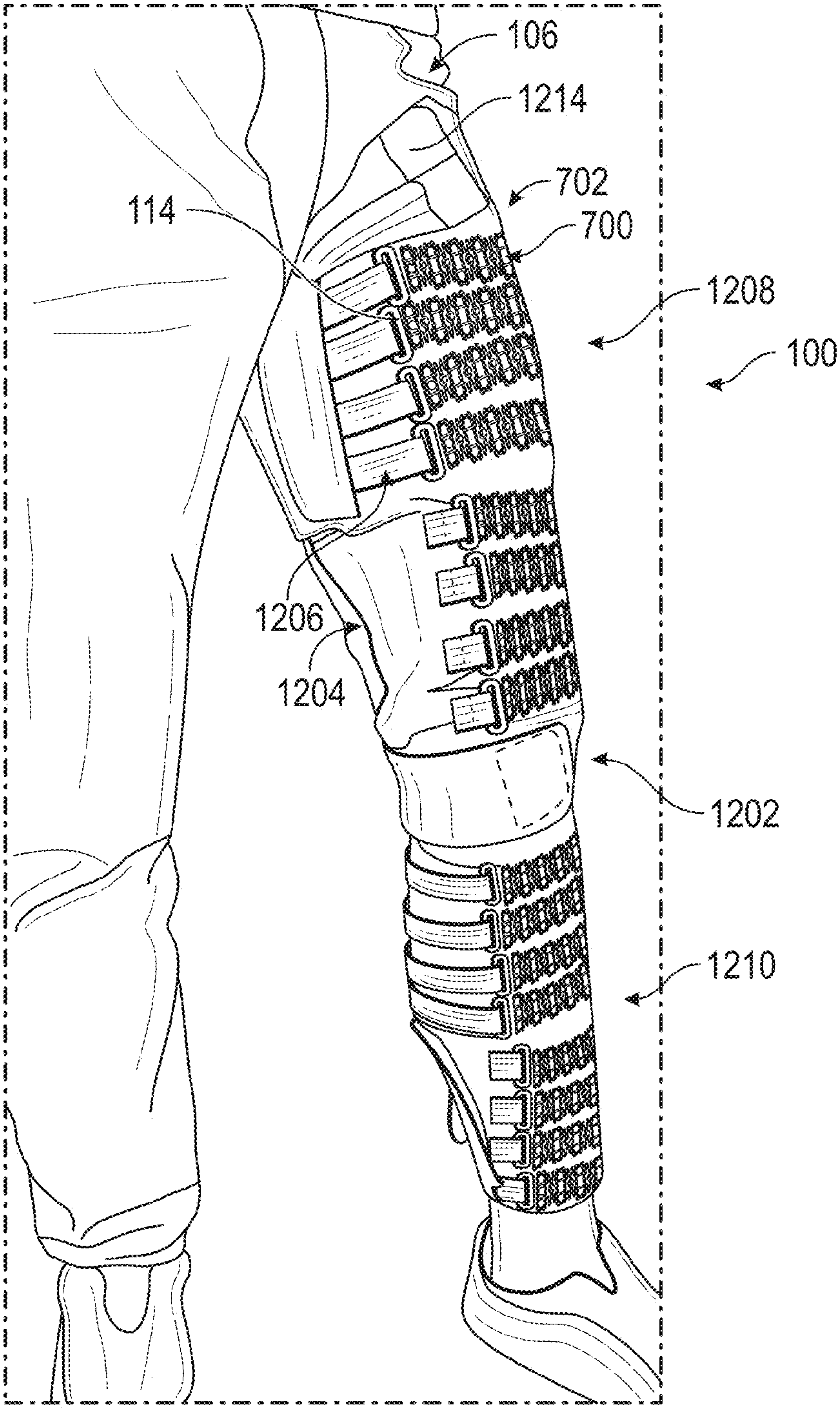

FIGS. 33A and 33B illustrate a compression garment 100 without an external covering (e.g., backing 116), exposing the internal features of the compression garment 100. The compression garment 100 can include an upper portion 1208 and a lower portion 1210. The upper portion 1208 and lower portion 1210 can be disposed on opposing sides of a joint of the user. A joint strap or region 1202 can be disposed between the upper portion 1208 and lower portion 1210 that extends around the joint of the user. The joint strap 1202 can have increased flexibility.

The compression garment 100 can include a hip strap 1214. The hip strap 1214 can be disposed on an upper portion of the compression garment 100. The hip strap 1214 can wrap around a portion of the user's upper thigh and/or part of the user's hip. For use on an arm, the compression garment 100 can include a shoulder strap 1214 that can wrap around a portion of the user's upper arm and/or shoulder.

As described herein, the compression garment 100 can include one or more flex frame assemblies 702. A flex frame assembly 702 can include a flex frame 700. A wire 118 can be routed around features of the flex frame 700 such that contraction of the wire 118, from winding up via a motor or, when the wire 118 is made of a shape memory alloy, applying a current therethrough, shortens the flex frame 700 to apply compression to the limb 106 and/or other anatomical feature of the user as described herein. The wire 118 can be operatively connected to a micro-electronic controller 320, which can control the application of a current through the wire 118 and/or winding of the wire 118 with a motor. In some variants, multiple flex frames 700 are controlled by a single micro-electronic controller 320. In some variants, each flex frame 700 is controlled by a micro-electronic controller 320. A wired connection 104 can provide power and/or data communication between the micro-electronic controller(s) 320 and a controller (e.g., controller 800). The controller can allow the user or another individual involved in the treatment of the user to run a treatment sequence, command the compression garment 100 to apply a desire compression, etc.

The compression garment 100 can include a liner 110 disposed between the flex frame assemblies 702 and the user. The liner 110 can insulate the user from heat and/or protect the user from the flex frame assemblies 702 during shortening and lengthening. As shown in FIGS. 33A and 33B, the compression garment 100 can accommodate movement of the user, such as straightening and/or bending the limb 106 of the user.

Figure 34A:
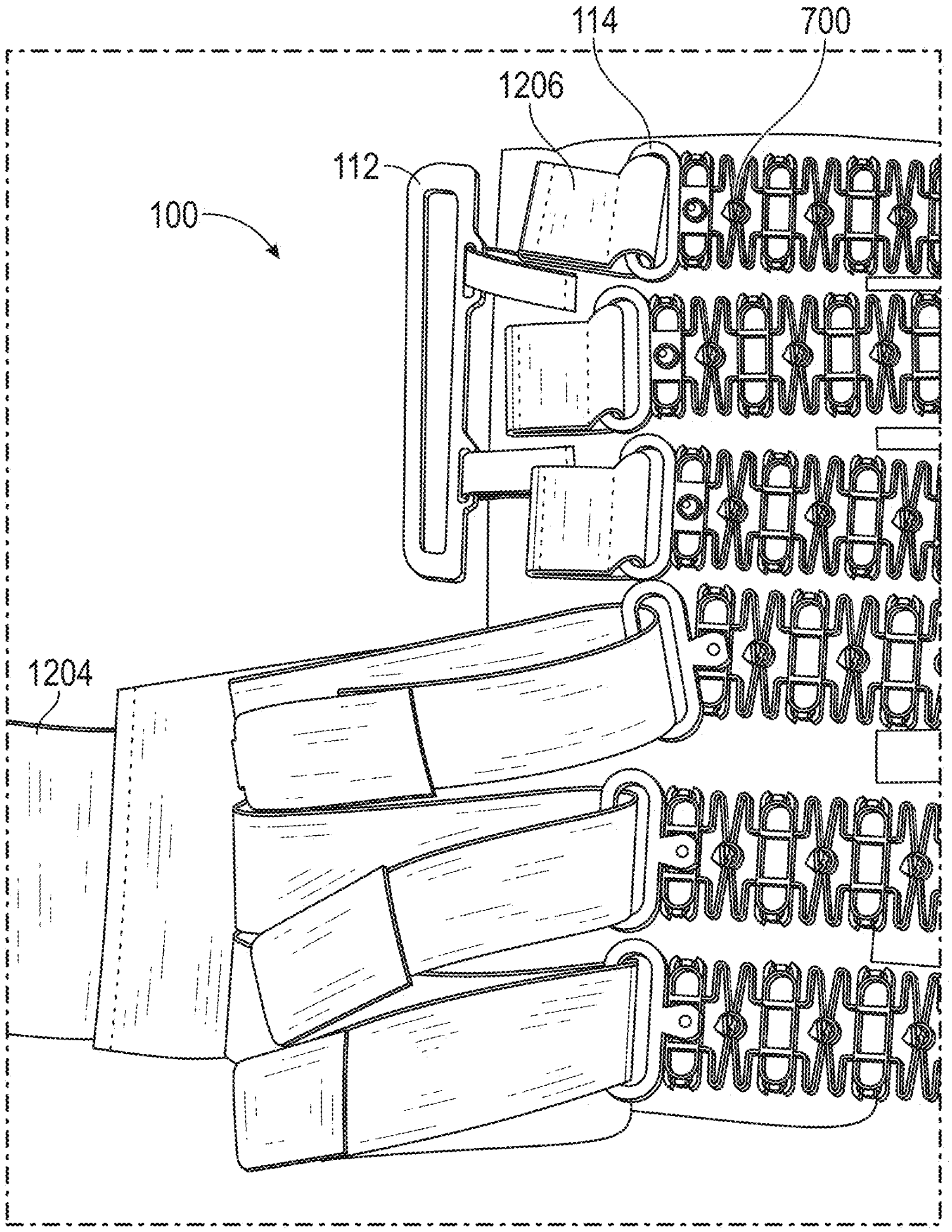
FIG. 34A illustrates a compression garment.
Figure 34B:
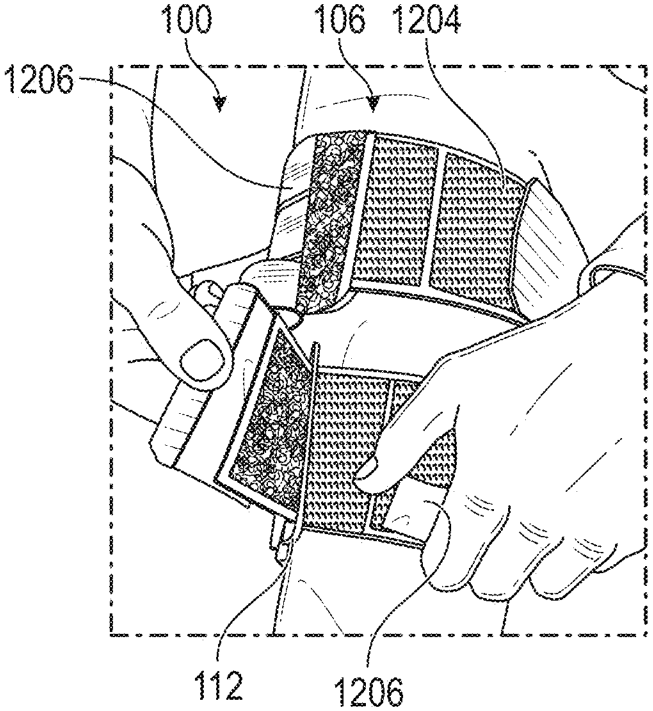
FIG. 34B illustrates the compression garment of FIG. 34A with a primary strap being secured around a limb of the user.
Figure 34C:
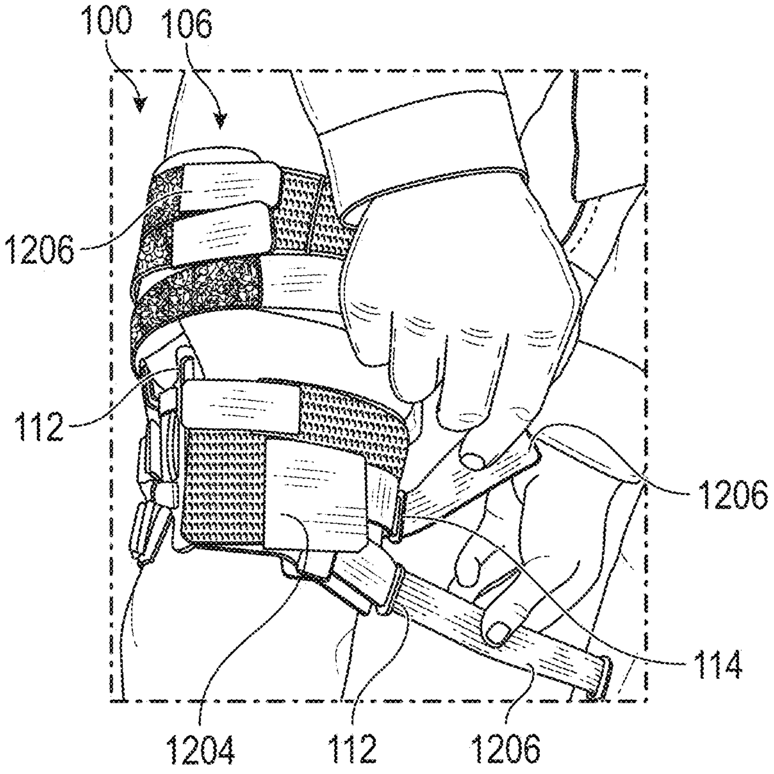
FIG. 34C illustrates the compression garment of FIG. 34A with a secondary strap being secured around the limb of the user.

FIGS. 34A-34C illustrate a compression garment 100 or strap assembly. The compression garment 100 is without a liner 110 and backing 116. The flex frame 700 includes a plurality of flex frames 700. The flex frame 700 can be coupled to one or more primary straps 1204 and/or secondary straps 1206. As illustrated in FIG. 34B, the one or more primary straps 1204 can be wrapped around the limb 106 of the user, inserted through the first strap interface 112 (e.g., D ring), and double back on itself to be secured via a hook and loop mechanism (e.g., VELCRO) or other technique, which can couple the compression garment 100 to the limb 106. As illustrated in FIG. 34C, the one or more secondary straps 1206 can be used to further tighten the compression garment 100 around the limb 106 of the user. The one or more secondary straps 1206 can be inserted, respectively, through a second strap interface 114 (e.g., D ring) and double back on itself to be secured via a hook and loop mechanism (e.g., VELCRO) or other technique. Securing with the primary strap 1204 and the secondary strap 1206 can enable the user to tighten the compression garment 100 more than with just one or the other. However, the compression garment 100 can be secured with just one of the primary straps 1204 or secondary straps 1206.

Figure 35A:
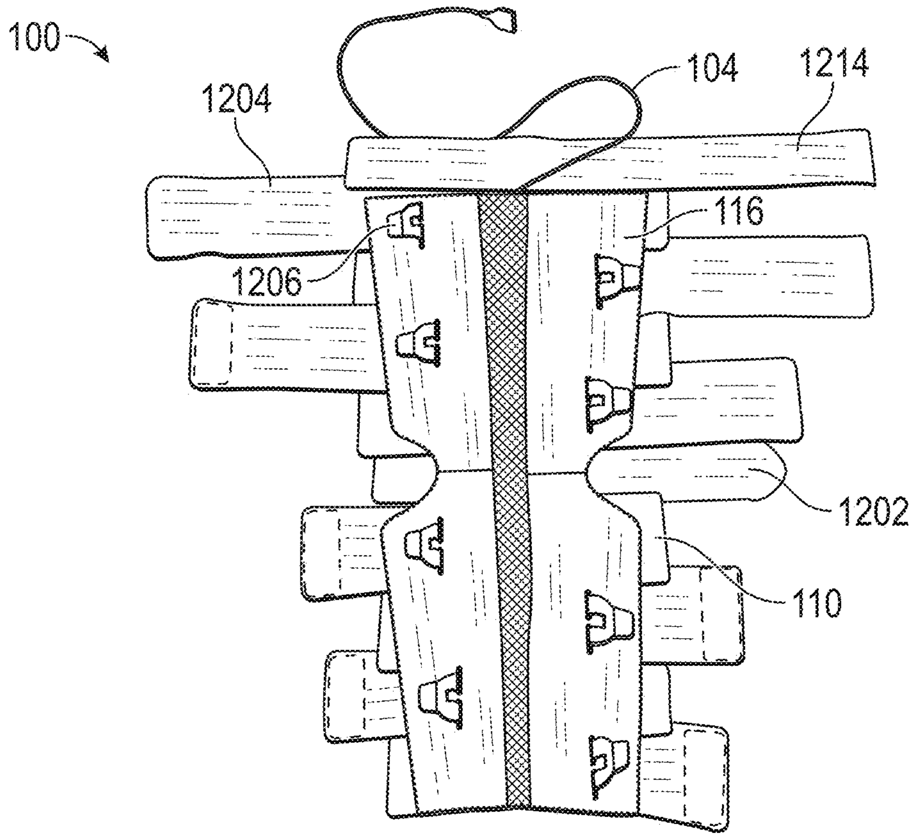
FIG. 35A illustrates a compression garment.
Figure 35B:
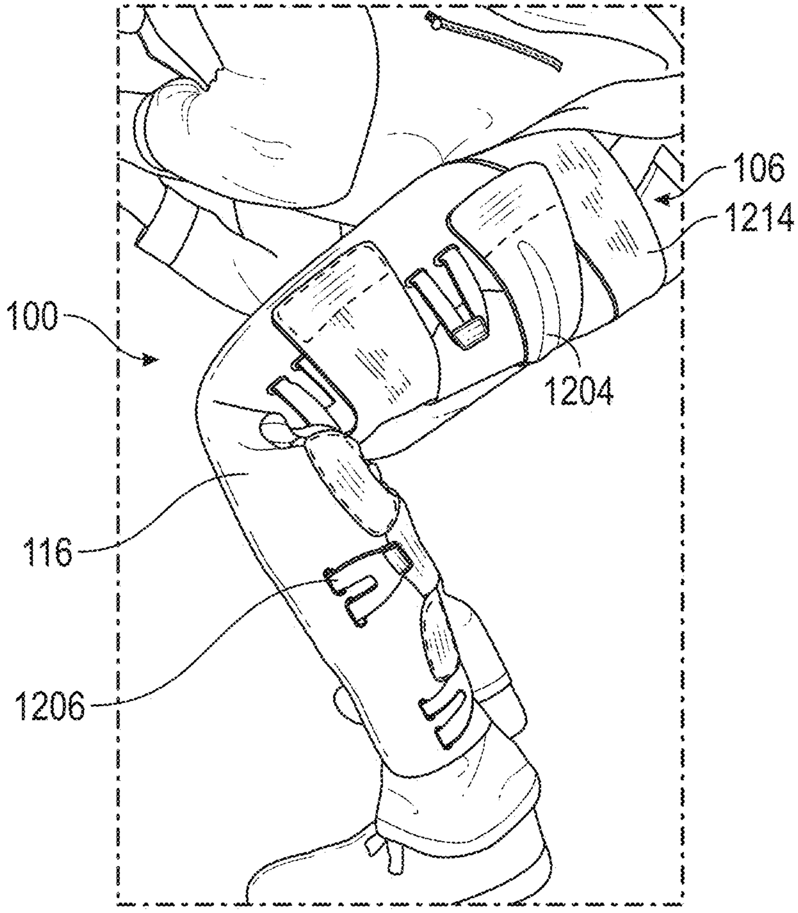
FIG. 35B illustrates the compression garment of FIG. 35A worn on a limb of a user.

FIGS. 35A and 35B illustrate a compression garment 100. As shown in FIG. 35A, the compression garment 100 can include a hip strap 1214, which can be wrapped around the hip and/or upper thigh of the user. In some variants, the hip strap 1214 can be a shoulder strap. The compression garment 100 can include primary straps 1204 that extend from the liner 110 in an alternating arrangement with each primary strap 1204 configured to extend in a different circumferential direction relative to an adjacent primary strap 1204, which can help to prevent shifting on the limb 106 of the user when donning the compression garment 100. The compression garment 100 can include secondary straps 1206, which can be used to further secure or tighten the compression garment 100 on the user. The secondary straps 1206 can be in an alternating arrangement such that each secondary strap 1206 is disposed on an opposing side of the compression garment 100, as described herein. In some variants, the secondary straps 1206 can be coupled to flex frame assemblies 702 that are disposed between the liner 110 and the backing 116. The compression garment 100 can include a joint strap or region 1202 that can be wrapped around the joint (e.g., elbow, knee, etc.) of the user. The backing 116 can include a narrowed portion to help improve flexibility of the compression garment 100 around the joint of the user. A wired connection 104 can extend into the compression garment 100 to communicate power and/or data to the flex frame assemblies 702 to facilitate the contraction of the compression garment 100. FIG. 35B illustrates the compression garment 100 on the limb 106 (e.g., leg) of the user.

Figure 36:
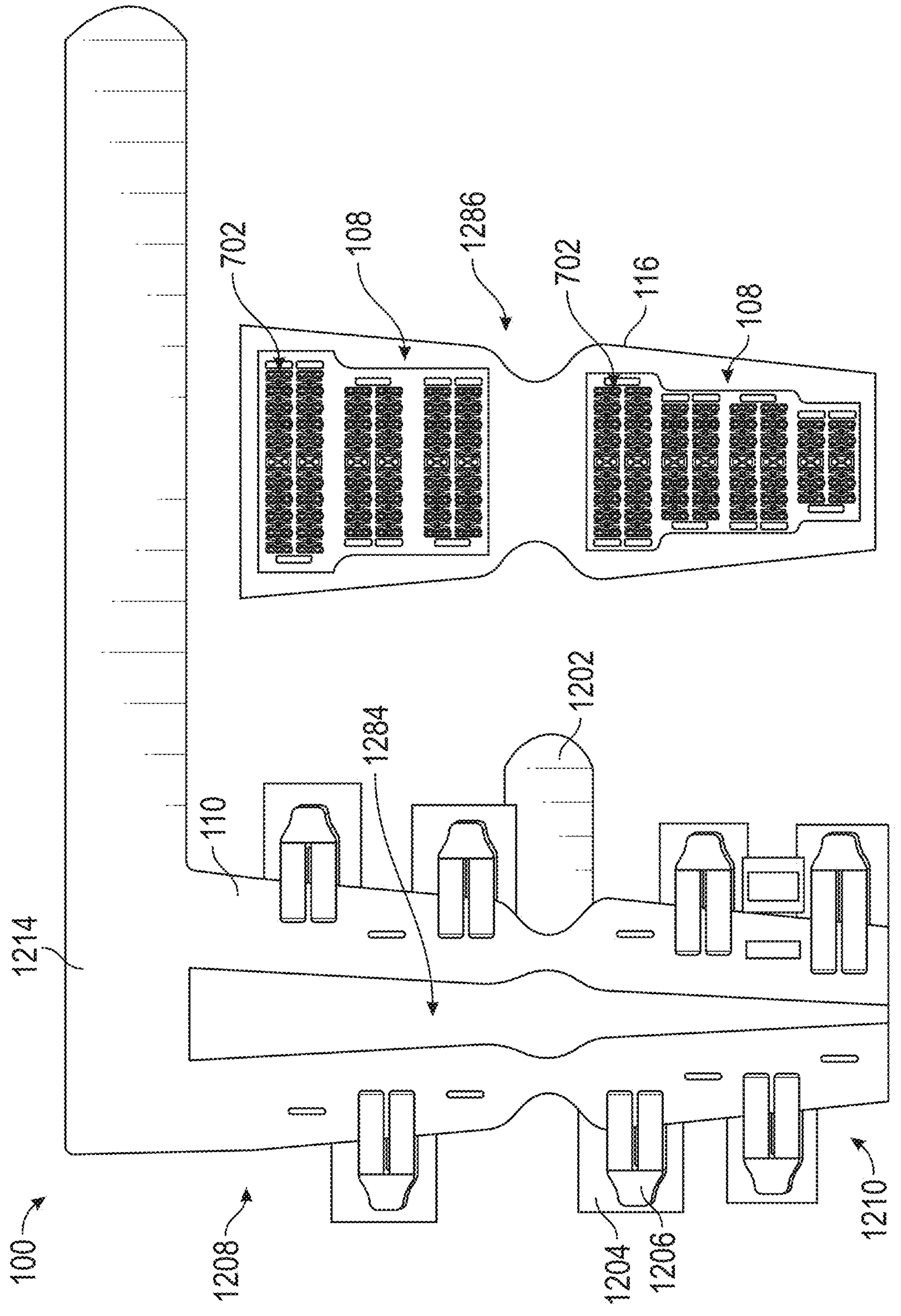
FIG. 36 illustrates a compression garment with an insert removed therefrom.

FIG. 36 illustrates a compression garment 100. The compression garment 100 can include a hip or shoulder strap 1214. The compression garment 100 can include primary straps 1204 and/or secondary straps 1206, which can be in an alternating arrangement as described herein. The compression garment 100 can include a joint strap 1202. The compression garment 100 can include an upper portion 1208 and a lower portion 1210 that are configured to be disposed on opposing sides of a joint of the user. In some variants, the upper portion 1208 can correspond to above the elbow or knee and the lower portion 1210 can correspond to the forearm or calf.

The compression garment 100 can include a liner 110. The hip strap 1214, primary strap 1204, secondary strap 1206, and/or joint strap 1202 can be coupled to the liner 110. The liner 110 can face the user's anatomy when the compression garment 100 is worn. The liner 110 can include an opening 1284 (e.g., envelope) to receive an insert 1286 therein.

The insert 1286 can include backing 116, which can be configured to face outward when the insert 1286 is positioned in the opening 1284 of the liner 110. The insert 1286 can include an upper panel 108 that can correspond to the upper portion 1208. The insert 1286 can include a lower panel 108 that can correspond to the lower portion 1210. The backing 116 can include a narrowed portion disposed between the upper panel 108 and lower panel 108 to facilitate flexibility about the joint. Each of the upper and lower panels 108 can include a plurality of flex frame assemblies 702 that can be used to apply compressive forces to anatomical features of the user as described herein.

Figure 37A:
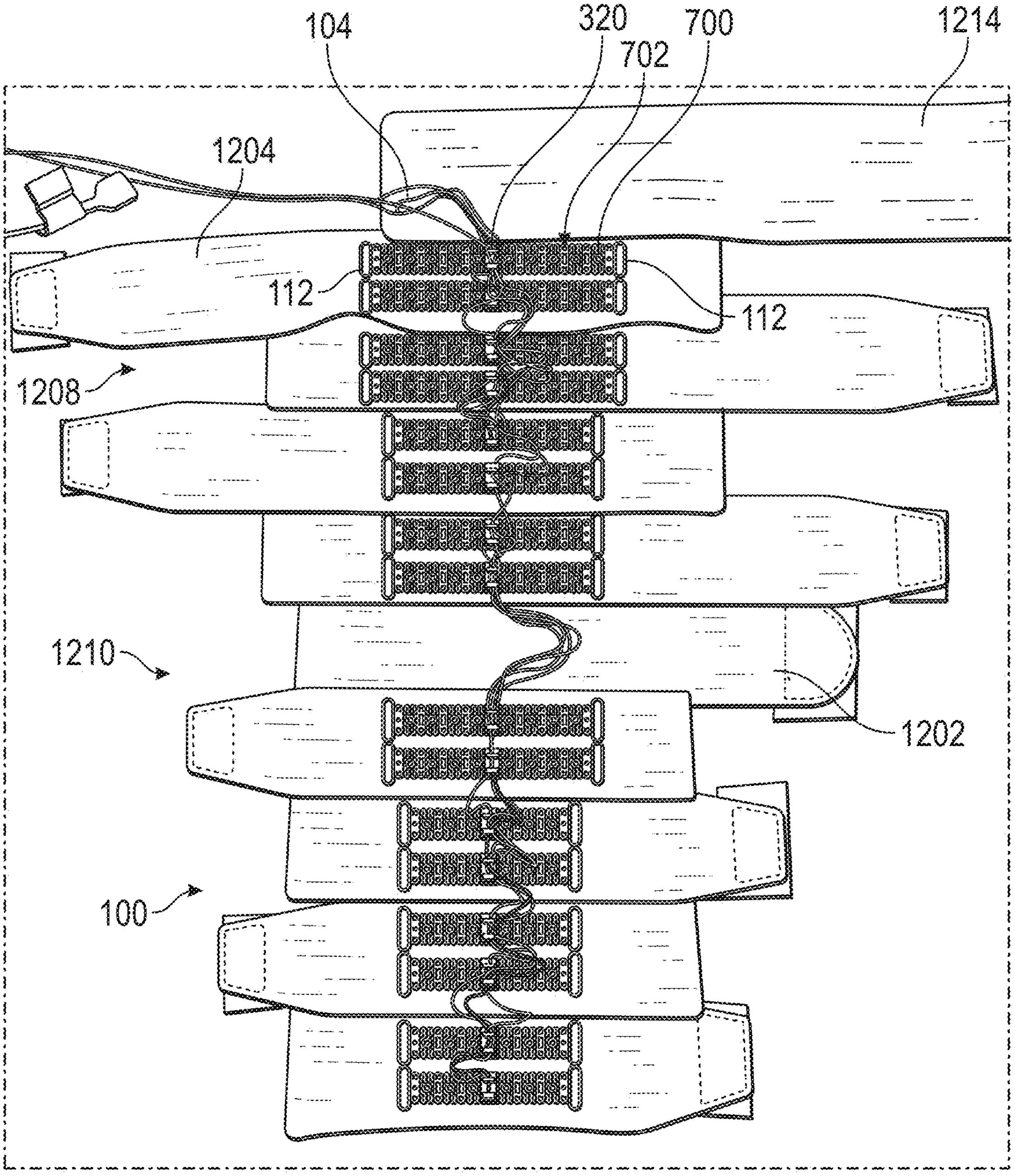
FIG. 37A illustrates a compression garment with a backing removed therefrom to expose a plurality of flex frame assemblies.
Figure 37B:
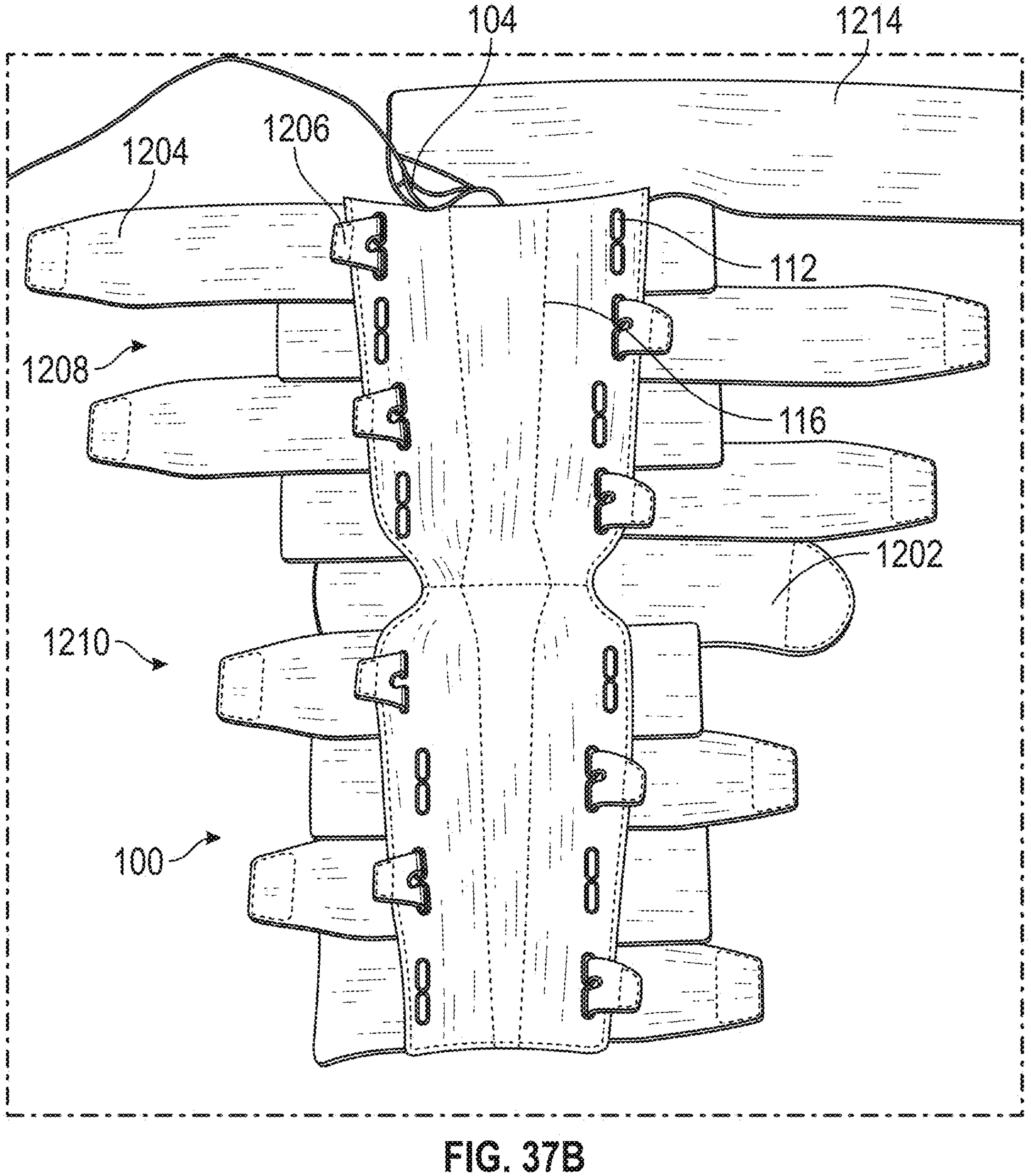
FIG. 37B illustrates the compression garment of FIG. 37A with the backing disposed over the plurality of flex frame assemblies.

FIGS. 37A and 37B illustrate a compression garment 100. FIG. 37A illustrates the compression garment 100 without a backing 116 to show internal features of the compression garment 100. The compression garment 100 can include a hip strap 1214 or shoulder strap 1214. The compression garment 100 can include a plurality of primary straps 1204 that can be arranged in an alternating pattern to extend in opposing circumferential directions about a limb or other anatomical feature of the user. The compression garment 100 can include a joint strap or region 1202, as describe herein. The compression garment 100 can include an upper portion 1208 and a lower portion 1210 which can be configured to be disposed on opposing sides of a joint of the user, which can include being on opposing sides of a joint strap or region 1202. The upper portion 1208 can include a plurality of flex frame assemblies 702 and the lower portion 1210 can include a plurality of flex frame assemblies 702. First strap interfaces 112 can be to coupled ends of the flex frame assemblies 702. The flex frame assembly 702 can include a flex frame 700, micro-electronic controller 320, wire 118, and wired connection 104 operatively coupled to a controller to provide instructions and power to the compression garment 100.

FIG. 37B illustrates the compression garment 100 with the backing 116 disposed thereon. The backing 116 can be configured to face out from the user. The backing 116 can cover the one or more flex frame assemblies 702 as described herein. The backing 116 can vent heat from the compression garment 100 as described herein. The backing 116 can include one or more holes through which the first strap interfaces 112 can extend and/or the secondary strap 1206. Secondary straps 1206 can engage with the first strap interface 112 which can enable the secondary strap 1206 to be pulled and wrapped around at least a portion of the user to further secure the compression garment 100 to the user. For example, the primary strap 1204 can be wrapped around the limb and/or other anatomical feature of the user and secured via a hook and loop mechanism (e.g., VELCRO) and/or other technique to secure the compression garment 100. The secondary straps 1206 can be wrapped around the limb and/or other anatomical features of the user and secured via a hook and loop mechanism (e.g., VELCRO) and/or other technique to further tighten and secure the compression garment 100.

Figure 38A:
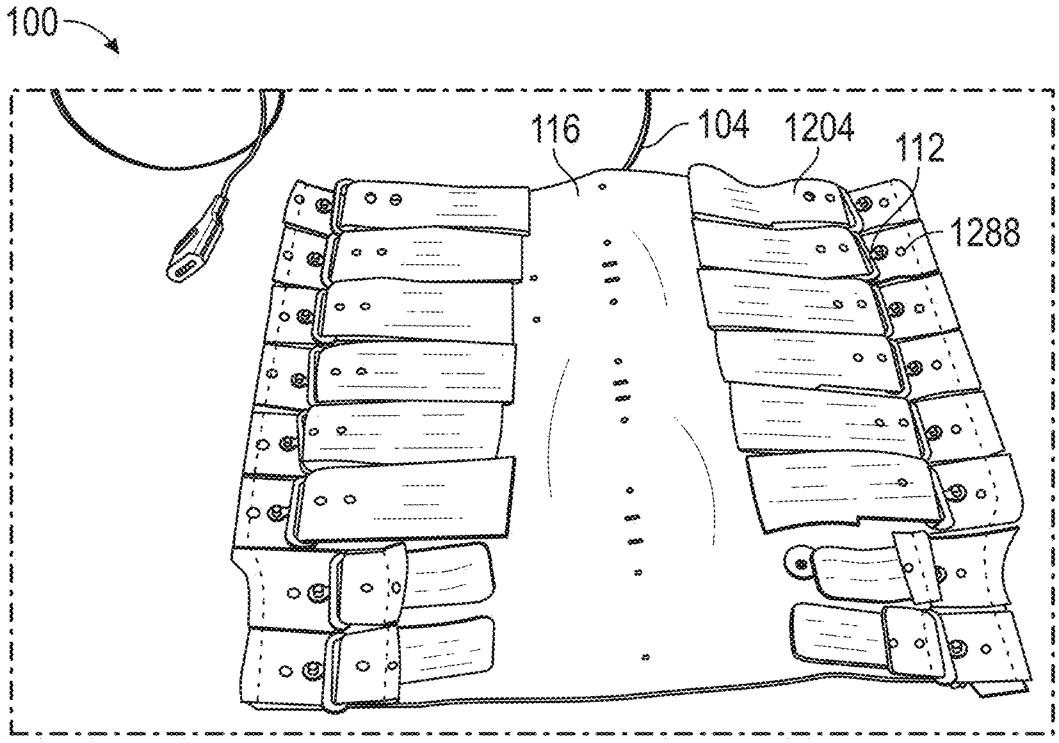
FIGS. 38A and 38B illustrates opposing sides of a compression garment.
Figure 38B:
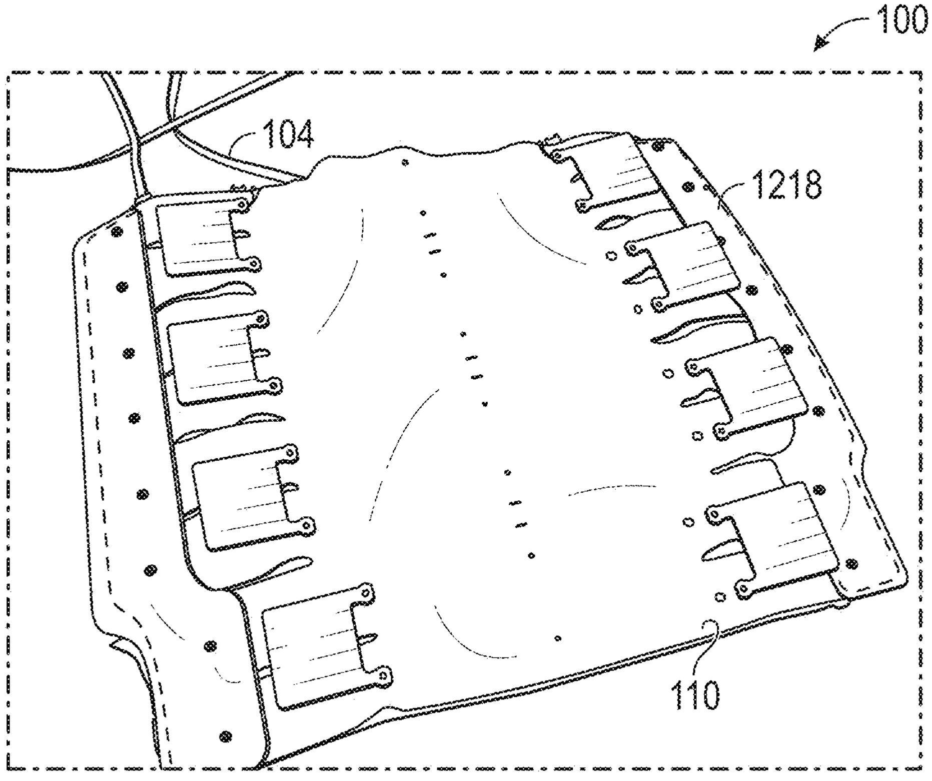
Figure 38C:
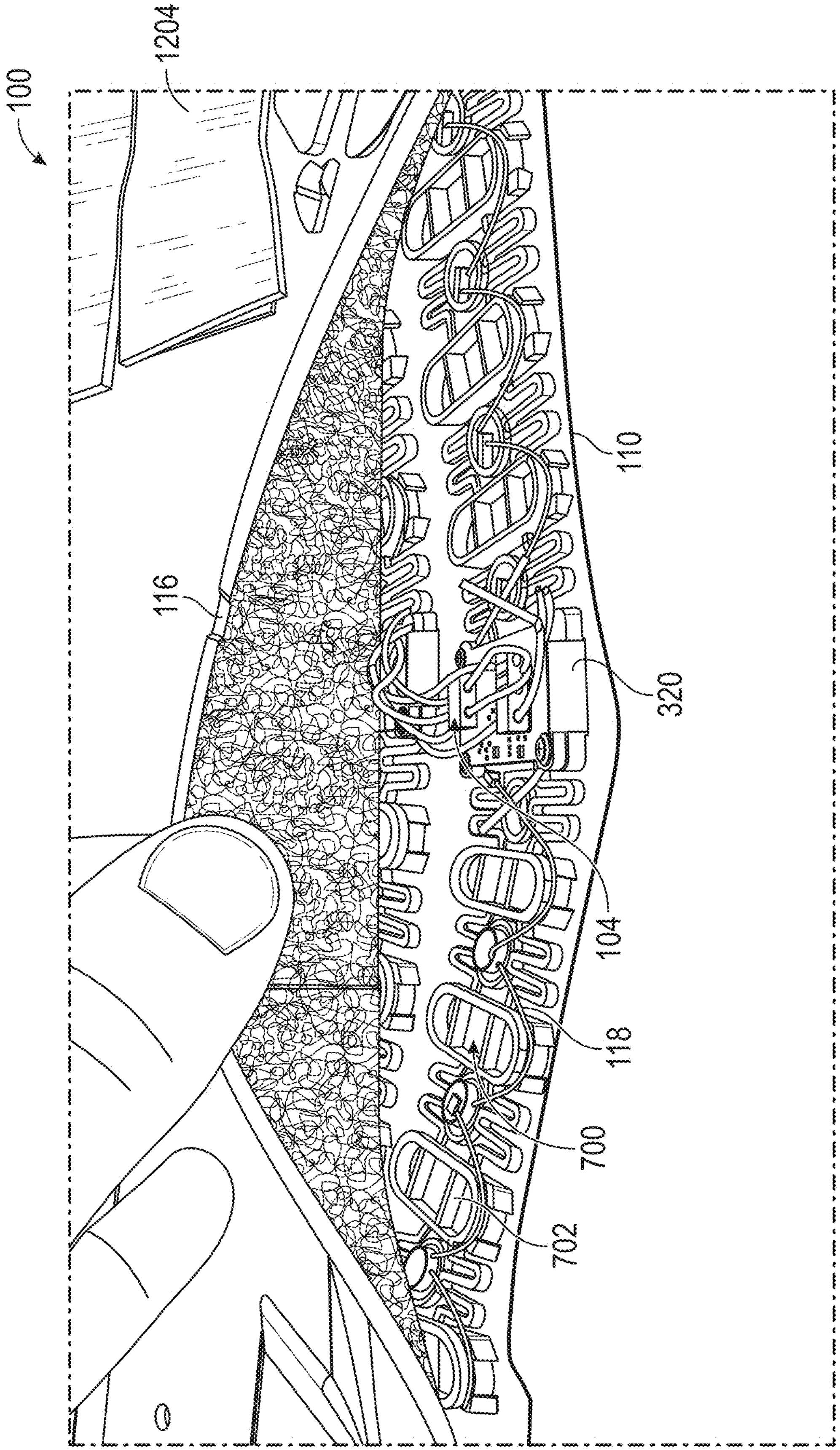
FIG. 38C illustrates an interior of the compression garment of FIGS. 38A and 38C.

FIGS. 38A-38C illustrate a compression garment 100. The compression garment 100 includes a backing 116, liner 110, and primary straps 1204. The primary straps 1204 can be secured to the compression garment 100. The primary strap 1204 can extend, respectively, through first strap interfaces 112. The first strap interface 112 can be coupled to the compression garment 100 at various positions via the positioning holes 1288, which can reconfigure the positioning of the primary strap 1204 extending therethrough. As illustrated in FIG. 38C, one or more flex frame assemblies 702 can be disposed between the backing 116 and the liner 110. A wired connection 104 can be operatively connected to the micro-electronic controller 320 of the flex frame assembly 702 to communicate data (e.g., commands, feedback, etc.) and provide power.

Figure 39:
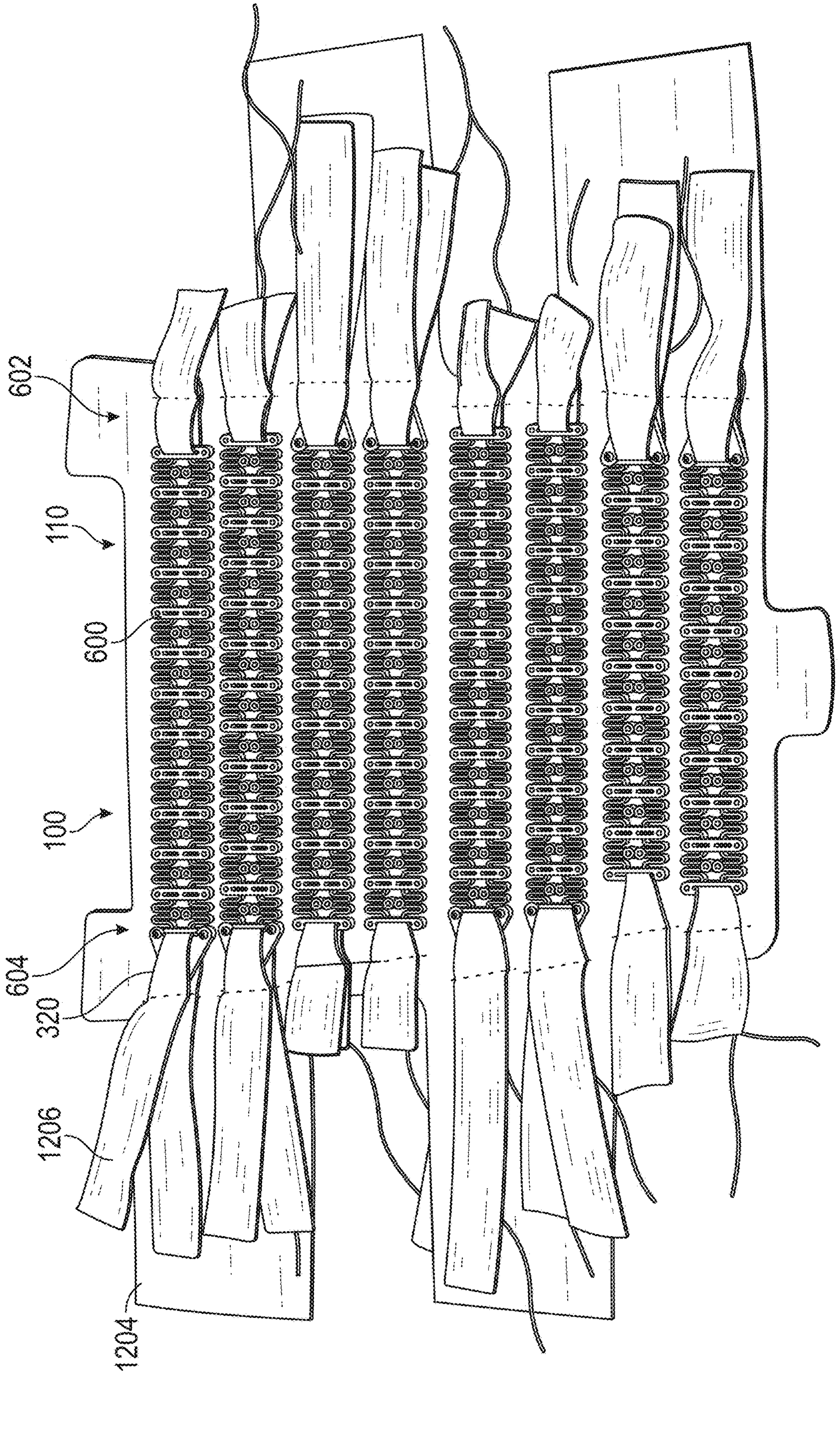
FIG. 39 illustrates a compression garment.

FIG. 39 illustrates a compression garment 100. The compression garment 100 can include a liner 110, a plurality of flex frames 600, one or more primary straps 1204, and one or more secondary straps 1206. The plurality of flex frames 600 can be mounted and/or otherwise coupled on the liner 110, which can be disposed between the user and the flex frames 600 during use. The flex frames 600 can have a second end 604 with a micro-electronic controller 320, as described herein, that can control the shortening and lengthening of a wire to compress and release the flex frames 600. The primary straps 1204 and secondary straps 1206 can be used to secure the compression garment 100 to the user. The flex frames 600 can be organized in alternating pair patterns with the micro-electronic controller 320 disposed on opposing sides of the compression garment 100 after every pair of flex frames 600.

Figure 40:
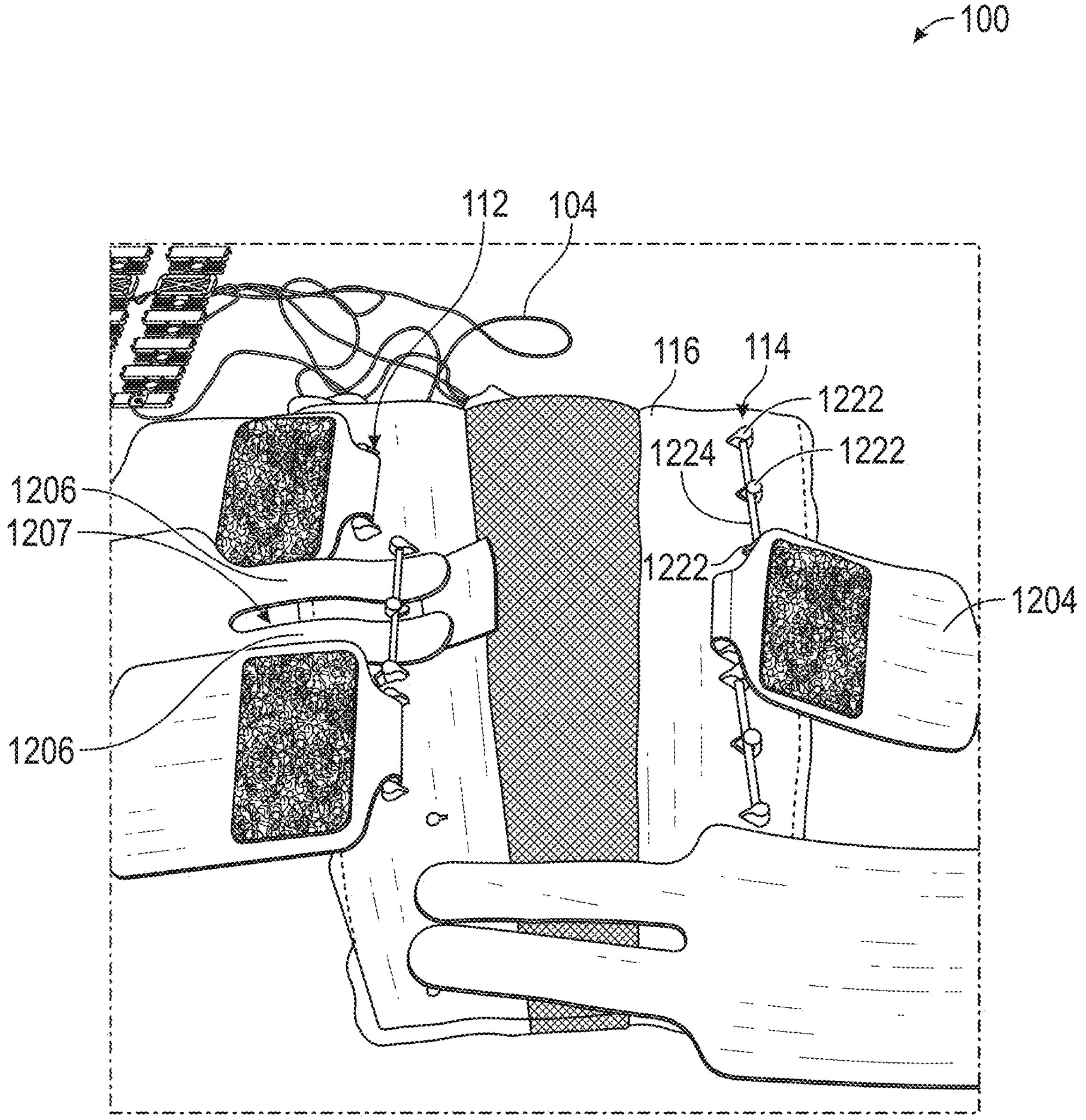
FIG. 40 illustrates a compression garment.

FIG. 40 illustrates a compression garment 100. The compression garment 100 can include a plurality of primary strap 1204 and secondary strap 1206. The primary straps 1204 can be coupled to the backing 116 via a first strap interface 112, which can be a loop or ring. The primary strap 1204 can include one of a pair of corresponding hook and loop mechanisms (e.g., VELCRO fasteners). The secondary straps 1206 can include the other of the pair of corresponding hook and loop mechanisms (e.g., VELCRO fasteners). The secondary straps 1206 can be coupled together in pairs with a gap 1207 therebetween. The pair of secondary straps 1206 can be joined at opposing ends such that the pair of secondary straps 1206 are coupled to a second strap interface 114. For example, the second strap interface 114 can include three supports 1222 with a bar 1224 extending therethrough. The pair of secondary straps 1206 can be positioned such that the central support of the three supports 1222 is disposed in the gap 1207 while the two remaining supports 1222 are disposed on opposing outer lateral sides of the pair of secondary straps 1206. The pair of secondary straps 1206 can be disposed between the bar 1224 and the backing 116 such that the pair of secondary straps 1206 are secured to the compression garment 100 via the three supports 1222 and bar 1224 of the second strap interface 114. One end of the pair of secondary straps 1206 can be joined by the other of the pair of the hook and loop mechanism (e.g., VELCRO fasteners). In use, the compression garment 100 can be secured to a limb or other anatomical feature by wrapping the primary straps 1204 and secondary straps 1206 around the limb or other anatomical feature and coupling them together via the hook and loop mechanisms (e.g., VELCRO fasteners). Other coupling mechanisms can be employed with can include at least those described herein.

Figure 41:
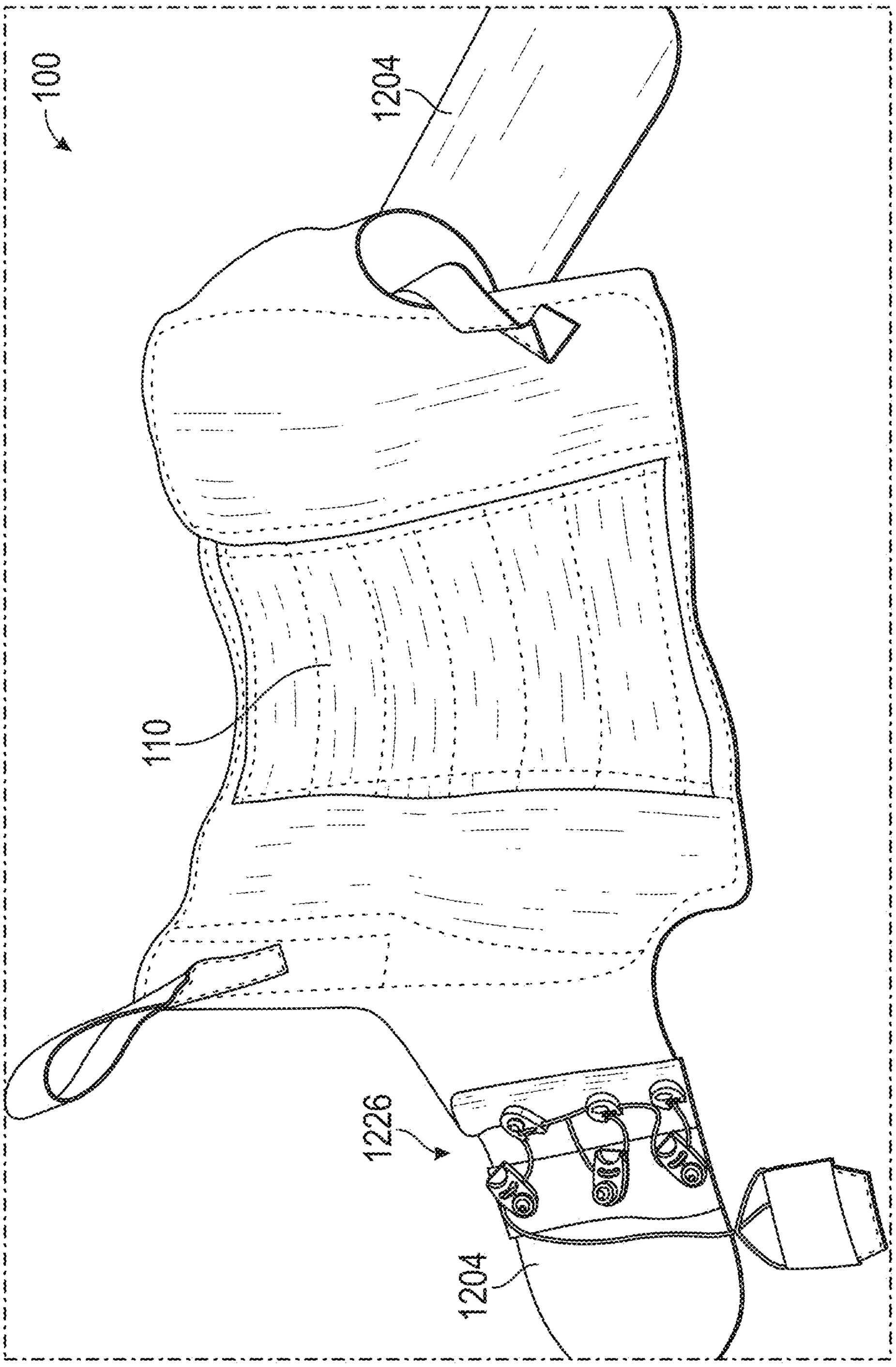
FIG. 41 illustrates a compression garment with a corset mechanism.

FIG. 41 illustrates a compression garment 100. The compression garment 100 can include primary straps 1204 to secure the compression garment 100 to a user. The compression garment 100 can include a corset mechanism 1226. In use, the compression garment 100 can be coupled to the user with the primary straps 1204. The compression garment 100 can then be further tightened on the user by pulling on the corset mechanism 1226. The compression garment 100 can include a flex frame assembly 702 and the other components described herein. The compression garment 100 can include a rigid insert (e.g., plastic) to maintain a form of the compression garment 100. The rigid insert can be curved to complement the curvature of an anatomical feature. The rigid insert can be deflected under compression.

Figure 42:
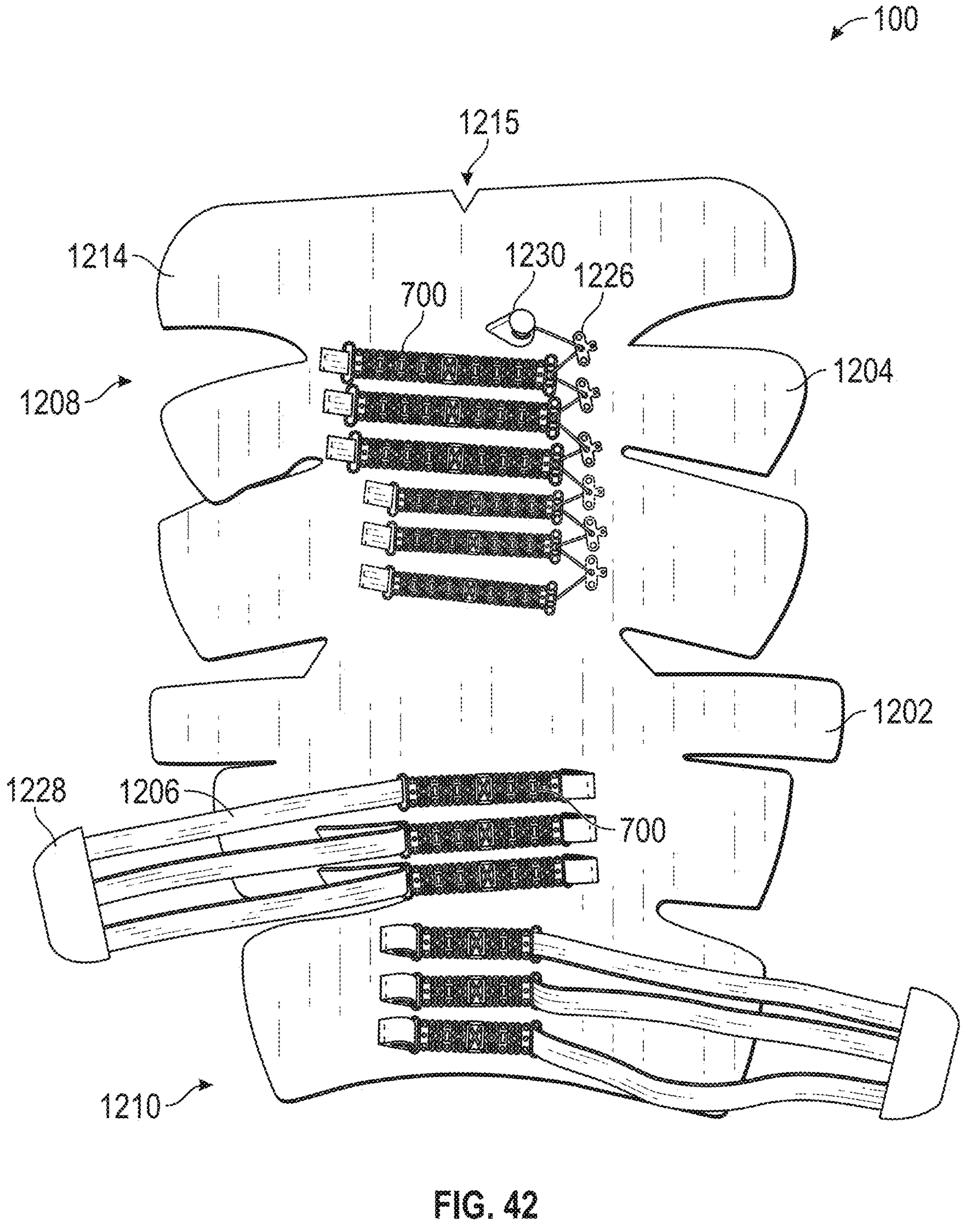
FIG. 42 illustrates a compression garment.

FIG. 42 illustrates a compression garment 100. The compression garment 100 includes an upper portion 1208 with a plurality of flex frames 700 and a corset mechanism 1226. The compression garment 100 includes a lower portion 1210 with a plurality of flex frames 700 and secondary straps 1206. In use, the compression garment 100 can be secured to the user with the plurality of primary straps 1204, hip or shoulder strap 1214, and/o joint strap 1202. The hip strap 1214 can include a gap 1215, also referred to as a notch, to facilitate a secure fit to the user.

The upper portion 1208 can be further tightened onto the user by way of the corset mechanism 1226. The user or another individual can pull on the tab 1230 of the corset mechanism 1226 to tighten the upper portion 1208 onto the user's limb. The lower portion 1210 can be further tightened onto the user by way of the secondary straps 1206. The secondary straps 1206 can be threaded through a strap interface, doubled back onto themselves, and secured via a hook and loop mechanism (e.g., VELCRO fastener) to further tighten the lower portion 1210 onto the user's limb. An end portion 1228, also referred to as a joining portion or grasping portion, can join the ends of the secondary strap 1206. The flex frames 700 can provide selective compression to the limb or other anatomical feature of the user as described herein.

Figure 43A:
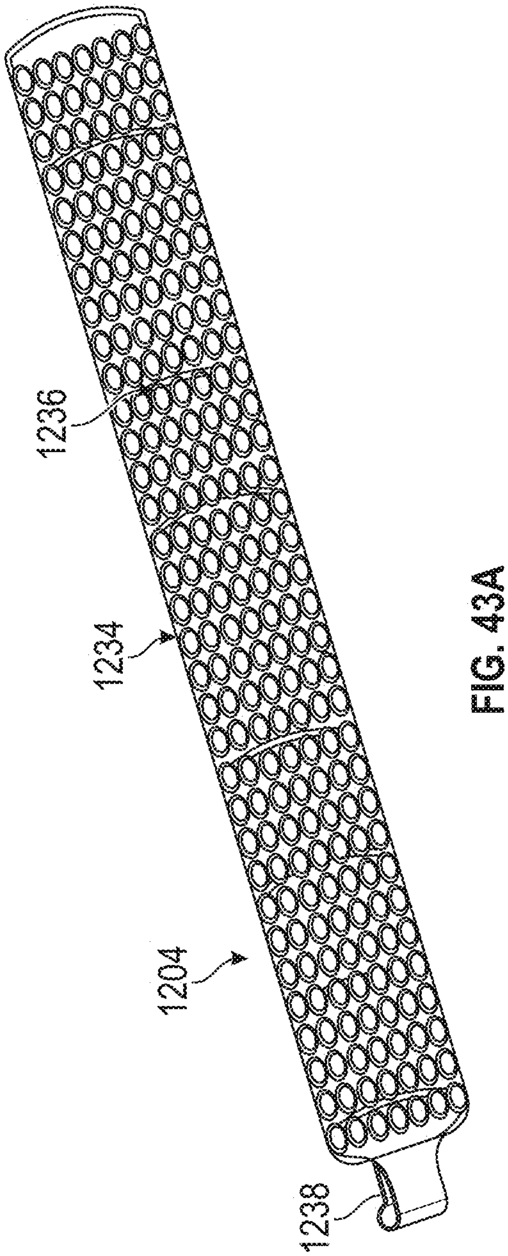
FIGS. 43A and 43B illustrate a strap with protrusions disposed thereon to help break up fibrotic tissue.
Figure 43B:
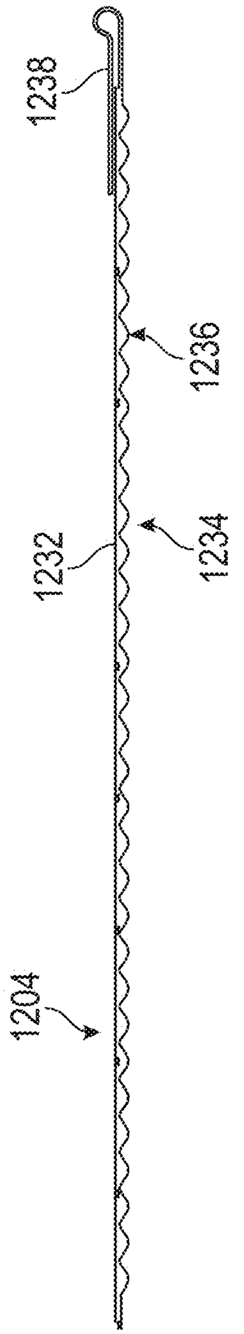

FIGS. 43A and 43B illustrate a primary strap 1204. The primary strap 1204 can be incorporated into any of the compression garments described herein. The primary strap 1204 can include a clip 1238, e.g., fastener, that can be used to facilitate incorporation into a compression garment. In some variants, the primary strap 1204 can be directly coupled to a flex frame.

The primary strap 1204 can include an outer surface 1232 and an inner surface 1234. The inner surface 1234 can be configured to face the user when the compression garment is worn by the user. The inner surface 1234 can include a plurality of protrusions 1236, which can also be referred to as bumps, round protrusions, protuberances, projections, bulges, etc. The protrusions 1236 can aid in breaking up fibrotic tissue. The protrusions 1236 can allow for areas of higher and lower pressure during compression. For example, the protrusions 1236 can increase localized pressure applied to the user under the protrusions 1236, which can aid in the breakup of fibrotic tissue. The protrusions 1236 can reduce friction between the flex frame 700 and other components of the compression garment 100 and/or the user, allowing for improved efficiency of the system. For example, the protrusions 1236 can be rounded and/or curved to further reduce friction. In some variants, the protrusions 1236 are uniform in size and/or placement. In some variants, the protrusions 1236 are not uniform in size and/or placement.

FIGS. 44A-44E illustrate various views of a flex frame 700. The flex frame 700 can include units 501 (e.g., two, three, four, five, six, etc.). The units 501 can include a first spring arm 506, second spring arm 507, bridge 508, guide structure 522, and/or support 510. The first spring arm 506 and/or second spring arm 507 can flex, deflect, deform, bend, and/or otherwise move to allow the flex frame 500 to lengthen or shorten to apply or release compressive forces to the limb 106 of the user. The guide structure 522 and support 510 can translate toward the controller mount 1240 during contraction of the flex frame 700 and translate away from the controller mount 1240 when the flex frame 700 is released.

The first spring arm 506 can extend from a central portion of a side of the micro-electronic controller 320 and/or controller mount 1240, extend outward toward the outer longitudinal edges of the flex frame 700, and curve back inward to join the second spring arm 507. The second spring arm 507 can be in a mirrored configuration relative to the first spring arm 506. The second spring arm 507 can, from the first spring arm 506, extend outward toward the outer longitudinal edges of the flex frame 700 and curve back inward to join with a central portion of a first support 510. In some variants, a bridge 508 and guide structure 522 are disposed at the joint of the first spring arm 506 and second spring arm 507 to guide a wire. The first spring arm 506 and/or second spring arm 507 can have an opening extending therethrough to facilitate flexion, deflection, and/or other movement.

The first unit 501 can include a first support 510. A first spring arm 506 can extend from a central portion of the first support 510, extend outward toward the outer longitudinal edges of the flex frame 700, and curve back to join a bridge 508. The first spring arm 506 can have an opening extending therethrough to facilitate flexion, deflection, and/or other movement. The bridge 508 can be disposed between the first spring arm 506 and the second spring arm 507. The bridge 508 can include a guide structure 522 that is described herein. The second spring arm 507 can be in a mirrored arrangement as the first spring arm 506 relative to the bridge 508. The second spring arm 507 can extend from a central portion of a second support 510, curve outward toward the outer longitudinal edges of the flex frame 500, and curve back inward to the bridge 508. The second spring arm 507 can have an opening extending therethrough to facilitate flexion, deflection, and/or other movement.

The support 510 can include a first groove 512 and/or a second groove 514. The first groove 512 and second groove 514 can be disposed on opposing sides of the support 510. The first groove 512 and second groove 514 can receive the wire routed through the flex frame 700. The first groove 512 and second groove 514 can be curved. The support 510 and/or features of the bridge 508 and/or guide structure 522 can extend from the plane of the flex frame 700 to improve movement of the wire during use without undue friction.

The flex frame 700 can include repeating units 501 as described herein that extend in opposing directions from the controller mount 1240. The flex frame 700 can terminate on opposing sides with a first end 502 and second end 504. The first end 502 and second end 504 can be in mirrored configurations. The first end 502 and second end 504 can be modified supports 510 with first grooves 512 and second grooves 514 on opposing sides thereof. The outer sides of the first end 502 and second end 504 can be gently curved between the first grooves 512 and second grooves 514 to accommodate the wire wrapping around the first end 502 and second end 504 before being routed back toward the controller mount 1240. In some variants, the outer sides of the first end 502 and second end 504 can include a groove to receive the wire. The first end 502 and the second end 504 can include fastener openings 1290 which can facilitate coupling the flex frame 700 to one or more straps and/or the compression garment 100.

Figure 44A:
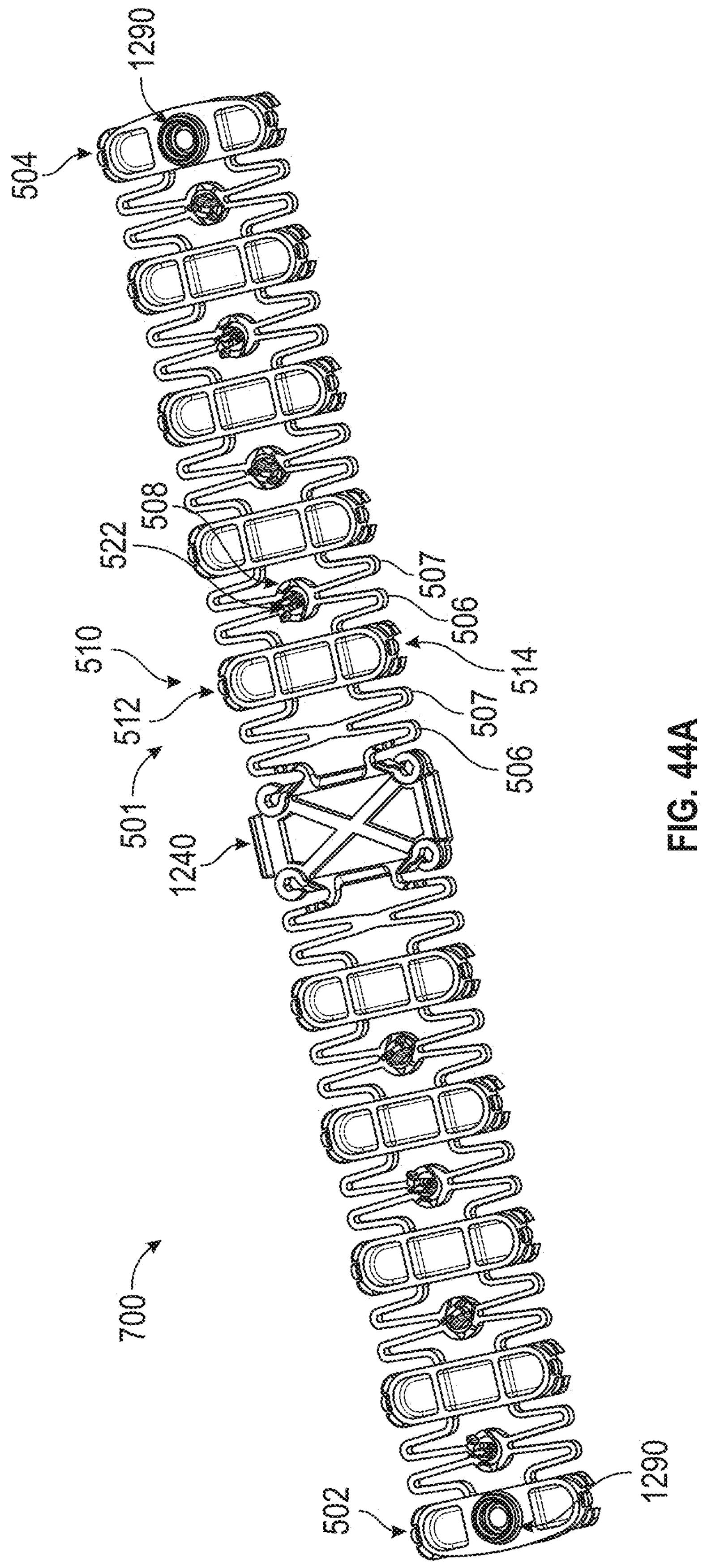
FIG. 44A illustrates a flex frame.
Figure 44B:
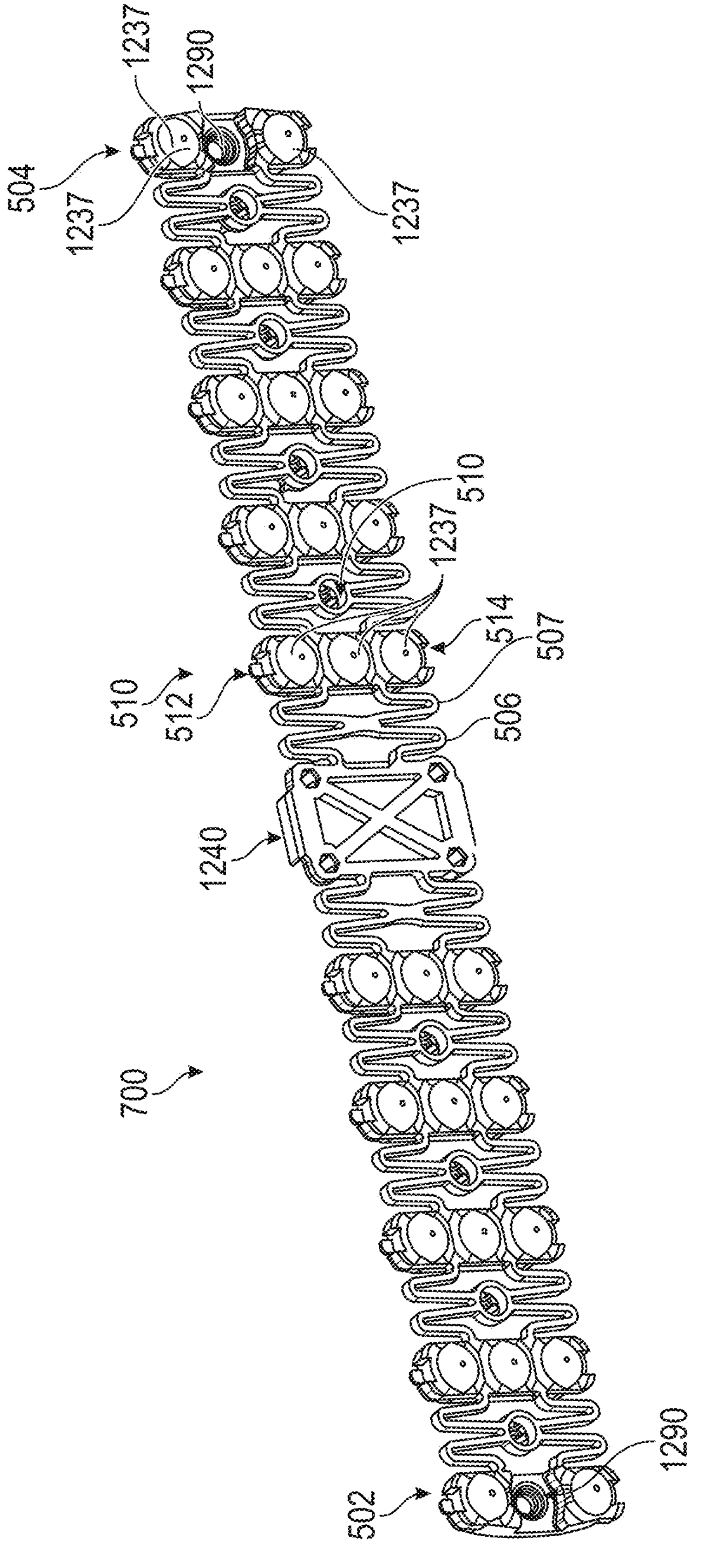
FIG. 44B illustrates an underside view of the flex frame of FIG. 44A.
Figure 44C:
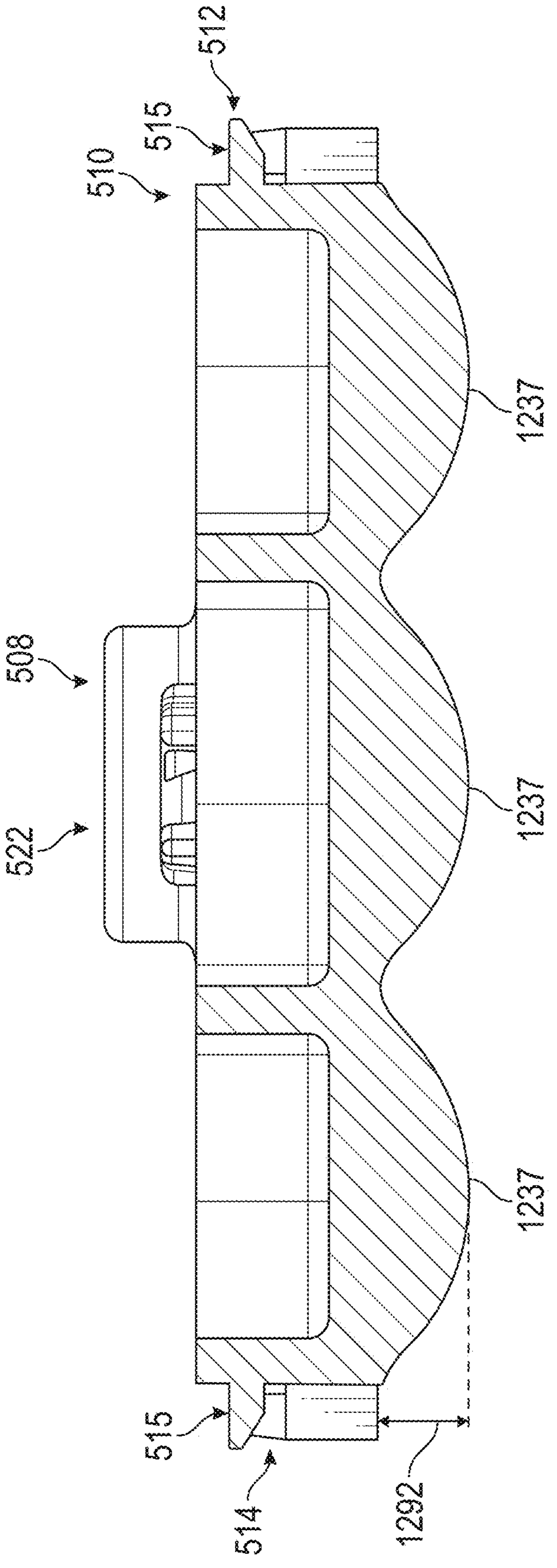
FIG. 44C illustrates a cross-section of the flex frame of FIG. 44A.

As illustrated in FIG. 44B, the flex frame 700 can include one or more protrusions 1237, which can be similar to the protrusions 1236 described herein. The protrusions 1237 can aid in the breakup fibrotic tissue during use of the compression garment 100. The protrusions 1237 can allow for areas of high and low pressure (e.g., high under the protrusions 1237). The protrusions 1237 can reduce friction, which can facilitate improved efficiency. The protrusions 1237 can be rounded, which can reduce friction and/or improve user comfort. The protrusions 1237 can be uniform or uninform in size, shape, and/or placement.

The protrusions 1237 can be disposed on a side of the flex frame 700 that is configured to face inward toward the user during use of the compression garment 100. The protrusions 1237 can be disposed on the support 510, first end 502, and second end 504. In some variants, three protrusions 1237 can be disposed on the supports 510 but other quantities can be implemented, such as one, two, four, five, or more. In some variants, first end 502 and/or second end 504 can include two protrusions 1237, which can be disposed on opposing sides of the fastener opening 1290, but other quantities of protrusions 1237 can be implemented. The protrusions 1237 can extend varying distances 1292 away from the flex frame 700, which can at least include 0.5 to 30 mm. The protrusions 1237 can have varying diameters, which can at least include 0.5 to 60 mm. Similarly, the protrusions 1236 can extend varying distances away from the primary strap 1204, which can at least include 0.5 to 30 mm. The protrusions 1236 can have varying diameters, which can at least include 0.5 to 60 mm.

Figure 44D:
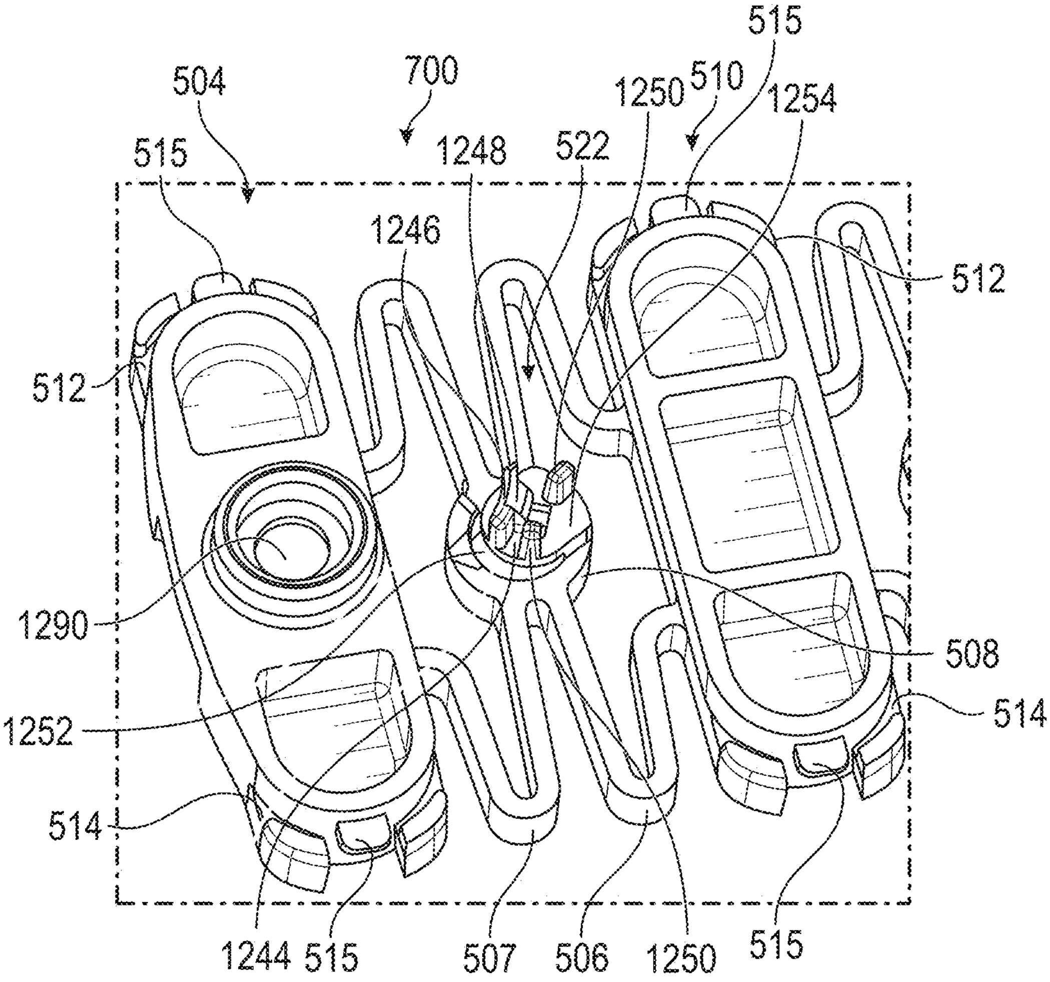
FIGS. 44D and 44E illustrate enlarged views of portions of the flex frame of FIG. 44A.
Figure 44E:
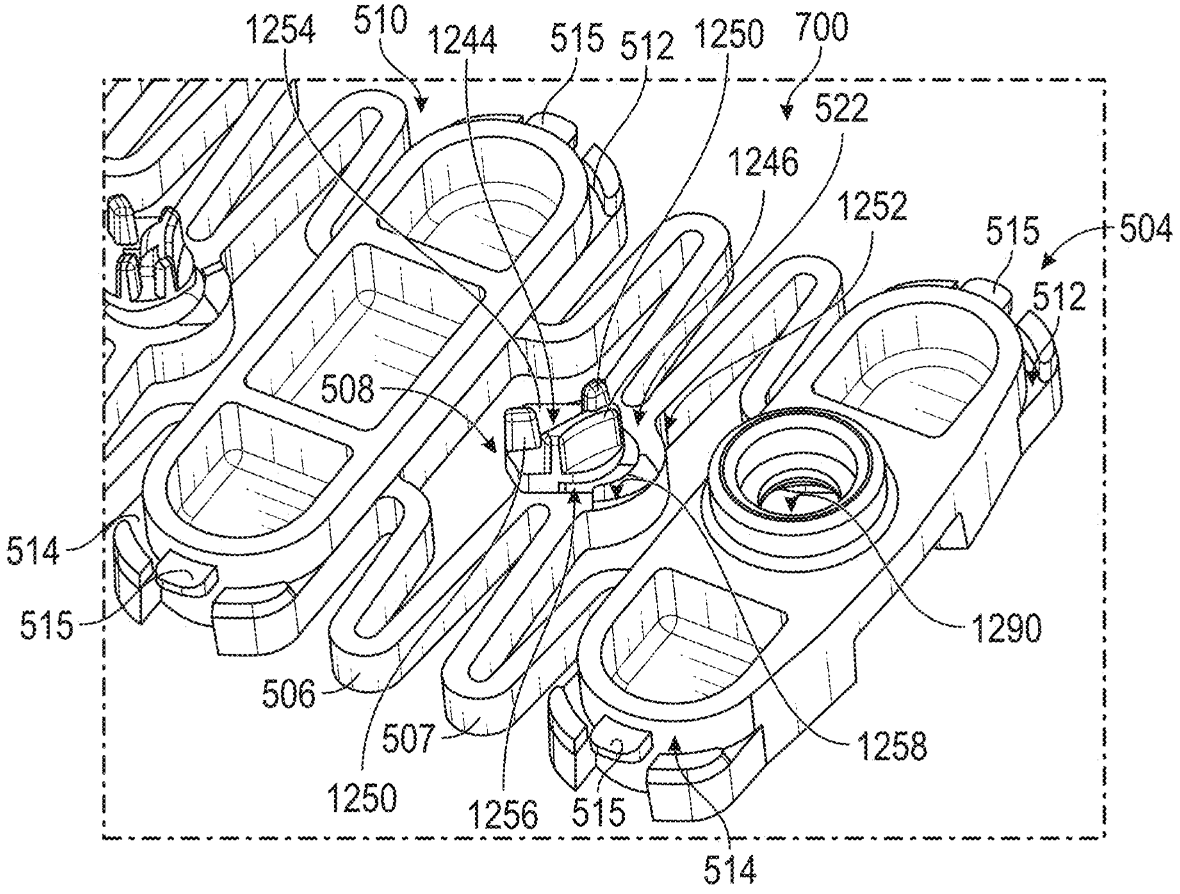

FIGS. 44D and 44E illustrate enlarged views of the bridge 508 proximate the second end 504. The bridge 508 can have a guide structure 522 through which the wire can be routed. The guide structure 522 can prevent the wire from contacting itself as the wire crosses over itself as the wire is routed from the micro-electronic controller 320 to the second end 504 or first end 502 and back. The guide structure 522 can insulate the wire from itself as the wire crosses over itself. For example, the guide structure 522 can have an upper channel 1244 and a lower channel 1256. The wire can be routed through the upper channel 1244 while being routed toward the micro-electronic controller 320 or the second end 504 and routed through the lower channel 1256 while being routed toward the other of the micro-electronic controller 320 or the second end 504. The same applies to the first end 502. The upper channel 1244 and lower channel 1256 can be separated by a partition 1254, which can also be referred to as a divider or separator. The partition 1254 can extend parallel to the plane of the flex frame 700. The partition 1254 can be disposed between the crossing wires routed through the flex frame 700.

The upper channel 1244 can be bounded by the partition 1254, guide 1246, and guides 1250. The guide 1246, which can also be referred to as a retainer, protrusion, and/or protuberance, can be curved to promote sliding of the wire within the upper channel 1244. The guide 1246 can extend away from the partition 1254. The guide 1246 can include a tab 1248, which can also be referred to as a retainer, that can help to retain the wire with the upper channel 1244. The tab 1248 can extend parallel to a top surface of the partition 1254. The guides 1250, which can also be referred to as retainers, protrusions, and/or protuberances, can be disposed on an opposing side of the upper channel 1244 relative to the guide 1246. The guides 1250 can extend from the partition 1254. The guides 1250 can be curved to promote sliding of the wire within the upper channel 1244. The guides 1250 can curve in an opposite direction compared to the guide 1246.

The partition 1254 can be raised relative to the bridge 508 to define a gap 1252 between the partition 1254 and the bridge 508 for the lower channel 1256. A ramp 1258 can be disposed on the bridge 508 to help retain the wire in the lower channel 1256. The ramp 1258 can help facilitate placement of the wire within the lower channel 1256. For example, the wire can be slid up the ramp 1258 until dropping into the lower channel 1256 beneath the partition 1254. The end of the ramp 1258 can then help to retain the wire within the lower channel 1256.

As described herein, the support 510, first end 502, and/or second end 504 can include a first groove 512 and second groove 514 which can be disposed on opposing ends of the support 510, first end 502, and/or second end 504. The first groove 512 and/or second groove 514 can be distributed into multiple portions (e.g., two) with a gap separating the portions. The first groove 512 and second groove 514 can be configured to receive and retain the wire or the like therein that is routed through the flex frame 700. The first groove 512 and/or second groove 514 can be curved to promote sliding of the wire or the like therein. A tab 515, also known as a retention feature, can be disposed on one or more of the ends of the support 510, first end 502, and/or second end 504 to help contain and/or electrically isolate the wire 118 in the first groove 512 and/or second groove 514. The tab 515 can extend over the first groove 512 and/or second groove 514.

As described herein, a wire can extend from a micro-electronic controller 320 disposed on the controller mount 1240. The wire can be routed through the first groove 512 of a first support 510, the upper channel 1244 of a guide structure 522, and a second groove 514 of a second support 510. The wire can be routed in like manner until reaching a first end 502 or second end 504. The wire can extend through a first groove 512 of the first end 502 or second end 504, around the outer side of the first end 502 or second end 504, and through a second groove 514 of first end 502 or second end 504. The wire can then be routed through the flex frame 700 back to the micro-electronic controller 320 mounted on the controller mount 1240. The wire can be routed through the lower channel 1256 of the guide structure 522, the first groove 512 of a support 510, through the lower channel 1256 of a second guide structure 522, and through the second groove 514 of a another support 510. The wire can be routed in like manner until reaching the micro-electronic controller 320 mounted on the controller mount 1240. In some variants, the wire can be routed through the lower channel 1256 toward the first end 502 or second end 504 and through the upper channel 1244 back toward the micro-electronic controller 320 mounted on the controller mount 1240. As described herein, the guide structure 522 can electrically isolate, which can include complete electrical isolation, the wire 118 from itself at intersections. The guide structure 522 can be made of a polymer (e.g., creating a polymer barrier), which can facilitate electrical isolation.

Figure 45A:
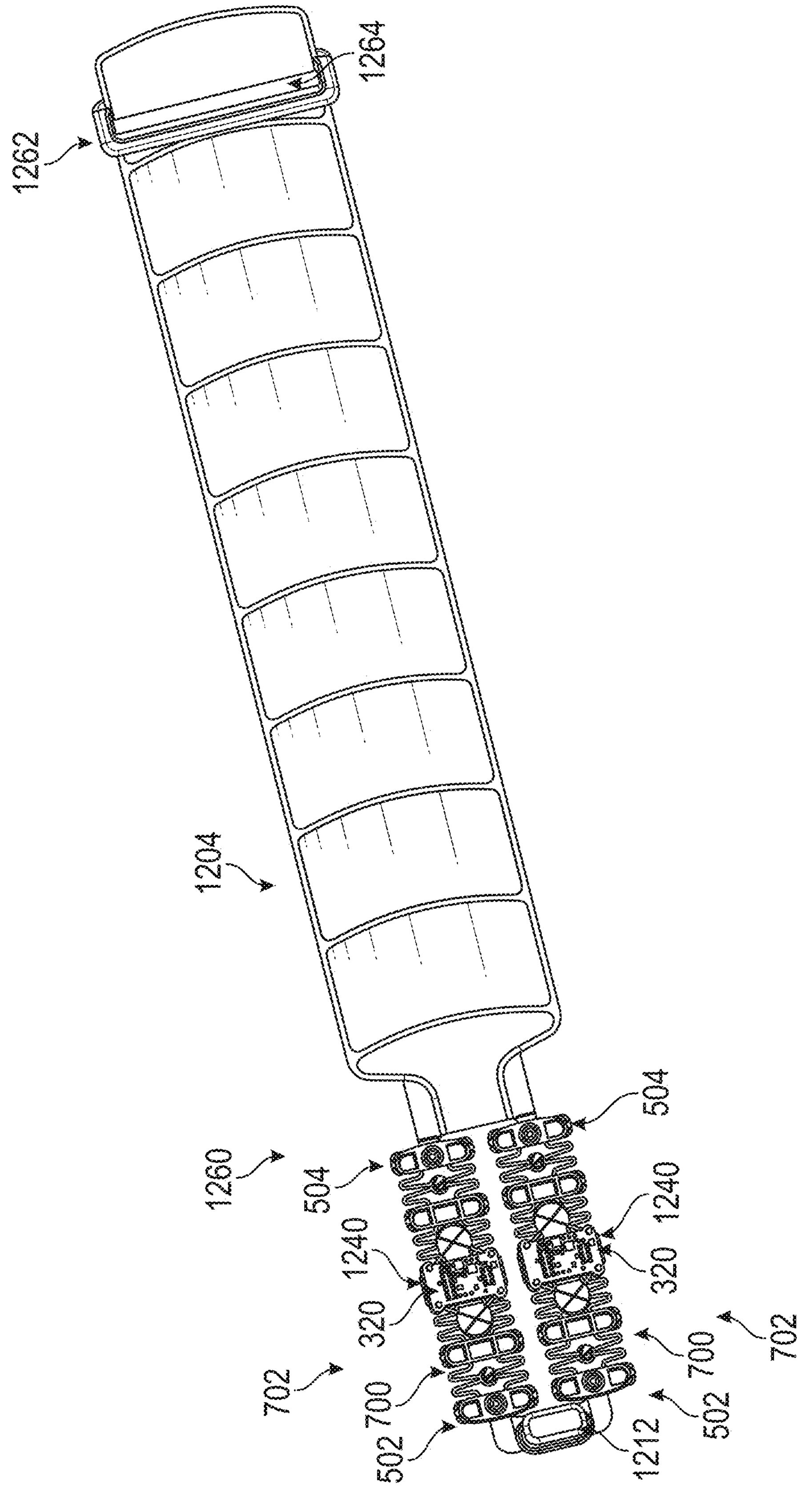
FIG. 45A illustrates a strap assembly.
Figure 45B:
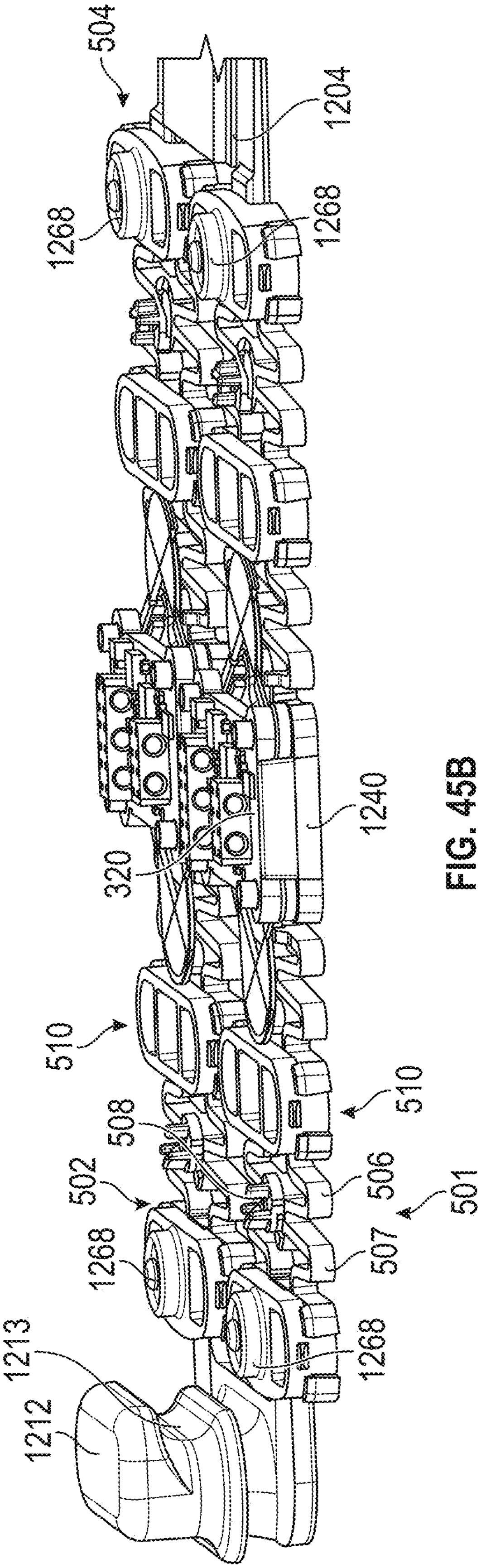
FIG. 45B illustrates an enlarged view of a portion of the strap assembly of FIG. 45A.

FIG. 45A illustrates a strap assembly 1260, which can also be referred to as a compression garment. The strap assembly 1260 can include one or more flex frame assemblies 702. The first ends 502 of the flex frames 700 can be coupled to a buckle anchor 1212. For example, as described herein, the first ends 502 can include fastener openings 1290. Fasteners 1268 can be inserted through the fastener openings 1290 to couple the flex frame assemblies 702 to the buckle anchor 1212, as illustrated in FIG. 45B. The buckle anchor 1212 can include a groove 1213, which can also be referred to as a hook. The buckle anchor 1212 can couple with a buckle 1262 attached to the primary strap 1204.

Figure 45C:
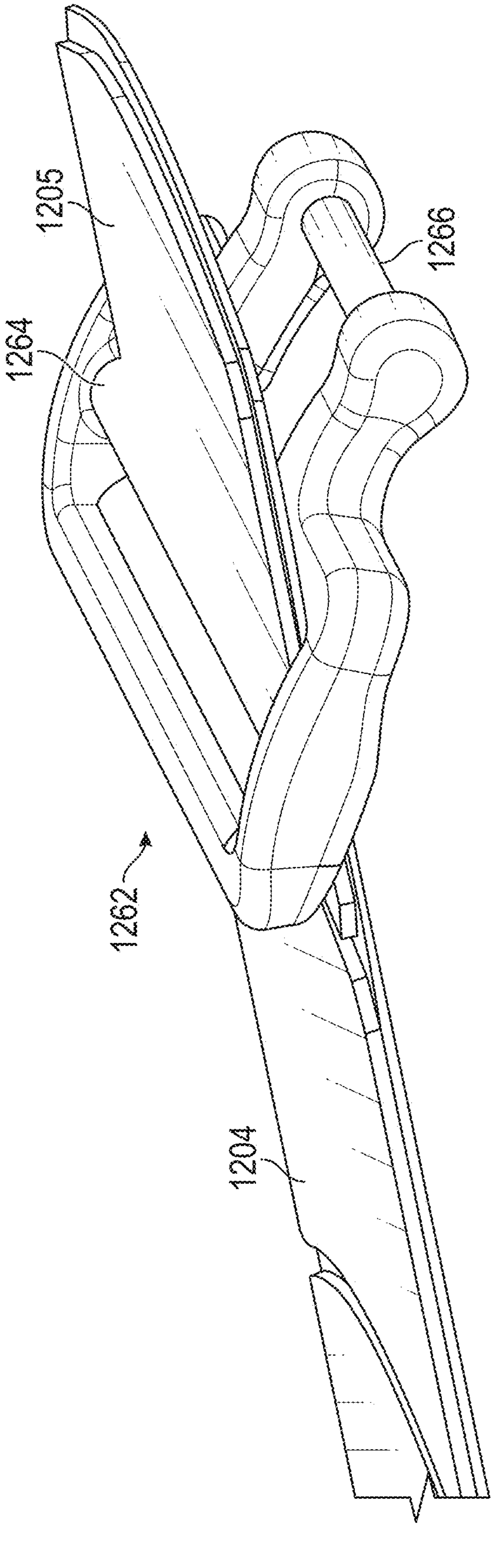
FIG. 45C illustrates an enlarged view of another portion of the strap assembly of FIG. 45A.

The primary strap 1204 can be coupled to the second ends 504 of the flex frame assemblies 702, which can be in a similar manner as described in reference to the buckle anchor 1212. For example, fasteners 1268 can be inserted through the fastener openings 1290 of the second ends 504 to couple the primary strap 1204 to the flex frames 700. As shown in FIG. 45C, the buckle 1262 can include a first bar 1264 and/or second bar 1266. The second bar 1266 can be disposed within the groove 1213 of the buckle anchor 1212 to couple the buckle 1262 to the buckle anchor 1212. The end 1205 of the primary strap 1204 can then be routed around the first bar 1264 and pulled to tighten and secure the strap assembly 1260 around an anatomical feature of the user. The buckle 1262 can include a locking mechanism to prevent the primary strap 1204 from inadvertently releasing. The flex frame assemblies 702 can then be activated to apply compression as described herein.

Figure 46A:
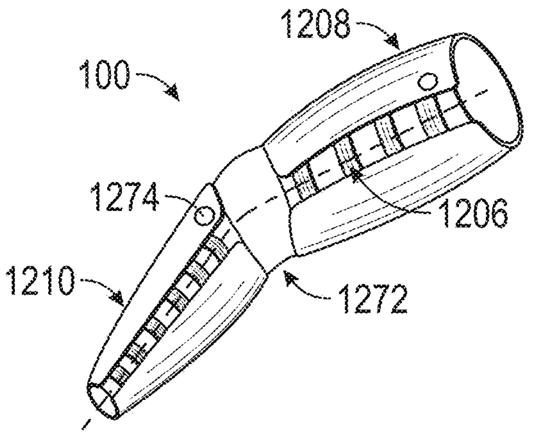
FIGS. 46A-46E illustrate various compression garments.

FIGS. 46A-46E illustrate variants of a compression garment 100. FIG. 46A illustrates a compression garment 100 with an upper portion 1208 and lower portion 1210 with a joint section 1272 therebetween. The joint section 1272 can have increased flexibility to facilitate movement of a limb of the user. The compression garment 100 can include a plurality of primary straps 1204 or secondary straps 1206 to secure the compression garment 100 to the user. The upper portion 1208 and lower portion 1210 can include dials (e.g., BOA dials) 1274, which can further tighten the compression garment 100 to the user in addition to the straps.

Figure 46B:
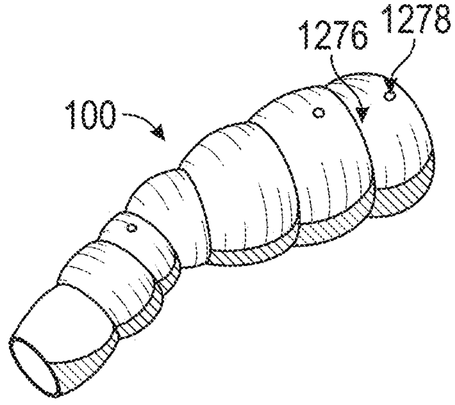

FIG. 46B illustrates a compression garment 100 with a plurality of inflatable sections 1276. The inflatable sections 1276 can be inflated to apply compressive forces to an anatomical feature of the user. In some variants, the inflatable sections 1276 can be inflated to apply uniform compression. In some variants, the inflatable sections 1276 can be inflated to various degrees to apply varying compressive forces along the length of the compression garment 100. The compression garment 100 can incorporate one or more pumps 1278 to inflate the plurality of inflatable sections 1276. In some variants, a separate pump 1278 can inflate the inflatable sections 1276. In some variants, a single pump

1278 can fill the inflatable sections 1276. In some variants, a pump 1278 can be incorporated with each inflatable sections 1276.

Figure 46C:
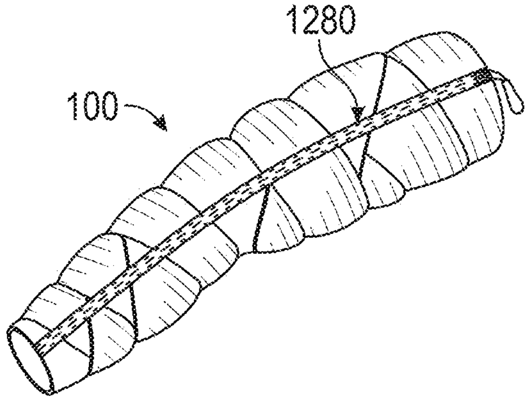

FIG. 46C illustrates a compression garment 100. The compression garment 100 can include elastic which can be pre-tightened to fit around the leg or other anatomic feature of the user. For example, in some variants, the compression garment 100 can include a crisscross pattern of elastic, which can also be referred to as a mummy wrap, to pre-tighten the compression garment 100. The compression garment 100 can include a zipper 1280. The anatomical feature of the user can be placed into the compression garment 100 and zipped in via the zipper 1280 to apply a compressive force to the anatomical feature of the user.

Figure 46D:
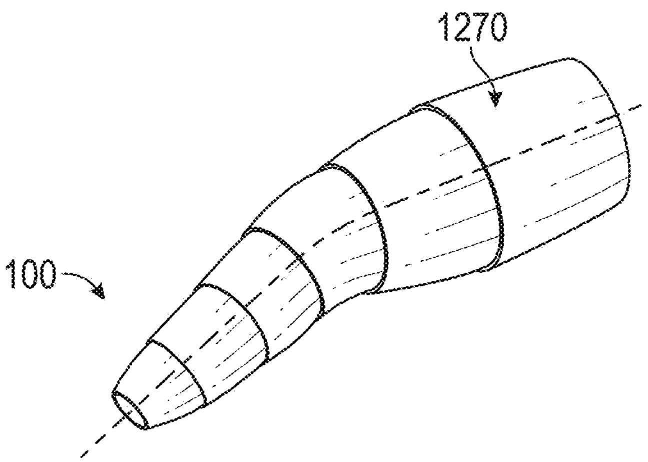

FIG. 46D illustrates a compression garment 100. The compression garment 100 can include a plurality of bands 1270. The bands 1270 can include different elastic properties such that when the compression garment 100 is disposed on the user, the bands 1270 apply varying compressive forces. The bands 1270 can be sized differently to apply varying compressive forces. In some variants, the bands 1270 can apply uniform compression to the anatomical feature of the user.

Figure 46E:
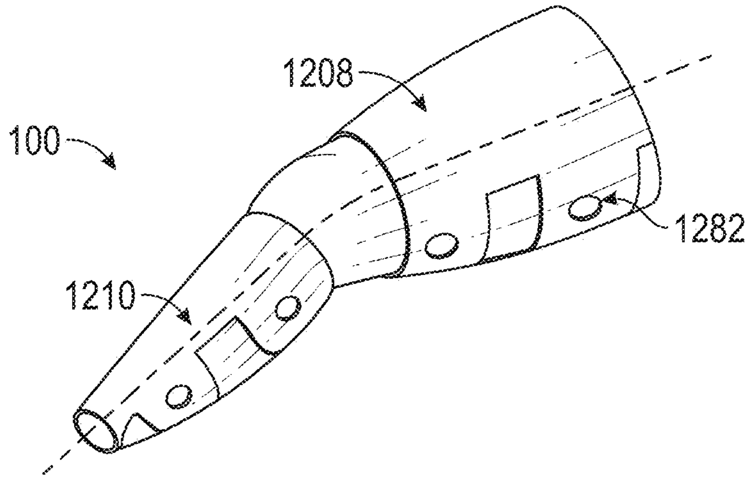

FIG. 46E illustrates a compression garment 100. The compression garment 100 can include an upper portion 1208 and a lower portion 1210. The upper portion 1208 and lower portion 1210 can each include one or more dials 1282 (e.g., two), which can be the same as the dials 1274 described in reference to FIG. 46A. The dials 1282 can be turned to tighten or loosen the upper portion 1208 or lower portion 1210 on the user. The upper portion 1208 and lower portion 1210 can be disposed over a sleeve that is placed on the anatomical feature of the user before placing the upper portion 1208 and lower portion 1210 thereon. In some variants, the upper portion 1208 and lower portion 1210 can be incorporated into a sleeve that can be disposed over the anatomical feature of the user.

It is intended that the scope of this present invention herein disclosed should not be limited by the particular disclosed embodiments described above. This invention is susceptible to various modifications and alternative forms, and specific examples have been shown in the drawings and are herein described in detail. This invention is not limited to the detailed forms or methods disclosed, but rather covers all equivalents, modifications, and alternatives falling within the scope and spirit of the various embodiments described and the appended claims.

Various other modifications, adaptations, and alternative designs are of course possible in light of the above teachings. Therefore, it should be understood at this time that within the scope of the appended claims the invention may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "tying a tie onto an orthodontic bracket" includes "instructing the tying of a tie onto an orthodontic bracket." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

All of the methods and tasks described herein may be performed and fully automated by a computer system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions, and/or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid state memory chips and/or magnetic disks, into a different state. In some embodiments, the computer system may be a cloud-based computing system whose processing resources are shared by multiple distinct business entities or other users.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry or digital logic circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC.

Additionally, all publications, patents, and patent applications mentioned in this specification are herein incorporated by reference to the same extent as if each individual publication, patent, or patent application was specifically and individually indicated to be incorporated by reference.

What is claimed is:

1. A compression garment configured to be worn on an anatomical feature of a user, the compression garment comprising:

a flex frame comprising:

a first support structure;

a second support structure;

a first spring arm connected to the first support structure;

a second spring arm connected to the second support structure; and a bridge disposed between and connected to the first spring arm and the second spring arm, the bridge comprising a guide structure having an upper channel and a lower channel separated by a partition;

a wire comprising shape memory material, the wire configured to be routed around at least the first and second support structures of the flex frame and through the upper and the lower channels of the guide structure to cross over itself at the partition, wherein the partition extends parallel to a horizontal plane of the flex frame and is configured to separate portions of the wire disposed through the upper and the lower channels; and a controller configured to apply an electrical current to the wire to generate heat, causing the wire to contract such that the flex frame deflects to a shorter length to apply a compressive force to the anatomical feature of the user to urge a flow of fluids within the anatomical feature when the compression garment is worn by the user;

wherein the first spring arm and the second spring arm are configured to deflect in response to a contraction of the wire.

2. The compression garment of claim 1, further comprising a plurality of primary straps configured to secure the compression garment around the anatomical feature of the user.

3. The compression garment of claim 2, wherein the plurality of primary straps comprise protrusions configured to break up fibrotic tissue of the user.

4. The compression garment of claim 2, further comprising a plurality of secondary straps configured to secure the compression garment around the anatomical feature of the user.

5. The compression garment of claim 1, further comprising a liner disposed between the flex frame and the anatomical feature of the user.

6. The compression garment of claim 1, further comprising protrusions configured to face inward toward the anatomical feature of the user when the compression garment is worn by the user, the protrusions configured to break up fibrotic tissue of the user.

7. The compression garment of claim 1, wherein the flex frame comprises protrusions configured to break up fibrotic tissue of the user when the compression garment is worn by the user.

8. The compression garment of claim 1, further comprising a plurality of flex frames and a plurality of wires.

9. The compression garment of claim 8, wherein the controller comprises a plurality of microcontrollers each configured to apply electrical current to one wire of the plurality of wires to facilitate localized compression to the anatomical feature of the user.

10. The compression garment of claim 1, wherein the first support structure comprises a first groove and a second groove disposed on opposing ends of the first support structure and the second support structure comprises a first groove and a second groove disposed on opposing ends of the second support structure.

11. The compression garment of claim 10, wherein the wire is configured to be routed through the first and the second grooves of each of the first and the second support structures.

12. The compression garment of claim 1, further comprising backing disposed on an outer surface of the compression garment, the backing configured to vent heat.

13. A compression garment configured to be worn on an anatomical feature of a user, the compression garment comprising:

a plurality of flex frames, each of the plurality of flex frames comprising:

a plurality of guide structures, each of the plurality of guide structures having an upper channel and a lower channel separated by a partition, wherein the upper channel is configured to be positioned more distally relative to the anatomical feature compared to the lower channel when the compression garment is worn on the anatomical feature;

a first support structure;

a second support structure;

a first spring arm connected to the first support structure;

a second spring arm connected to the second support structures; and a bridge disposed between and connected to the first spring arm and the second spring arm, the bridge comprising one of the plurality of guide structures;

a plurality of wires, each of the plurality of wires comprising shape memory material and configured to be respectively wrapped around at least the first and second support structures of one flex frame of the plurality of flex frames and through the upper and the lower channels of the plurality of guide structures of the one flex frame to cross over itself at the partition, wherein each of the partitions of the plurality of guide structures extends parallel to a horizontal plane of the one flex frame and is configured to electrically isolate the wire from itself as the wire crosses over itself; and a plurality of microcontrollers, each of the plurality of microcontrollers configured to apply an electrical current to one wire of the plurality of wires to generate heat, causing the one wire to contract, deflecting the first spring arm and the second spring arm, such that the corresponding one flex frame of the plurality of flex frames deflects to a shorter length to apply a compressive force to the anatomical feature of the user to urge a flow of fluids within the anatomical feature when the compression garment is worn by the user.

14. The compression garment of claim 13, further comprising a plurality of primary straps configured to secure the compression garment around the anatomical feature of the user.

15. The compression garment of claim 14, wherein the primary straps comprise protrusions configured to break up fibrotic tissue of the user.

16. The compression garment of claim 14, further comprising a plurality of secondary straps configured to secure the compression garment around the anatomical feature of the user.

17. The compression garment of claim 13, further comprising a liner disposed between the plurality of flex frames and the anatomical feature of the user.

18. The compression garment of claim 13, further comprising protrusions configured to face inward toward the anatomical feature of the user, the protrusions configured to break up fibrotic tissue of the user.

19. The compression garment of claim 13, wherein the plurality of flex frames comprise protrusions configured to break up fibrotic tissue of the user.

20. The compression garment of claim 13, wherein the plurality of microcontrollers are configured to apply electrical current to the plurality of wires in a sequence in a longitudinal direction of the compression garment to direct the flow of fluids in the anatomical feature.

21. The compression garment of claim 13, further comprising backing disposed on an outer surface of the compression garment, the backing configured to vent heat.

22. The compression garment of claim 13, further comprising one or more sensors to measure one or more parameters of the user.

23. A compression garment configured to be worn on an anatomical feature of a user, the compression garment comprising:

a flex frame comprising:

a plurality of guide structures, each of the plurality of guide structures having an upper channel and a lower channel separated by a partition, wherein the upper channel is configured to be positioned more distally relative to the anatomical feature of the user compared to the lower channel when the compression garment is worn on the anatomical feature;

a first support structure;

a second support structure;

a first spring arm connected to the first support structure;

a second spring arm connected to the second support structure; and a bridge disposed between and connected to the first spring arm and the second spring arm, the bridge comprising one guide structure of the plurality of guide structures;

a wire comprising shape memory material, the wire configured to be routed around at least the first and second support structures of the flex frame and through the upper and the lower channels of each of the plurality of guide structures to cross over itself at each of the partitions, wherein each partition extends parallel to a horizontal plane of the flex frame and is configured to separate portions of the wire disposed through the upper and the lower channels; and a controller configured to apply an electrical current to the wire to generate heat, causing the wire to contract such that the flex frame deflects to a shorter length to apply a compressive force to the anatomical feature of the user to urge a flow of fluids within the anatomical feature when the compression garment is worn by the user.

24. The compression garment of claim 23, wherein the first spring arm and the second spring arm are configured to deflect in response to a contraction of the wire.

25. The compression garment of claim 23, further comprising protrusions configured to break up fibrotic tissue of the user.

* * * * *